US009969791B2

(12) United States Patent
Chuang et al.

(10) Patent No.: US 9,969,791 B2
(45) Date of Patent: May 15, 2018

(54) MODIFIED FIBRONECTIN FRAGMENTS OR VARIANTS AND USES THEREOF

(71) Applicants: DCB-USA LLC, Wilmington, DE (US); NATIONAL CHENG KUNG UNIVERSITY, Tainan (TW)

(72) Inventors: Woei-Jer Chuang, Tainan (TW); Yung-Sheng Chang, Tainan (TW)

(73) Assignee: NATIONAL CHENG KUNG UNIVERSITY, Tainan (TW)

(*) Notice: Subject to any disclaimer, the term of this patent is extended or adjusted under 35 U.S.C. 154(b) by 254 days.

(21) Appl. No.: 14/406,215

(22) PCT Filed: Jun. 7, 2013

(86) PCT No.: PCT/US2013/044699
§ 371 (c)(1),
(2) Date: Dec. 7, 2014

(87) PCT Pub. No.: WO2013/185027
PCT Pub. Date: Dec. 12, 2013

(65) Prior Publication Data
US 2015/0218251 A1      Aug. 6, 2015

Related U.S. Application Data

(60) Provisional application No. 61/656,671, filed on Jun. 7, 2012.

(51) Int. Cl.
*A61K 39/00* (2006.01)
*A61K 38/00* (2006.01)
*C07K 14/78* (2006.01)

(52) U.S. Cl.
CPC .............. *C07K 14/78* (2013.01); *A61K 38/00* (2013.01)

(58) Field of Classification Search
None
See application file for complete search history.

(56) References Cited

U.S. PATENT DOCUMENTS

| 4,554,101 A | 11/1985 | Hopp | |
|---|---|---|---|
| 2005/0118661 A1* | 6/2005 | Mardon | G01N 33/689 435/7.92 |
| 2013/0337038 A1* | 12/2013 | Hocking | A61K 38/39 424/446 |

OTHER PUBLICATIONS

Richards, JL., Identification and Functional Characterization of Novel Receptor Ligands of CD40 and Alpha(v)beta(3) Integrin: Implications for Gene Delivery. Ph.D Dissertation. Department of Microbiology and Immunology, School of Medicine and Dentistry, University of Rochester, Rochester, NY,p. 1-197, 2002.*

Silverman et al. Engineered Cystine-Knot Peptides That Bind αvβ3 Integrin With Antibody-Like Affinities. J Mol Biol. Jan. 30, 2009; 385(4): 1064-1075.*
Richards et al. Engineered Fibronectin Type III Domain with a RGDWXE Sequence Binds with Enhanced Affinity and Specificity to Human αvβ3 Integrin. J. Mol. Biol. (2003) 326, 1475-1488.*
Koivunen et al. Identification of Receptor Ligands with Phage Display Peptide Libraries. J Nucl Med; 40:883-888, 1999.*
Christmann et al. The cystine knot of a squash-type protease inhibitor as a structural scaffold for *Escherichia coli* cell surface display of conformationally constrained peptides. Protein Eng. Sep. 1999;12(9):797-806.*
Koivunen et al. Phage libraries displaying cyclic peptides with different ring sizes: Ligand specificities of the rgd-directed . integrine. BioTechnology, 13(3), Mar. 1995, pp. 265-270.*
Yung-Sheng Chang and Woei-Jer Chuang. The Ninth and/or Tenth Modules of Fibronectin Type III Domains as the Scaffolds to Design Integrins αvβ3 and/or α5β1-specific Antagonists Yung-Sheng Chang and Woei-Jer Chuang. ISSX Online Abstracts, Supplement 6, No. 1, 2011 4th Asian Pacific Regional ISSX Meeting T'ainan, Taiwan | Apr. 2011.*
Yamada et al. Tailoring echistatin to possess higher affinity for integrin αIIbβ3. FEBS Letters 387 (1996) 11-15.*
Siggers, et al., "Conformational Dynamics in Loop Swap Mutants of Homologous Fibronectin Type III Domains," Biophysical Journal, 93: 2447-2456 (2007).*
Lu X et al. Preferential antagonism of the interactions of the integrin αIIb β3 with immobilized glycoprotein ligands by snake-venom RGD (Arg-Gly-Asp) proteins. Evidence supporting a functional role for the amino acid residues flanking the tripeptide RGD in determining the inhibitory properties of snake-venom RGD p(1994) Biochem J 304: 929-936).*
Roy et al., "Synthetic Matrix Mimetics Specify Integrin Adhesion and Direct Extracellular Matrix Assembly," TERMIS-NA Annual Meeting (Dec. 13, 2011).*
Altroff et al. (2004) "Interdomain Tilt Angle Determines Integrin-dependent Function of the Ninth and Tenth FIII Domains of Human Fibronectin," J. Biol. Chem. 279:55995-56003.
Arnaoutova et al. (2010) "In vitro angiogenesis: endothelial cell tube formation on gelled basement membrane extract," Nature Protocols. 5:628-635.
Bisanz et al. (2005) "Targeting ECM-Integrin Interaction with Liposome-Encapsulated Small Interfering RNAs Inhibits the Growth of Human Prostate Cancer in a Bone Xenograft Imaging Model," Mol. Ther. 12:634-643.
Brooks et al. (1994) "Integrin αvβ3 antagonists promote tumor regression by inducing apoptosis of angiogenic blood vessels," Cell. 79:1157-1164.
Bruylants et al. (2005) "Differential scanning calorimetry in life science: thermodynamics, stability, molecular recognition and application in drug design," Curr. Med. Chem. 12(17):2011-2020.
Chu et al. (1981) "SV40 DNA transfection of cells in suspension: analysis of efficiency of transcription and translation of T-antigen," Gene. 13:197-202.

(Continued)

*Primary Examiner* — Maher M Haddad
(74) *Attorney, Agent, or Firm* — Lathrop Gage LLP; James H. Velema, Esq.

(57) ABSTRACT

The present invention provides isolated polypeptides comprising a modified fibronectin fragment that comprises FNIII 10 and optionally further comprising FNIII 9. Also provided are pharmaceutical compositions comprising the polypeptides and methods of making and using the polypeptides.

15 Claims, 23 Drawing Sheets

(56) References Cited

OTHER PUBLICATIONS

Figure 1:
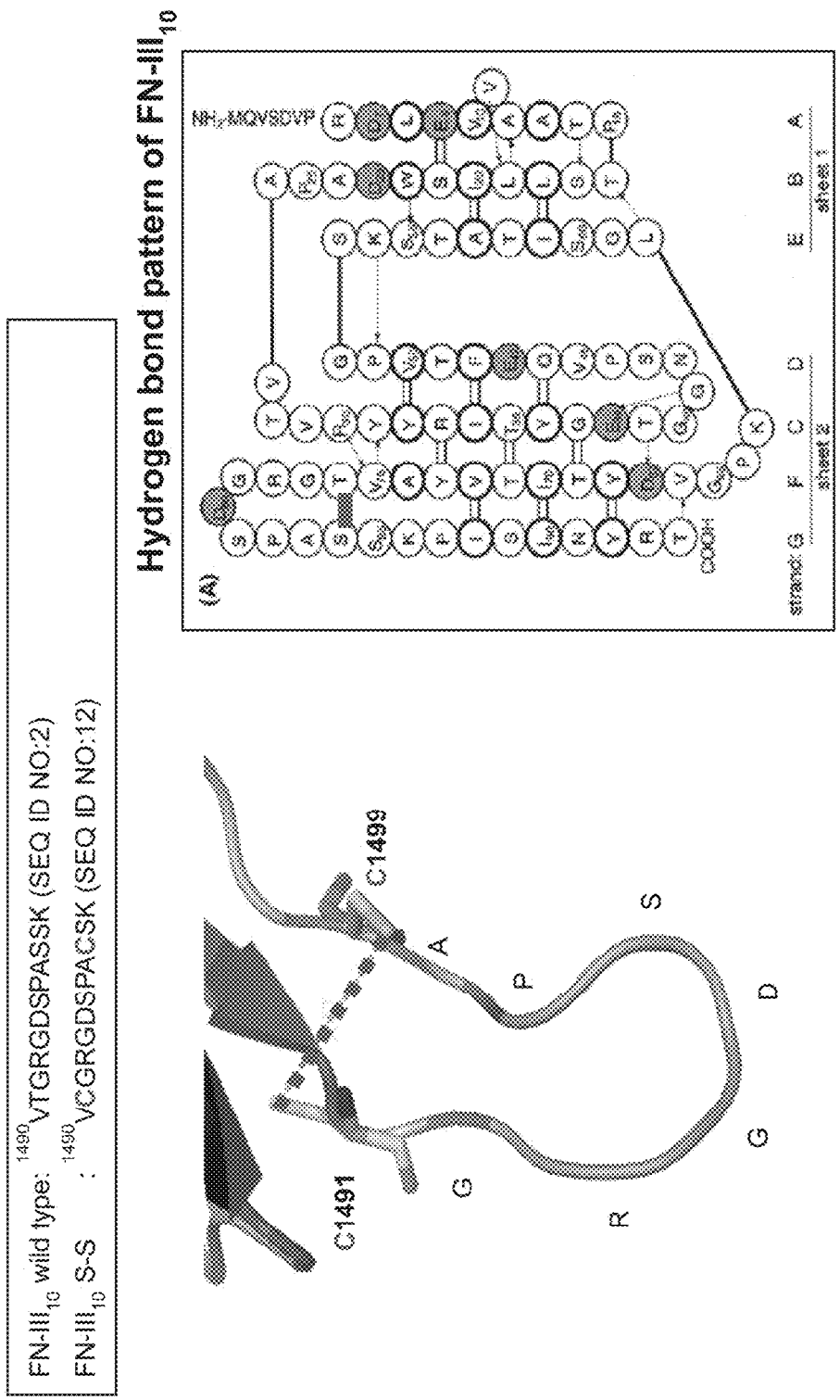

Coller et al. (2008) "The GPIIb/IIIa (integrin αIIbβ3) odyssey: a technology-driven saga of a receptor with twists, turns, and even a bend," Blood. 112:3011-3025.
Demarest et al. (2004) "Packing, specificity, and mutability at the binding interface between the p160 coactivator and CREB-binding protein," Protein Sci. 13(1):203-210.
Eble et al. (1998) "Recombinant Soluble Human α3β1 Integrin: Purification, Processing, Regulation, and Specific Binding to Laminin-5 and Invasin in a Mutually Exclusive Manner," Biochemistry. 37:10945-10955.
Genbank Databse [online] (Feb. 10, 2016) "fibronectin isoform 5 precursor [*Homo sapiens*]," Accession No. NP_997641. National Center for Biotechnology Information. Accessible on the Internet at URL: https://www.ncbi.nlm.nih.gov/protein/NP_997641. [Last Accessed Oct. 25, 2016].
Genbank Databse [online] (Feb. 10, 2016) "*Homo sapiens* fibronectin 1 (FN1), transcript variant 5, mRNA," Accession No. NM_212476. National Center for Biotechnology Information. Accessible on the Internet at URL: https://www.ncbi.nlm.nih.gov/nuccore/NM_212476. [Last Accessed Oct. 25, 2016].
Genbank Databse [online] (Jul. 26, 2016) "fibronectin 1, isoform CRA_d [Rattus norvegicus]," Accession No. EDL75262. National Center for Biotechnology Information. Accessible on the Internet at URL: https://www.ncbi.nlm.nih.gov/protein/EDL75262. [Last Accessed Oct. 25, 2016].
Genbank Databse [online] (Jun. 2, 2016) "Predicted: fibronectin isoform X18 [Pan troglodytes]," Accession No. XP_003309506. National Center for Biotechnology Information. Accessible on the Internet at URL: https://www.ncbi.nlm.nih.gov/protein/XP_003309506. [Last Accessed Oct. 25, 2016].
Genbank Databse [online] (May 21, 2010) "TPA: fibronectin [Bos taurus]" Accession No. DAA32456. National Center for Biotechnology Information. Accessible on the Internet at URL: https://www.ncbi.nlm.nih.gov/protein/DAA32456. [Last Accessed Oct. 25, 2016].
Genbank Databse [online] (Oct. 6, 2010) "unnamed protein product [Mus musculus]," Accession No. BAE28040. National Center for Biotechnology Information. Accessible on the Internet at URL: https://www.ncbi.nlm.nih.gov/protein/BAE28040. [Last Accessed Oct. 25, 2016].
Genbank Databse [online] (Sep. 11, 2015) "Predicted: fibronectin isoform X12 [Sus scrofa]," Accession No. XP_003133691. National Center for Biotechnology Information. Accessible on the Internet at URL: https://www.ncbi.nlm.nih.gov/protein/XP_003133691. [Last Accessed Oct. 25, 2016].
Golovanov et al. (2004) "A Simple Method for Improving Protein Solubility and Long-Term Stability," J. Am. Chem. Soc. 126:8933-8939.
Graham et al. (1973) "A new technique for the assay of infectivity of human adenovirus 5 DNA," Virology. 52:456-467.
Hamburger et al. (1999) "Crystal structure of invasin: a bacterial integrin-binding protein," Science. 286(5438)291-295.
Kleinman et al. (1986) "Basement membrane complexes with biological activity," Biochemistry. 25(2):312-318.
Koide et al. (2001) "Stabilization of a fibronectin type III domain by the removal of unfavorable electrostatic interactions on the protein surface," Biochemistry. 40:10326-10333.
Kyte et al. (1982) "A simple method for displaying the hydropathic character of a protein," J. Mol. Biol. 157:105-131.
Maubant et al. (2006) "Blockade of αvβ3 and αvβ5 integrins by RGD mimetics induces anoikis and not integrin-mediated death in human endothelial cells," Blood. 108:3035-3044.
Morgan et al. (2009) "Giving off mixed signals—Distinct functions of α5β1 and αvβ3 integrins in regulating cell behaviour," IUBMB Life. 61:731-738.
Morton et al. (2007) "Establishment of human tumor xenografts in immunodeficient mice," Nature Protocols. 2:247-250.
Passaniti et al. (1992) "A simple, quantitative method for assessing angiogenesis and antiangiogenic agents using reconstituted basement membrane, heparin, and fibroblast growth factor," Lab. Invest. 67:519-528.
Richards et al. (2003) "Engineered Fibronectin Type III Domain with a RGDWXE Sequence Binds with Enhanced Affinity and Specificity to Human αvβ3 Integrin," J. Mol. Biol. 326(5):1475-1488.
Sanchez-Ruiz et al. (1988) "Differential scanning calorimetry of the irreversible thermal denaturation of thermolysin," Biochemistry. 27:1648-1652.
Smith (2008) "3. Adhesion molecules and receptors," J. Allergy. Clin. Immunol. 121(2 Suppl):S375-379.
Spink (2008) "Differential scanning calorimetry," Methods Cell Biol. 84:115-141.
Thornton et at. (1991) "Protein structure. Prediction of progress at last," Nature 354(6349):105-106.
Trevino et al. (2008) "Measuring and increasing protein solubility," Journal of Pharmaceutical Sciences. 97:4155-4166.
Van Der Walle et al. (2002) "Novel mutant human fibronectin FIII9-10 domain pair with increased conformational stability and biological activity," Protein Engineering. 15:1021-1024.
Van Nhieu et al. (1996) "Mutations in the Cytoplasmic Domain of the Integrin β1 Chain Indicate a Role for Endocytosis Factors in Bacterial Internalization," J. Biol. Chem. 271:7665-7672.
Vermeer et al. (2000) "The thermal stability of immunoglobulin: unfolding and aggregation of a multi-domain protein," Biophys. J. 78(1):394-404.
Vlieghe et al. (2010) "Synthetic therapeutic peptides: science and market," Drug Discovery Today. 15:40-56.
Zhang et al. (1998) "Specific Interaction of the Recombinant Disintegrin-like Domain of MDC-15 (Metargidin, ADAM-15) with Integrin αvβ3," J. Biol. Chem. 273:7345-7350.
Lemmon et al. (2011) "Probing the folded state of fibronectin type III domains in stretched fibrils by measuring buried cysteine accessibility," J. Biol. Chem. 286(3):26375-26382.
Ohashi et al. (2005) "Domain unfolding plays a role in superfibronectin formation," J. Biol. Chem. 280(47):39143-39151.
Yamada et al. (1995) "Structure of a conformationally constrained Arg-Gly-Asp sequence inserted into human lysozyme," J. Biol. Chem. 270(11):5687-5690.
Kumagai et al. (May 31, 1991) "Effect of Cyclic RGD Peptide on Cell Adhesion and Tumor Metastasis," Biochemical and Biophysical Research Communications. 177(1):74-82.

* cited by examiner

```
Human       GLDSPTGIDFSDITANSFTVHWIAPRATITGYKIRHHPEHFSGRPREDRVPHSRNSITLT   60
Chimpanzee  GLDSPTGIDFSDITANSFTVHWIAPRATITGYKIRHHPEHLSGRPREDRVPPSRNSITLT   60
Cow         ALDSPSGIBFSDITANSFTVHWIAPRATITGYKIRHHPENMGGRPREDRVPPSRNSITLT   60
Boar        GLDSPTGIDFSDITANSFTVHWIAPRATITGYKIRHHPEHMGRPREDRVPPSRNSITLT   60
Mouse       GLDSPTGFDSSDITARSFTVHWVAPRAPITGYIIRHHAEHSVGRFRQDRVFFSRNSITLT   60
Rat         GLDSPTGFDSSDVTANSFTVHWVAPRAPITGYIIRHHAEHSAGRFRQDRVPPSRNSITLT   60
             ****:*:*: **.****:***.*****.**   *:: .***:.; *****  *****

Human       NLTPGTEYVVSIVALNGREESPLLIGQQSTVSDVERDLEVVAATPTSLLISWDAPAVTVR  120
Chimpanzee  NLTPGTEYVVSIVALRGREESPLIGQQSTVSDVPRDLEVVAATPTSLLISWDAPAVTVR  120
Cow         NLNPGTEYVVSIVALNSKEESLFLVGQQSTVSDVPKDLEVLAAHPTSLLISWDAPAVTVR  120
Boar        NLIPGVEYVVSIVAVRGREESPPLVGQQSTVSDVPRDLQVIATTPTSLLISWDAPAVTVR  120
Mouse       NLNPGTEYVVSILAVEGREESPPLIGQQATVSDIPRDLEVLASTPTSLLISWEPPAVSVR  120
Rat         NLNPGTEYIVTILAVEGREESPPLIGQQSTVSDVPRDLEVLASTPTSLLISWEPPAVSVR  120
            ** **.**:*:*.:. :***  ::*** :***: :**:*:*: :*********: **:**

Human       YYPRITYGETGGNSPVQEFTVPGSKSTATISGLKFGVDYTITVYAVTGRGRGRGDSPASSKPISI  180
Chimpanzee  YYPRITYGETGGNSPVQEFTVPGSKSTATISGLKFGVDYTITVYAVTGRGDSPASSKPISI  180
Cow         YYPRITYGETGGSSPVQEFTVPGSKSTATISGLKFGVDYTITVYAVTGRGDSPASSKPVSI  180
Boar        YYRRITYGETGGNSPVQEFTVPGSKSTATINNIKPGADYTITLYAVTGRGDSPASSKPVSI  180
Mouse       YYRRITYGETGGNSPVQEFTVPGSKSTATINNIKPGADYTITLYAVTGRGDSPASSKPVSI  180
Rat         YYPRITYGEHGGNSPVQEFTVPGSKSTATINNIKFGADYTITINAVTGRGDSPASSKPVSI  180
            ** ***** ***.****************:. :: *.***:.******** ********:

Human       NYRT  184  (SEQ ID NO: 4)
Chimpanzee  NYRT  184  (SEQ ID NO: 66)
Cow         NYRT  184  (SEQ ID NO: 67)
Boar        DYRT  184  (SEQ ID NO: 68)
Mouse       NYKT  184  (SEQ ID NO: 69)
Rat         NYQT  184  (SEQ ID NO: 70)
            :*:*
```

Figure 2

Figure 3:
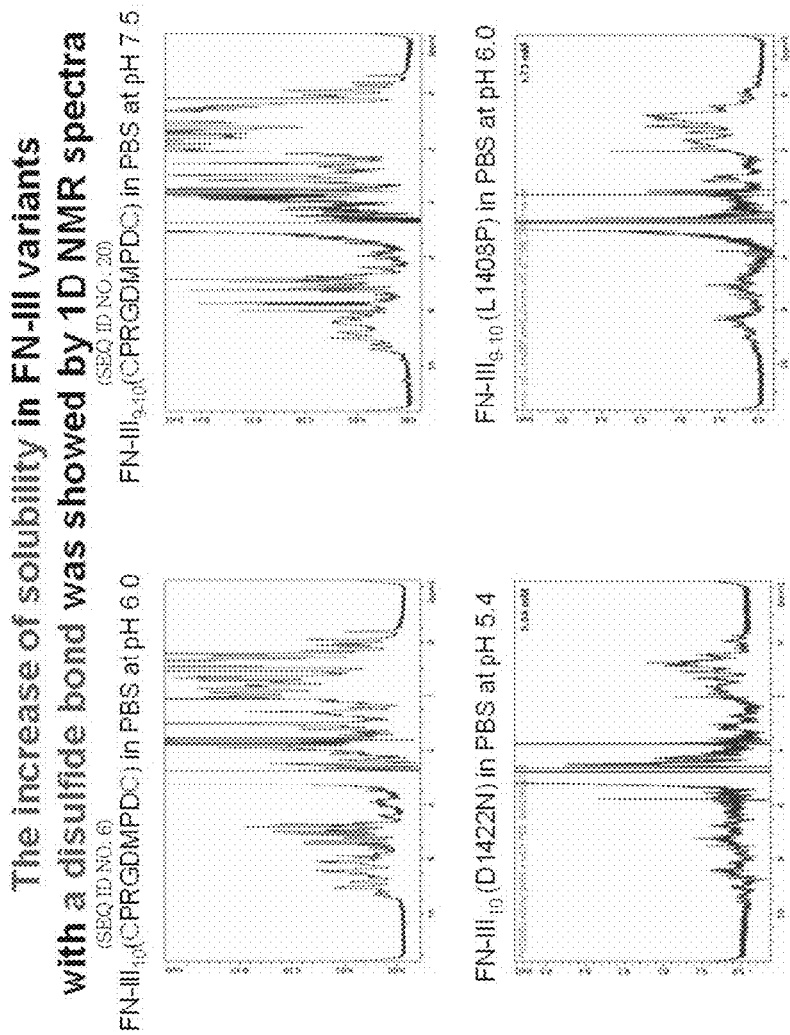
Figure 3:
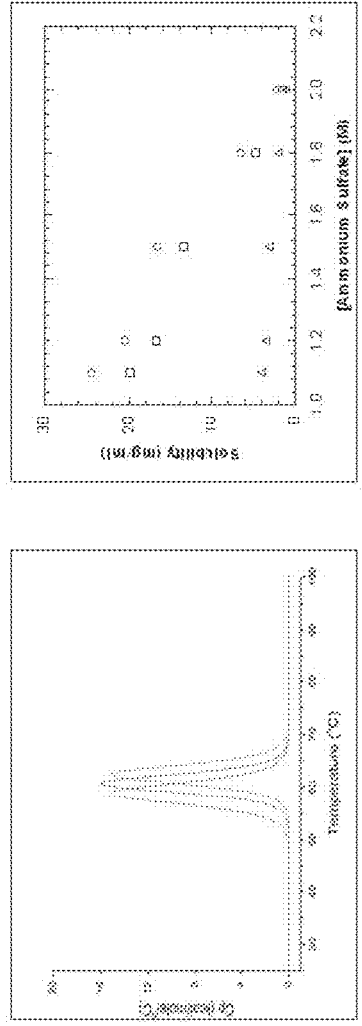

Thermostability and Solubility of FN-III$_{10}$ Variants
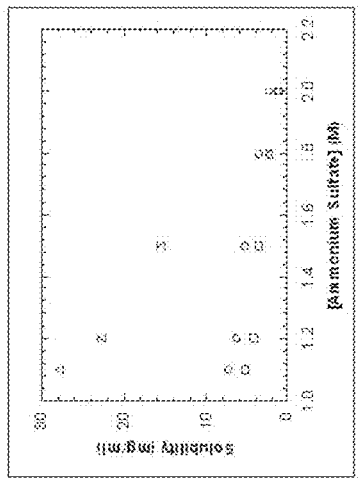
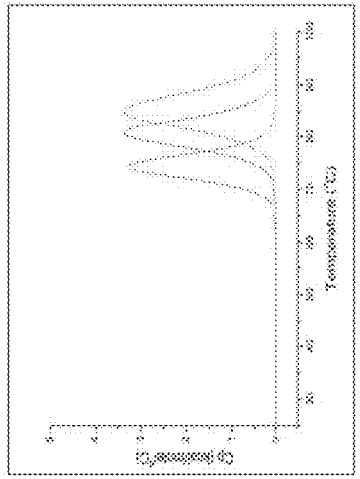
Figure 3 (Continued)

C.

D.

A
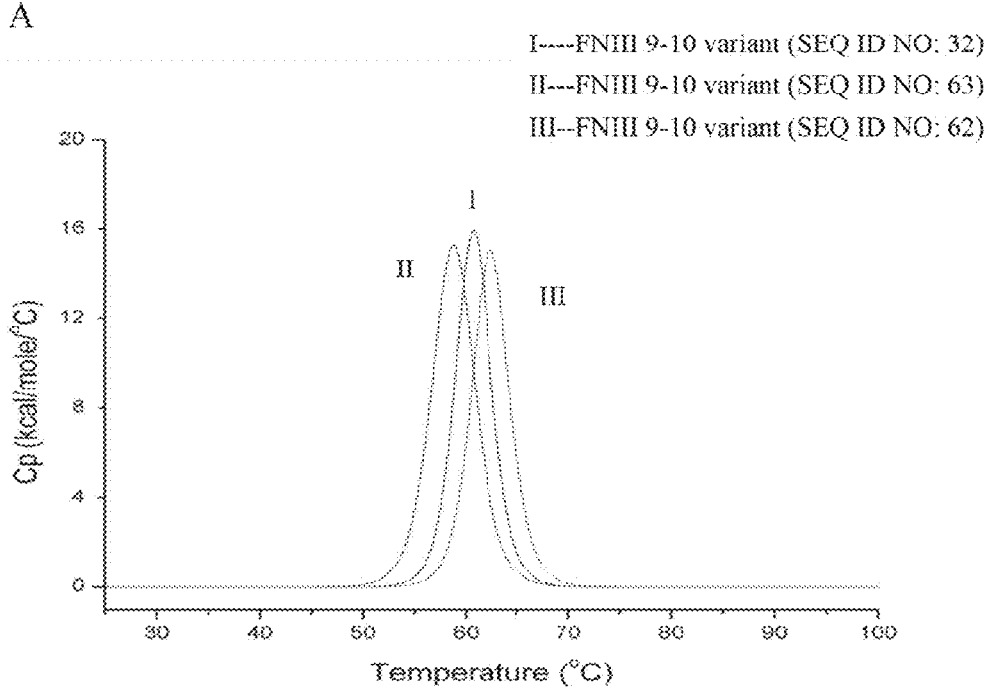
B
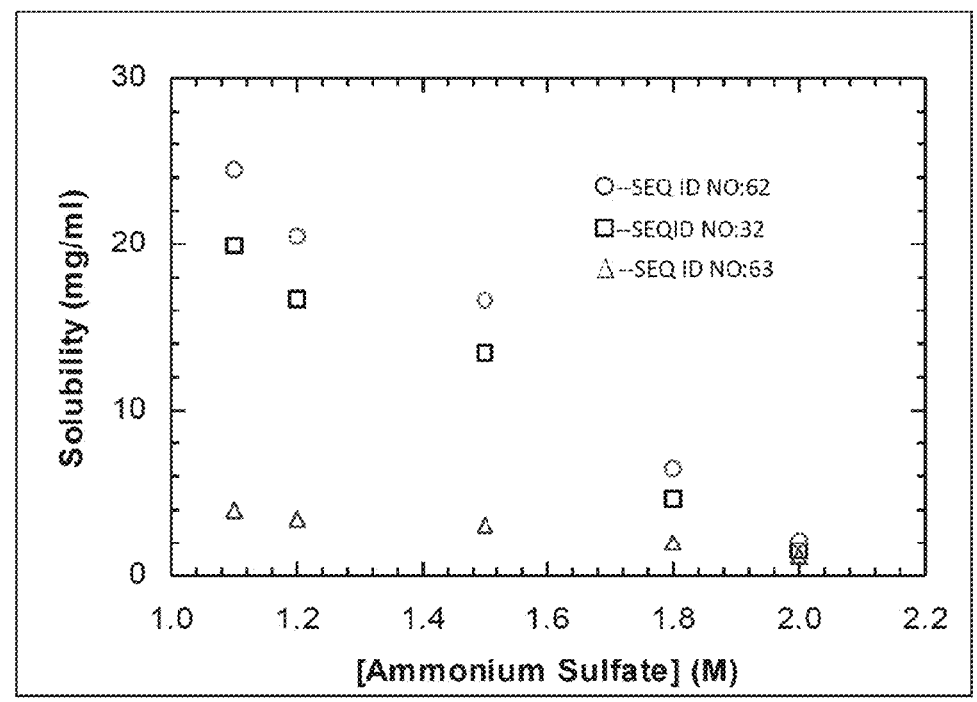
Figure 8

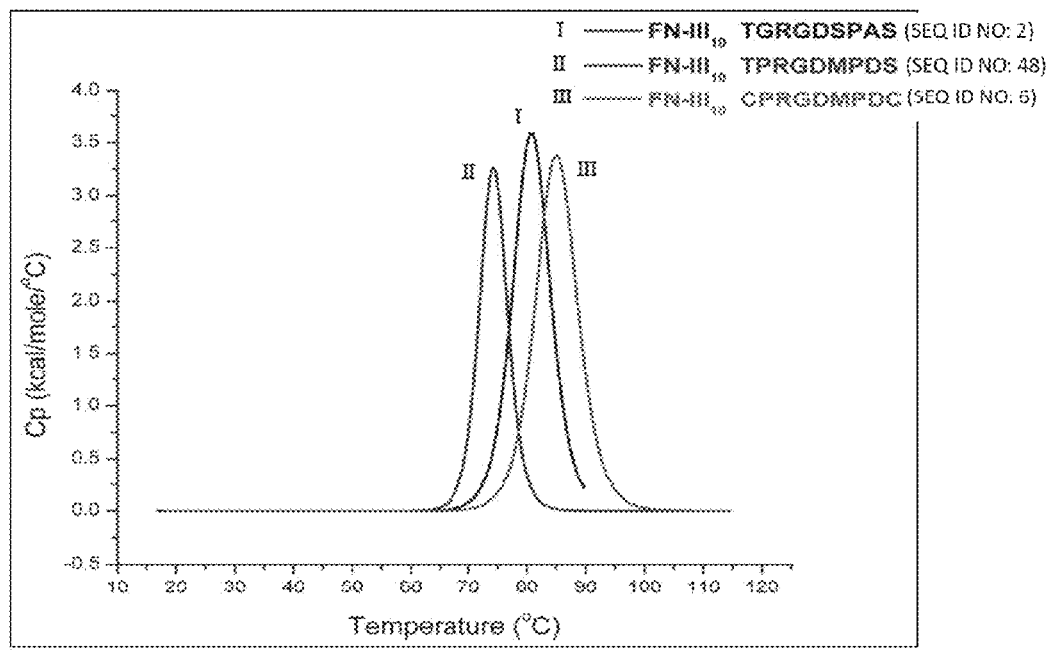
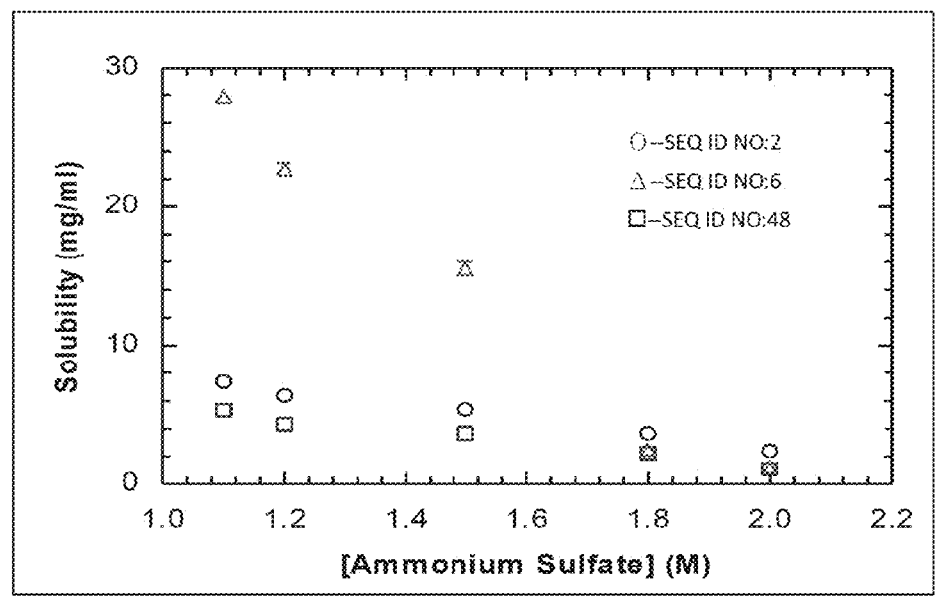
Figure 9

SEQUENCE LISTING

```
<160> NUMBER OF SEQ ID NOS: 123

<210> SEQ ID NO 1
<211> LENGTH: 282
<212> TYPE: DNA
<213> ORGANISM: Homo sapiens
<220> FEATURE:
<221> NAME/KEY: CDS
<222> LOCATION: (1)..(282)

<400> SEQUENCE: 1 gtt tct gat gtt ccg agg gac ctg gaa gtt gtt gct gcg acc ccc acc      48
Val Ser Asp Val Pro Arg Asp Leu Glu Val Val Ala Ala Thr Pro Thr
1               5                   10                  15 agc cta ctg atc agc tgg gat gct cct gct gtc aca gtg aga tat tac      96
Ser Leu Leu Ile Ser Trp Asp Ala Pro Ala Val Thr Val Arg Tyr Tyr
            20                  25                  30 agg atc act tac gga gaa aca gga gga aat agc cct gtc cag gag ttc     144
Arg Ile Thr Tyr Gly Glu Thr Gly Gly Asn Ser Pro Val Gln Glu Phe
        35                  40                  45 act gtg cct ggg agc aag tct aca gct acc atc agc ggc ctt aaa cct     192
Thr Val Pro Gly Ser Lys Ser Thr Ala Thr Ile Ser Gly Leu Lys Pro
    50                  55                  60 gga gtt gat tat acc atc act gtg tat gct gtc act ggc cgt gga gac     240
```

```
Gly Val Asp Tyr Thr Ile Thr Val Tyr Ala Val Thr Gly Arg Gly Asp
 65                  70                  75                  80 agc ccc gca agc agc aag cca att tcc att aat tac cga aca               282
Ser Pro Ala Ser Ser Lys Pro Ile Ser Ile Asn Tyr Arg Thr
                 85                  90

<210> SEQ ID NO 2
<211> LENGTH: 94
<212> TYPE: PRT
<213> ORGANISM: Homo sapiens

<400> SEQUENCE: 2

Val Ser Asp Val Pro Arg Asp Leu Glu Val Val Ala Ala Thr Pro Thr
 1               5                  10                  15

Ser Leu Leu Ile Ser Trp Asp Ala Pro Ala Val Thr Val Arg Tyr Tyr
                20                  25                  30

Arg Ile Thr Tyr Gly Glu Thr Gly Gly Asn Ser Pro Val Gln Glu Phe
             35                  40                  45

Thr Val Pro Gly Ser Lys Ser Thr Ala Thr Ile Ser Gly Leu Lys Pro
 50                  55                  60

Gly Val Asp Tyr Thr Ile Thr Val Tyr Ala Val Thr Gly Arg Gly Asp
 65                  70                  75                  80

Ser Pro Ala Ser Ser Lys Pro Ile Ser Ile Asn Tyr Arg Thr
                 85                  90

<210> SEQ ID NO 3
<211> LENGTH: 552
<212> TYPE: DNA
<213> ORGANISM: Homo sapiens
<220> FEATURE:
<221> NAME/KEY: CDS
<222> LOCATION: (1)..(552)

<400> SEQUENCE: 3 ggt ctt gat tcc cca act ggc att gac ttt tct gat att act gcc aac        48
Gly Leu Asp Ser Pro Thr Gly Ile Asp Phe Ser Asp Ile Thr Ala Asn
 1               5                  10                  15 tct ttt act gtg cac tgg att gct cct cga gcc acc atc act ggc tac        96
Ser Phe Thr Val His Trp Ile Ala Pro Arg Ala Thr Ile Thr Gly Tyr
                20                  25                  30 agg atc cgc cat cat ccc gag cac ttc agt ggg aga cct cga gaa gat       144
Arg Ile Arg His His Pro Glu His Phe Ser Gly Arg Pro Arg Glu Asp
             35                  40                  45 cgg gtg ccc cac tct cgg aat tcc atc acc ctc acc aac ctc act cca       192
Arg Val Pro His Ser Arg Asn Ser Ile Thr Leu Thr Asn Leu Thr Pro
 50                  55                  60 ggc aca gag tat gtg gtc agc atc gtt gct ctt aat ggc aga gag gaa       240
Gly Thr Glu Tyr Val Val Ser Ile Val Ala Leu Asn Gly Arg Glu Glu
 65                  70                  75                  80 agt ccc tta ttg att ggc caa caa tca aca gtt tct gat gtt ccg agg       288
Ser Pro Leu Leu Ile Gly Gln Gln Ser Thr Val Ser Asp Val Pro Arg
                85                  90                  95 gac ctg gaa gtt gtt gct gcg acc ccc acc agc cta ctg atc agc tgg       336
Asp Leu Glu Val Val Ala Ala Thr Pro Thr Ser Leu Leu Ile Ser Trp
           100                 105                 110 gat gct cct gct gtc aca gtg aga tat tac agg atc act tac gga gaa       384
Asp Ala Pro Ala Val Thr Val Arg Tyr Tyr Arg Ile Thr Tyr Gly Glu
        115                 120                 125 aca gga gga aat agc cct gtc cag gag ttc act gtg cct ggg agc aag       432
Thr Gly Gly Asn Ser Pro Val Gln Glu Phe Thr Val Pro Gly Ser Lys
    130                 135                 140
```

```
tct aca gct acc atc agc ggc ctt aaa cct gga gtt gat tat acc atc      480
Ser Thr Ala Thr Ile Ser Gly Leu Lys Pro Gly Val Asp Tyr Thr Ile
145                 150                 155                 160 act gtg tat gct gtc act ggc cgt gga gac agc ccc gca agc agc aag      528
Thr Val Tyr Ala Val Thr Gly Arg Gly Asp Ser Pro Ala Ser Ser Lys
                165                 170                 175 cca att tcc att aat tac cga aca                                      552
Pro Ile Ser Ile Asn Tyr Arg Thr
            180
```

<210> SEQ ID NO 4
<211> LENGTH: 184
<212> TYPE: PRT
<213> ORGANISM: Homo sapiens

<400> SEQUENCE: 4

```
Gly Leu Asp Ser Pro Thr Gly Ile Asp Phe Ser Asp Ile Thr Ala Asn
1               5                   10                  15

Ser Phe Thr Val His Trp Ile Ala Pro Arg Ala Thr Ile Thr Gly Tyr
                20                  25                  30

Arg Ile Arg His His Pro Glu His Phe Ser Gly Arg Pro Arg Glu Asp
            35                  40                  45

Arg Val Pro His Ser Arg Asn Ser Ile Thr Leu Thr Asn Leu Thr Pro
        50                  55                  60

Gly Thr Glu Tyr Val Val Ser Ile Val Ala Leu Asn Gly Arg Glu Glu
65                  70                  75                  80

Ser Pro Leu Leu Ile Gly Gln Gln Ser Thr Val Ser Asp Val Pro Arg
                85                  90                  95

Asp Leu Glu Val Val Ala Ala Thr Pro Thr Ser Leu Leu Ile Ser Trp
                100                 105                 110

Asp Ala Pro Ala Val Thr Val Arg Tyr Tyr Arg Ile Thr Tyr Gly Glu
            115                 120                 125

Thr Gly Gly Asn Ser Pro Val Gln Glu Phe Thr Val Pro Gly Ser Lys
        130                 135                 140

Ser Thr Ala Thr Ile Ser Gly Leu Lys Pro Gly Val Asp Tyr Thr Ile
145                 150                 155                 160

Thr Val Tyr Ala Val Thr Gly Arg Gly Asp Ser Pro Ala Ser Ser Lys
                165                 170                 175

Pro Ile Ser Ile Asn Tyr Arg Thr
            180
```

<210> SEQ ID NO 5
<211> LENGTH: 282
<212> TYPE: DNA
<213> ORGANISM: Homo sapiens
<220> FEATURE:
<221> NAME/KEY: CDS
<222> LOCATION: (1)..(282)

<400> SEQUENCE: 5

```
gtt tct gat gtt ccg agg gac ctg gaa gtt gtt gct gcg acc ccc acc       48
Val Ser Asp Val Pro Arg Asp Leu Glu Val Val Ala Ala Thr Pro Thr
1               5                   10                  15 agc cta ctg atc agc tgg gat gct cct gct gtc aca gtg aga tat tac       96
Ser Leu Leu Ile Ser Trp Asp Ala Pro Ala Val Thr Val Arg Tyr Tyr
                20                  25                  30 agg atc act tac gga gaa aca gga gga aat agc cct gtc cag gag ttc      144
Arg Ile Thr Tyr Gly Glu Thr Gly Gly Asn Ser Pro Val Gln Glu Phe
            35                  40                  45
```

```
act gtg cct ggg agc aag tct aca gct acc atc agc ggc ctt aaa cct      192
Thr Val Pro Gly Ser Lys Ser Thr Ala Thr Ile Ser Gly Leu Lys Pro
     50                  55                  60 gga gtt gat tat acc atc act gtg tat gct gtc tgt cct cgt ggt gat      240
Gly Val Asp Tyr Thr Ile Thr Val Tyr Ala Val Cys Pro Arg Gly Asp
 65                  70                  75                  80 atg cct gac tgt agc aag cca att tcc att aat tac cga aca              282
Met Pro Asp Cys Ser Lys Pro Ile Ser Ile Asn Tyr Arg Thr
                 85                  90
```

<210> SEQ ID NO 6
<211> LENGTH: 94
<212> TYPE: PRT
<213> ORGANISM: Homo sapiens

<400> SEQUENCE: 6

```
Val Ser Asp Val Pro Arg Asp Leu Glu Val Val Ala Ala Thr Pro Thr
 1               5                  10                  15

Ser Leu Leu Ile Ser Trp Asp Ala Pro Ala Val Thr Val Arg Tyr Tyr
                 20                  25                  30

Arg Ile Thr Tyr Gly Glu Thr Gly Gly Asn Ser Pro Val Gln Glu Phe
                 35                  40                  45

Thr Val Pro Gly Ser Lys Ser Thr Ala Thr Ile Ser Gly Leu Lys Pro
     50                  55                  60

Gly Val Asp Tyr Thr Ile Thr Val Tyr Ala Val Cys Pro Arg Gly Asp
 65                  70                  75                  80

Met Pro Asp Cys Ser Lys Pro Ile Ser Ile Asn Tyr Arg Thr
                 85                  90
```

<210> SEQ ID NO 7
<211> LENGTH: 282
<212> TYPE: DNA
<213> ORGANISM: Homo sapiens
<220> FEATURE:
<221> NAME/KEY: CDS
<222> LOCATION: (1)..(282)

<400> SEQUENCE: 7

```
gtt tct gat gtt ccg agg gac ctg gaa gtt gtt gct gcg acc ccc acc      48
Val Ser Asp Val Pro Arg Asp Leu Glu Val Val Ala Ala Thr Pro Thr
 1               5                  10                  15 agc cta ctg atc agc tgg gat gct cct gct gtc aca gtg aga tat tac      96
Ser Leu Leu Ile Ser Trp Asp Ala Pro Ala Val Thr Val Arg Tyr Tyr
                 20                  25                  30 agg atc act tac gga gaa aca gga gga aat agc cct gtc cag gag ttc      144
Arg Ile Thr Tyr Gly Glu Thr Gly Gly Asn Ser Pro Val Gln Glu Phe
                 35                  40                  45 act gtg cct ggg agc aag tct aca gct acc atc agc ggc ctt aaa cct      192
Thr Val Pro Gly Ser Lys Ser Thr Ala Thr Ile Ser Gly Leu Lys Pro
     50                  55                  60 gga gtt gat tat acc atc act gtg tat gct gtc tgt ccg cgt gga gac      240
Gly Val Asp Tyr Thr Ile Thr Val Tyr Ala Val Cys Pro Arg Gly Asp
 65                  70                  75                  80 tgg aat gaa tgt agc aag cca att tcc att aat tac cga aca              282
Trp Asn Glu Cys Ser Lys Pro Ile Ser Ile Asn Tyr Arg Thr
                 85                  90
```

<210> SEQ ID NO 8
<211> LENGTH: 94
<212> TYPE: PRT
<213> ORGANISM: Homo sapiens

<400> SEQUENCE: 8

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Cys Pro Arg Gly Asp
65                  70                  75                  80

Trp Asn Glu Cys Ser Lys Pro Ile Ser Ile Asn Tyr Arg Thr
                85                  90

<210> SEQ ID NO 9
<211> LENGTH: 282
<212> TYPE: DNA
<213> ORGANISM: Homo sapiens
<220> FEATURE:
<221> NAME/KEY: CDS
<222> LOCATION: (1)..(282)

<400> SEQUENCE: 9 gtt tct gat gtt ccg agg gac ctg gaa gtt gtt gct gcg acc ccc acc     48
Val Ser Asp Val Pro Arg Asp Leu Glu Val Val Ala Ala Thr Pro Thr
1               5                   10                  15 agc cta ctg atc agc tgg gat gct cct gct gtc aca gtg aga tat tac     96
Ser Leu Leu Ile Ser Trp Asp Ala Pro Ala Val Thr Val Arg Tyr Tyr
            20                  25                  30 agg atc act tac gga gaa aca gga gga aat agc cct gtc cag gag ttc    144
Arg Ile Thr Tyr Gly Glu Thr Gly Gly Asn Ser Pro Val Gln Glu Phe
        35                  40                  45 act gtg cct ggg agc aag tct aca gct acc atc agc ggc ctt aaa cct    192
Thr Val Pro Gly Ser Lys Ser Thr Ala Thr Ile Ser Gly Leu Lys Pro
    50                  55                  60 gga gtt gat tat acc atc act gtg tat gct gtc tgt gct cgt ggt gat    240
Gly Val Asp Tyr Thr Ile Thr Val Tyr Ala Val Cys Ala Arg Gly Asp
65                  70                  75                  80 aat cct gac tgt agc aag cca att tcc att aat tac cga aca              282
Asn Pro Asp Cys Ser Lys Pro Ile Ser Ile Asn Tyr Arg Thr
                85                  90

<210> SEQ ID NO 10
<211> LENGTH: 94
<212> TYPE: PRT
<213> ORGANISM: Homo sapiens

<400> SEQUENCE: 10

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Cys Ala Arg Gly Asp
65                  70                  75                  80

Asn Pro Asp Cys Ser Lys Pro Ile Ser Ile Asn Tyr Arg Thr
                85                  90

<210> SEQ ID NO 11
<211> LENGTH: 282
<212> TYPE: DNA
<213> ORGANISM: Homo sapiens
<220> FEATURE:
<221> NAME/KEY: CDS
<222> LOCATION: (1)..(282)

<400> SEQUENCE: 11 gtt tct gat gtt ccg agg gac ctg gaa gtt gtt gct gcg acc ccc acc     48
Val Ser Asp Val Pro Arg Asp Leu Glu Val Val Ala Ala Thr Pro Thr
1               5                   10                  15 agc cta ctg atc agc tgg gat gct cct gct gtc aca gtg aga tat tac     96
Ser Leu Leu Ile Ser Trp Asp Ala Pro Ala Val Thr Val Arg Tyr Tyr
            20                  25                  30 agg atc act tac gga gaa aca gga gga aat agc cct gtc cag gag ttc    144
Arg Ile Thr Tyr Gly Glu Thr Gly Gly Asn Ser Pro Val Gln Glu Phe
        35                  40                  45 act gtg cct ggg agc aag tct aca gct acc atc agc ggc ctt aaa cct    192
Thr Val Pro Gly Ser Lys Ser Thr Ala Thr Ile Ser Gly Leu Lys Pro
    50                  55                  60 gga gtt gat tat acc atc act gtg tat gct gtc tgt ggt cgt gga gac    240
Gly Val Asp Tyr Thr Ile Thr Val Tyr Ala Val Cys Gly Arg Gly Asp
65                  70                  75                  80 agc ccc gca tgt agc aag cca att tcc att aat tac cga aca             282
Ser Pro Ala Cys Ser Lys Pro Ile Ser Ile Asn Tyr Arg Thr
                85                  90

<210> SEQ ID NO 12
<211> LENGTH: 94
<212> TYPE: PRT
<213> ORGANISM: Homo sapiens

<400> SEQUENCE: 12

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Cys Gly Arg Gly Asp
65                  70                  75                  80

Ser Pro Ala Cys Ser Lys Pro Ile Ser Ile Asn Tyr Arg Thr
                85                  90

<210> SEQ ID NO 13
<211> LENGTH: 282
<212> TYPE: DNA
<213> ORGANISM: Homo sapiens
<220> FEATURE:
<221> NAME/KEY: CDS
<222> LOCATION: (1)..(282)

<400> SEQUENCE: 13 gtt tct gat gtt ccg agg gac ctg gaa gtt gtt gct gcg acc ccc acc     48
Val Ser Asp Val Pro Arg Asp Leu Glu Val Val Ala Ala Thr Pro Thr
1               5                   10                  15

| | | | | | | | | | | | | | | | |
|---|---|---|---|---|---|---|---|---|---|---|---|---|---|---|---|
| agc | cta | ctg | atc | agc | tgg | gat | gct | cct | gct | gtc | aca | gtg | aga | tat | tac | 96
| Ser | Leu | Leu | Ile | Ser | Trp | Asp | Ala | Pro | Ala | Val | Thr | Val | Arg | Tyr | Tyr |
| | | | 20 | | | | 25 | | | | 30 | | | | |

| agg | atc | act | tac | gga | gaa | aca | gga | gga | aat | agc | cct | gtc | cag | gag | ttc | 144
|---|---|---|---|---|---|---|---|---|---|---|---|---|---|---|---|
| Arg | Ile | Thr | Tyr | Gly | Glu | Thr | Gly | Gly | Asn | Ser | Pro | Val | Gln | Glu | Phe |
| | 35 | | | | | 40 | | | | | 45 | | | | |

| act | gtg | cct | ggg | agc | aag | tct | aca | gct | acc | atc | agc | ggc | ctt | aaa | cct | 192
|---|---|---|---|---|---|---|---|---|---|---|---|---|---|---|---|
| Thr | Val | Pro | Gly | Ser | Lys | Ser | Thr | Ala | Thr | Ile | Ser | Gly | Leu | Lys | Pro |
| 50 | | | | | 55 | | | | | 60 | | | | | |

| gga | gtt | gat | tat | acc | atc | act | gtg | tat | gct | tgt | att | cct | cgt | ggt | gat | 240
|---|---|---|---|---|---|---|---|---|---|---|---|---|---|---|---|
| Gly | Val | Asp | Tyr | Thr | Ile | Thr | Val | Tyr | Ala | Cys | Ile | Pro | Arg | Gly | Asp |
| 65 | | | | 70 | | | | | 75 | | | | | 80 | |

| atg | cct | gac | tgt | agc | aag | cca | att | tcc | att | aat | tac | cga | aca | | | 282
|---|---|---|---|---|---|---|---|---|---|---|---|---|---|---|---|
| Met | Pro | Asp | Cys | Ser | Lys | Pro | Ile | Ser | Ile | Asn | Tyr | Arg | Thr | | |
| | | | | 85 | | | | | 90 | | | | | | |

<210> SEQ ID NO 14
<211> LENGTH: 94
<212> TYPE: PRT
<213> ORGANISM: Homo sapiens

<400> SEQUENCE: 14

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Cys Ile Pro Arg Gly Asp
65                  70                  75                  80

Met Pro Asp Cys Ser Lys Pro Ile Ser Ile Asn Tyr Arg Thr
                85                  90

<210> SEQ ID NO 15
<211> LENGTH: 282
<212> TYPE: DNA
<213> ORGANISM: Homo sapiens
<220> FEATURE:
<221> NAME/KEY: CDS
<222> LOCATION: (1)..(282)

<400> SEQUENCE: 15

| gtt | tct | gat | gtt | ccg | agg | gac | ctg | gaa | gtt | gtt | gct | gcg | acc | ccc | acc | 48
|---|---|---|---|---|---|---|---|---|---|---|---|---|---|---|---|
| Val | Ser | Asp | Val | Pro | Arg | Asp | Leu | Glu | Val | Val | Ala | Ala | Thr | Pro | Thr |
| 1 | | | | 5 | | | | | 10 | | | | | 15 | |

| agc | cta | ctg | atc | agc | tgg | gat | gct | cct | gct | gtc | aca | gtg | aga | tat | tac | 96
|---|---|---|---|---|---|---|---|---|---|---|---|---|---|---|---|
| Ser | Leu | Leu | Ile | Ser | Trp | Asp | Ala | Pro | Ala | Val | Thr | Val | Arg | Tyr | Tyr |
| | | | 20 | | | | 25 | | | | 30 | | | | |

| agg | atc | act | tac | gga | gaa | aca | gga | gga | aat | agc | cct | gtc | cag | gag | ttc | 144
|---|---|---|---|---|---|---|---|---|---|---|---|---|---|---|---|
| Arg | Ile | Thr | Tyr | Gly | Glu | Thr | Gly | Gly | Asn | Ser | Pro | Val | Gln | Glu | Phe |
| | 35 | | | | | 40 | | | | | 45 | | | | |

| act | gtg | cct | ggg | agc | aag | tct | aca | gct | acc | atc | agc | ggc | ctt | aaa | cct | 192
|---|---|---|---|---|---|---|---|---|---|---|---|---|---|---|---|
| Thr | Val | Pro | Gly | Ser | Lys | Ser | Thr | Ala | Thr | Ile | Ser | Gly | Leu | Lys | Pro |
| 50 | | | | | 55 | | | | | 60 | | | | | | |

| gga | gtt | gat | tat | acc | atc | act | gtg | tat | gct | tgt | cgt | gct | cgt | ggt | gat | 240
|---|---|---|---|---|---|---|---|---|---|---|---|---|---|---|---|
| Gly | Val | Asp | Tyr | Thr | Ile | Thr | Val | Tyr | Ala | Cys | Arg | Ala | Arg | Gly | Asp |
| 65 | | | | 70 | | | | | 75 | | | | | 80 | |

| aat | cct | gac | tgt | agc | aag | cca | att | tcc | att | aat | tac | cga | aca | | | 282
|---|---|---|---|---|---|---|---|---|---|---|---|---|---|---|---|
| Asn | Pro | Asp | Cys | Ser | Lys | Pro | Ile | Ser | Ile | Asn | Tyr | Arg | Thr | | |

```
<210> SEQ ID NO 16
<211> LENGTH: 94
<212> TYPE: PRT
<213> ORGANISM: Homo sapiens

<400> SEQUENCE: 16

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
                20                  25                  30

Arg Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Cys Arg Ala Arg Gly Asp
65                  70                  75                  80

Asn Pro Asp Cys Ser Lys Pro Ile Ser Ile Asn Tyr Arg Thr
                85                  90

<210> SEQ ID NO 17
<211> LENGTH: 282
<212> TYPE: DNA
<213> ORGANISM: Homo sapiens
<220> FEATURE:
<221> NAME/KEY: CDS
<222> LOCATION: (1)..(282)

<400> SEQUENCE: 17 gtt tct gat gtt ccg agg gac ctg gaa gtt gtt gct gcg acc ccc acc      48
Val Ser Asp Val Pro Arg Asp Leu Glu Val Val Ala Ala Thr Pro Thr
1               5                   10                  15 agc cta ctg atc agc tgg gat gct cct gct gtc aca gtg aga tat tac      96
Ser Leu Leu Ile Ser Trp Asp Ala Pro Ala Val Thr Val Arg Tyr Tyr
                20                  25                  30 agg atc act tac gga gaa aca gga gga aat agc cct gtc cag gag ttc     144
Arg Ile Thr Tyr Gly Glu Thr Gly Gly Asn Ser Pro Val Gln Glu Phe
            35                  40                  45 act gtg cct ggg agc aag tct aca gct acc atc agc ggc ctt aaa cct     192
Thr Val Pro Gly Ser Lys Ser Thr Ala Thr Ile Ser Gly Leu Lys Pro
    50                  55                  60 gga gtt gat tat acc atc act gtg tat gct tgt act ggt cgt gga gac     240
Gly Val Asp Tyr Thr Ile Thr Val Tyr Ala Cys Thr Gly Arg Gly Asp
65                  70                  75                  80 agc ccc gca tgt agc aag cca att tcc att aat tac cga aca             282
Ser Pro Ala Cys Ser Lys Pro Ile Ser Ile Asn Tyr Arg Thr
                85                  90

<210> SEQ ID NO 18
<211> LENGTH: 94
<212> TYPE: PRT
<213> ORGANISM: Homo sapiens

<400> SEQUENCE: 18

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
                20                  25                  30

Arg Ile Thr Tyr Gly Glu Thr Gly Gly Asn Ser Pro Val Gln Glu Phe
            35                  40                  45
```

```
Thr Val Pro Gly Ser Lys Ser Thr Ala Thr Ile Ser Gly Leu Lys Pro
        50                  55                  60
Gly Val Asp Tyr Thr Ile Thr Val Tyr Ala Cys Thr Gly Arg Gly Asp
 65                  70                  75                  80
Ser Pro Ala Cys Ser Lys Pro Ile Ser Ile Asn Tyr Arg Thr
                 85                  90
```

<210> SEQ ID NO 19
<211> LENGTH: 552
<212> TYPE: DNA
<213> ORGANISM: Homo sapiens
<220> FEATURE:
<221> NAME/KEY: CDS
<222> LOCATION: (1)..(552)

<400> SEQUENCE: 19

```
ggt ctt gat tcc cca act ggc att gac ttt tct gat att act gcc aac         48
Gly Leu Asp Ser Pro Thr Gly Ile Asp Phe Ser Asp Ile Thr Ala Asn
 1               5                  10                  15 tct ttt act gtg cac tgg att gct cct cga gcc acc atc act ggc tac         96
Ser Phe Thr Val His Trp Ile Ala Pro Arg Ala Thr Ile Thr Gly Tyr
            20                  25                  30 agg atc cgc cat cat ccc gag cac ttc agt ggg aga cct cga gaa gat        144
Arg Ile Arg His His Pro Glu His Phe Ser Gly Arg Pro Arg Glu Asp
        35                  40                  45 cgg gtg ccc cac tct cgg aat tcc atc acc ctc acc aac ctc act cca        192
Arg Val Pro His Ser Arg Asn Ser Ile Thr Leu Thr Asn Leu Thr Pro
    50                  55                  60 ggc aca gag tat gtg gtc agc atc gtt gct ctt aat ggc aga gag gaa        240
Gly Thr Glu Tyr Val Val Ser Ile Val Ala Leu Asn Gly Arg Glu Glu
65                  70                  75                  80 agt ccc tta ttg att ggc caa caa tca aca gtt tct gat gtt ccg agg        288
Ser Pro Leu Leu Ile Gly Gln Gln Ser Thr Val Ser Asp Val Pro Arg
                85                  90                  95 gac ctg gaa gtt gtt gct gcg acc ccc acc agc cta ctg atc agc tgg        336
Asp Leu Glu Val Val Ala Ala Thr Pro Thr Ser Leu Leu Ile Ser Trp
            100                 105                 110 gat gct cct gct gtc aca gtg aga tat tac agg atc act tac gga gaa        384
Asp Ala Pro Ala Val Thr Val Arg Tyr Tyr Arg Ile Thr Tyr Gly Glu
        115                 120                 125 aca gga gga aat agc cct gtc cag gag ttc act gtg cct ggg agc aag        432
Thr Gly Gly Asn Ser Pro Val Gln Glu Phe Thr Val Pro Gly Ser Lys
    130                 135                 140 tct aca gct acc atc agc ggc ctt aaa cct gga gtt gat tat acc atc        480
Ser Thr Ala Thr Ile Ser Gly Leu Lys Pro Gly Val Asp Tyr Thr Ile
145                 150                 155                 160 act gtg tat gct gtc tgt cct cgt ggt gat atg cct gac tgt agc aag        528
Thr Val Tyr Ala Val Cys Pro Arg Gly Asp Met Pro Asp Cys Ser Lys
                165                 170                 175 cca att tcc att aat tac cga aca                                         552
Pro Ile Ser Ile Asn Tyr Arg Thr
            180
```

<210> SEQ ID NO 20
<211> LENGTH: 184
<212> TYPE: PRT
<213> ORGANISM: Homo sapiens

<400> SEQUENCE: 20

```
Gly Leu Asp Ser Pro Thr Gly Ile Asp Phe Ser Asp Ile Thr Ala Asn
 1               5                  10                  15
```

```
Ser Phe Thr Val His Trp Ile Ala Pro Arg Ala Thr Ile Thr Gly Tyr
            20                  25                  30

Arg Ile Arg His His Pro Glu His Phe Ser Gly Arg Pro Arg Glu Asp
        35                  40                  45

Arg Val Pro His Ser Arg Asn Ser Ile Thr Leu Thr Asn Leu Thr Pro
    50                  55                  60

Gly Thr Glu Tyr Val Val Ser Ile Val Ala Leu Asn Gly Arg Glu Glu
65                  70                  75                  80

Ser Pro Leu Leu Ile Gly Gln Gln Ser Thr Val Ser Asp Val Pro Arg
                85                  90                  95

Asp Leu Glu Val Val Ala Ala Thr Pro Thr Ser Leu Leu Ile Ser Trp
            100                 105                 110

Asp Ala Pro Ala Val Thr Val Arg Tyr Tyr Arg Ile Thr Tyr Gly Glu
        115                 120                 125

Thr Gly Gly Asn Ser Pro Val Gln Glu Phe Thr Val Pro Gly Ser Lys
    130                 135                 140

Ser Thr Ala Thr Ile Ser Gly Leu Lys Pro Gly Val Asp Tyr Thr Ile
145                 150                 155                 160

Thr Val Tyr Ala Val Cys Pro Arg Gly Asp Met Pro Asp Cys Ser Lys
                165                 170                 175

Pro Ile Ser Ile Asn Tyr Arg Thr
            180
```

<210> SEQ ID NO 21
<211> LENGTH: 552
<212> TYPE: DNA
<213> ORGANISM: Homo sapiens
<220> FEATURE:
<221> NAME/KEY: CDS
<222> LOCATION: (1)..(552)

<400> SEQUENCE: 21

```
ggt ctt gat tcc cca act ggc att gac ttt tct gat att act gcc aac      48
Gly Leu Asp Ser Pro Thr Gly Ile Asp Phe Ser Asp Ile Thr Ala Asn
1               5                   10                  15 tct ttt act gtg cac tgg att gct cct cga gcc acc atc act ggc tac      96
Ser Phe Thr Val His Trp Ile Ala Pro Arg Ala Thr Ile Thr Gly Tyr
            20                  25                  30 agg atc cgc cat cat ccc gag cac ttc agt ggg aga cct cga gaa gat     144
Arg Ile Arg His His Pro Glu His Phe Ser Gly Arg Pro Arg Glu Asp
        35                  40                  45 cgg gtg ccc cac tct cgg aat tcc atc acc ctc acc aac ctc act cca     192
Arg Val Pro His Ser Arg Asn Ser Ile Thr Leu Thr Asn Leu Thr Pro
    50                  55                  60 ggc aca gag tat gtg gtc agc atc gtt gct ctt aat ggc aga gag gaa     240
Gly Thr Glu Tyr Val Val Ser Ile Val Ala Leu Asn Gly Arg Glu Glu
65                  70                  75                  80 agt ccc ccg ttg att ggc caa caa tca aca gtt tct gat gtt ccg agg     288
Ser Pro Pro Leu Ile Gly Gln Gln Ser Thr Val Ser Asp Val Pro Arg
                85                  90                  95 gac ctg gaa gtt gtt gct gcg acc ccc acc agc cta ctg atc agc tgg     336
Asp Leu Glu Val Val Ala Ala Thr Pro Thr Ser Leu Leu Ile Ser Trp
            100                 105                 110 gat gct cct gct gtc aca gtg aga tat tac agg atc act tac gga gaa     384
Asp Ala Pro Ala Val Thr Val Arg Tyr Tyr Arg Ile Thr Tyr Gly Glu
        115                 120                 125 aca gga gga aat agc cct gtc cag gag ttc act gtg cct ggg agc aag     432
Thr Gly Gly Asn Ser Pro Val Gln Glu Phe Thr Val Pro Gly Ser Lys
```

```
tct aca gct acc atc agc ggc ctt aaa cct gga gtt gat tat acc atc      480
Ser Thr Ala Thr Ile Ser Gly Leu Lys Pro Gly Val Asp Tyr Thr Ile
145                 150                 155                 160 act gtg tat gct gtc tgt gct cgt ggt gat aat cct gac tgt agc aag      528
Thr Val Tyr Ala Val Cys Ala Arg Gly Asp Asn Pro Asp Cys Ser Lys
                165                 170                 175 cca att tcc att aat tac cga aca                                      552
Pro Ile Ser Ile Asn Tyr Arg Thr
            180

<210> SEQ ID NO 22
<211> LENGTH: 184
<212> TYPE: PRT
<213> ORGANISM: Homo sapiens

<400> SEQUENCE: 22

Gly Leu Asp Ser Pro Thr Gly Ile Asp Phe Ser Asp Ile Thr Ala Asn
1               5                   10                  15

Ser Phe Thr Val His Trp Ile Ala Pro Arg Ala Thr Ile Thr Gly Tyr
                20                  25                  30

Arg Ile Arg His His Pro Glu His Phe Ser Gly Arg Pro Arg Glu Asp
            35                  40                  45

Arg Val Pro His Ser Arg Asn Ser Ile Thr Leu Thr Asn Leu Thr Pro
        50                  55                  60

Gly Thr Glu Tyr Val Val Ser Ile Val Ala Leu Asn Gly Arg Glu Glu
65                  70                  75                  80

Ser Pro Pro Leu Ile Gly Gln Gln Ser Thr Val Ser Asp Val Pro Arg
                85                  90                  95

Asp Leu Glu Val Val Ala Ala Thr Pro Thr Ser Leu Leu Ile Ser Trp
            100                 105                 110

Asp Ala Pro Ala Val Thr Val Arg Tyr Tyr Arg Ile Thr Tyr Gly Glu
        115                 120                 125

Thr Gly Gly Asn Ser Pro Val Gln Glu Phe Thr Val Pro Gly Ser Lys
130                 135                 140

Ser Thr Ala Thr Ile Ser Gly Leu Lys Pro Gly Val Asp Tyr Thr Ile
145                 150                 155                 160

Thr Val Tyr Ala Val Cys Ala Arg Gly Asp Asn Pro Asp Cys Ser Lys
                165                 170                 175

Pro Ile Ser Ile Asn Tyr Arg Thr
            180

<210> SEQ ID NO 23
<211> LENGTH: 552
<212> TYPE: DNA
<213> ORGANISM: Homo sapiens
<220> FEATURE:
<221> NAME/KEY: CDS
<222> LOCATION: (1)..(552)

<400> SEQUENCE: 23 ggt ctt gat tcc cca act ggc att gac ttt tct gat att act gcc aac       48
Gly Leu Asp Ser Pro Thr Gly Ile Asp Phe Ser Asp Ile Thr Ala Asn
1               5                   10                  15 tct ttt act gtg cac tgg att gct cct cga gcc acc atc act ggc tac       96
Ser Phe Thr Val His Trp Ile Ala Pro Arg Ala Thr Ile Thr Gly Tyr
                20                  25                  30 agg atc cgc cat cat ccc gag cac ttc agt ggg aga cct cga gaa gat      144
Arg Ile Arg His His Pro Glu His Phe Ser Gly Arg Pro Arg Glu Asp
```

-continued

```
                    35                      40                      45
cgg gtg ccc cac tct cgg aat tcc atc acc ctc acc aac ctc act cca        192
Arg Val Pro His Ser Arg Asn Ser Ile Thr Leu Thr Asn Leu Thr Pro
 50                      55                      60 ggc aca gag tat gtg gtc agc atc gtt gct ctt aat ggc aga gag gaa        240
Gly Thr Glu Tyr Val Val Ser Ile Val Ala Leu Asn Gly Arg Glu Glu
 65                      70                      75                  80 agt ccc ccg ttg att ggc caa caa tca aca gtt tct gat gtt ccg agg        288
Ser Pro Pro Leu Ile Gly Gln Gln Ser Thr Val Ser Asp Val Pro Arg
                     85                      90                      95 gac ctg gaa gtt gtt gct gcg acc ccc acc agc cta ctg atc agc tgg        336
Asp Leu Glu Val Val Ala Ala Thr Pro Thr Ser Leu Leu Ile Ser Trp
                100                     105                     110 gat gct cct gct gtc aca gtg aga tat tac agg atc act tac gga gaa        384
Asp Ala Pro Ala Val Thr Val Arg Tyr Tyr Arg Ile Thr Tyr Gly Glu
            115                     120                     125 aca gga gga aat agc cct gtc cag gag ttc act gtg cct ggg agc aag        432
Thr Gly Gly Asn Ser Pro Val Gln Glu Phe Thr Val Pro Gly Ser Lys
        130                     135                     140 tct aca gct acc atc agc ggc ctt aaa cct gga gtt gat tat acc atc        480
Ser Thr Ala Thr Ile Ser Gly Leu Lys Pro Gly Val Asp Tyr Thr Ile
145                     150                     155                 160 act gtg tat gct gtc tgt ggt cgt gga gac agc ccc gca tgt agc aag        528
Thr Val Tyr Ala Val Cys Gly Arg Gly Asp Ser Pro Ala Cys Ser Lys
                    165                     170                     175 cca att tcc att aat tac cga aca                                        552
Pro Ile Ser Ile Asn Tyr Arg Thr
                180
```

<210> SEQ ID NO 24
<211> LENGTH: 184
<212> TYPE: PRT
<213> ORGANISM: Homo sapiens

<400> SEQUENCE: 24

```
Gly Leu Asp Ser Pro Thr Gly Ile Asp Phe Ser Asp Ile Thr Ala Asn
 1               5                  10                  15

Ser Phe Thr Val His Trp Ile Ala Pro Arg Ala Thr Ile Thr Gly Tyr
                20                  25                  30

Arg Ile Arg His His Pro Glu His Phe Ser Gly Arg Pro Arg Glu Asp
            35                  40                  45

Arg Val Pro His Ser Arg Asn Ser Ile Thr Leu Thr Asn Leu Thr Pro
        50                  55                  60

Gly Thr Glu Tyr Val Val Ser Ile Val Ala Leu Asn Gly Arg Glu Glu
 65                  70                  75                  80

Ser Pro Pro Leu Ile Gly Gln Gln Ser Thr Val Ser Asp Val Pro Arg
                85                  90                  95

Asp Leu Glu Val Val Ala Ala Thr Pro Thr Ser Leu Leu Ile Ser Trp
            100                 105                 110

Asp Ala Pro Ala Val Thr Val Arg Tyr Tyr Arg Ile Thr Tyr Gly Glu
        115                 120                 125

Thr Gly Gly Asn Ser Pro Val Gln Glu Phe Thr Val Pro Gly Ser Lys
    130                 135                 140

Ser Thr Ala Thr Ile Ser Gly Leu Lys Pro Gly Val Asp Tyr Thr Ile
145                 150                 155                 160

Thr Val Tyr Ala Val Cys Gly Arg Gly Asp Ser Pro Ala Cys Ser Lys
                165                 170                 175
```

```
<210> SEQ ID NO 25
<211> LENGTH: 552
<212> TYPE: DNA
<213> ORGANISM: Homo sapiens
<220> FEATURE:
<221> NAME/KEY: CDS
<222> LOCATION: (1)..(552)

<400> SEQUENCE: 25 ggt ctt gat tcc cca act ggc att gac ttt tct gat att act gcc aac      48
Gly Leu Asp Ser Pro Thr Gly Ile Asp Phe Ser Asp Ile Thr Ala Asn
1               5                   10                  15 tct ttt act gtg cac tgg att gct cct cga gcc acc atc act ggc tac      96
Ser Phe Thr Val His Trp Ile Ala Pro Arg Ala Thr Ile Thr Gly Tyr
            20                  25                  30 agg atc cgc cat cat ccc gag cac ttc agt ggg aga cct cga gaa gat     144
Arg Ile Arg His His Pro Glu His Phe Ser Gly Arg Pro Arg Glu Asp
        35                  40                  45 cgg gtg ccc cac tct cgg aat tcc atc acc ctc acc aac ctc act cca     192
Arg Val Pro His Ser Arg Asn Ser Ile Thr Leu Thr Asn Leu Thr Pro
    50                  55                  60 ggc aca gag tat gtg gtc agc atc gtt gct ctt aat ggc aga gag gaa     240
Gly Thr Glu Tyr Val Val Ser Ile Val Ala Leu Asn Gly Arg Glu Glu
65                  70                  75                  80 agt ccc tta ttg att ggc caa caa tca aca gtt tct gat gtt ccg agg     288
Ser Pro Leu Leu Ile Gly Gln Gln Ser Thr Val Ser Asp Val Pro Arg
                85                  90                  95 gac ctg gaa gtt gtt gct gcg acc ccc acc agc cta ctg atc agc tgg     336
Asp Leu Glu Val Val Ala Ala Thr Pro Thr Ser Leu Leu Ile Ser Trp
            100                 105                 110 gat gct cct gct gtc aca gtg aga tat tac agg atc act tac gga gaa     384
Asp Ala Pro Ala Val Thr Val Arg Tyr Tyr Arg Ile Thr Tyr Gly Glu
        115                 120                 125 aca gga gga aat agc cct gtc cag gag ttc act gtg cct ggg agc aag     432
Thr Gly Gly Asn Ser Pro Val Gln Glu Phe Thr Val Pro Gly Ser Lys
    130                 135                 140 tct aca gct acc atc agc ggc ctt aaa cct gga gtt gat tat acc atc     480
Ser Thr Ala Thr Ile Ser Gly Leu Lys Pro Gly Val Asp Tyr Thr Ile
145                 150                 155                 160 act gtg tat gct gtc tgt ggt cgt gga gac agc ccc gca tgt agc aag     528
Thr Val Tyr Ala Val Cys Gly Arg Gly Asp Ser Pro Ala Cys Ser Lys
                165                 170                 175 cca att tcc att aat tac cga aca                                     552
Pro Ile Ser Ile Asn Tyr Arg Thr
            180

<210> SEQ ID NO 26
<211> LENGTH: 184
<212> TYPE: PRT
<213> ORGANISM: Homo sapiens

<400> SEQUENCE: 26

Gly Leu Asp Ser Pro Thr Gly Ile Asp Phe Ser Asp Ile Thr Ala Asn
1               5                   10                  15

Ser Phe Thr Val His Trp Ile Ala Pro Arg Ala Thr Ile Thr Gly Tyr
            20                  25                  30

Arg Ile Arg His His Pro Glu His Phe Ser Gly Arg Pro Arg Glu Asp
        35                  40                  45
```

```
Arg Val Pro His Ser Arg Asn Ser Ile Thr Leu Thr Asn Leu Thr Pro
     50                  55                  60

Gly Thr Glu Tyr Val Val Ser Ile Val Ala Leu Asn Gly Arg Glu Glu
65                  70                  75                  80

Ser Pro Leu Leu Ile Gly Gln Gln Ser Thr Val Ser Asp Val Pro Arg
                85                  90                  95

Asp Leu Glu Val Val Ala Ala Thr Pro Thr Ser Leu Leu Ile Ser Trp
            100                 105                 110

Asp Ala Pro Ala Val Thr Val Arg Tyr Tyr Arg Ile Thr Tyr Gly Glu
            115                 120                 125

Thr Gly Gly Asn Ser Pro Val Gln Glu Phe Thr Val Pro Gly Ser Lys
    130                 135                 140

Ser Thr Ala Thr Ile Ser Gly Leu Lys Pro Gly Val Asp Tyr Thr Ile
145                 150                 155                 160

Thr Val Tyr Ala Val Cys Gly Arg Gly Asp Ser Pro Ala Cys Ser Lys
                165                 170                 175

Pro Ile Ser Ile Asn Tyr Arg Thr
            180
```

<210> SEQ ID NO 27
<211> LENGTH: 552
<212> TYPE: DNA
<213> ORGANISM: Homo sapiens
<220> FEATURE:
<221> NAME/KEY: CDS
<222> LOCATION: (1)..(552)

<400> SEQUENCE: 27

```
ggt ctt gat tcc cca act ggc att gac ttt tct gat att act gcc aac    48
Gly Leu Asp Ser Pro Thr Gly Ile Asp Phe Ser Asp Ile Thr Ala Asn
1               5                   10                  15 tct ttt act gtg cac tgg att gct cct cga gcc acc atc act ggc tac    96
Ser Phe Thr Val His Trp Ile Ala Pro Arg Ala Thr Ile Thr Gly Tyr
                20                  25                  30 agg atc cgc cat cat ccc gag cac ttc agt ggg aga cct cga gaa gat   144
Arg Ile Arg His His Pro Glu His Phe Ser Gly Arg Pro Arg Glu Asp
            35                  40                  45 cgg gtg ccc cac tct cgg aat tcc atc acc ctc acc aac ctc act cca   192
Arg Val Pro His Ser Arg Asn Ser Ile Thr Leu Thr Asn Leu Thr Pro
    50                  55                  60 gga aca gag tat gtg gtc agc atc gtt gct ctt aat ggc aga gag gaa   240
Gly Thr Glu Tyr Val Val Ser Ile Val Ala Leu Asn Gly Arg Glu Glu
65                  70                  75                  80 agt ccc ccg ttg att ggc caa caa tca aca gtt tct gat gtt ccg agg   288
Ser Pro Pro Leu Ile Gly Gln Gln Ser Thr Val Ser Asp Val Pro Arg
                85                  90                  95 gac ctg gaa gtt gtt gct gcg acc ccc acc agc cta ctg atc agc tgg   336
Asp Leu Glu Val Val Ala Ala Thr Pro Thr Ser Leu Leu Ile Ser Trp
            100                 105                 110 gat gct cct gct gtc aca gtg aga tat tac agg atc act tac gga gaa   384
Asp Ala Pro Ala Val Thr Val Arg Tyr Tyr Arg Ile Thr Tyr Gly Glu
            115                 120                 125 aca gga gga aat agc cct gtc cag gag ttc act gtg cct ggg agc aag   432
Thr Gly Gly Asn Ser Pro Val Gln Glu Phe Thr Val Pro Gly Ser Lys
    130                 135                 140 tct aca gct acc atc agc ggc ctt aaa cct gga gtt gat tat acc atc   480
Ser Thr Ala Thr Ile Ser Gly Leu Lys Pro Gly Val Asp Tyr Thr Ile
145                 150                 155                 160 act gtg tat gct tgt act ggt cgt gga gac agc ccc gca tgt agc aag   528
Thr Val Tyr Ala Cys Thr Gly Arg Gly Asp Ser Pro Ala Cys Ser Lys
                165                 170                 175
```

```
Thr Val Tyr Ala Cys Thr Gly Arg Gly Asp Ser Pro Ala Cys Ser Lys
            165                 170                 175 cca att tcc att aat tac cga aca                                      552
Pro Ile Ser Ile Asn Tyr Arg Thr
            180
```

<210> SEQ ID NO 28
<211> LENGTH: 184
<212> TYPE: PRT
<213> ORGANISM: Homo sapiens

<400> SEQUENCE: 28

```
Gly Leu Asp Ser Pro Thr Gly Ile Asp Phe Ser Asp Ile Thr Ala Asn
1               5                   10                  15

Ser Phe Thr Val His Trp Ile Ala Pro Arg Ala Thr Ile Thr Gly Tyr
            20                  25                  30

Arg Ile Arg His His Pro Glu His Phe Ser Gly Arg Pro Arg Glu Asp
        35                  40                  45

Arg Val Pro His Ser Arg Asn Ser Ile Thr Leu Thr Asn Leu Thr Pro
    50                  55                  60

Gly Thr Glu Tyr Val Val Ser Ile Val Ala Leu Asn Gly Arg Glu Glu
65                  70                  75                  80

Ser Pro Pro Leu Ile Gly Gln Gln Ser Thr Val Ser Asp Val Pro Arg
            85                  90                  95

Asp Leu Glu Val Val Ala Ala Thr Pro Thr Ser Leu Leu Ile Ser Trp
            100                 105                 110

Asp Ala Pro Ala Val Thr Val Arg Tyr Tyr Arg Ile Thr Tyr Gly Glu
        115                 120                 125

Thr Gly Gly Asn Ser Pro Val Gln Glu Phe Thr Val Pro Gly Ser Lys
    130                 135                 140

Ser Thr Ala Thr Ile Ser Gly Leu Lys Pro Gly Val Asp Tyr Thr Ile
145                 150                 155                 160

Thr Val Tyr Ala Cys Thr Gly Arg Gly Asp Ser Pro Ala Cys Ser Lys
            165                 170                 175

Pro Ile Ser Ile Asn Tyr Arg Thr
            180
```

<210> SEQ ID NO 29
<211> LENGTH: 552
<212> TYPE: DNA
<213> ORGANISM: Homo sapiens
<220> FEATURE:
<221> NAME/KEY: CDS
<222> LOCATION: (1)..(552)

<400> SEQUENCE: 29

```
ggt ctt gat tcc cca act ggc att gac ttt tct gat att act gcc aac      48
Gly Leu Asp Ser Pro Thr Gly Ile Asp Phe Ser Asp Ile Thr Ala Asn
1               5                   10                  15 tct ttt act gtg cac tgg att gct cct cga gcc acc atc act ggc tac      96
Ser Phe Thr Val His Trp Ile Ala Pro Arg Ala Thr Ile Thr Gly Tyr
            20                  25                  30 agg atc cgc cat cat ccc gag cac ttc agt ggg aga cct cga gaa gat      144
Arg Ile Arg His His Pro Glu His Phe Ser Gly Arg Pro Arg Glu Asp
        35                  40                  45 cgg gtg ccc cac tct cgg aat tcc atc acc ctc acc aac ctc act cca      192
Arg Val Pro His Ser Arg Asn Ser Ile Thr Leu Thr Asn Leu Thr Pro
    50                  55                  60 ggc aca gag tat gtg gtc agc atc gtt gct ctt aat ggc aga gag gaa      240
```

```
         Gly Thr Glu Tyr Val Val Ser Ile Val Ala Leu Asn Gly Arg Glu Glu
         65                  70                  75                  80 agt ccc ccg ttg att ggc caa caa tca aca gtt tct gat gtt ccg agg        288
Ser Pro Pro Leu Ile Gly Gln Gln Ser Thr Val Ser Asp Val Pro Arg
                 85                  90                  95 gac ctg gaa gtt gtt gct gcg acc ccc acc agc cta ctg atc agc tgg        336
Asp Leu Glu Val Val Ala Ala Thr Pro Thr Ser Leu Leu Ile Ser Trp
             100                 105                 110 gat gct cct gct gtc aca gtg aga tat tac agg atc act tac gga gaa        384
Asp Ala Pro Ala Val Thr Val Arg Tyr Tyr Arg Ile Thr Tyr Gly Glu
         115                 120                 125 aca gga gga aat agc cct gtc cag gag ttc act gtg cct ggg agc aag        432
Thr Gly Gly Asn Ser Pro Val Gln Glu Phe Thr Val Pro Gly Ser Lys
     130                 135                 140 tct aca gct acc atc agc ggc ctt aaa cct gga gtt gat tat acc atc        480
Ser Thr Ala Thr Ile Ser Gly Leu Lys Pro Gly Val Asp Tyr Thr Ile
145                 150                 155                 160 act gtg tat gct tgt att cct cgt ggt gat atg cct gac tgt agc aag        528
Thr Val Tyr Ala Cys Ile Pro Arg Gly Asp Met Pro Asp Cys Ser Lys
                 165                 170                 175 cca att tcc att aat tac cga aca                                        552
Pro Ile Ser Ile Asn Tyr Arg Thr
             180

<210> SEQ ID NO 30
<211> LENGTH: 184
<212> TYPE: PRT
<213> ORGANISM: Homo sapiens

<400> SEQUENCE: 30

Gly Leu Asp Ser Pro Thr Gly Ile Asp Phe Ser Asp Ile Thr Ala Asn
1               5                   10                  15

Ser Phe Thr Val His Trp Ile Ala Pro Arg Ala Thr Ile Thr Gly Tyr
            20                  25                  30

Arg Ile Arg His His Pro Glu His Phe Ser Gly Arg Pro Arg Glu Asp
        35                  40                  45

Arg Val Pro His Ser Arg Asn Ser Ile Thr Leu Thr Asn Leu Thr Pro
    50                  55                  60

Gly Thr Glu Tyr Val Val Ser Ile Val Ala Leu Asn Gly Arg Glu Glu
65                  70                  75                  80

Ser Pro Pro Leu Ile Gly Gln Gln Ser Thr Val Ser Asp Val Pro Arg
                85                  90                  95

Asp Leu Glu Val Val Ala Ala Thr Pro Thr Ser Leu Leu Ile Ser Trp
            100                 105                 110

Asp Ala Pro Ala Val Thr Val Arg Tyr Tyr Arg Ile Thr Tyr Gly Glu
        115                 120                 125

Thr Gly Gly Asn Ser Pro Val Gln Glu Phe Thr Val Pro Gly Ser Lys
    130                 135                 140

Ser Thr Ala Thr Ile Ser Gly Leu Lys Pro Gly Val Asp Tyr Thr Ile
145                 150                 155                 160

Thr Val Tyr Ala Cys Ile Pro Arg Gly Asp Met Pro Asp Cys Ser Lys
                165                 170                 175

Pro Ile Ser Ile Asn Tyr Arg Thr
            180

<210> SEQ ID NO 31
<211> LENGTH: 552
<212> TYPE: DNA
```

```
<213> ORGANISM: Homo sapiens
<220> FEATURE:
<221> NAME/KEY: CDS
<222> LOCATION: (1)..(552)

<400> SEQUENCE: 31 ggt ctt gat tcc cca act ggc att gac ttt tct gat att act gcc aac      48
Gly Leu Asp Ser Pro Thr Gly Ile Asp Phe Ser Asp Ile Thr Ala Asn
1               5                   10                  15 tct ttt act gtg cac tgg att gct cct cga gcc acc atc act ggc tac      96
Ser Phe Thr Val His Trp Ile Ala Pro Arg Ala Thr Ile Thr Gly Tyr
            20                  25                  30 agg atc cgc cat cat ccc gag cac ttc agt ggg aga cct cga gaa gat     144
Arg Ile Arg His His Pro Glu His Phe Ser Gly Arg Pro Arg Glu Asp
        35                  40                  45 cgg gtg ccc cac tct cgg aat tcc atc acc ctc acc aac ctc act cca     192
Arg Val Pro His Ser Arg Asn Ser Ile Thr Leu Thr Asn Leu Thr Pro
    50                  55                  60 ggc aca gag tat gtg gtc agc atc gtt gct ctt aat ggc aga gag gaa     240
Gly Thr Glu Tyr Val Val Ser Ile Val Ala Leu Asn Gly Arg Glu Glu
65                  70                  75                  80 agt ccc ccg ttg att ggc caa caa tca aca gtt tct gat gtt ccg agg     288
Ser Pro Pro Leu Ile Gly Gln Gln Ser Thr Val Ser Asp Val Pro Arg
                85                  90                  95 gac ctg gaa gtt gtt gct gcg acc ccc acc agc cta ctg atc agc tgg     336
Asp Leu Glu Val Val Ala Ala Thr Pro Thr Ser Leu Leu Ile Ser Trp
            100                 105                 110 gat gct cct gct gtc aca gtg aga tat tac agg atc act tac gga gaa     384
Asp Ala Pro Ala Val Thr Val Arg Tyr Tyr Arg Ile Thr Tyr Gly Glu
        115                 120                 125 aca gga gga aat agc cct gtc cag gag ttc act gtg cct ggg agc aag     432
Thr Gly Gly Asn Ser Pro Val Gln Glu Phe Thr Val Pro Gly Ser Lys
    130                 135                 140 tct aca gct acc atc agc ggc ctt aaa cct gga gtt gat tat acc atc     480
Ser Thr Ala Thr Ile Ser Gly Leu Lys Pro Gly Val Asp Tyr Thr Ile
145                 150                 155                 160 act gtg tat gct tgt cgt gct cgt ggt gat aat cct gac tgt agc aag     528
Thr Val Tyr Ala Cys Arg Ala Arg Gly Asp Asn Pro Asp Cys Ser Lys
                165                 170                 175 cca att tcc att aat tac cga aca                                     552
Pro Ile Ser Ile Asn Tyr Arg Thr
            180

<210> SEQ ID NO 32
<211> LENGTH: 184
<212> TYPE: PRT
<213> ORGANISM: Homo sapiens

<400> SEQUENCE: 32

Gly Leu Asp Ser Pro Thr Gly Ile Asp Phe Ser Asp Ile Thr Ala Asn
1               5                   10                  15

Ser Phe Thr Val His Trp Ile Ala Pro Arg Ala Thr Ile Thr Gly Tyr
            20                  25                  30

Arg Ile Arg His His Pro Glu His Phe Ser Gly Arg Pro Arg Glu Asp
        35                  40                  45

Arg Val Pro His Ser Arg Asn Ser Ile Thr Leu Thr Asn Leu Thr Pro
    50                  55                  60

Gly Thr Glu Tyr Val Val Ser Ile Val Ala Leu Asn Gly Arg Glu Glu
65                  70                  75                  80

Ser Pro Pro Leu Ile Gly Gln Gln Ser Thr Val Ser Asp Val Pro Arg
```

```
                    85                  90                  95
Asp Leu Glu Val Val Ala Ala Thr Pro Thr Ser Leu Leu Ile Ser Trp
            100                 105                 110

Asp Ala Pro Ala Val Thr Val Arg Tyr Tyr Arg Ile Thr Tyr Gly Glu
            115                 120                 125

Thr Gly Gly Asn Ser Pro Val Gln Glu Phe Thr Val Pro Gly Ser Lys
        130                 135                 140

Ser Thr Ala Thr Ile Ser Gly Leu Lys Pro Gly Val Asp Tyr Thr Ile
145                 150                 155                 160

Thr Val Tyr Ala Cys Arg Ala Arg Gly Asp Asn Pro Asp Cys Ser Lys
                165                 170                 175

Pro Ile Ser Ile Asn Tyr Arg Thr
            180

<210> SEQ ID NO 33
<211> LENGTH: 552
<212> TYPE: DNA
<213> ORGANISM: Homo sapiens
<220> FEATURE:
<221> NAME/KEY: CDS
<222> LOCATION: (1)..(552)

<400> SEQUENCE: 33 ggt ctt gat tcc cca act ggc att gac ttt tct gat att act gcc aac      48
Gly Leu Asp Ser Pro Thr Gly Ile Asp Phe Ser Asp Ile Thr Ala Asn
1               5                   10                  15 tct ttt act gtg cac tgg att gct cct cga gcc acc atc act ggc tac      96
Ser Phe Thr Val His Trp Ile Ala Pro Arg Ala Thr Ile Thr Gly Tyr
                20                  25                  30 agg atc cgc cat cat ccc gag cac ttc agt ggg aga cct cga gaa gat     144
Arg Ile Arg His His Pro Glu His Phe Ser Gly Arg Pro Arg Glu Asp
            35                  40                  45 cgg gtg ccc cac tct cgg aat tcc atc acc ctc acc aac ctc act cca     192
Arg Val Pro His Ser Arg Asn Ser Ile Thr Leu Thr Asn Leu Thr Pro
        50                  55                  60 ggc aca gag tat gtg gtc agc atc gtt gct ctt aat ggc aga gag gaa     240
Gly Thr Glu Tyr Val Val Ser Ile Val Ala Leu Asn Gly Arg Glu Glu
65                  70                  75                  80 agt ccc ccg ttg att ggc caa caa tca aca gtt tct gat gtt ccg agg     288
Ser Pro Pro Leu Ile Gly Gln Gln Ser Thr Val Ser Asp Val Pro Arg
                85                  90                  95 gac ctg gaa gtt gtt gct gcg acc ccc acc agc cta ctg atc agc tgg     336
Asp Leu Glu Val Val Ala Ala Thr Pro Thr Ser Leu Leu Ile Ser Trp
            100                 105                 110 gat gct cct gct gtc aca gtg aga tat tac agg atc act tac gga gaa     384
Asp Ala Pro Ala Val Thr Val Arg Tyr Tyr Arg Ile Thr Tyr Gly Glu
        115                 120                 125 aca gga gga aat agc cct gtc cag gag ttc act gtg cct ggg agc aag     432
Thr Gly Gly Asn Ser Pro Val Gln Glu Phe Thr Val Pro Gly Ser Lys
    130                 135                 140 tct aca gct acc atc agc ggc ctt aaa cct gga gtt gat tat acc atc     480
Ser Thr Ala Thr Ile Ser Gly Leu Lys Pro Gly Val Asp Tyr Thr Ile
145                 150                 155                 160 act gtg tat gct tgt act ggt cgt gga gac agc ccc gca tgt agc aag     528
Thr Val Tyr Ala Cys Thr Gly Arg Gly Asp Ser Pro Ala Cys Ser Lys
                165                 170                 175 cca att tcc att aat tac cga aca                                     552
Pro Ile Ser Ile Asn Tyr Arg Thr
            180
```

<210> SEQ ID NO 34
<211> LENGTH: 184
<212> TYPE: PRT
<213> ORGANISM: Homo sapiens

<400> SEQUENCE: 34

Gly Leu Asp Ser Pro Thr Gly Ile Asp Phe Ser Asp Ile Thr Ala Asn
1               5                   10                  15

Ser Phe Thr Val His Trp Ile Ala Pro Arg Ala Thr Ile Thr Gly Tyr
                20                  25                  30

Arg Ile Arg His His Pro Glu His Phe Ser Gly Arg Pro Arg Glu Asp
            35                  40                  45

Arg Val Pro His Ser Arg Asn Ser Ile Thr Leu Thr Asn Leu Thr Pro
    50                  55                  60

Gly Thr Glu Tyr Val Val Ser Ile Val Ala Leu Asn Gly Arg Glu Glu
65                  70                  75                  80

Ser Pro Pro Leu Ile Gly Gln Gln Ser Thr Val Ser Asp Val Pro Arg
                85                  90                  95

Asp Leu Glu Val Val Ala Ala Thr Pro Thr Ser Leu Leu Ile Ser Trp
                100                 105                 110

Asp Ala Pro Ala Val Thr Val Arg Tyr Tyr Arg Ile Thr Tyr Gly Glu
            115                 120                 125

Thr Gly Gly Asn Ser Pro Val Gln Glu Phe Thr Val Pro Gly Ser Lys
    130                 135                 140

Ser Thr Ala Thr Ile Ser Gly Leu Lys Pro Gly Val Asp Tyr Thr Ile
145                 150                 155                 160

Thr Val Tyr Ala Cys Thr Gly Arg Gly Asp Ser Pro Ala Cys Ser Lys
                165                 170                 175

Pro Ile Ser Ile Asn Tyr Arg Thr
            180

<210> SEQ ID NO 35
<211> LENGTH: 552
<212> TYPE: DNA
<213> ORGANISM: Homo sapiens
<220> FEATURE:
<221> NAME/KEY: CDS
<222> LOCATION: (1)..(552)

<400> SEQUENCE: 35 ggt ctt gat tcc cca act ggc att gac ttt tct gat att act gat aac    48
Gly Leu Asp Ser Pro Thr Gly Ile Asp Phe Ser Asp Ile Thr Asp Asn
1               5                   10                  15 tct ttt act gtg cac tgg att gct cct cga gcc acc atc act ggc tac    96
Ser Phe Thr Val His Trp Ile Ala Pro Arg Ala Thr Ile Thr Gly Tyr
                20                  25                  30 agg atc cgc cat cat ccc gag cac ttc agt ggg aga cct cga gaa gat    144
Arg Ile Arg His His Pro Glu His Phe Ser Gly Arg Pro Arg Glu Asp
            35                  40                  45 cgg gtg ccc cac tct cgg aat tcc atc acc ctc acc aac ctc act cca    192
Arg Val Pro His Ser Arg Asn Ser Ile Thr Leu Thr Asn Leu Thr Pro
    50                  55                  60 ggc aca gag tat gtg gtc agc atc gtt gct ctt aat ggc aga gag gaa    240
Gly Thr Glu Tyr Val Val Ser Ile Val Ala Leu Asn Gly Arg Glu Glu
65                  70                  75                  80 agt ccc ccg ttg att ggc caa caa tca aca gtt tct gat gtt ccg agg    288
Ser Pro Pro Leu Ile Gly Gln Gln Ser Thr Val Ser Asp Val Pro Arg
                85                  90                  95

```
gac ctg gaa gtt gtt gct gcg acc ccc acc agc cta ctg atc agc tgg      336
Asp Leu Glu Val Val Ala Ala Thr Pro Thr Ser Leu Leu Ile Ser Trp
        100                 105                 110 gat gct cct gct gtc aca gtg aga tat tac agg atc act tac gga gaa      384
Asp Ala Pro Ala Val Thr Val Arg Tyr Tyr Arg Ile Thr Tyr Gly Glu
            115                 120                 125 aca gga gga aat agc cct gtc cag gag ttc act gtg cct ggg agc aag      432
Thr Gly Gly Asn Ser Pro Val Gln Glu Phe Thr Val Pro Gly Ser Lys
130                 135                 140 tct aca gct acc atc agc ggc ctt aaa cct gga gtt gat tat acc atc      480
Ser Thr Ala Thr Ile Ser Gly Leu Lys Pro Gly Val Asp Tyr Thr Ile
145                 150                 155                 160 act gtg tat gct gtc act ggc cgt gga gac agc ccc gca agc agc aag      528
Thr Val Tyr Ala Val Thr Gly Arg Gly Asp Ser Pro Ala Ser Ser Lys
                165                 170                 175 cca att tcc att aat tac cga aca                                      552
Pro Ile Ser Ile Asn Tyr Arg Thr
            180

<210> SEQ ID NO 36
<211> LENGTH: 184
<212> TYPE: PRT
<213> ORGANISM: Homo sapiens

<400> SEQUENCE: 36

Gly Leu Asp Ser Pro Thr Gly Ile Asp Phe Ser Asp Ile Thr Asp Asn
1               5                   10                  15

Ser Phe Thr Val His Trp Ile Ala Pro Arg Ala Thr Ile Thr Gly Tyr
            20                  25                  30

Arg Ile Arg His His Pro Glu His Phe Ser Gly Arg Pro Arg Glu Asp
        35                  40                  45

Arg Val Pro His Ser Arg Asn Ser Ile Thr Leu Thr Asn Leu Thr Pro
    50                  55                  60

Gly Thr Glu Tyr Val Val Ser Ile Val Ala Leu Asn Gly Arg Glu Glu
65                  70                  75                  80

Ser Pro Pro Leu Ile Gly Gln Gln Ser Thr Val Ser Asp Val Pro Arg
                85                  90                  95

Asp Leu Glu Val Val Ala Ala Thr Pro Thr Ser Leu Leu Ile Ser Trp
            100                 105                 110

Asp Ala Pro Ala Val Thr Val Arg Tyr Tyr Arg Ile Thr Tyr Gly Glu
        115                 120                 125

Thr Gly Gly Asn Ser Pro Val Gln Glu Phe Thr Val Pro Gly Ser Lys
    130                 135                 140

Ser Thr Ala Thr Ile Ser Gly Leu Lys Pro Gly Val Asp Tyr Thr Ile
145                 150                 155                 160

Thr Val Tyr Ala Val Thr Gly Arg Gly Asp Ser Pro Ala Ser Ser Lys
                165                 170                 175

Pro Ile Ser Ile Asn Tyr Arg Thr
            180

<210> SEQ ID NO 37
<211> LENGTH: 552
<212> TYPE: DNA
<213> ORGANISM: Homo sapiens
<220> FEATURE:
<221> NAME/KEY: CDS
<222> LOCATION: (1)..(552)

<400> SEQUENCE: 37
```

| | | |
|---|---|---|
| ggt ctt gat tcc cca act ggc att gac ttt tct gat att act gcc aac<br>Gly Leu Asp Ser Pro Thr Gly Ile Asp Phe Ser Asp Ile Thr Ala Asn<br>1               5                   10                  15 | | 48 |
| tct ttt act gtg cac tgg att gct cct cga gcc acc atc act ggc tac<br>Ser Phe Thr Val His Trp Ile Ala Pro Arg Ala Thr Ile Thr Gly Tyr<br>            20                  25                  30 | | 96 |
| agg atc cgc cat cat ccc gag cac ttc agt ggg aga cct cga gaa gat<br>Arg Ile Arg His His Pro Glu His Phe Ser Gly Arg Pro Arg Glu Asp<br>        35                  40                  45 | | 144 |
| cgg gtg ccc cac tct cgg aat tcc atc acc ctc acc aac ctc act cca<br>Arg Val Pro His Ser Arg Asn Ser Ile Thr Leu Thr Asn Leu Thr Pro<br>    50                  55                  60 | | 192 |
| ggc aca gag tat gtg gtc agc atc gtt gct ctt aat ggc aga gag gaa<br>Gly Thr Glu Tyr Val Val Ser Ile Val Ala Leu Asn Gly Arg Glu Glu<br>65                  70                  75                  80 | | 240 |
| agt ccc ccg ttg att ggc caa caa tca aca gtt tct gat gtt ccg agg<br>Ser Pro Pro Leu Ile Gly Gln Gln Ser Thr Val Ser Asp Val Pro Arg<br>                85                  90                  95 | | 288 |
| gac ctg gaa gtt gtt gct gcg acc ccc acc agc cta ctg atc agc tgg<br>Asp Leu Glu Val Val Ala Ala Thr Pro Thr Ser Leu Leu Ile Ser Trp<br>            100                 105                 110 | | 336 |
| gat gct cct gct aaa aca gtg aga tat tac agg atc act tac gga gaa<br>Asp Ala Pro Ala Lys Thr Val Arg Tyr Tyr Arg Ile Thr Tyr Gly Glu<br>        115                 120                 125 | | 384 |
| aca gga gga aat agc cct gtc cag gag ttc act gtg cct ggg agc aag<br>Thr Gly Gly Asn Ser Pro Val Gln Glu Phe Thr Val Pro Gly Ser Lys<br>    130                 135                 140 | | 432 |
| tct aca gct acc atc agc ggc ctt aaa cct gga gtt gat tat acc atc<br>Ser Thr Ala Thr Ile Ser Gly Leu Lys Pro Gly Val Asp Tyr Thr Ile<br>145                 150                 155                 160 | | 480 |
| act gtg tat gct gtc act ggc cgt gga gac agc ccc gca agc agc aag<br>Thr Val Tyr Ala Val Thr Gly Arg Gly Asp Ser Pro Ala Ser Ser Lys<br>                165                 170                 175 | | 528 |
| cca att tcc att aat tac cga aca<br>Pro Ile Ser Ile Asn Tyr Arg Thr<br>            180 | | 552 |

<210> SEQ ID NO 38
<211> LENGTH: 184
<212> TYPE: PRT
<213> ORGANISM: Homo sapiens

<400> SEQUENCE: 38

Gly Leu Asp Ser Pro Thr Gly Ile Asp Phe Ser Asp Ile Thr Ala Asn
1               5                   10                  15

Ser Phe Thr Val His Trp Ile Ala Pro Arg Ala Thr Ile Thr Gly Tyr
            20                  25                  30

Arg Ile Arg His His Pro Glu His Phe Ser Gly Arg Pro Arg Glu Asp
        35                  40                  45

Arg Val Pro His Ser Arg Asn Ser Ile Thr Leu Thr Asn Leu Thr Pro
    50                  55                  60

Gly Thr Glu Tyr Val Val Ser Ile Val Ala Leu Asn Gly Arg Glu Glu
65                  70                  75                  80

Ser Pro Pro Leu Ile Gly Gln Gln Ser Thr Val Ser Asp Val Pro Arg
                85                  90                  95

Asp Leu Glu Val Val Ala Ala Thr Pro Thr Ser Leu Leu Ile Ser Trp
            100                 105                 110

Asp Ala Pro Ala Lys Thr Val Arg Tyr Tyr Arg Ile Thr Tyr Gly Glu
        115                 120                 125

```
Thr Gly Gly Asn Ser Pro Val Gln Glu Phe Thr Val Pro Gly Ser Lys
        130                 135                 140

Ser Thr Ala Thr Ile Ser Gly Leu Lys Pro Gly Val Asp Tyr Thr Ile
145                 150                 155                 160

Thr Val Tyr Ala Val Thr Gly Arg Gly Asp Ser Pro Ala Ser Ser Lys
                165                 170                 175

Pro Ile Ser Ile Asn Tyr Arg Thr
            180

<210> SEQ ID NO 39
<211> LENGTH: 552
<212> TYPE: DNA
<213> ORGANISM: Homo sapiens
<220> FEATURE:
<221> NAME/KEY: CDS
<222> LOCATION: (1)..(552)

<400> SEQUENCE: 39 ggt ctt gat tcc cca act ggc att gac ttt tct gat att act gat aac      48
Gly Leu Asp Ser Pro Thr Gly Ile Asp Phe Ser Asp Ile Thr Asp Asn
1               5                   10                  15 tct ttt act gtg cac tgg att gct cct cga gcc acc atc act ggc tac      96
Ser Phe Thr Val His Trp Ile Ala Pro Arg Ala Thr Ile Thr Gly Tyr
                20                  25                  30 agg atc cgc cat cat ccc gag cac ttc agt ggg aga cct cga gaa gat     144
Arg Ile Arg His His Pro Glu His Phe Ser Gly Arg Pro Arg Glu Asp
            35                  40                  45 cgg gtg ccc cac tct cgg aat tcc atc acc ctc acc aac ctc act cca     192
Arg Val Pro His Ser Arg Asn Ser Ile Thr Leu Thr Asn Leu Thr Pro
        50                  55                  60 ggc aca gag tat gtg gtc agc atc gtt gct ctt aat ggc aga gag gaa     240
Gly Thr Glu Tyr Val Val Ser Ile Val Ala Leu Asn Gly Arg Glu Glu
65                  70                  75                  80 agt ccc ccg ttg att ggc caa caa tca aca gtt tct gat gtt ccg agg     288
Ser Pro Pro Leu Ile Gly Gln Gln Ser Thr Val Ser Asp Val Pro Arg
                85                  90                  95 gac ctg gaa gtt gtt gct gcg acc ccc acc agc cta ctg atc agc tgg     336
Asp Leu Glu Val Val Ala Ala Thr Pro Thr Ser Leu Leu Ile Ser Trp
            100                 105                 110 gat gct cct gct aaa aca gtg aga tat tac agg atc act tac gga gaa     384
Asp Ala Pro Ala Lys Thr Val Arg Tyr Tyr Arg Ile Thr Tyr Gly Glu
        115                 120                 125 aca gga gga aat agc cct gtc cag gag ttc act gtg cct ggg agc aag     432
Thr Gly Gly Asn Ser Pro Val Gln Glu Phe Thr Val Pro Gly Ser Lys
130                 135                 140 tct aca gct acc atc agc ggc ctt aaa cct gga gtt gat tat acc atc     480
Ser Thr Ala Thr Ile Ser Gly Leu Lys Pro Gly Val Asp Tyr Thr Ile
145                 150                 155                 160 act gtg tat gct gtc act ggc cgt gga gac agc ccc gca agc agc aag     528
Thr Val Tyr Ala Val Thr Gly Arg Gly Asp Ser Pro Ala Ser Ser Lys
                165                 170                 175 cca att tcc att aat tac cga aca                                     552
Pro Ile Ser Ile Asn Tyr Arg Thr
            180

<210> SEQ ID NO 40
<211> LENGTH: 184
<212> TYPE: PRT
<213> ORGANISM: Homo sapiens

<400> SEQUENCE: 40
```

```
Gly Leu Asp Ser Pro Thr Gly Ile Asp Phe Ser Asp Ile Thr Asp Asn
1               5                   10                  15

Ser Phe Thr Val His Trp Ile Ala Pro Arg Ala Thr Ile Thr Gly Tyr
            20                  25                  30

Arg Ile Arg His His Pro Glu His Phe Ser Gly Arg Pro Arg Glu Asp
        35                  40                  45

Arg Val Pro His Ser Arg Asn Ser Ile Thr Leu Thr Asn Leu Thr Pro
    50                  55                  60

Gly Thr Glu Tyr Val Val Ser Ile Val Ala Leu Asn Gly Arg Glu Glu
65                  70                  75                  80

Ser Pro Pro Leu Ile Gly Gln Gln Ser Thr Val Ser Asp Val Pro Arg
                85                  90                  95

Asp Leu Glu Val Val Ala Ala Thr Pro Thr Ser Leu Leu Ile Ser Trp
            100                 105                 110

Asp Ala Pro Ala Lys Thr Val Arg Tyr Tyr Arg Ile Thr Tyr Gly Glu
        115                 120                 125

Thr Gly Gly Asn Ser Pro Val Gln Glu Phe Thr Val Pro Gly Ser Lys
    130                 135                 140

Ser Thr Ala Thr Ile Ser Gly Leu Lys Pro Gly Val Asp Tyr Thr Ile
145                 150                 155                 160

Thr Val Tyr Ala Val Thr Gly Arg Gly Asp Ser Pro Ala Ser Ser Lys
                165                 170                 175

Pro Ile Ser Ile Asn Tyr Arg Thr
            180

<210> SEQ ID NO 41
<211> LENGTH: 552
<212> TYPE: DNA
<213> ORGANISM: Homo sapiens
<220> FEATURE:
<221> NAME/KEY: CDS
<222> LOCATION: (1)..(552)

<400> SEQUENCE: 41 ggt ctt gat tcc cca act ggc att gac ttt tct gat att act gcc aac     48
Gly Leu Asp Ser Pro Thr Gly Ile Asp Phe Ser Asp Ile Thr Ala Asn
1               5                   10                  15 tct ttt act gtg cac tgg att gct cct cga gcc acc atc act ggc tac    96
Ser Phe Thr Val His Trp Ile Ala Pro Arg Ala Thr Ile Thr Gly Tyr
            20                  25                  30 agg atc cgc cat cat ccc gag cac ttc agt ggg aga cct cga gaa cgt    144
Arg Ile Arg His His Pro Glu His Phe Ser Gly Arg Pro Arg Glu Arg
        35                  40                  45 cgg gtg ccc cac tct cgg aat tcc atc acc ctc acc aac ctc act cca    192
Arg Val Pro His Ser Arg Asn Ser Ile Thr Leu Thr Asn Leu Thr Pro
    50                  55                  60 ggc aca gag tat gtg gtc agc atc gtt gct ctt aat ggc aga gag gaa    240
Gly Thr Glu Tyr Val Val Ser Ile Val Ala Leu Asn Gly Arg Glu Glu
65                  70                  75                  80 agt ccc ccg ttg att ggc caa caa tca aca gtt tct gat gtt ccg agg    288
Ser Pro Pro Leu Ile Gly Gln Gln Ser Thr Val Ser Asp Val Pro Arg
                85                  90                  95 gac ctg gaa gtt gct gct gcg acc ccc acc agc cta ctg atc agc tgg    336
Asp Leu Glu Val Ala Ala Ala Thr Pro Thr Ser Leu Leu Ile Ser Trp
            100                 105                 110 gat gct cct gct gtc aca gtg aga tat tac agg atc act tac gga gaa    384
Asp Ala Pro Ala Val Thr Val Arg Tyr Tyr Arg Ile Thr Tyr Gly Glu
        115                 120                 125
```

```
aca gga gga aat agc cct gtc cag gag ttc act gtg cct ggg agc aag        432
Thr Gly Gly Asn Ser Pro Val Gln Glu Phe Thr Val Pro Gly Ser Lys
    130                 135                 140 tct aca gct acc atc agc ggc ttt aaa cct gga gtt gat tat acc atc        480
Ser Thr Ala Thr Ile Ser Gly Phe Lys Pro Gly Val Asp Tyr Thr Ile
145                 150                 155                 160 act gtg tat gct gtc act ggc cgt gga gac agc ccc gca agc agc aag        528
Thr Val Tyr Ala Val Thr Gly Arg Gly Asp Ser Pro Ala Ser Ser Lys
                165                 170                 175 cca att tcc att aat tac cga aca                                        552
Pro Ile Ser Ile Asn Tyr Arg Thr
            180

<210> SEQ ID NO 42
<211> LENGTH: 184
<212> TYPE: PRT
<213> ORGANISM: Homo sapiens

<400> SEQUENCE: 42

Gly Leu Asp Ser Pro Thr Gly Ile Asp Phe Ser Asp Ile Thr Ala Asn
1               5                   10                  15

Ser Phe Thr Val His Trp Ile Ala Pro Arg Ala Thr Ile Thr Gly Tyr
            20                  25                  30

Arg Ile Arg His His Pro Glu His Phe Ser Gly Arg Pro Arg Glu Arg
        35                  40                  45

Arg Val Pro His Ser Arg Asn Ser Ile Thr Leu Thr Asn Leu Thr Pro
    50                  55                  60

Gly Thr Glu Tyr Val Val Ser Ile Val Ala Leu Asn Gly Arg Glu Glu
65                  70                  75                  80

Ser Pro Pro Leu Ile Gly Gln Gln Ser Thr Val Ser Asp Val Pro Arg
                85                  90                  95

Asp Leu Glu Val Ala Ala Ala Thr Pro Thr Ser Leu Leu Ile Ser Trp
            100                 105                 110

Asp Ala Pro Ala Val Thr Val Arg Tyr Tyr Arg Ile Thr Tyr Gly Glu
        115                 120                 125

Thr Gly Gly Asn Ser Pro Val Gln Glu Phe Thr Val Pro Gly Ser Lys
    130                 135                 140

Ser Thr Ala Thr Ile Ser Gly Phe Lys Pro Gly Val Asp Tyr Thr Ile
145                 150                 155                 160

Thr Val Tyr Ala Val Thr Gly Arg Gly Asp Ser Pro Ala Ser Ser Lys
                165                 170                 175

Pro Ile Ser Ile Asn Tyr Arg Thr
            180

<210> SEQ ID NO 43
<211> LENGTH: 552
<212> TYPE: DNA
<213> ORGANISM: Homo sapiens
<220> FEATURE:
<221> NAME/KEY: CDS
<222> LOCATION: (1)..(552)

<400> SEQUENCE: 43 ggt ctt gat tcc cca act ggc att gac ttt tct gat att act gcc aac        48
Gly Leu Asp Ser Pro Thr Gly Ile Asp Phe Ser Asp Ile Thr Ala Asn
1               5                   10                  15 tct ttt act gtg cac tgg att gct cct cga gcc acc atc act ggc tac        96
Ser Phe Thr Val His Trp Ile Ala Pro Arg Ala Thr Ile Thr Gly Tyr
            20                  25                  30
```

```
agg atc cgc cat cat ccc gag cac ttc agt ggg aga cct cga gaa gat    144
Arg Ile Arg His His Pro Glu His Phe Ser Gly Arg Pro Arg Glu Asp
             35                  40                  45 cgg gtg ccc cac tct gat aat tcc atc acc ctc acc aac ctc act cca    192
Arg Val Pro His Ser Asp Asn Ser Ile Thr Leu Thr Asn Leu Thr Pro
 50                  55                  60 ggc aca gag tat gtg gtc agc atc gtt gct ctt aat ggc aga gag gaa    240
Gly Thr Glu Tyr Val Val Ser Ile Val Ala Leu Asn Gly Arg Glu Glu
 65                  70                  75                  80 agt ccc ccg ttg att ggc caa caa tca aca gtt tct gat gtt ccg agg    288
Ser Pro Pro Leu Ile Gly Gln Gln Ser Thr Val Ser Asp Val Pro Arg
                 85                  90                  95 gac ctg gaa gtt gtt gct gcg acc ccc acc agc cta ctg atc agc tgg    336
Asp Leu Glu Val Val Ala Ala Thr Pro Thr Ser Leu Leu Ile Ser Trp
            100                 105                 110 gat gct cct gct gtc aca gtg aga tat tac agg atc act tac gga gaa    384
Asp Ala Pro Ala Val Thr Val Arg Tyr Tyr Arg Ile Thr Tyr Gly Glu
            115                 120                 125 aca gga gga aat agc cct gtc cag gag ttc act gtg cct ggg agc aag    432
Thr Gly Gly Asn Ser Pro Val Gln Glu Phe Thr Val Pro Gly Ser Lys
        130                 135                 140 tct aca gct acc atc agc ggc ctt aaa cct gga gtt gat tat acc atc    480
Ser Thr Ala Thr Ile Ser Gly Leu Lys Pro Gly Val Asp Tyr Thr Ile
145                 150                 155                 160 act gtg tat gct gtc act ggc cgt gga gac agc ccc gca agc agc aag    528
Thr Val Tyr Ala Val Thr Gly Arg Gly Asp Ser Pro Ala Ser Ser Lys
                165                 170                 175 cca att tcc att aat tac cga aca                                    552
Pro Ile Ser Ile Asn Tyr Arg Thr
                180

<210> SEQ ID NO 44
<211> LENGTH: 184
<212> TYPE: PRT
<213> ORGANISM: Homo sapiens

<400> SEQUENCE: 44

Gly Leu Asp Ser Pro Thr Gly Ile Asp Phe Ser Asp Ile Thr Ala Asn
1               5                   10                  15

Ser Phe Thr Val His Trp Ile Ala Pro Arg Ala Thr Ile Thr Gly Tyr
            20                  25                  30

Arg Ile Arg His His Pro Glu His Phe Ser Gly Arg Pro Arg Glu Asp
        35                  40                  45

Arg Val Pro His Ser Asp Asn Ser Ile Thr Leu Thr Asn Leu Thr Pro
 50                  55                  60

Gly Thr Glu Tyr Val Val Ser Ile Val Ala Leu Asn Gly Arg Glu Glu
 65                  70                  75                  80

Ser Pro Pro Leu Ile Gly Gln Gln Ser Thr Val Ser Asp Val Pro Arg
                 85                  90                  95

Asp Leu Glu Val Val Ala Ala Thr Pro Thr Ser Leu Leu Ile Ser Trp
            100                 105                 110

Asp Ala Pro Ala Val Thr Val Arg Tyr Tyr Arg Ile Thr Tyr Gly Glu
            115                 120                 125

Thr Gly Gly Asn Ser Pro Val Gln Glu Phe Thr Val Pro Gly Ser Lys
        130                 135                 140

Ser Thr Ala Thr Ile Ser Gly Leu Lys Pro Gly Val Asp Tyr Thr Ile
145                 150                 155                 160
```

```
Thr Val Tyr Ala Val Thr Gly Arg Gly Asp Ser Pro Ala Ser Ser Lys
                165                 170                 175

Pro Ile Ser Ile Asn Tyr Arg Thr
            180
```

<210> SEQ ID NO 45
<211> LENGTH: 552
<212> TYPE: DNA
<213> ORGANISM: Homo sapiens
<220> FEATURE:
<221> NAME/KEY: CDS
<222> LOCATION: (1)..(552)

<400> SEQUENCE: 45

```
ggt ctt gat tcc cca act ggc att gac ttt tct gat att act gcc aac    48
Gly Leu Asp Ser Pro Thr Gly Ile Asp Phe Ser Asp Ile Thr Ala Asn
1               5                   10                  15 tct ttt act gtg cac tgg att gct cct cga gcc acc atc act ggc tac    96
Ser Phe Thr Val His Trp Ile Ala Pro Arg Ala Thr Ile Thr Gly Tyr
            20                  25                  30 agg atc cgc cat cat ccc gag cac ttc agt ggg aga cct cga gaa cgt   144
Arg Ile Arg His His Pro Glu His Phe Ser Gly Arg Pro Arg Glu Arg
        35                  40                  45 cga gtg ccc cac tct gat aat tcc atc acc ctc acc aac ctc act cca   192
Arg Val Pro His Ser Asp Asn Ser Ile Thr Leu Thr Asn Leu Thr Pro
    50                  55                  60 ggc aca gag tat gtg gtc agc atc gtt gct ctt aat ggc aga gag gaa   240
Gly Thr Glu Tyr Val Val Ser Ile Val Ala Leu Asn Gly Arg Glu Glu
65                  70                  75                  80 agt ccc ccg ttg att ggc caa caa tca aca gtt tct gat gtt ccg agg   288
Ser Pro Pro Leu Ile Gly Gln Gln Ser Thr Val Ser Asp Val Pro Arg
                85                  90                  95 gac ctg gaa gtt gtt gct gcg acc ccc acc agc cta ctg atc agc tgg   336
Asp Leu Glu Val Val Ala Ala Thr Pro Thr Ser Leu Leu Ile Ser Trp
            100                 105                 110 gat gct cct gct gtc aca gtg aga tat tac agg atc act tac gga gaa   384
Asp Ala Pro Ala Val Thr Val Arg Tyr Tyr Arg Ile Thr Tyr Gly Glu
        115                 120                 125 aca gga gga aat agc cct gtc cag gag ttc act gtg cct ggg agc aag   432
Thr Gly Gly Asn Ser Pro Val Gln Glu Phe Thr Val Pro Gly Ser Lys
    130                 135                 140 tct aca gct acc atc agc ggc ctt aaa cct gga gtt gat tat acc atc   480
Ser Thr Ala Thr Ile Ser Gly Leu Lys Pro Gly Val Asp Tyr Thr Ile
145                 150                 155                 160 act gtg tat gct gtc act ggc cgt gga gac agc ccc gca agc agc aag   528
Thr Val Tyr Ala Val Thr Gly Arg Gly Asp Ser Pro Ala Ser Ser Lys
                165                 170                 175 cca att tcc att aat tac cga aca                                   552
Pro Ile Ser Ile Asn Tyr Arg Thr
            180
```

<210> SEQ ID NO 46
<211> LENGTH: 184
<212> TYPE: PRT
<213> ORGANISM: Homo sapiens

<400> SEQUENCE: 46

```
Gly Leu Asp Ser Pro Thr Gly Ile Asp Phe Ser Asp Ile Thr Ala Asn
1               5                   10                  15

Ser Phe Thr Val His Trp Ile Ala Pro Arg Ala Thr Ile Thr Gly Tyr
            20                  25                  30
```

```
Arg Ile Arg His His Pro Glu His Phe Ser Gly Arg Pro Arg Glu Arg
             35                  40                  45

Arg Val Pro His Ser Asp Asn Ser Ile Thr Leu Thr Asn Leu Thr Pro
         50                  55                  60

Gly Thr Glu Tyr Val Val Ser Ile Val Ala Leu Asn Gly Arg Glu Glu
 65                  70                  75                  80

Ser Pro Pro Leu Ile Gly Gln Gln Ser Thr Val Ser Asp Val Pro Arg
                 85                  90                  95

Asp Leu Glu Val Val Ala Ala Thr Pro Thr Ser Leu Leu Ile Ser Trp
            100                 105                 110

Asp Ala Pro Ala Val Thr Val Arg Tyr Tyr Arg Ile Thr Tyr Gly Glu
        115                 120                 125

Thr Gly Gly Asn Ser Pro Val Gln Glu Phe Thr Val Pro Gly Ser Lys
    130                 135                 140

Ser Thr Ala Thr Ile Ser Gly Leu Lys Pro Gly Val Asp Tyr Thr Ile
145                 150                 155                 160

Thr Val Tyr Ala Val Thr Gly Arg Gly Asp Ser Pro Ala Ser Ser Lys
                165                 170                 175

Pro Ile Ser Ile Asn Tyr Arg Thr
            180
```

```
<210> SEQ ID NO 47
<211> LENGTH: 282
<212> TYPE: DNA
<213> ORGANISM: Homo sapiens
<220> FEATURE:
<221> NAME/KEY: CDS
<222> LOCATION: (1)..(282)

<400> SEQUENCE: 47 gtt tct gat gtt ccg agg gac ctg gaa gtt gtt gct gcg acc ccc acc      48
Val Ser Asp Val Pro Arg Asp Leu Glu Val Val Ala Ala Thr Pro Thr
 1               5                  10                  15 agc cta ctg atc agc tgg gat gct cct gct gtc aca gtg aga tat tac      96
Ser Leu Leu Ile Ser Trp Asp Ala Pro Ala Val Thr Val Arg Tyr Tyr
             20                  25                  30 agg atc act tac gga gaa aca gga gga aat agc cct gtc cag gag ttc     144
Arg Ile Thr Tyr Gly Glu Thr Gly Gly Asn Ser Pro Val Gln Glu Phe
         35                  40                  45 act gtg cct ggg agc aag tct aca gct acc atc agc ggc ctt aaa cct     192
Thr Val Pro Gly Ser Lys Ser Thr Ala Thr Ile Ser Gly Leu Lys Pro
     50                  55                  60 gga gtt gat tat acc atc act gtg tat gct gtc act cct cgt ggt gat     240
Gly Val Asp Tyr Thr Ile Thr Val Tyr Ala Val Thr Pro Arg Gly Asp
 65                  70                  75                  80 atg cct gac agc agc aag cca att tcc att aat tac cga aca                 282
Met Pro Asp Ser Ser Lys Pro Ile Ser Ile Asn Tyr Arg Thr
                 85                  90
```

```
<210> SEQ ID NO 48
<211> LENGTH: 94
<212> TYPE: PRT
<213> ORGANISM: Homo sapiens

<400> SEQUENCE: 48

Val Ser Asp Val Pro Arg Asp Leu Glu Val Val Ala Ala Thr Pro Thr
 1               5                  10                  15

Ser Leu Leu Ile Ser Trp Asp Ala Pro Ala Val Thr Val Arg Tyr Tyr
             20                  25                  30
```

```
Arg Ile Thr Tyr Gly Glu Thr Gly Gly Asn Ser Pro Val Gln Glu Phe
         35                  40                  45

Thr Val Pro Gly Ser Lys Ser Thr Ala Thr Ile Ser Gly Leu Lys Pro
 50                  55                  60

Gly Val Asp Tyr Thr Ile Thr Val Tyr Ala Val Thr Pro Arg Gly Asp
 65                  70                  75                  80

Met Pro Asp Ser Ser Lys Pro Ile Ser Ile Asn Tyr Arg Thr
                 85                  90
```

<210> SEQ ID NO 49
<211> LENGTH: 282
<212> TYPE: DNA
<213> ORGANISM: Homo sapiens
<220> FEATURE:
<221> NAME/KEY: CDS
<222> LOCATION: (1)..(282)

<400> SEQUENCE: 49

```
gtt tct gat gtt ccg agg gac ctg gaa gtt gtt gct gcg acc ccc acc      48
Val Ser Asp Val Pro Arg Asp Leu Glu Val Val Ala Ala Thr Pro Thr
 1               5                  10                  15 agc cta ctg atc agc tgg gat gct cct gct gtc aca gtg aga tat tac      96
Ser Leu Leu Ile Ser Trp Asp Ala Pro Ala Val Thr Val Arg Tyr Tyr
             20                  25                  30 agg atc act tac gga gaa aca gga gga aat agc cct gtc cag gag ttc     144
Arg Ile Thr Tyr Gly Glu Thr Gly Gly Asn Ser Pro Val Gln Glu Phe
         35                  40                  45 act gtg cct ggg agc aag tct aca gct acc atc agc ggc ctt aaa cct     192
Thr Val Pro Gly Ser Lys Ser Thr Ala Thr Ile Ser Gly Leu Lys Pro
 50                  55                  60 gga gtt gat tat acc atc act gtg tat gct gtc act ccg cgt gga gac     240
Gly Val Asp Tyr Thr Ile Thr Val Tyr Ala Val Thr Pro Arg Gly Asp
 65                  70                  75                  80 tgg aat gaa gga agc aag cca att tcc att aat tac cga aca              282
Trp Asn Glu Gly Ser Lys Pro Ile Ser Ile Asn Tyr Arg Thr
                 85                  90
```

<210> SEQ ID NO 50
<211> LENGTH: 94
<212> TYPE: PRT
<213> ORGANISM: Homo sapiens

<400> SEQUENCE: 50

```
Val Ser Asp Val Pro Arg Asp Leu Glu Val Val Ala Ala Thr Pro Thr
 1               5                  10                  15

Ser Leu Leu Ile Ser Trp Asp Ala Pro Ala Val Thr Val Arg Tyr Tyr
             20                  25                  30

Arg Ile Thr Tyr Gly Glu Thr Gly Gly Asn Ser Pro Val Gln Glu Phe
         35                  40                  45

Thr Val Pro Gly Ser Lys Ser Thr Ala Thr Ile Ser Gly Leu Lys Pro
 50                  55                  60

Gly Val Asp Tyr Thr Ile Thr Val Tyr Ala Val Thr Pro Arg Gly Asp
 65                  70                  75                  80

Trp Asn Glu Gly Ser Lys Pro Ile Ser Ile Asn Tyr Arg Thr
                 85                  90
```

<210> SEQ ID NO 51
<211> LENGTH: 282
<212> TYPE: DNA
<213> ORGANISM: Homo sapiens
<220> FEATURE:

```
<221> NAME/KEY: CDS
<222> LOCATION: (1)..(282)

<400> SEQUENCE: 51 gtt tct gat gtt ccg agg gac ctg gaa gtt gtt gct gcg acc ccc acc      48
Val Ser Asp Val Pro Arg Asp Leu Glu Val Val Ala Ala Thr Pro Thr
1               5                   10                  15 agc cta ctg atc agc tgg gat gct cct gct gtc aca gtg aga tac tac      96
Ser Leu Leu Ile Ser Trp Asp Ala Pro Ala Val Thr Val Arg Tyr Tyr
            20                  25                  30 agg atc act tac gga gaa aca gga gga aat agc cct gtc cag gag ttc     144
Arg Ile Thr Tyr Gly Glu Thr Gly Gly Asn Ser Pro Val Gln Glu Phe
        35                  40                  45 act gtg cct ggg agc aag tct aca gct acc atc agc ggc ctt aaa cct     192
Thr Val Pro Gly Ser Lys Ser Thr Ala Thr Ile Ser Gly Leu Lys Pro
    50                  55                  60 gga gtt gat tat acc atc act gtg tat gct gtc act gct cgt ggt gat     240
Gly Val Asp Tyr Thr Ile Thr Val Tyr Ala Val Thr Ala Arg Gly Asp
65                  70                  75                  80 aat cct gac agc agc aag cca att tcc att aat tac cga aca             282
Asn Pro Asp Ser Ser Lys Pro Ile Ser Ile Asn Tyr Arg Thr
                85                  90

<210> SEQ ID NO 52
<211> LENGTH: 94
<212> TYPE: PRT
<213> ORGANISM: Homo sapiens

<400> SEQUENCE: 52

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Ala Arg Gly Asp
65                  70                  75                  80

Asn Pro Asp Ser Ser Lys Pro Ile Ser Ile Asn Tyr Arg Thr
                85                  90

<210> SEQ ID NO 53
<211> LENGTH: 282
<212> TYPE: DNA
<213> ORGANISM: Homo sapiens
<220> FEATURE:
<221> NAME/KEY: CDS
<222> LOCATION: (1)..(282)

<400> SEQUENCE: 53 gtt tct gat gtt ccg agg gac ctg gaa gtt gtt gct gcg acc ccc acc      48
Val Ser Asp Val Pro Arg Asp Leu Glu Val Val Ala Ala Thr Pro Thr
1               5                   10                  15 agc cta ctg atc agc tgg gat gct cct gct gtc aca gtg aga tac tac      96
Ser Leu Leu Ile Ser Trp Asp Ala Pro Ala Val Thr Val Arg Tyr Tyr
            20                  25                  30 agg atc act tac gga gaa aca gga gga aat agc cct gtc cag gag ttc     144
Arg Ile Thr Tyr Gly Glu Thr Gly Gly Asn Ser Pro Val Gln Glu Phe
        35                  40                  45 act gtg cct ggg agc aag tct aca gct acc atc agc ggc ctt aaa cct     192
```

```
Thr Val Pro Gly Ser Lys Ser Thr Ala Thr Ile Ser Gly Leu Lys Pro
         50                  55                  60 gga gtt gat tat acc atc act gtg tat gct gtc cgt gct cgt ggt gat     240
Gly Val Asp Tyr Thr Ile Thr Val Tyr Ala Val Arg Ala Arg Gly Asp
 65              70                  75                  80 aat cct gac agc agc aag cca att tcc att aat tac cga aca             282
Asn Pro Asp Ser Ser Lys Pro Ile Ser Ile Asn Tyr Arg Thr
                     85                  90
```

<210> SEQ ID NO 54
<211> LENGTH: 94
<212> TYPE: PRT
<213> ORGANISM: Homo sapiens

<400> SEQUENCE: 54

```
Val Ser Asp Val Pro Arg Asp Leu Glu Val Val Ala Ala Thr Pro Thr
 1               5                  10                  15

Ser Leu Leu Ile Ser Trp Asp Ala Pro Ala Val Thr Val Arg Tyr Tyr
                20                  25                  30

Arg Ile Thr Tyr Gly Glu Thr Gly Gly Asn Ser Pro Val Gln Glu Phe
             35                  40                  45

Thr Val Pro Gly Ser Lys Ser Thr Ala Thr Ile Ser Gly Leu Lys Pro
         50                  55                  60

Gly Val Asp Tyr Thr Ile Thr Val Tyr Ala Val Arg Ala Arg Gly Asp
 65              70                  75                  80

Asn Pro Asp Ser Ser Lys Pro Ile Ser Ile Asn Tyr Arg Thr
                 85                  90
```

<210> SEQ ID NO 55
<211> LENGTH: 552
<212> TYPE: DNA
<213> ORGANISM: Homo sapiens
<220> FEATURE:
<221> NAME/KEY: CDS
<222> LOCATION: (1)..(552)

<400> SEQUENCE: 55

```
ggt ctt gat tcc cca act ggc att gac ttt tct gat att act gcc aac     48
Gly Leu Asp Ser Pro Thr Gly Ile Asp Phe Ser Asp Ile Thr Ala Asn
 1               5                  10                  15 tct ttt act gtg cac tgg att gct cct cga gcc acc atc act ggc tac     96
Ser Phe Thr Val His Trp Ile Ala Pro Arg Ala Thr Ile Thr Gly Tyr
                20                  25                  30 agg atc cgc cat cat ccc gag cac ttc agt ggg aga cct cga gaa gat    144
Arg Ile Arg His His Pro Glu His Phe Ser Gly Arg Pro Arg Glu Asp
             35                  40                  45 cgg gtg ccc cac tct cgg aat tcc atc acc ctc acc aac ctc act cca    192
Arg Val Pro His Ser Arg Asn Ser Ile Thr Leu Thr Asn Leu Thr Pro
         50                  55                  60 ggc aca gag tat gtg gtc agc atc gtt gct ctt aat ggc aga gag gaa    240
Gly Thr Glu Tyr Val Val Ser Ile Val Ala Leu Asn Gly Arg Glu Glu
 65              70                  75                  80 agt ccc tta ttg att ggc caa caa tca aca gtt tct gat gtt ccg agg    288
Ser Pro Leu Leu Ile Gly Gln Gln Ser Thr Val Ser Asp Val Pro Arg
                 85                  90                  95 gac ctg gaa gtt gtt gct gcg acc ccc acc agc cta ctg atc agc tgg    336
Asp Leu Glu Val Val Ala Ala Thr Pro Thr Ser Leu Leu Ile Ser Trp
                100                 105                 110 gat gct cct gct gtc aca gtg aga tat tac agg atc act tac gga gaa    384
Asp Ala Pro Ala Val Thr Val Arg Tyr Tyr Arg Ile Thr Tyr Gly Glu
            115                 120                 125
```

```
aca gga gga aat agc cct gtc cag gag ttc act gtg cct ggg agc aag       432
Thr Gly Gly Asn Ser Pro Val Gln Glu Phe Thr Val Pro Gly Ser Lys
    130                 135                 140 tct aca gct acc atc agc ggc ctt aaa cct gga gtt gat tat acc atc       480
Ser Thr Ala Thr Ile Ser Gly Leu Lys Pro Gly Val Asp Tyr Thr Ile
145                 150                 155                 160 act gtg tat gct gtc act cct cgt ggt gat atg cct gac agc agc aag       528
Thr Val Tyr Ala Val Thr Pro Arg Gly Asp Met Pro Asp Ser Ser Lys
                165                 170                 175 cca att tcc att aat tac cga aca                                       552
Pro Ile Ser Ile Asn Tyr Arg Thr
            180
```

```
<210> SEQ ID NO 56
<211> LENGTH: 184
<212> TYPE: PRT
<213> ORGANISM: Homo sapiens

<400> SEQUENCE: 56

Gly Leu Asp Ser Pro Thr Gly Ile Asp Phe Ser Asp Ile Thr Ala Asn
1               5                   10                  15

Ser Phe Thr Val His Trp Ile Ala Pro Arg Ala Thr Ile Thr Gly Tyr
            20                  25                  30

Arg Ile Arg His His Pro Glu His Phe Ser Gly Arg Pro Arg Glu Asp
        35                  40                  45

Arg Val Pro His Ser Arg Asn Ser Ile Thr Leu Thr Asn Leu Thr Pro
    50                  55                  60

Gly Thr Glu Tyr Val Val Ser Ile Val Ala Leu Asn Gly Arg Glu Glu
65                  70                  75                  80

Ser Pro Leu Leu Ile Gly Gln Gln Ser Thr Val Ser Asp Val Pro Arg
                85                  90                  95

Asp Leu Glu Val Val Ala Ala Thr Pro Thr Ser Leu Leu Ile Ser Trp
            100                 105                 110

Asp Ala Pro Ala Val Thr Val Arg Tyr Tyr Arg Ile Thr Tyr Gly Glu
        115                 120                 125

Thr Gly Gly Asn Ser Pro Val Gln Glu Phe Thr Val Pro Gly Ser Lys
    130                 135                 140

Ser Thr Ala Thr Ile Ser Gly Leu Lys Pro Gly Val Asp Tyr Thr Ile
145                 150                 155                 160

Thr Val Tyr Ala Val Thr Pro Arg Gly Asp Met Pro Asp Ser Ser Lys
                165                 170                 175

Pro Ile Ser Ile Asn Tyr Arg Thr
            180
```

```
<210> SEQ ID NO 57
<211> LENGTH: 552
<212> TYPE: DNA
<213> ORGANISM: Homo sapiens
<220> FEATURE:
<221> NAME/KEY: CDS
<222> LOCATION: (1)..(552)

<400> SEQUENCE: 57 ggt ctt gat tcc cca act ggc att gac ttt tct gat att act gcc aac       48
Gly Leu Asp Ser Pro Thr Gly Ile Asp Phe Ser Asp Ile Thr Ala Asn
1               5                   10                  15 tct ttt act gtg cac tgg att gct cct cga gcc acc atc act ggc tac       96
Ser Phe Thr Val His Trp Ile Ala Pro Arg Ala Thr Ile Thr Gly Tyr
            20                  25                  30
```

```
agg atc cgc cat cat ccc gag cac ttc agt ggg aga cct cga gaa gat    144
Arg Ile Arg His His Pro Glu His Phe Ser Gly Arg Pro Arg Glu Asp
         35                  40                  45 cgg gtg ccc cac tct cgg aat tcc atc acc ctc acc aac ctc act cca    192
Arg Val Pro His Ser Arg Asn Ser Ile Thr Leu Thr Asn Leu Thr Pro
 50                  55                  60 ggc aca gag tat gtg gtc agc atc gtt gct ctt aat ggc aga gag gaa    240
Gly Thr Glu Tyr Val Val Ser Ile Val Ala Leu Asn Gly Arg Glu Glu
 65                  70                  75                  80 agt ccc tta ttg att ggc caa caa tca aca gtt tct gat gtt ccg agg    288
Ser Pro Leu Leu Ile Gly Gln Gln Ser Thr Val Ser Asp Val Pro Arg
                 85                  90                  95 gac ctg gaa gtt gtt gct gcg acc ccc acc agc cta ctg atc agc tgg    336
Asp Leu Glu Val Val Ala Ala Thr Pro Thr Ser Leu Leu Ile Ser Trp
            100                 105                 110 gat gct cct gct gtc aca gtg aga tat tac agg atc act tac gga gaa    384
Asp Ala Pro Ala Val Thr Val Arg Tyr Tyr Arg Ile Thr Tyr Gly Glu
        115                 120                 125 aca gga gga aat agc cct gtc cag gag ttc act gtg cct ggg agc aag    432
Thr Gly Gly Asn Ser Pro Val Gln Glu Phe Thr Val Pro Gly Ser Lys
    130                 135                 140 tct aca gct acc atc agc ggc ctt aaa cct gga gtt gat tat acc atc    480
Ser Thr Ala Thr Ile Ser Gly Leu Lys Pro Gly Val Asp Tyr Thr Ile
145                 150                 155                 160 act gtg tat gct gtc act ccg cgt gga gac tgg aat gaa gga agc aag    528
Thr Val Tyr Ala Val Thr Pro Arg Gly Asp Trp Asn Glu Gly Ser Lys
                165                 170                 175 cca att tcc att aat tac cga aca                                    552
Pro Ile Ser Ile Asn Tyr Arg Thr
            180

<210> SEQ ID NO 58
<211> LENGTH: 184
<212> TYPE: PRT
<213> ORGANISM: Homo sapiens

<400> SEQUENCE: 58

Gly Leu Asp Ser Pro Thr Gly Ile Asp Phe Ser Asp Ile Thr Ala Asn
 1               5                  10                  15

Ser Phe Thr Val His Trp Ile Ala Pro Arg Ala Thr Ile Thr Gly Tyr
            20                  25                  30

Arg Ile Arg His His Pro Glu His Phe Ser Gly Arg Pro Arg Glu Asp
        35                  40                  45

Arg Val Pro His Ser Arg Asn Ser Ile Thr Leu Thr Asn Leu Thr Pro
 50                  55                  60

Gly Thr Glu Tyr Val Val Ser Ile Val Ala Leu Asn Gly Arg Glu Glu
 65                  70                  75                  80

Ser Pro Leu Leu Ile Gly Gln Gln Ser Thr Val Ser Asp Val Pro Arg
                 85                  90                  95

Asp Leu Glu Val Val Ala Ala Thr Pro Thr Ser Leu Leu Ile Ser Trp
            100                 105                 110

Asp Ala Pro Ala Val Thr Val Arg Tyr Tyr Arg Ile Thr Tyr Gly Glu
        115                 120                 125

Thr Gly Gly Asn Ser Pro Val Gln Glu Phe Thr Val Pro Gly Ser Lys
    130                 135                 140

Ser Thr Ala Thr Ile Ser Gly Leu Lys Pro Gly Val Asp Tyr Thr Ile
145                 150                 155                 160
```

```
Thr Val Tyr Ala Val Thr Pro Arg Gly Asp Trp Asn Glu Gly Ser Lys
                165                 170                 175

Pro Ile Ser Ile Asn Tyr Arg Thr
            180

<210> SEQ ID NO 59
<211> LENGTH: 552
<212> TYPE: DNA
<213> ORGANISM: Homo sapiens
<220> FEATURE:
<221> NAME/KEY: CDS
<222> LOCATION: (1)..(552)

<400> SEQUENCE: 59 ggt ctt gat tcc cca act ggc att gac ttt tct gat att act gcc aac      48
Gly Leu Asp Ser Pro Thr Gly Ile Asp Phe Ser Asp Ile Thr Ala Asn
1               5                   10                  15 tct ttt act gtg cac tgg att gct cct cga gcc acc atc act ggc tac     96
Ser Phe Thr Val His Trp Ile Ala Pro Arg Ala Thr Ile Thr Gly Tyr
                20                  25                  30 agg atc cgc cat cat ccc gag cac ttc agt ggg aga cct cga gaa gat    144
Arg Ile Arg His His Pro Glu His Phe Ser Gly Arg Pro Arg Glu Asp
            35                  40                  45 cgg gtg ccc cac tct cgg aat tcc atc acc ctc acc aac ctc act cca    192
Arg Val Pro His Ser Arg Asn Ser Ile Thr Leu Thr Asn Leu Thr Pro
        50                  55                  60 ggc aca gag tat gtg gtc agc atc gtt gct ctt aat ggc aga gag gaa    240
Gly Thr Glu Tyr Val Val Ser Ile Val Ala Leu Asn Gly Arg Glu Glu
65                  70                  75                  80 agt ccc ccg ttg att ggc caa caa tca aca gtt tct gat gtt ccg agg    288
Ser Pro Pro Leu Ile Gly Gln Gln Ser Thr Val Ser Asp Val Pro Arg
                85                  90                  95 gac ctg gaa gtt gtt gct gcg acc ccc acc agc cta ctg atc agc tgg    336
Asp Leu Glu Val Val Ala Ala Thr Pro Thr Ser Leu Leu Ile Ser Trp
            100                 105                 110 gat gct cct gct gtc aca gtg aga tac tac agg atc act tac gga gaa    384
Asp Ala Pro Ala Val Thr Val Arg Tyr Tyr Arg Ile Thr Tyr Gly Glu
        115                 120                 125 aca gga gga aat agc cct gtc cag gag ttc act gtg cct ggg agc aag    432
Thr Gly Gly Asn Ser Pro Val Gln Glu Phe Thr Val Pro Gly Ser Lys
    130                 135                 140 tct aca gct acc atc agc ggc ctt aaa cct gga gtt gat tat acc atc    480
Ser Thr Ala Thr Ile Ser Gly Leu Lys Pro Gly Val Asp Tyr Thr Ile
145                 150                 155                 160 act gtg tat gct gtc act gct cgt ggt gat aat cct gac agc agc aag    528
Thr Val Tyr Ala Val Thr Ala Arg Gly Asp Asn Pro Asp Ser Ser Lys
                165                 170                 175 cca att tcc att aat tac cga aca                                    552
Pro Ile Ser Ile Asn Tyr Arg Thr
            180

<210> SEQ ID NO 60
<211> LENGTH: 184
<212> TYPE: PRT
<213> ORGANISM: Homo sapiens

<400> SEQUENCE: 60

Gly Leu Asp Ser Pro Thr Gly Ile Asp Phe Ser Asp Ile Thr Ala Asn
1               5                   10                  15

Ser Phe Thr Val His Trp Ile Ala Pro Arg Ala Thr Ile Thr Gly Tyr
                20                  25                  30
```

```
Arg Ile Arg His His Pro Glu His Phe Ser Gly Arg Pro Arg Glu Asp
         35                  40                  45

Arg Val Pro His Ser Arg Asn Ser Ile Thr Leu Thr Asn Leu Thr Pro
 50                  55                  60

Gly Thr Glu Tyr Val Val Ser Ile Val Ala Leu Asn Gly Arg Glu Glu
 65                  70                  75                  80

Ser Pro Pro Leu Ile Gly Gln Gln Ser Thr Val Ser Asp Val Pro Arg
                 85                  90                  95

Asp Leu Glu Val Val Ala Ala Thr Pro Thr Ser Leu Leu Ile Ser Trp
                100                 105                 110

Asp Ala Pro Ala Val Thr Val Arg Tyr Tyr Arg Ile Thr Tyr Gly Glu
                115                 120                 125

Thr Gly Gly Asn Ser Pro Val Gln Glu Phe Thr Val Pro Gly Ser Lys
130                 135                 140

Ser Thr Ala Thr Ile Ser Gly Leu Lys Pro Gly Val Asp Tyr Thr Ile
145                 150                 155                 160

Thr Val Tyr Ala Val Thr Ala Arg Gly Asp Asn Pro Asp Ser Ser Lys
                165                 170                 175

Pro Ile Ser Ile Asn Tyr Arg Thr
                180

<210> SEQ ID NO 61
<211> LENGTH: 552
<212> TYPE: DNA
<213> ORGANISM: Homo sapiens
<220> FEATURE:
<221> NAME/KEY: CDS
<222> LOCATION: (1)..(552)

<400> SEQUENCE: 61 ggt ctt gat tcc cca act ggc att gac ttt tct gat att act gcc aac      48
Gly Leu Asp Ser Pro Thr Gly Ile Asp Phe Ser Asp Ile Thr Ala Asn
 1               5                  10                  15 tct ttt act gtg cac tgg att gct cct cga gcc acc atc act ggc tac      96
Ser Phe Thr Val His Trp Ile Ala Pro Arg Ala Thr Ile Thr Gly Tyr
                20                  25                  30 agg atc cgc cat cat ccc gag cac ttc agt ggg aga cct cga gaa gat     144
Arg Ile Arg His His Pro Glu His Phe Ser Gly Arg Pro Arg Glu Asp
         35                  40                  45 cgg gtg ccc cac tct cgg aat tcc atc acc ctc acc aac ctc act cca     192
Arg Val Pro His Ser Arg Asn Ser Ile Thr Leu Thr Asn Leu Thr Pro
 50                  55                  60 ggc aca gag tat gtg gtc agc atc gtt gct ctt aat ggc aga gag gaa     240
Gly Thr Glu Tyr Val Val Ser Ile Val Ala Leu Asn Gly Arg Glu Glu
 65                  70                  75                  80 agt ccc ccg ttg att ggc caa caa tca aca gtt tct gat gtt ccg agg     288
Ser Pro Pro Leu Ile Gly Gln Gln Ser Thr Val Ser Asp Val Pro Arg
                 85                  90                  95 gac ctg gaa gtt gtt gct gcg acc ccc acc agc cta ctg atc agc tgg     336
Asp Leu Glu Val Val Ala Ala Thr Pro Thr Ser Leu Leu Ile Ser Trp
                100                 105                 110 gat gct cct gct gtc aca gtg aga tac tac agg atc act tac gga gaa     384
Asp Ala Pro Ala Val Thr Val Arg Tyr Tyr Arg Ile Thr Tyr Gly Glu
                115                 120                 125 aca gga gga aat agc cct gtc cag gag ttc act gtg cct ggg agc aag     432
Thr Gly Gly Asn Ser Pro Val Gln Glu Phe Thr Val Pro Gly Ser Lys
130                 135                 140 tct aca gct acc atc agc ggc ctt aaa cct gga gtt gat tat acc atc     480
Ser Thr Ala Thr Ile Ser Gly Leu Lys Pro Gly Val Asp Tyr Thr Ile
```

```
                145                 150                 155                 160
act gtg tat gct gtc cgt gct cgt ggt gat aat cct gac agc agc aag        528
Thr Val Tyr Ala Val Arg Ala Arg Gly Asp Asn Pro Asp Ser Ser Lys
                165                 170                 175 cca att tcc att aat tac cga aca                                        552
Pro Ile Ser Ile Asn Tyr Arg Thr
                180

<210> SEQ ID NO 62
<211> LENGTH: 184
<212> TYPE: PRT
<213> ORGANISM: Homo sapiens

<400> SEQUENCE: 62

Gly Leu Asp Ser Pro Thr Gly Ile Asp Phe Ser Asp Ile Thr Ala Asn
1               5                   10                  15

Ser Phe Thr Val His Trp Ile Ala Pro Arg Ala Thr Ile Thr Gly Tyr
                20                  25                  30

Arg Ile Arg His His Pro Glu His Phe Ser Gly Arg Pro Arg Glu Asp
            35                  40                  45

Arg Val Pro His Ser Arg Asn Ser Ile Thr Leu Thr Asn Leu Thr Pro
        50                  55                  60

Gly Thr Glu Tyr Val Val Ser Ile Val Ala Leu Asn Gly Arg Glu Glu
65                  70                  75                  80

Ser Pro Pro Leu Ile Gly Gln Gln Ser Thr Val Ser Asp Val Pro Arg
                85                  90                  95

Asp Leu Glu Val Val Ala Ala Thr Pro Thr Ser Leu Leu Ile Ser Trp
            100                 105                 110

Asp Ala Pro Ala Val Thr Val Arg Tyr Tyr Arg Ile Thr Tyr Gly Glu
        115                 120                 125

Thr Gly Gly Asn Ser Pro Val Gln Glu Phe Thr Val Pro Gly Ser Lys
    130                 135                 140

Ser Thr Ala Thr Ile Ser Gly Leu Lys Pro Gly Val Asp Tyr Thr Ile
145                 150                 155                 160

Thr Val Tyr Ala Val Arg Ala Arg Gly Asp Asn Pro Asp Ser Ser Lys
                165                 170                 175

Pro Ile Ser Ile Asn Tyr Arg Thr
                180

<210> SEQ ID NO 63
<211> LENGTH: 184
<212> TYPE: PRT
<213> ORGANISM: Homo sapiens

<400> SEQUENCE: 63

Gly Leu Asp Ser Pro Thr Gly Ile Asp Phe Ser Asp Ile Thr Ala Asn
1               5                   10                  15

Ser Phe Thr Val His Trp Ile Ala Pro Arg Ala Thr Ile Thr Gly Tyr
                20                  25                  30

Arg Ile Arg His His Pro Glu His Phe Ser Gly Arg Pro Arg Glu Asp
            35                  40                  45

Arg Val Pro His Ser Arg Asn Ser Ile Thr Leu Thr Asn Leu Thr Pro
        50                  55                  60

Gly Thr Glu Tyr Val Val Ser Ile Val Ala Leu Asn Gly Arg Glu Glu
65                  70                  75                  80

Ser Pro Pro Leu Ile Gly Gln Gln Ser Thr Val Ser Asp Val Pro Arg
                85                  90                  95
```

Asp Leu Glu Val Val Ala Ala Thr Pro Thr Ser Leu Leu Ile Ser Trp
            100                 105                 110

Asp Ala Pro Ala Val Thr Val Arg Tyr Tyr Arg Ile Thr Tyr Gly Glu
            115                 120                 125

Thr Gly Gly Asn Ser Pro Val Gln Glu Phe Thr Val Pro Gly Ser Lys
        130                 135                 140

Ser Thr Ala Thr Ile Ser Gly Leu Lys Pro Gly Val Asp Tyr Thr Ile
145                 150                 155                 160

Thr Val Tyr Ala Val Thr Gly Arg Gly Asp Ser Pro Ala Ser Ser Lys
                165                 170                 175

Pro Ile Ser Ile Asn Tyr Arg Thr
            180

<210> SEQ ID NO 64
<211> LENGTH: 184
<212> TYPE: PRT
<213> ORGANISM: Homo sapiens

<400> SEQUENCE: 64

Gly Leu Asp Ser Pro Thr Gly Ile Asp Phe Ser Asp Ile Thr Cys Asn
1               5                   10                  15

Ser Phe Thr Val His Trp Ile Ala Pro Arg Ala Thr Ile Thr Gly Tyr
            20                  25                  30

Arg Ile Arg His His Pro Glu His Phe Ser Gly Arg Pro Arg Glu Asp
        35                  40                  45

Arg Val Pro His Ser Arg Asn Ser Ile Thr Leu Thr Asn Leu Thr Pro
    50                  55                  60

Gly Thr Glu Tyr Val Val Ser Ile Val Ala Leu Asn Gly Arg Glu Glu
65                  70                  75                  80

Ser Pro Pro Leu Ile Gly Gln Gln Ser Thr Val Ser Asp Val Pro Arg
                85                  90                  95

Asp Leu Glu Val Val Ala Ala Thr Pro Thr Ser Leu Leu Ile Ser Trp
            100                 105                 110

Asp Ala Pro Ala Cys Thr Val Arg Tyr Tyr Arg Ile Thr Tyr Gly Glu
            115                 120                 125

Thr Gly Gly Asn Ser Pro Val Gln Glu Phe Thr Val Pro Gly Ser Lys
        130                 135                 140

Ser Thr Ala Thr Ile Ser Gly Leu Lys Pro Gly Val Asp Tyr Thr Ile
145                 150                 155                 160

Thr Val Tyr Ala Val Thr Gly Arg Gly Asp Ser Pro Ala Ser Ser Lys
                165                 170                 175

Pro Ile Ser Ile Asn Tyr Arg Thr
            180

<210> SEQ ID NO 65
<211> LENGTH: 94
<212> TYPE: PRT
<213> ORGANISM: Homo sapiens

<400> SEQUENCE: 65

Val Ser Asp Val Pro Arg Asn Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
            50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr
                85                  90

<210> SEQ ID NO 66
<211> LENGTH: 184
<212> TYPE: PRT
<213> ORGANISM: Pan troglodytes

<400> SEQUENCE: 66

Gly Leu Asp Ser Pro Thr Gly Ile Asp Phe Ser Asp Ile Thr Ala Asn
1               5                   10                  15

Ser Phe Thr Val His Trp Ile Ala Pro Arg Ala Thr Ile Thr Gly Tyr
            20                  25                  30

Arg Ile Arg His His Pro Glu His Leu Ser Gly Arg Pro Arg Glu Asp
        35                  40                  45

Arg Val Pro Pro Ser Arg Asn Ser Ile Thr Leu Thr Asn Leu Thr Pro
    50                  55                  60

Gly Thr Glu Tyr Val Val Ser Ile Val Ala Leu Asn Gly Arg Glu Glu
65                  70                  75                  80

Ser Pro Ser Leu Ile Gly Gln Gln Ser Thr Val Ser Asp Val Pro Arg
                85                  90                  95

Asp Leu Glu Val Val Ala Ala Thr Pro Thr Ser Leu Leu Ile Ser Trp
            100                 105                 110

Asp Ala Pro Ala Val Thr Val Arg Tyr Tyr Arg Ile Thr Tyr Gly Glu
        115                 120                 125

Thr Gly Gly Asn Ser Pro Val Gln Glu Phe Thr Val Pro Gly Ser Lys
    130                 135                 140

Ser Thr Ala Thr Ile Ser Gly Leu Lys Pro Gly Val Asp Tyr Thr Ile
145                 150                 155                 160

Thr Val Tyr Ala Val Thr Gly Arg Gly Asp Ser Pro Ala Ser Ser Lys
                165                 170                 175

Pro Ile Ser Ile Asn Tyr Arg Thr
            180

<210> SEQ ID NO 67
<211> LENGTH: 184
<212> TYPE: PRT
<213> ORGANISM: Bos taurus

<400> SEQUENCE: 67

Ala Leu Asp Ser Pro Ser Gly Ile Asp Phe Ser Asp Ile Thr Ala Asn
1               5                   10                  15

Ser Phe Thr Val His Trp Ile Ala Pro Arg Ala Thr Ile Thr Gly Tyr
            20                  25                  30

Arg Ile Arg His His Pro Glu Asn Met Gly Gly Arg Pro Arg Glu Asp
        35                  40                  45

Arg Val Pro Pro Ser Arg Asn Ser Ile Thr Leu Thr Asn Leu Asn Pro
    50                  55                  60

Gly Thr Glu Tyr Val Val Ser Ile Val Ala Leu Asn Ser Lys Glu Glu
65                  70                  75                  80

Ser Leu Pro Leu Val Gly Gln Gln Ser Thr Val Ser Asp Val Pro Arg
                85                  90                  95

-continued

```
Asp Leu Glu Val Ile Ala Ala Thr Pro Thr Ser Leu Leu Ile Ser Trp
            100                 105                 110

Asp Ala Pro Ala Val Thr Val Arg Tyr Tyr Arg Ile Thr Tyr Gly Glu
        115                 120                 125

Thr Gly Gly Ser Ser Pro Val Gln Glu Phe Thr Val Pro Gly Ser Lys
    130                 135                 140

Ser Thr Ala Thr Ile Ser Gly Leu Lys Pro Gly Val Asp Tyr Thr Ile
145                 150                 155                 160

Thr Val Tyr Ala Val Thr Gly Arg Gly Asp Ser Pro Ala Ser Ser Lys
                165                 170                 175

Pro Val Ser Ile Asn Tyr Arg Thr
            180

<210> SEQ ID NO 68
<211> LENGTH: 184
<212> TYPE: PRT
<213> ORGANISM: Sus scrofa

<400> SEQUENCE: 68

Gly Leu Asp Ser Pro Thr Gly Ile Asp Phe Ser Asp Ile Thr Ala Asn
1               5                   10                  15

Ser Phe Thr Val Tyr Trp Ile Ala Pro Arg Ala Thr Ile Thr Gly Tyr
            20                  25                  30

Lys Ile Arg His His Pro Glu His Met Gly Gly Arg Pro Arg Glu Asp
        35                  40                  45

Arg Val Pro Pro Ser Arg Asn Ser Ile Thr Leu Thr Asn Leu Ile Pro
    50                  55                  60

Gly Val Glu Tyr Val Val Ser Ile Val Ala Val Asn Gly Arg Glu Glu
65                  70                  75                  80

Ser Pro Pro Leu Val Gly Gln Gln Ser Thr Val Ser Asp Val Pro Arg
                85                  90                  95

Asp Leu Gln Val Ile Ala Thr Thr Pro Thr Ser Leu Leu Ile Ser Trp
            100                 105                 110

Asp Ala Pro Ala Val Thr Val Arg Tyr Tyr Arg Ile Thr Tyr Gly Glu
        115                 120                 125

Thr Gly Gly Asn Ser Pro Val Gln Glu Phe Thr Val Pro Gly Ser Lys
    130                 135                 140

Ser Thr Ala Thr Ile Ser Gly Leu Lys Pro Gly Val Asp Tyr Thr Ile
145                 150                 155                 160

Thr Val Tyr Ala Val Thr Gly Arg Gly Asp Ser Pro Ala Ser Ser Lys
                165                 170                 175

Pro Val Ser Ile Asp Tyr Arg Thr
            180

<210> SEQ ID NO 69
<211> LENGTH: 184
<212> TYPE: PRT
<213> ORGANISM: Mus musculus

<400> SEQUENCE: 69

Gly Leu Asp Ser Pro Thr Gly Phe Asp Ser Ser Asp Ile Thr Ala Asn
1               5                   10                  15

Ser Phe Thr Val His Trp Val Ala Pro Arg Ala Pro Ile Thr Gly Tyr
            20                  25                  30

Ile Ile Arg His His Ala Glu His Ser Val Gly Arg Pro Arg Gln Asp
        35                  40                  45
```

-continued

Arg Val Pro Pro Ser Arg Asn Ser Ile Thr Leu Thr Asn Leu Asn Pro
         50                  55                  60

Gly Thr Glu Tyr Val Val Ser Ile Ile Ala Val Asn Gly Arg Glu Glu
 65                  70                  75                  80

Ser Pro Pro Leu Ile Gly Gln Gln Ala Thr Val Ser Asp Ile Pro Arg
                 85                  90                  95

Asp Leu Glu Val Ile Ala Ser Thr Pro Thr Ser Leu Leu Ile Ser Trp
                100                 105                 110

Glu Pro Pro Ala Val Ser Val Arg Tyr Tyr Arg Ile Thr Tyr Gly Glu
            115                 120                 125

Thr Gly Gly Asn Ser Pro Val Gln Glu Phe Thr Val Pro Gly Ser Lys
        130                 135                 140

Ser Thr Ala Thr Ile Asn Asn Ile Lys Pro Gly Ala Asp Tyr Thr Ile
145                 150                 155                 160

Thr Leu Tyr Ala Val Thr Gly Arg Gly Asp Ser Pro Ala Ser Ser Lys
                165                 170                 175

Pro Val Ser Ile Asn Tyr Lys Thr
            180

<210> SEQ ID NO 70
<211> LENGTH: 184
<212> TYPE: PRT
<213> ORGANISM: Rattus norvegicus

<400> SEQUENCE: 70

Gly Leu Asp Ser Pro Thr Gly Phe Asp Ser Ser Asp Val Thr Ala Asn
 1               5                  10                  15

Ser Phe Thr Val His Trp Val Ala Pro Arg Ala Pro Ile Thr Gly Tyr
                20                  25                  30

Ile Ile Arg His His Ala Glu His Ser Ala Gly Arg Pro Arg Gln Asp
            35                  40                  45

Arg Val Pro Pro Ser Arg Asn Ser Ile Thr Leu Thr Asn Leu Asn Pro
         50                  55                  60

Gly Thr Glu Tyr Ile Val Thr Ile Ile Ala Val Asn Gly Arg Glu Glu
 65                  70                  75                  80

Ser Pro Pro Leu Ile Gly Gln Gln Ser Thr Val Ser Asp Val Pro Arg
                 85                  90                  95

Asp Leu Glu Val Ile Ala Ser Thr Pro Thr Ser Leu Leu Ile Ser Trp
                100                 105                 110

Glu Pro Pro Ala Val Ser Val Arg Tyr Tyr Arg Ile Thr Tyr Gly Glu
            115                 120                 125

Thr Gly Gly Asn Ser Pro Val Gln Glu Phe Thr Val Pro Gly Ser Lys
        130                 135                 140

Ser Thr Ala Thr Ile Asn Asn Ile Lys Pro Gly Ala Asp Tyr Thr Ile
145                 150                 155                 160

Thr Leu Tyr Ala Val Thr Gly Arg Gly Asp Ser Pro Ala Ser Ser Lys
                165                 170                 175

Pro Val Ser Ile Asn Tyr Gln Thr
            180

<210> SEQ ID NO 71
<211> LENGTH: 552
<212> TYPE: DNA
<213> ORGANISM: Homo sapiens
<220> FEATURE:
<221> NAME/KEY: CDS -continued

<222> LOCATION: (1)..(552)

<400> SEQUENCE: 71

```
ggt ctt gat tcc cca act ggc att gac ttt tct gat att act gcc aac      48
Gly Leu Asp Ser Pro Thr Gly Ile Asp Phe Ser Asp Ile Thr Ala Asn
1               5                   10                  15 tct ttt act gtg cac tgg att gct cct cga gcc acc atc act ggc tac      96
Ser Phe Thr Val His Trp Ile Ala Pro Arg Ala Thr Ile Thr Gly Tyr
            20                  25                  30 agg atc cgc cat cat ccc gag cac ttc agt ggg aga cct cga gaa gat     144
Arg Ile Arg His His Pro Glu His Phe Ser Gly Arg Pro Arg Glu Asp
        35                  40                  45 cgg gtg ccc cac tct cgg aat tcc atc acc ctc acc aac ctc act cca     192
Arg Val Pro His Ser Arg Asn Ser Ile Thr Leu Thr Asn Leu Thr Pro
    50                  55                  60 ggc aca gag tat gtg gtc agc atc gtt gct ctt aat ggc aga gag gaa     240
Gly Thr Glu Tyr Val Val Ser Ile Val Ala Leu Asn Gly Arg Glu Glu
65                  70                  75                  80 agt ccc ccg ttg att ggc caa caa tca aca gtt tct gat gtt ccg agg     288
Ser Pro Pro Leu Ile Gly Gln Gln Ser Thr Val Ser Asp Val Pro Arg
                85                  90                  95 gac ctg gaa gtt gtt gct gcg acc ccc acc agc cta ctg atc agc tgg     336
Asp Leu Glu Val Val Ala Ala Thr Pro Thr Ser Leu Leu Ile Ser Trp
            100                 105                 110 gat gct cct gct gtc aca gtg aga tat tac agg atc act tac gga gaa     384
Asp Ala Pro Ala Val Thr Val Arg Tyr Tyr Arg Ile Thr Tyr Gly Glu
        115                 120                 125 aca gga gga aat agc cct gtc cag gag ttc act gtg cct ggg agc aag     432
Thr Gly Gly Asn Ser Pro Val Gln Glu Phe Thr Val Pro Gly Ser Lys
    130                 135                 140 tct aca gct acc atc agc ggc ctt aaa cct gga gtt gat tat acc atc     480
Ser Thr Ala Thr Ile Ser Gly Leu Lys Pro Gly Val Asp Tyr Thr Ile
145                 150                 155                 160 act gtg tat gct gtc agg ggc cgt gga gac agc ccc gca agc agc aag     528
Thr Val Tyr Ala Val Arg Gly Arg Gly Asp Ser Pro Ala Ser Ser Lys
                165                 170                 175 cca att tcc att aat tac cga aca                                     552
Pro Ile Ser Ile Asn Tyr Arg Thr
            180
```

<210> SEQ ID NO 72
<211> LENGTH: 184
<212> TYPE: PRT
<213> ORGANISM: Homo sapiens

<400> SEQUENCE: 72

```
Gly Leu Asp Ser Pro Thr Gly Ile Asp Phe Ser Asp Ile Thr Ala Asn
1               5                   10                  15

Ser Phe Thr Val His Trp Ile Ala Pro Arg Ala Thr Ile Thr Gly Tyr
            20                  25                  30

Arg Ile Arg His His Pro Glu His Phe Ser Gly Arg Pro Arg Glu Asp
        35                  40                  45

Arg Val Pro His Ser Arg Asn Ser Ile Thr Leu Thr Asn Leu Thr Pro
    50                  55                  60

Gly Thr Glu Tyr Val Val Ser Ile Val Ala Leu Asn Gly Arg Glu Glu
65                  70                  75                  80

Ser Pro Pro Leu Ile Gly Gln Gln Ser Thr Val Ser Asp Val Pro Arg
                85                  90                  95

Asp Leu Glu Val Val Ala Ala Thr Pro Thr Ser Leu Leu Ile Ser Trp
```

100                 105                 110
Asp Ala Pro Ala Val Thr Val Arg Tyr Tyr Arg Ile Thr Tyr Gly Glu
            115                 120                 125

Thr Gly Gly Asn Ser Pro Val Gln Glu Phe Thr Val Pro Gly Ser Lys
        130                 135                 140

Ser Thr Ala Thr Ile Ser Gly Leu Lys Pro Gly Val Asp Tyr Thr Ile
145                 150                 155                 160

Thr Val Tyr Ala Val Arg Gly Arg Gly Asp Ser Pro Ala Ser Ser Lys
                165                 170                 175

Pro Ile Ser Ile Asn Tyr Arg Thr
            180

<210> SEQ ID NO 73
<211> LENGTH: 8272
<212> TYPE: DNA
<213> ORGANISM: Homo sapiens
<220> FEATURE:
<221> NAME/KEY: CDS
<222> LOCATION: (360)..(7154)

<400> SEQUENCE: 73
gcccgcgccg gctgtgctgc acaggggggag gagagggaac cccaggcgcg agcgggaaga    60
ggggacctgc agccacaact tctctggtcc tctgcatccc ttctgtccct ccacccgtcc   120
ccttccccac cctctggccc ccaccttctt ggaggcgaca accccgggga ggcattagaa   180
gggatttttc ccgcaggttg cgaagggaag caaacttggt ggcaacttgc ctcccggtgc   240
gggcgtctct cccccaccgt ctcaacatgc ttagggggtcc ggggcccggg ctgctgctgc   300
tggccgtcca gtgcctgggg acagcggtgc cctccacggg agcctcgaag agcaagagg    359 cag gct cag caa atg gtt cag ccc cag tcc ccg gtg gct gtc agt caa   407
Gln Ala Gln Gln Met Val Gln Pro Gln Ser Pro Val Ala Val Ser Gln
 1               5                  10                  15 agc aag ccc ggt tgt tat gac aat gga aaa cac tat cag ata aat caa   455
Ser Lys Pro Gly Cys Tyr Asp Asn Gly Lys His Tyr Gln Ile Asn Gln
                20                  25                  30 cag tgg gag cgg acc tac cta ggc aat gcg ttg gtt tgt act tgt tat   503
Gln Trp Glu Arg Thr Tyr Leu Gly Asn Ala Leu Val Cys Thr Cys Tyr
            35                  40                  45 gga gga agc cga ggt ttt aac tgc gag agt aaa cct gaa gct gaa gag   551
Gly Gly Ser Arg Gly Phe Asn Cys Glu Ser Lys Pro Glu Ala Glu Glu
        50                  55                  60 act tgc ttt gac aag tac act ggg aac act tac cga gtg ggt gac act   599
Thr Cys Phe Asp Lys Tyr Thr Gly Asn Thr Tyr Arg Val Gly Asp Thr
65                  70                  75                  80 tat gag cgt cct aaa gac tcc atg atc tgg gac tgt acc tgc atc ggg   647
Tyr Glu Arg Pro Lys Asp Ser Met Ile Trp Asp Cys Thr Cys Ile Gly
                85                  90                  95 gct ggg cga ggg aga ata agc tgt acc atc gca aac cgc tgc cat gaa   695
Ala Gly Arg Gly Arg Ile Ser Cys Thr Ile Ala Asn Arg Cys His Glu
            100                 105                 110 ggg ggt cag tcc tac aag att ggt gac acc tgg agg aga cca cat gag   743
Gly Gly Gln Ser Tyr Lys Ile Gly Asp Thr Trp Arg Arg Pro His Glu
        115                 120                 125 act ggt ggt tac atg tta gag tgt gtg tgt ctt ggt aat gga aaa gga   791
Thr Gly Gly Tyr Met Leu Glu Cys Val Cys Leu Gly Asn Gly Lys Gly
130                 135                 140 gaa tgg acc tgc aag ccc ata gct gag aag tgt ttt gat cat gct gct   839
Glu Trp Thr Cys Lys Pro Ile Ala Glu Lys Cys Phe Asp His Ala Ala
145                 150                 155                 160

| | | |
|---|---|---|
| ggg act tcc tat gtg gtc gga gaa acg tgg gag aag ccc tac caa ggc<br>Gly Thr Ser Tyr Val Val Gly Glu Thr Trp Glu Lys Pro Tyr Gln Gly<br>165 170 175 | | 887 |
| tgg atg atg gta gat tgt act tgc ctg gga gaa ggc agc gga cgc atc<br>Trp Met Met Val Asp Cys Thr Cys Leu Gly Glu Gly Ser Gly Arg Ile<br>180 185 190 | | 935 |
| act tgc act tct aga aat aga tgc aac gat cag gac aca agg aca tcc<br>Thr Cys Thr Ser Arg Asn Arg Cys Asn Asp Gln Asp Thr Arg Thr Ser<br>195 200 205 | | 983 |
| tat aga att gga gac acc tgg agc aag aag gat aat cga gga aac ctg<br>Tyr Arg Ile Gly Asp Thr Trp Ser Lys Lys Asp Asn Arg Gly Asn Leu<br>210 215 220 | | 1031 |
| ctc cag tgc atc tgc aca ggc aac ggc cga gga gag tgg aag tgt gag<br>Leu Gln Cys Ile Cys Thr Gly Asn Gly Arg Gly Glu Trp Lys Cys Glu<br>225 230 235 240 | | 1079 |
| agg cac acc tct gtg cag acc aca tcg agc gga tct ggc ccc ttc acc<br>Arg His Thr Ser Val Gln Thr Thr Ser Ser Gly Ser Gly Pro Phe Thr<br>245 250 255 | | 1127 |
| gat gtt cgt gca gct gtt tac caa ccg cag cct cac ccc cag cct cct<br>Asp Val Arg Ala Ala Val Tyr Gln Pro Gln Pro His Pro Gln Pro Pro<br>260 265 270 | | 1175 |
| ccc tat ggc cac tgt gtc aca gac agt ggt gtg gtc tac tct gtg ggg<br>Pro Tyr Gly His Cys Val Thr Asp Ser Gly Val Val Tyr Ser Val Gly<br>275 280 285 | | 1223 |
| atg cag tgg ctg aag aca caa gga aat aag caa atg ctt tgc acg tgc<br>Met Gln Trp Leu Lys Thr Gln Gly Asn Lys Gln Met Leu Cys Thr Cys<br>290 295 300 | | 1271 |
| ctg ggc aac gga gtc agc tgc caa gag aca gct gta acc cag act tac<br>Leu Gly Asn Gly Val Ser Cys Gln Glu Thr Ala Val Thr Gln Thr Tyr<br>305 310 315 320 | | 1319 |
| ggt ggc aac tca aat gga gag cca tgt gtc tta cca ttc acc tac aat<br>Gly Gly Asn Ser Asn Gly Glu Pro Cys Val Leu Pro Phe Thr Tyr Asn<br>325 330 335 | | 1367 |
| ggc agg acg ttc tac tcc tgc acc aca gaa ggg cga cag gac gga cat<br>Gly Arg Thr Phe Tyr Ser Cys Thr Thr Glu Gly Arg Gln Asp Gly His<br>340 345 350 | | 1415 |
| ctt tgg tgc agc aca act tcg aat tat gag cag gac cag aaa tac tct<br>Leu Trp Cys Ser Thr Thr Ser Asn Tyr Glu Gln Asp Gln Lys Tyr Ser<br>355 360 365 | | 1463 |
| ttc tgc aca gac cac act gtt ttg gtt cag act cga gga gga aat tcc<br>Phe Cys Thr Asp His Thr Val Leu Val Gln Thr Arg Gly Gly Asn Ser<br>370 375 380 | | 1511 |
| aat ggt gcc ttg tgc cac ttc ccc ttc cta tac aac aac cac aat tac<br>Asn Gly Ala Leu Cys His Phe Pro Phe Leu Tyr Asn Asn His Asn Tyr<br>385 390 395 400 | | 1559 |
| act gat tgc act tct gag ggc aga aga gac aac atg aag tgg tgt ggg<br>Thr Asp Cys Thr Ser Glu Gly Arg Arg Asp Asn Met Lys Trp Cys Gly<br>405 410 415 | | 1607 |
| acc aca cag aac tat gat gcc gac cag aag ttt ggg ttc tgc ccc atg<br>Thr Thr Gln Asn Tyr Asp Ala Asp Gln Lys Phe Gly Phe Cys Pro Met<br>420 425 430 | | 1655 |
| gct gcc cac gag gaa atc tgc aca acc aat gaa ggg gtc atg tac cgc<br>Ala Ala His Glu Glu Ile Cys Thr Thr Asn Glu Gly Val Met Tyr Arg<br>435 440 445 | | 1703 |
| att gga gat cag tgg gat aag cag cat gac atg ggt cac atg atg agg<br>Ile Gly Asp Gln Trp Asp Lys Gln His Asp Met Gly His Met Met Arg<br>450 455 460 | | 1751 |
| tgc acg tgt gtt ggg aat ggt cgt ggg gaa tgg aca tgc att gcc tac<br>Cys Thr Cys Val Gly Asn Gly Arg Gly Glu Trp Thr Cys Ile Ala Tyr | | 1799 |

```
                    465                 470                 475                 480
tcg cag ctt cga gat cag tgc att gtt gat gac atc act tac aat gtg   1847
Ser Gln Leu Arg Asp Gln Cys Ile Val Asp Asp Ile Thr Tyr Asn Val
                    485                 490                 495 aac gac aca ttc cac aag cgt cat gaa gag ggg cac atg ctg aac tgt   1895
Asn Asp Thr Phe His Lys Arg His Glu Glu Gly His Met Leu Asn Cys
                500                 505                 510 aca tgc ttc ggt cag ggt cgg ggc agg tgg aag tgt gat ccc gtc gac   1943
Thr Cys Phe Gly Gln Gly Arg Gly Arg Trp Lys Cys Asp Pro Val Asp
            515                 520                 525 caa tgc cag gat tca gag act ggg acg ttt tat caa att gga gat tca   1991
Gln Cys Gln Asp Ser Glu Thr Gly Thr Phe Tyr Gln Ile Gly Asp Ser
        530                 535                 540 tgg gag aag tat gtg cat ggt gtc aga tac cag tgc tac tgc tat ggc   2039
Trp Glu Lys Tyr Val His Gly Val Arg Tyr Gln Cys Tyr Cys Tyr Gly
545                 550                 555                 560 cgt ggc att ggg gag tgg cat tgc caa cct tta cag acc tat cca agc   2087
Arg Gly Ile Gly Glu Trp His Cys Gln Pro Leu Gln Thr Tyr Pro Ser
                565                 570                 575 tca agt ggt cct gtc gaa gta ttt atc act gag act ccg agt cag ccc   2135
Ser Ser Gly Pro Val Glu Val Phe Ile Thr Glu Thr Pro Ser Gln Pro
            580                 585                 590 aac tcc cac ccc atc cag tgg aat gca cca cag cca tct cac att tcc   2183
Asn Ser His Pro Ile Gln Trp Asn Ala Pro Gln Pro Ser His Ile Ser
        595                 600                 605 aag tac att ctc agg tgg aga cct aaa aat tct gta ggc cgt tgg aag   2231
Lys Tyr Ile Leu Arg Trp Arg Pro Lys Asn Ser Val Gly Arg Trp Lys
    610                 615                 620 gaa gct acc ata cca ggc cac tta aac tcc tac acc atc aaa ggc ctg   2279
Glu Ala Thr Ile Pro Gly His Leu Asn Ser Tyr Thr Ile Lys Gly Leu
625                 630                 635                 640 aag cct ggt gtg gta tac gag ggc cag ctc atc agc atc cag cag tac   2327
Lys Pro Gly Val Val Tyr Glu Gly Gln Leu Ile Ser Ile Gln Gln Tyr
                645                 650                 655 ggc cac caa gaa gtg act cgc ttt gac ttc acc acc agc acc agc       2375
Gly His Gln Glu Val Thr Arg Phe Asp Phe Thr Thr Thr Ser Thr Ser
            660                 665                 670 aca cct gtg acc agc aac acc gtg aca gga gag acg act ccc ttt tct   2423
Thr Pro Val Thr Ser Asn Thr Val Thr Gly Glu Thr Thr Pro Phe Ser
        675                 680                 685 cct ctt gtg gcc act tct gaa tct gtg acc gaa atc aca gcc agt agc   2471
Pro Leu Val Ala Thr Ser Glu Ser Val Thr Glu Ile Thr Ala Ser Ser
    690                 695                 700 ttt gtg gtc tcc tgg gtc tca gct tcc gac acc gtg tcg gga ttc cgg   2519
Phe Val Val Ser Trp Val Ser Ala Ser Asp Thr Val Ser Gly Phe Arg
705                 710                 715                 720 gtg gaa tat gag ctg agt gag gag gga gat gag cca cag tac ctg gat   2567
Val Glu Tyr Glu Leu Ser Glu Glu Gly Asp Glu Pro Gln Tyr Leu Asp
                725                 730                 735 ctt cca agc aca gcc act tct gtg aac atc cct gac ctg ctt cct ggc   2615
Leu Pro Ser Thr Ala Thr Ser Val Asn Ile Pro Asp Leu Leu Pro Gly
            740                 745                 750 cga aaa tac att gta aat gtc tat cag ata tct gag gat ggg gag cag   2663
Arg Lys Tyr Ile Val Asn Val Tyr Gln Ile Ser Glu Asp Gly Glu Gln
        755                 760                 765 agt ttg atc ctg tct act tca caa aca aca gcg cct gat gcc cct cct   2711
Ser Leu Ile Leu Ser Thr Ser Gln Thr Thr Ala Pro Asp Ala Pro Pro
    770                 775                 780 gac ccg act gtg gac caa gtt gat gac acc tca att gtt gtt cgc tgg   2759
```

```
Asp Pro Thr Val Asp Gln Val Asp Asp Thr Ser Ile Val Val Arg Trp
785                 790                 795                 800 agc aga ccc cag gct ccc atc aca ggg tac aga ata gtc tat tcg cca      2807
Ser Arg Pro Gln Ala Pro Ile Thr Gly Tyr Arg Ile Val Tyr Ser Pro
            805                 810                 815 tca gta gaa ggt agc agc aca gaa ctc aac ctt cct gaa act gca aac      2855
Ser Val Glu Gly Ser Ser Thr Glu Leu Asn Leu Pro Glu Thr Ala Asn
        820                 825                 830 tcc gtc acc ctc agt gac ttg caa cct ggt gtt cag tat aac atc act      2903
Ser Val Thr Leu Ser Asp Leu Gln Pro Gly Val Gln Tyr Asn Ile Thr
            835                 840                 845 atc tat gct gtg gaa gaa aat caa gaa agt aca cct gtt gtc att caa      2951
Ile Tyr Ala Val Glu Glu Asn Gln Glu Ser Thr Pro Val Val Ile Gln
850                 855                 860 caa gaa acc act ggc acc cca cgc tca gat aca gtg ccc tct ccc agg      2999
Gln Glu Thr Thr Gly Thr Pro Arg Ser Asp Thr Val Pro Ser Pro Arg
865                 870                 875                 880 gac ctg cag ttt gtg gaa gtg aca gac gtg aag gtc acc atc atg tgg      3047
Asp Leu Gln Phe Val Glu Val Thr Asp Val Lys Val Thr Ile Met Trp
            885                 890                 895 aca ccg cct gag agt gca gtg acc ggc tac cgt gtg gat gtg atc ccc      3095
Thr Pro Pro Glu Ser Ala Val Thr Gly Tyr Arg Val Asp Val Ile Pro
        900                 905                 910 gtc aac ctg cct ggc gag cac ggg cag agg ctg ccc atc agc agg aac      3143
Val Asn Leu Pro Gly Glu His Gly Gln Arg Leu Pro Ile Ser Arg Asn
            915                 920                 925 acc ttt gca gaa gtc acc ggg ctg tcc cct ggg gtc acc tat tac ttc      3191
Thr Phe Ala Glu Val Thr Gly Leu Ser Pro Gly Val Thr Tyr Tyr Phe
930                 935                 940 aaa gtc ttt gca gtg agc cat ggg agg gag agc aag cct ctg act gct      3239
Lys Val Phe Ala Val Ser His Gly Arg Glu Ser Lys Pro Leu Thr Ala
945                 950                 955                 960 caa cag aca acc aaa ctg gat gct ccc act aac ctc cag ttt gtc aat      3287
Gln Gln Thr Thr Lys Leu Asp Ala Pro Thr Asn Leu Gln Phe Val Asn
            965                 970                 975 gaa act gat tct act gtc ctg gtg aga tgg act cca cct cgg gcc cag      3335
Glu Thr Asp Ser Thr Val Leu Val Arg Trp Thr Pro Pro Arg Ala Gln
        980                 985                 990 ata aca gga tac cga ctg acc gtg ggc ctt acc cga aga gga cag ccc      3383
Ile Thr Gly Tyr Arg Leu Thr Val Gly Leu Thr Arg Arg Gly Gln Pro
            995                 1000                1005 agg cag tac aat gtg ggt ccc tct gtc tcc aag tac cca ctg agg          3428
Arg Gln Tyr Asn Val Gly Pro Ser Val Ser Lys Tyr Pro Leu Arg
    1010                1015                1020 aat ctg cag cct gca tct gag tac acc gta tcc ctc gtg gcc ata          3473
Asn Leu Gln Pro Ala Ser Glu Tyr Thr Val Ser Leu Val Ala Ile
    1025                1030                1035 aag ggc aac caa gag agc ccc aaa gcc act gga gtc ttt acc aca          3518
Lys Gly Asn Gln Glu Ser Pro Lys Ala Thr Gly Val Phe Thr Thr
    1040                1045                1050 ctg cag cct ggg agc tct att cca cct tac aac acc gag gtg act          3563
Leu Gln Pro Gly Ser Ser Ile Pro Pro Tyr Asn Thr Glu Val Thr
    1055                1060                1065 gag acc acc att gtg atc aca tgg acg cct gct cca aga att ggt          3608
Glu Thr Thr Ile Val Ile Thr Trp Thr Pro Ala Pro Arg Ile Gly
    1070                1075                1080 ttt aag ctg ggt gta cga cca agc cag gga gga gag gca cca cga          3653
Phe Lys Leu Gly Val Arg Pro Ser Gln Gly Gly Glu Ala Pro Arg
    1085                1090                1095
```

```
-continued gaa gtg act tca gac tca gga agc atc gtt gtg tcc ggc ttg act     3698
Glu Val Thr Ser Asp Ser Gly Ser Ile Val Val Ser Gly Leu Thr
    1100            1105                1110 cca gga gta gaa tac gtc tac acc atc caa gtc ctg aga gat gga     3743
Pro Gly Val Glu Tyr Val Tyr Thr Ile Gln Val Leu Arg Asp Gly
    1115            1120                1125 cag gaa aga gat gcg cca att gta aac aaa gtg gtg aca cca ttg     3788
Gln Glu Arg Asp Ala Pro Ile Val Asn Lys Val Val Thr Pro Leu
    1130            1135                1140 tct cca cca aca aac ttg cat ctg gag gca aac cct gac act gga     3833
Ser Pro Pro Thr Asn Leu His Leu Glu Ala Asn Pro Asp Thr Gly
    1145            1150                1155 gtg ctc aca gtc tcc tgg gag agg agc acc acc cca gac att act     3878
Val Leu Thr Val Ser Trp Glu Arg Ser Thr Thr Pro Asp Ile Thr
    1160            1165                1170 ggt tat aga att acc aca acc cct aca aac ggc cag cag gga aat     3923
Gly Tyr Arg Ile Thr Thr Thr Pro Thr Asn Gly Gln Gln Gly Asn
    1175            1180                1185 tct ttg gaa gaa gtg gtc cat gct gat cag agc tcc tgc act ttt     3968
Ser Leu Glu Glu Val Val His Ala Asp Gln Ser Ser Cys Thr Phe
    1190            1195                1200 gat aac ctg agt ccc ggc ctg gag tac aat gtc agt gtt tac act     4013
Asp Asn Leu Ser Pro Gly Leu Glu Tyr Asn Val Ser Val Tyr Thr
    1205            1210                1215 gtc aag gat gac aag gaa agt gtc cct atc tct gat acc atc atc     4058
Val Lys Asp Asp Lys Glu Ser Val Pro Ile Ser Asp Thr Ile Ile
    1220            1225                1230 cca gct gtt cct cct ccc act gac ctg cga ttc acc aac att ggt     4103
Pro Ala Val Pro Pro Pro Thr Asp Leu Arg Phe Thr Asn Ile Gly
    1235            1240                1245 cca gac acc atg cgt gtc acc tgg gct cca ccc cca tcc att gat     4148
Pro Asp Thr Met Arg Val Thr Trp Ala Pro Pro Pro Ser Ile Asp
    1250            1255                1260 tta acc aac ttc ctg gtg cgt tac tca cct gtg aaa aat gag gaa     4193
Leu Thr Asn Phe Leu Val Arg Tyr Ser Pro Val Lys Asn Glu Glu
    1265            1270                1275 gat gtt gca gag ttg tca att tct cct tca gac aat gca gtg gtc     4238
Asp Val Ala Glu Leu Ser Ile Ser Pro Ser Asp Asn Ala Val Val
    1280            1285                1290 tta aca aat ctc ctg cct ggt aca gaa tat gta gtg agt gtc tcc     4283
Leu Thr Asn Leu Leu Pro Gly Thr Glu Tyr Val Val Ser Val Ser
    1295            1300                1305 agt gtc tac gaa caa cat gag agc aca cct ctt aga gga aga cag     4328
Ser Val Tyr Glu Gln His Glu Ser Thr Pro Leu Arg Gly Arg Gln
    1310            1315                1320 aaa aca ggt ctt gat tcc cca act ggc att gac ttt tct gat att     4373
Lys Thr Gly Leu Asp Ser Pro Thr Gly Ile Asp Phe Ser Asp Ile
    1325            1330                1335 act gcc aac tct ttt act gtg cac tgg att gct cct cga gcc acc     4418
Thr Ala Asn Ser Phe Thr Val His Trp Ile Ala Pro Arg Ala Thr
    1340            1345                1350 atc act ggc tac agg atc cgc cat cat ccc gag cac ttc agt ggg     4463
Ile Thr Gly Tyr Arg Ile Arg His His Pro Glu His Phe Ser Gly
    1355            1360                1365 aga cct cga gaa gat cgg gtg ccc cac tct cgg aat tcc atc acc     4508
Arg Pro Arg Glu Asp Arg Val Pro His Ser Arg Asn Ser Ile Thr
    1370            1375                1380 ctc acc aac ctc act cca ggc aca gag tat gtg gtc agc atc gtt     4553
Leu Thr Asn Leu Thr Pro Gly Thr Glu Tyr Val Val Ser Ile Val
    1385            1390                1395
```

| | | | | | | | | | | |
|---|---|---|---|---|---|---|---|---|---|---|
| gct | ctt | aat | ggc | aga | gag | gaa | agt | ccc | tta | ttg | att | ggc | caa | caa | 4598 |
| Ala | Leu | Asn | Gly | Arg | Glu | Glu | Ser | Pro | Leu | Leu | Ile | Gly | Gln | Gln | |
| | 1400 | | | | 1405 | | | | | 1410 | | | | | |
| tca | aca | gtt | tct | gat | gtt | ccg | agg | gac | ctg | gaa | gtt | gtt | gct | gcg | 4643 |
| Ser | Thr | Val | Ser | Asp | Val | Pro | Arg | Asp | Leu | Glu | Val | Val | Ala | Ala | |
| | 1415 | | | | 1420 | | | | | 1425 | | | | | |
| acc | ccc | acc | agc | cta | ctg | atc | agc | tgg | gat | gct | cct | gct | gtc | aca | 4688 |
| Thr | Pro | Thr | Ser | Leu | Leu | Ile | Ser | Trp | Asp | Ala | Pro | Ala | Val | Thr | |
| | 1430 | | | | 1435 | | | | | 1440 | | | | | |
| gtg | aga | tat | tac | agg | atc | act | tac | gga | gag | aca | gga | gga | aat | agc | 4733 |
| Val | Arg | Tyr | Tyr | Arg | Ile | Thr | Tyr | Gly | Glu | Thr | Gly | Gly | Asn | Ser | |
| | 1445 | | | | 1450 | | | | | 1455 | | | | | |
| cct | gtc | cag | gag | ttc | act | gtg | cct | ggg | agc | aag | tct | aca | gct | acc | 4778 |
| Pro | Val | Gln | Glu | Phe | Thr | Val | Pro | Gly | Ser | Lys | Ser | Thr | Ala | Thr | |
| | 1460 | | | | 1465 | | | | | 1470 | | | | | |
| atc | agc | ggc | ctt | aaa | cct | gga | gtt | gat | tat | acc | atc | act | gtg | tat | 4823 |
| Ile | Ser | Gly | Leu | Lys | Pro | Gly | Val | Asp | Tyr | Thr | Ile | Thr | Val | Tyr | |
| | 1475 | | | | 1480 | | | | | 1485 | | | | | |
| gct | gtc | act | ggc | cgt | gga | gac | agc | ccc | gca | agc | agc | aag | cca | att | 4868 |
| Ala | Val | Thr | Gly | Arg | Gly | Asp | Ser | Pro | Ala | Ser | Ser | Lys | Pro | Ile | |
| | 1490 | | | | 1495 | | | | | 1500 | | | | | |
| tcc | att | aat | tac | cga | aca | gaa | att | gac | aaa | cca | tcc | cag | atg | caa | 4913 |
| Ser | Ile | Asn | Tyr | Arg | Thr | Glu | Ile | Asp | Lys | Pro | Ser | Gln | Met | Gln | |
| | 1505 | | | | 1510 | | | | | 1515 | | | | | |
| gtg | acc | gat | gtt | cag | gac | aac | agc | att | agt | gtc | aag | tgg | ctg | cct | 4958 |
| Val | Thr | Asp | Val | Gln | Asp | Asn | Ser | Ile | Ser | Val | Lys | Trp | Leu | Pro | |
| | 1520 | | | | 1525 | | | | | 1530 | | | | | |
| tca | agt | tcc | cct | gtt | act | ggt | tac | aga | gta | acc | acc | act | ccc | aaa | 5003 |
| Ser | Ser | Ser | Pro | Val | Thr | Gly | Tyr | Arg | Val | Thr | Thr | Thr | Pro | Lys | |
| | 1535 | | | | 1540 | | | | | 1545 | | | | | |
| aat | gga | cca | gga | cca | aca | aaa | act | aaa | act | gca | ggt | cca | gat | caa | 5048 |
| Asn | Gly | Pro | Gly | Pro | Thr | Lys | Thr | Lys | Thr | Ala | Gly | Pro | Asp | Gln | |
| | 1550 | | | | 1555 | | | | | 1560 | | | | | |
| aca | gaa | atg | act | att | gaa | ggc | ttg | cag | ccc | aca | gtg | gag | tat | gtg | 5093 |
| Thr | Glu | Met | Thr | Ile | Glu | Gly | Leu | Gln | Pro | Thr | Val | Glu | Tyr | Val | |
| | 1565 | | | | 1570 | | | | | 1575 | | | | | |
| gtt | agt | gtc | tat | gct | cag | aat | cca | agc | gga | gag | agt | cag | cct | ctg | 5138 |
| Val | Ser | Val | Tyr | Ala | Gln | Asn | Pro | Ser | Gly | Glu | Ser | Gln | Pro | Leu | |
| | 1580 | | | | 1585 | | | | | 1590 | | | | | |
| gtt | cag | act | gca | gta | acc | act | att | cct | gca | cca | act | gac | ctg | aag | 5183 |
| Val | Gln | Thr | Ala | Val | Thr | Thr | Ile | Pro | Ala | Pro | Thr | Asp | Leu | Lys | |
| | 1595 | | | | 1600 | | | | | 1605 | | | | | |
| ttc | act | cag | gtc | aca | ccc | aca | agc | ctg | agc | gcc | cag | tgg | aca | cca | 5228 |
| Phe | Thr | Gln | Val | Thr | Pro | Thr | Ser | Leu | Ser | Ala | Gln | Trp | Thr | Pro | |
| | 1610 | | | | 1615 | | | | | 1620 | | | | | |
| ccc | aat | gtt | cag | ctc | act | gga | tat | cga | gtg | cgg | gtg | acc | ccc | aag | 5273 |
| Pro | Asn | Val | Gln | Leu | Thr | Gly | Tyr | Arg | Val | Arg | Val | Thr | Pro | Lys | |
| | 1625 | | | | 1630 | | | | | 1635 | | | | | |
| gag | aag | acc | gga | cca | atg | aaa | gaa | atc | aac | ctt | gct | cct | gac | agc | 5318 |
| Glu | Lys | Thr | Gly | Pro | Met | Lys | Glu | Ile | Asn | Leu | Ala | Pro | Asp | Ser | |
| | 1640 | | | | 1645 | | | | | 1650 | | | | | |
| tca | tcc | gtg | gtt | gta | tca | gga | ctt | atg | gtg | gcc | acc | aaa | tat | gaa | 5363 |
| Ser | Ser | Val | Val | Val | Ser | Gly | Leu | Met | Val | Ala | Thr | Lys | Tyr | Glu | |
| | 1655 | | | | 1660 | | | | | 1665 | | | | | |
| gtg | agt | gtc | tat | gct | ctt | aag | gac | act | ttg | aca | agc | aga | cca | gct | 5408 |
| Val | Ser | Val | Tyr | Ala | Leu | Lys | Asp | Thr | Leu | Thr | Ser | Arg | Pro | Ala | |
| | 1670 | | | | 1675 | | | | | 1680 | | | | | |
| cag | gga | gtt | gtc | acc | act | ctg | gag | aat | gtc | agc | cca | cca | aga | agg | 5453 |
| Gln | Gly | Val | Val | Thr | Thr | Leu | Glu | Asn | Val | Ser | Pro | Pro | Arg | Arg | |

-continued

|  |  |  |  |
|---|---|---|---|
| | 1685 | 1690 | 1695 |

```
gct cgt gtg aca gat gct act gag acc acc atc acc att agc tgg   5498
Ala Arg Val Thr Asp Ala Thr Glu Thr Thr Ile Thr Ile Ser Trp
    1700                1705                1710 aga acc aag act gag acg atc act ggc ttc caa gtt gat gcc gtt   5543
Arg Thr Lys Thr Glu Thr Ile Thr Gly Phe Gln Val Asp Ala Val
    1715                1720                1725 cca gcc aat ggc cag act cca atc cag aga acc atc aag cca gat   5588
Pro Ala Asn Gly Gln Thr Pro Ile Gln Arg Thr Ile Lys Pro Asp
    1730                1735                1740 gtc aga agc tac acc atc aca ggt tta caa cca ggc act gac tac   5633
Val Arg Ser Tyr Thr Ile Thr Gly Leu Gln Pro Gly Thr Asp Tyr
    1745                1750                1755 aag atc tac ctg tac acc ttg aat gac aat gct cgg agc tcc cct   5678
Lys Ile Tyr Leu Tyr Thr Leu Asn Asp Asn Ala Arg Ser Ser Pro
    1760                1765                1770 gtg gtc atc gac gcc tcc act gcc att gat gca cca tcc aac ctg   5723
Val Val Ile Asp Ala Ser Thr Ala Ile Asp Ala Pro Ser Asn Leu
    1775                1780                1785 cgt ttc ctg gcc acc aca ccc aat tcc ttg ctg gta tca tgg cag   5768
Arg Phe Leu Ala Thr Thr Pro Asn Ser Leu Leu Val Ser Trp Gln
    1790                1795                1800 ccg cca cgt gcc agg att acc ggc tac atc atc aag tat gag aag   5813
Pro Pro Arg Ala Arg Ile Thr Gly Tyr Ile Ile Lys Tyr Glu Lys
    1805                1810                1815 cct ggg tct cct ccc aga gaa gtg gtc cct cgg ccc cgc cct ggt   5858
Pro Gly Ser Pro Pro Arg Glu Val Val Pro Arg Pro Arg Pro Gly
    1820                1825                1830 gtc aca gag gct act att act ggc ctg gaa ccg gga acc gaa tat   5903
Val Thr Glu Ala Thr Ile Thr Gly Leu Glu Pro Gly Thr Glu Tyr
    1835                1840                1845 aca att tat gtc att gcc ctg aag aat aat cag aag agc gag ccc   5948
Thr Ile Tyr Val Ile Ala Leu Lys Asn Asn Gln Lys Ser Glu Pro
    1850                1855                1860 ctg att gga agg aaa aag aca gac gag ctt ccc caa ctg gta acc   5993
Leu Ile Gly Arg Lys Lys Thr Asp Glu Leu Pro Gln Leu Val Thr
    1865                1870                1875 ctt cca cac ccc aat ctt cat gga cca gag atc ttg gat gtt cct   6038
Leu Pro His Pro Asn Leu His Gly Pro Glu Ile Leu Asp Val Pro
    1880                1885                1890 tcc aca gtt caa aag acc cct ttc gtc acc cac cct ggg tat gac   6083
Ser Thr Val Gln Lys Thr Pro Phe Val Thr His Pro Gly Tyr Asp
    1895                1900                1905 act gga aat ggt att cag ctt cct ggc act tct ggt cag caa ccc   6128
Thr Gly Asn Gly Ile Gln Leu Pro Gly Thr Ser Gly Gln Gln Pro
    1910                1915                1920 agt gtt ggg caa caa atg atc ttt gag gaa cat ggt ttt agg cgg   6173
Ser Val Gly Gln Gln Met Ile Phe Glu Glu His Gly Phe Arg Arg
    1925                1930                1935 acc aca ccg ccc aca acg gcc acc ccc ata agg cat agg cca aga   6218
Thr Thr Pro Pro Thr Thr Ala Thr Pro Ile Arg His Arg Pro Arg
    1940                1945                1950 cca tac ccg ccg aat gta ggt gag gaa atc caa att ggt cac atc   6263
Pro Tyr Pro Pro Asn Val Gly Glu Glu Ile Gln Ile Gly His Ile
    1955                1960                1965 ccc agg gaa gat gta gac tat cac ctg tac cca cac ggt ccg gga   6308
Pro Arg Glu Asp Val Asp Tyr His Leu Tyr Pro His Gly Pro Gly
    1970                1975                1980 ctc aat cca aat gcc tct aca gga caa gaa gct ctc tct cag aca   6353
```

-continued

```
                Leu Asn Pro Asn Ala Ser Thr Gly Gln Glu Ala Leu Ser Gln Thr
                1985                1990                1995 acc atc tca tgg gcc cca ttc cag gac act tct gag tac atc att        6398
Thr Ile Ser Trp Ala Pro Phe Gln Asp Thr Ser Glu Tyr Ile Ile
2000                2005                2010 tca tgt cat cct gtt ggc act gat gaa gaa ccc tta cag ttc agg        6443
Ser Cys His Pro Val Gly Thr Asp Glu Glu Pro Leu Gln Phe Arg
2015                2020                2025 gtt cct gga act tct acc agt gcc act ctg aca ggc ctc acc aga        6488
Val Pro Gly Thr Ser Thr Ser Ala Thr Leu Thr Gly Leu Thr Arg
2030                2035                2040 ggt gcc acc tac aac atc ata gtg gag gca ctg aaa gac cag cag        6533
Gly Ala Thr Tyr Asn Ile Ile Val Glu Ala Leu Lys Asp Gln Gln
2045                2050                2055 agg cat aag gtt cgg gaa gag gtt gtt acc gtg ggc aac tct gtc        6578
Arg His Lys Val Arg Glu Glu Val Val Thr Val Gly Asn Ser Val
2060                2065                2070 aac gaa ggc ttg aac caa cct acg gat gac tcg tgc ttt gac ccc        6623
Asn Glu Gly Leu Asn Gln Pro Thr Asp Asp Ser Cys Phe Asp Pro
2075                2080                2085 tac aca gtt tcc cat tat gcc gtt gga gat gag tgg gaa cga atg        6668
Tyr Thr Val Ser His Tyr Ala Val Gly Asp Glu Trp Glu Arg Met
2090                2095                2100 tct gaa tca ggc ttt aaa ctg ttg tgc cag tgc tta ggc ttt gga        6713
Ser Glu Ser Gly Phe Lys Leu Leu Cys Gln Cys Leu Gly Phe Gly
2105                2110                2115 agt ggt cat ttc aga tgt gat tca tct aga tgg tgc cat gac aat        6758
Ser Gly His Phe Arg Cys Asp Ser Ser Arg Trp Cys His Asp Asn
2120                2125                2130 ggt gtg aac tac aag att gga gag aag tgg gac cgt cag gga gaa        6803
Gly Val Asn Tyr Lys Ile Gly Glu Lys Trp Asp Arg Gln Gly Glu
2135                2140                2145 aat ggc cag atg atg agc tgc aca tgt ctt ggg aac gga aaa gga        6848
Asn Gly Gln Met Met Ser Cys Thr Cys Leu Gly Asn Gly Lys Gly
2150                2155                2160 gaa ttc aag tgt gac cct cat gag gca acg tgt tat gat gat ggg        6893
Glu Phe Lys Cys Asp Pro His Glu Ala Thr Cys Tyr Asp Asp Gly
2165                2170                2175 aag aca tac cac gta gga gaa cag tgg cag aag gaa tat ctc ggt        6938
Lys Thr Tyr His Val Gly Glu Gln Trp Gln Lys Glu Tyr Leu Gly
2180                2185                2190 gcc att tgc tcc tgc aca tgc ttt gga ggc cag cgg ggc tgg cgc        6983
Ala Ile Cys Ser Cys Thr Cys Phe Gly Gly Gln Arg Gly Trp Arg
2195                2200                2205 tgt gac aac tgc cgc aga cct ggg ggt gaa ccc agt ccc gaa ggc        7028
Cys Asp Asn Cys Arg Arg Pro Gly Gly Glu Pro Ser Pro Glu Gly
2210                2215                2220 act act ggc cag tcc tac aac cag tat tct cag aga tac cat cag        7073
Thr Thr Gly Gln Ser Tyr Asn Gln Tyr Ser Gln Arg Tyr His Gln
2225                2230                2235 aga aca aac act aat gtt aat tgc cca att gag tgc ttc atg cct        7118
Arg Thr Asn Thr Asn Val Asn Cys Pro Ile Glu Cys Phe Met Pro
2240                2245                2250 tta gat gta cag gct gac aga gaa gat tcc cga gag taaatcatct        7164
Leu Asp Val Gln Ala Asp Arg Glu Asp Ser Arg Glu
2255                2260                2265 ttccaatcca gaggaacaag catgtctctc tgccaagatc catctaaact ggagtgatgt  7224
tagcagaccc agcttagagt tcttctttct ttcttaagcc ctttgctctg gaggaagttc  7284
```

-continued

```
tccagcttca gctcaactca cagcttctcc aagcatcacc ctgggagttt cctgagggtt      7344
ttctcataaa tgagggctgc acattgcctg ttctgcttcg aagtattcaa taccgctcag      7404
tattttaaat gaagtgattc taagatttgg tttgggatca ataggaaagc atatgcagcc      7464
aaccaagatg caaatgtttt gaaatgatat gaccaaaatt ttaagtagga aagtcaccca      7524
aacacttctg ctttcactta agtgtctggc ccgcaatact gtaggaacaa gcatgatctt      7584
gttactgtga tattttaaat atccacagta ctcactttttt ccaaatgatc ctagtaattg      7644
cctagaaata tctttctctt acctgttatt tatcaatttt tcccagtatt tttatacgga      7704
aaaaattgta ttgaaaacac ttagtatgca gttgataaga ggaatttggt ataattatgg      7764
tgggtgatta ttttttatac tgtatgtgcc aaagctttac tactgtggaa agacaactgt      7824
tttaataaaa gatttacatt ccacaacttg aagttcatct atttgatata agacaccttc      7884
gggggaaata attcctgtga atattctttt tcaattcagc aaacatttga aaatctatga      7944
tgtgcaagtc taattgttga tttcagtaca agattttcta aatcagttgc tacaaaaact      8004
gattggtttt tgtcacttca tctcttcact aatggagata gctttacact ttctgcttta      8064
atagatttaa gtggaccccca atatttatta aaattgctag tttaccgttc agaagtataa      8124
tagaaataat ctttagttgc tcttttctaa ccattgtaat tcttcccttc ttccctccac      8184
ctttccttca ttgaataaac ctctgttcaa agagattgcc tgcaagggaa ataaaaatga      8244
ctaagatatt aaaaaaaaaa aaaaaaaa                                         8272
```

<210> SEQ ID NO 74
<211> LENGTH: 2265
<212> TYPE: PRT
<213> ORGANISM: Homo sapiens

<400> SEQUENCE: 74

```
Gln Ala Gln Gln Met Val Gln Pro Gln Ser Pro Val Ala Val Ser Gln
1               5                   10                  15

Ser Lys Pro Gly Cys Tyr Asp Asn Gly Lys His Tyr Gln Ile Asn Gln
            20                  25                  30

Gln Trp Glu Arg Thr Tyr Leu Gly Asn Ala Leu Val Cys Thr Cys Tyr
        35                  40                  45

Gly Gly Ser Arg Gly Phe Asn Cys Glu Ser Lys Pro Glu Ala Glu Glu
    50                  55                  60

Thr Cys Phe Asp Lys Tyr Thr Gly Asn Thr Tyr Arg Val Gly Asp Thr
65                  70                  75                  80

Tyr Glu Arg Pro Lys Asp Ser Met Ile Trp Asp Cys Thr Cys Ile Gly
                85                  90                  95

Ala Gly Arg Gly Arg Ile Ser Cys Thr Ile Ala Asn Arg Cys His Glu
            100                 105                 110

Gly Gly Gln Ser Tyr Lys Ile Gly Asp Thr Trp Arg Arg Pro His Glu
        115                 120                 125

Thr Gly Gly Tyr Met Leu Glu Cys Val Cys Leu Gly Asn Gly Lys Gly
    130                 135                 140

Glu Trp Thr Cys Lys Pro Ile Ala Glu Lys Cys Phe Asp His Ala Ala
145                 150                 155                 160

Gly Thr Ser Tyr Val Val Gly Glu Thr Trp Glu Lys Pro Tyr Gln Gly
                165                 170                 175

Trp Met Met Val Asp Cys Thr Cys Leu Gly Glu Gly Ser Gly Arg Ile
            180                 185                 190

Thr Cys Thr Ser Arg Asn Arg Cys Asn Asp Gln Asp Thr Arg Thr Ser
```

-continued

```
            195                 200                 205
Tyr Arg Ile Gly Asp Thr Trp Ser Lys Lys Asp Asn Arg Gly Asn Leu
210                 215                 220
Leu Gln Cys Ile Cys Thr Gly Asn Gly Arg Gly Glu Trp Lys Cys Glu
225                 230                 235                 240
Arg His Thr Ser Val Gln Thr Ser Ser Gly Ser Gly Pro Phe Thr
                    245                 250                 255
Asp Val Arg Ala Ala Val Tyr Gln Pro Gln Pro His Pro Gln Pro Pro
                260                 265                 270
Pro Tyr Gly His Cys Val Thr Asp Ser Gly Val Val Tyr Ser Val Gly
            275                 280                 285
Met Gln Trp Leu Lys Thr Gln Gly Asn Lys Gln Met Leu Cys Thr Cys
        290                 295                 300
Leu Gly Asn Gly Val Ser Cys Gln Glu Thr Ala Val Thr Gln Thr Tyr
305                 310                 315                 320
Gly Gly Asn Ser Asn Gly Glu Pro Cys Val Leu Pro Phe Thr Tyr Asn
                325                 330                 335
Gly Arg Thr Phe Tyr Ser Cys Thr Thr Glu Gly Arg Gln Asp Gly His
                340                 345                 350
Leu Trp Cys Ser Thr Thr Ser Asn Tyr Glu Gln Asp Gln Lys Tyr Ser
            355                 360                 365
Phe Cys Thr Asp His Thr Val Leu Val Gln Thr Arg Gly Gly Asn Ser
370                 375                 380
Asn Gly Ala Leu Cys His Phe Pro Phe Leu Tyr Asn Asn His Asn Tyr
385                 390                 395                 400
Thr Asp Cys Thr Ser Glu Gly Arg Arg Asp Asn Met Lys Trp Cys Gly
                405                 410                 415
Thr Thr Gln Asn Tyr Asp Ala Asp Gln Lys Phe Gly Phe Cys Pro Met
                420                 425                 430
Ala Ala His Glu Glu Ile Cys Thr Thr Asn Glu Gly Val Met Tyr Arg
            435                 440                 445
Ile Gly Asp Gln Trp Asp Lys Gln His Asp Met Gly His Met Met Arg
450                 455                 460
Cys Thr Cys Val Gly Asn Gly Arg Gly Glu Trp Thr Cys Ile Ala Tyr
465                 470                 475                 480
Ser Gln Leu Arg Asp Gln Cys Ile Val Asp Asp Ile Thr Tyr Asn Val
                485                 490                 495
Asn Asp Thr Phe His Lys Arg His Glu Glu Gly His Met Leu Asn Cys
                500                 505                 510
Thr Cys Phe Gly Gln Gly Arg Gly Arg Trp Lys Cys Asp Pro Val Asp
            515                 520                 525
Gln Cys Gln Asp Ser Glu Thr Gly Thr Phe Tyr Gln Ile Gly Asp Ser
        530                 535                 540
Trp Glu Lys Tyr Val His Gly Val Arg Tyr Gln Cys Tyr Cys Tyr Gly
545                 550                 555                 560
Arg Gly Ile Gly Glu Trp His Cys Gln Pro Leu Gln Thr Tyr Pro Ser
                565                 570                 575
Ser Ser Gly Pro Val Glu Val Phe Ile Thr Glu Thr Pro Ser Gln Pro
            580                 585                 590
Asn Ser His Pro Ile Gln Trp Asn Ala Pro Gln Pro Ser His Ile Ser
        595                 600                 605
Lys Tyr Ile Leu Arg Trp Arg Pro Lys Asn Ser Val Gly Arg Trp Lys
610                 615                 620
```

```
Glu Ala Thr Ile Pro Gly His Leu Asn Ser Tyr Thr Ile Lys Gly Leu
625                 630                 635                 640

Lys Pro Gly Val Val Tyr Glu Gly Gln Leu Ile Ser Ile Gln Gln Tyr
            645                 650                 655

Gly His Gln Glu Val Thr Arg Phe Asp Phe Thr Thr Ser Thr Ser Ser
                660                 665                 670

Thr Pro Val Thr Ser Asn Thr Val Thr Gly Glu Thr Thr Pro Phe Ser
            675                 680                 685

Pro Leu Val Ala Thr Ser Glu Ser Val Thr Glu Ile Thr Ala Ser Ser
690                 695                 700

Phe Val Val Ser Trp Val Ser Ala Ser Asp Thr Val Ser Gly Phe Arg
705                 710                 715                 720

Val Glu Tyr Glu Leu Ser Glu Glu Gly Asp Glu Pro Gln Tyr Leu Asp
            725                 730                 735

Leu Pro Ser Thr Ala Thr Ser Val Asn Ile Pro Asp Leu Leu Pro Gly
            740                 745                 750

Arg Lys Tyr Ile Val Asn Val Tyr Gln Ile Ser Glu Asp Gly Glu Gln
            755                 760                 765

Ser Leu Ile Leu Ser Thr Ser Gln Thr Thr Ala Pro Asp Ala Pro Pro
770                 775                 780

Asp Pro Thr Val Asp Gln Val Asp Thr Ser Ile Val Val Arg Trp
785                 790                 795                 800

Ser Arg Pro Gln Ala Pro Ile Thr Gly Tyr Arg Ile Val Tyr Ser Pro
            805                 810                 815

Ser Val Glu Gly Ser Ser Thr Glu Leu Asn Leu Pro Glu Thr Ala Asn
            820                 825                 830

Ser Val Thr Leu Ser Asp Leu Gln Pro Gly Val Gln Tyr Asn Ile Thr
            835                 840                 845

Ile Tyr Ala Val Glu Glu Asn Gln Glu Ser Thr Pro Val Val Ile Gln
850                 855                 860

Gln Glu Thr Thr Gly Thr Pro Arg Ser Asp Thr Val Pro Ser Pro Arg
865                 870                 875                 880

Asp Leu Gln Phe Val Glu Val Thr Asp Val Lys Val Thr Ile Met Trp
                885                 890                 895

Thr Pro Pro Glu Ser Ala Val Thr Gly Tyr Arg Val Asp Val Ile Pro
                900                 905                 910

Val Asn Leu Pro Gly Glu His Gly Gln Arg Leu Pro Ile Ser Arg Asn
            915                 920                 925

Thr Phe Ala Glu Val Thr Gly Leu Ser Pro Gly Val Thr Tyr Tyr Phe
            930                 935                 940

Lys Val Phe Ala Val Ser His Gly Arg Glu Ser Lys Pro Leu Thr Ala
945                 950                 955                 960

Gln Gln Thr Thr Lys Leu Asp Ala Pro Thr Asn Leu Gln Phe Val Asn
                965                 970                 975

Glu Thr Asp Ser Thr Val Leu Val Arg Trp Thr Pro Arg Ala Gln
                980                 985                 990

Ile Thr Gly Tyr Arg Leu Thr Val  Gly Leu Thr Arg Arg  Gly Gln Pro
            995                 1000                1005

Arg Gln  Tyr Asn Val Gly Pro  Ser Val Ser Lys Tyr  Pro Leu Arg
    1010                 1015                 1020

Asn Leu  Gln Pro Ala Ser Glu  Tyr Thr Val Ser Leu  Val Ala Ile
    1025                 1030                 1035
```

```
Lys Gly Asn Gln Glu Ser Pro Lys Ala Thr Gly Val Phe Thr Thr
    1040                1045                1050

Leu Gln Pro Gly Ser Ser Ile Pro Pro Tyr Asn Thr Glu Val Thr
    1055                1060                1065

Glu Thr Thr Ile Val Ile Thr Trp Thr Pro Ala Pro Arg Ile Gly
    1070                1075                1080

Phe Lys Leu Gly Val Arg Pro Ser Gln Gly Gly Glu Ala Pro Arg
    1085                1090                1095

Glu Val Thr Ser Asp Ser Gly Ser Ile Val Val Ser Gly Leu Thr
    1100                1105                1110

Pro Gly Val Glu Tyr Val Tyr Thr Ile Gln Val Leu Arg Asp Gly
    1115                1120                1125

Gln Glu Arg Asp Ala Pro Ile Val Asn Lys Val Val Thr Pro Leu
    1130                1135                1140

Ser Pro Pro Thr Asn Leu His Leu Glu Ala Asn Pro Asp Thr Gly
    1145                1150                1155

Val Leu Thr Val Ser Trp Glu Arg Ser Thr Thr Pro Asp Ile Thr
    1160                1165                1170

Gly Tyr Arg Ile Thr Thr Thr Pro Thr Asn Gly Gln Gln Gly Asn
    1175                1180                1185

Ser Leu Glu Glu Val Val His Ala Asp Gln Ser Ser Cys Thr Phe
    1190                1195                1200

Asp Asn Leu Ser Pro Gly Leu Glu Tyr Asn Val Ser Val Tyr Thr
    1205                1210                1215

Val Lys Asp Asp Lys Glu Ser Val Pro Ile Ser Asp Thr Ile Ile
    1220                1225                1230

Pro Ala Val Pro Pro Pro Thr Asp Leu Arg Phe Thr Asn Ile Gly
    1235                1240                1245

Pro Asp Thr Met Arg Val Thr Trp Ala Pro Pro Ser Ile Asp
    1250                1255                1260

Leu Thr Asn Phe Leu Val Arg Tyr Ser Pro Val Lys Asn Glu Glu
    1265                1270                1275

Asp Val Ala Glu Leu Ser Ile Ser Pro Ser Asp Asn Ala Val Val
    1280                1285                1290

Leu Thr Asn Leu Leu Pro Gly Thr Glu Tyr Val Val Ser Val Ser
    1295                1300                1305

Ser Val Tyr Glu Gln His Glu Ser Thr Pro Leu Arg Gly Arg Gln
    1310                1315                1320

Lys Thr Gly Leu Asp Ser Pro Thr Gly Ile Asp Phe Ser Asp Ile
    1325                1330                1335

Thr Ala Asn Ser Phe Thr Val His Trp Ile Ala Pro Arg Ala Thr
    1340                1345                1350

Ile Thr Gly Tyr Arg Ile Arg His His Pro Glu His Phe Ser Gly
    1355                1360                1365

Arg Pro Arg Glu Asp Arg Val Pro His Ser Arg Asn Ser Ile Thr
    1370                1375                1380

Leu Thr Asn Leu Thr Pro Gly Thr Glu Tyr Val Val Ser Ile Val
    1385                1390                1395

Ala Leu Asn Gly Arg Glu Glu Ser Pro Leu Leu Ile Gly Gln Gln
    1400                1405                1410

Ser Thr Val Ser Asp Val Pro Arg Asp Leu Glu Val Val Ala Ala
    1415                1420                1425

Thr Pro Thr Ser Leu Leu Ile Ser Trp Asp Ala Pro Ala Val Thr
```

-continued

```
            1430                1435               1440
Val Arg Tyr Tyr Arg Ile Thr Tyr Gly Glu Thr Gly Gly Asn Ser
    1445                1450               1455
Pro Val Gln Glu Phe Thr Val Pro Gly Ser Lys Ser Thr Ala Thr
    1460                1465               1470
Ile Ser Gly Leu Lys Pro Gly Val Asp Tyr Thr Ile Thr Val Tyr
    1475                1480               1485
Ala Val Thr Gly Arg Gly Asp Ser Pro Ala Ser Ser Lys Pro Ile
    1490                1495               1500
Ser Ile Asn Tyr Arg Thr Glu Ile Asp Lys Pro Ser Gln Met Gln
    1505                1510               1515
Val Thr Asp Val Gln Asp Asn Ser Ile Ser Val Lys Trp Leu Pro
    1520                1525               1530
Ser Ser Ser Pro Val Thr Gly Tyr Arg Val Thr Thr Thr Pro Lys
    1535                1540               1545
Asn Gly Pro Gly Pro Thr Lys Thr Lys Thr Ala Gly Pro Asp Gln
    1550                1555               1560
Thr Glu Met Thr Ile Glu Gly Leu Gln Pro Thr Val Glu Tyr Val
    1565                1570               1575
Val Ser Val Tyr Ala Gln Asn Pro Ser Gly Glu Ser Gln Pro Leu
    1580                1585               1590
Val Gln Thr Ala Val Thr Thr Ile Pro Ala Pro Thr Asp Leu Lys
    1595                1600               1605
Phe Thr Gln Val Thr Pro Thr Ser Leu Ser Ala Gln Trp Thr Pro
    1610                1615               1620
Pro Asn Val Gln Leu Thr Gly Tyr Arg Val Arg Val Thr Pro Lys
    1625                1630               1635
Glu Lys Thr Gly Pro Met Lys Glu Ile Asn Leu Ala Pro Asp Ser
    1640                1645               1650
Ser Ser Val Val Val Ser Gly Leu Met Val Ala Thr Lys Tyr Glu
    1655                1660               1665
Val Ser Val Tyr Ala Leu Lys Asp Thr Leu Thr Ser Arg Pro Ala
    1670                1675               1680
Gln Gly Val Val Thr Thr Leu Glu Asn Val Ser Pro Pro Arg Arg
    1685                1690               1695
Ala Arg Val Thr Asp Ala Thr Glu Thr Thr Ile Thr Ile Ser Trp
    1700                1705               1710
Arg Thr Lys Thr Glu Thr Ile Thr Gly Phe Gln Val Asp Ala Val
    1715                1720               1725
Pro Ala Asn Gly Gln Thr Pro Ile Gln Arg Thr Ile Lys Pro Asp
    1730                1735               1740
Val Arg Ser Tyr Thr Ile Thr Gly Leu Gln Pro Gly Thr Asp Tyr
    1745                1750               1755
Lys Ile Tyr Leu Tyr Thr Leu Asn Asp Asn Ala Arg Ser Ser Pro
    1760                1765               1770
Val Val Ile Asp Ala Ser Thr Ala Ile Asp Ala Pro Ser Asn Leu
    1775                1780               1785
Arg Phe Leu Ala Thr Thr Pro Asn Ser Leu Leu Val Ser Trp Gln
    1790                1795               1800
Pro Pro Arg Ala Arg Ile Thr Gly Tyr Ile Ile Lys Tyr Glu Lys
    1805                1810               1815
Pro Gly Ser Pro Pro Arg Glu Val Val Pro Arg Pro Arg Pro Gly
    1820                1825               1830
```

```
Val Thr Glu Ala Thr Ile Thr Gly Leu Glu Pro Gly Thr Glu Tyr
    1835            1840                1845

Thr Ile Tyr Val Ile Ala Leu Lys Asn Asn Gln Lys Ser Glu Pro
    1850            1855                1860

Leu Ile Gly Arg Lys Lys Thr Asp Glu Leu Pro Gln Leu Val Thr
    1865            1870                1875

Leu Pro His Pro Asn Leu His Gly Pro Glu Ile Leu Asp Val Pro
    1880            1885                1890

Ser Thr Val Gln Lys Thr Pro Phe Val Thr His Pro Gly Tyr Asp
    1895            1900                1905

Thr Gly Asn Gly Ile Gln Leu Pro Gly Thr Ser Gly Gln Gln Pro
    1910            1915                1920

Ser Val Gly Gln Gln Met Ile Phe Glu Glu His Gly Phe Arg Arg
    1925            1930                1935

Thr Thr Pro Pro Thr Thr Ala Thr Pro Ile Arg His Arg Pro Arg
    1940            1945                1950

Pro Tyr Pro Pro Asn Val Gly Glu Glu Ile Gln Ile Gly His Ile
    1955            1960                1965

Pro Arg Glu Asp Val Asp Tyr His Leu Tyr Pro His Gly Pro Gly
    1970            1975                1980

Leu Asn Pro Asn Ala Ser Thr Gly Gln Glu Ala Leu Ser Gln Thr
    1985            1990                1995

Thr Ile Ser Trp Ala Pro Phe Gln Asp Thr Ser Glu Tyr Ile Ile
    2000            2005                2010

Ser Cys His Pro Val Gly Thr Asp Glu Glu Pro Leu Gln Phe Arg
    2015            2020                2025

Val Pro Gly Thr Ser Thr Ser Ala Thr Leu Thr Gly Leu Thr Arg
    2030            2035                2040

Gly Ala Thr Tyr Asn Ile Ile Val Glu Ala Leu Lys Asp Gln Gln
    2045            2050                2055

Arg His Lys Val Arg Glu Glu Val Val Thr Val Gly Asn Ser Val
    2060            2065                2070

Asn Glu Gly Leu Asn Gln Pro Thr Asp Asp Ser Cys Phe Asp Pro
    2075            2080                2085

Tyr Thr Val Ser His Tyr Ala Val Gly Asp Glu Trp Glu Arg Met
    2090            2095                2100

Ser Glu Ser Gly Phe Lys Leu Leu Cys Gln Cys Leu Gly Phe Gly
    2105            2110                2115

Ser Gly His Phe Arg Cys Asp Ser Ser Arg Trp Cys His Asp Asn
    2120            2125                2130

Gly Val Asn Tyr Lys Ile Gly Glu Lys Trp Asp Arg Gln Gly Glu
    2135            2140                2145

Asn Gly Gln Met Met Ser Cys Thr Cys Leu Gly Asn Gly Lys Gly
    2150            2155                2160

Glu Phe Lys Cys Asp Pro His Glu Ala Thr Cys Tyr Asp Asp Gly
    2165            2170                2175

Lys Thr Tyr His Val Gly Glu Gln Trp Gln Lys Glu Tyr Leu Gly
    2180            2185                2190

Ala Ile Cys Ser Cys Thr Cys Phe Gly Gly Gln Arg Gly Trp Arg
    2195            2200                2205

Cys Asp Asn Cys Arg Arg Pro Gly Gly Glu Pro Ser Pro Glu Gly
    2210            2215                2220
```

```
Thr Thr Gly Gln Ser Tyr Asn Gln Tyr Ser Gln Arg Tyr His Gln
    2225                2230                2235

Arg Thr Asn Thr Asn Val Asn Cys Pro Ile Glu Cys Phe Met Pro
    2240                2245                2250

Leu Asp Val Gln Ala Asp Arg Glu Asp Ser Arg Glu
    2255                2260                2265

<210> SEQ ID NO 75
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
catatgcata tgcaccacca ccaccaccac ggtcttgatt ccccaact                      48

<210> SEQ ID NO 76
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
aagcttaagc tttcatgttc ggtaattaat ggaaattgg                               39

<210> SEQ ID NO 77
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
catatgcata tgcaccacca ccaccaccac gtttctgatg ttccga                       46

<210> SEQ ID NO 78
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
cgtggtgata tgcctgacag cagcaag                                            27

<210> SEQ ID NO 79
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
aggcatatca ccacgaggag tgacagcata                                         30

<210> SEQ ID NO 80
<211> LENGTH: 27
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 80
cgtggtgata atcctgacag cagcaag                                          27

<210> SEQ ID NO 81
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
aggattatca ccacgagcag tgacagcata                                       30

<210> SEQ ID NO 82
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
ggagactgga atgaaggaag caagcca                                          27

<210> SEQ ID NO 83
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
attccagtct ccacgcggag tgacagcata                                       30

<210> SEQ ID NO 84
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
tatgctgtcc gtgctcgtgg tgat                                             24

<210> SEQ ID NO 85
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
accacgagca cggacagcat acac                                             24

<210> SEQ ID NO 86
<211> LENGTH: 18
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 86
agtcccccgt tgattggc                                                    18

<210> SEQ ID NO 87
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
caacggggga ctttcctc                                                    18

<210> SEQ ID NO 88
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
ccgaggaatc tggaagttg                                                   19

<210> SEQ ID NO 89
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
cagattcctc ggaacatc                                                    18

<210> SEQ ID NO 90
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
tctgatatta ctgataactc ttttactgtg                                       30

<210> SEQ ID NO 91
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
agagttatca gtaatatcag aaaagtcaat                                       30

<210> SEQ ID NO 92
<211> LENGTH: 27
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 92
gctaaaacag tgagatatta caggatc                                            27

<210> SEQ ID NO 93
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
cactgtttta gcaggagcat ccca                                               24

<210> SEQ ID NO 94
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
gaacgtcggg tgccc                                                         15

<210> SEQ ID NO 95
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
ccgacgttca cgaggtct                                                      18

<210> SEQ ID NO 96
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
gtgccccact ctgataattc catcacc                                            27

<210> SEQ ID NO 97
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
ggtgatggaa ttatcagagt ggggcac                                            27

<210> SEQ ID NO 98
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 98
cgtggtgata atcctgactg tagcaagcca                                30

<210> SEQ ID NO 99
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
aggattatca ccacgagcac agacagcata                                30

<210> SEQ ID NO 100
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
cgtggtgata tgcctgactg tagcaagcca                                30

<210> SEQ ID NO 101
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
aggcatatca ccacgaggac agacagcata                                30

<210> SEQ ID NO 102
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
ggagactgga atgaatgtag caagcca                                   27

<210> SEQ ID NO 103
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
attccagtct ccacgcggac agacagcata                                30

<210> SEQ ID NO 104
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 104
cgtggtgata atcctgactg tagcaagcca                                       30

<210> SEQ ID NO 105
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
aggattatca ccacgagcac gacaagcata cac                                   33

<210> SEQ ID NO 106
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
ggtcgtggag acagccccgc atgtagcaag cca                                   33

<210> SEQ ID NO 107
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
gtctccacga ccagtacaag catacac                                          27

<210> SEQ ID NO 108
<211> LENGTH: 185
<212> TYPE: PRT
<213> ORGANISM: Homo sapiens

<400> SEQUENCE: 108

Gly Leu Asp Ser Pro Thr Gly Ile Asp Phe Ser Asp Ile Thr Ala Asn
1               5                   10                  15

Ser Phe Thr Val His Trp Ile Ala Pro Arg Ala Thr Ile Thr Gly Tyr
            20                  25                  30

Arg Ile Arg His His Pro Glu His Phe Ser Gly Arg Pro Arg Glu Asp
        35                  40                  45

Arg Val Pro His Ser Arg Asn Ser Ile Thr Leu Thr Asn Leu Thr Pro
    50                  55                  60

Gly Thr Glu Tyr Val Val Ser Ile Val Ala Leu Asn Gly Arg Glu Glu
65                  70                  75                  80

Ser Pro Pro Leu Ile Gly Gln Gln Ser Thr Val Ser Asp Val Pro Arg
                85                  90                  95

Asp Leu Glu Val Val Ala Ala Thr Pro Thr Ser Leu Leu Ile Ser Trp
            100                 105                 110

Asp Ala Pro Ala Val Thr Val Arg Tyr Tyr Arg Ile Thr Tyr Gly Glu
        115                 120                 125

Thr Gly Gly Asn Ser Pro Val Gln Glu Phe Thr Val Pro Gly Ser Lys
    130                 135                 140

Ser Thr Ala Thr Ile Ser Gly Leu Lys Pro Gly Val Asp Tyr Thr Ile

```
                145                 150                 155                 160
Thr Val Tyr Ala Val Cys Arg Ala Arg Gly Asp Phe Pro Asp Cys Ser
                    165                 170                 175
Lys Pro Ile Ser Ile Asn Tyr Arg Thr
                    180                 185

<210> SEQ ID NO 109
<211> LENGTH: 185
<212> TYPE: PRT
<213> ORGANISM: HOMO SAPIENS

<400> SEQUENCE: 109

Gly Leu Asp Ser Pro Thr Gly Ile Asp Phe Ser Asp Ile Thr Ala Asn
1               5                   10                  15

Ser Phe Thr Val His Trp Ile Ala Pro Arg Ala Thr Ile Thr Gly Tyr
                20                  25                  30

Arg Ile Arg His His Pro Glu His Phe Ser Gly Arg Pro Arg Glu Asp
            35                  40                  45

Arg Val Pro His Ser Arg Asn Ser Ile Thr Leu Thr Asn Leu Thr Pro
        50                  55                  60

Gly Thr Glu Tyr Val Val Ser Ile Val Ala Leu Asn Gly Arg Glu Glu
65                  70                  75                  80

Ser Pro Pro Leu Ile Gly Gln Gln Ser Thr Val Ser Asp Val Pro Arg
                85                  90                  95

Asp Leu Glu Val Val Ala Ala Thr Pro Thr Ser Leu Leu Ile Ser Trp
            100                 105                 110

Asp Ala Pro Ala Val Thr Val Arg Tyr Tyr Arg Ile Thr Tyr Gly Glu
        115                 120                 125

Thr Gly Gly Asn Ser Pro Val Gln Glu Phe Thr Val Pro Gly Ser Lys
    130                 135                 140

Ser Thr Ala Thr Ile Ser Gly Leu Lys Pro Gly Val Asp Tyr Thr Ile
145                 150                 155                 160

Thr Val Tyr Ala Val Cys Arg Ala Arg Gly Asp Arg Pro Asp Cys Ser
                    165                 170                 175

Lys Pro Ile Ser Ile Asn Tyr Arg Thr
                    180                 185

<210> SEQ ID NO 110
<211> LENGTH: 185
<212> TYPE: PRT
<213> ORGANISM: Homo sapiens

<400> SEQUENCE: 110

Gly Leu Asp Ser Pro Thr Gly Ile Asp Phe Ser Asp Ile Thr Ala Asn
1               5                   10                  15

Ser Phe Thr Val His Trp Ile Ala Pro Arg Ala Thr Ile Thr Gly Tyr
                20                  25                  30

Arg Ile Arg His His Pro Glu His Phe Ser Gly Arg Pro Arg Glu Asp
            35                  40                  45

Arg Val Pro His Ser Arg Asn Ser Ile Thr Leu Thr Asn Leu Thr Pro
        50                  55                  60

Gly Thr Glu Tyr Val Val Ser Ile Val Ala Leu Asn Gly Arg Glu Glu
65                  70                  75                  80

Ser Pro Pro Leu Ile Gly Gln Gln Ser Thr Val Ser Asp Val Pro Arg
                85                  90                  95

Asp Leu Glu Val Val Ala Ala Thr Pro Thr Ser Leu Leu Ile Ser Trp
```

Asp Ala Pro Ala Val Thr Val Arg Tyr Tyr Arg Ile Thr Tyr Gly Glu
            115                 120                 125

Thr Gly Gly Asn Ser Pro Val Gln Glu Phe Thr Val Pro Gly Ser Lys
        130                 135                 140

Ser Thr Ala Thr Ile Ser Gly Leu Lys Pro Gly Val Asp Tyr Thr Ile
145                 150                 155                 160

Thr Val Tyr Ala Val Cys Arg Ala Arg Gly Asp Asp Pro Asp Cys Ser
                165                 170                 175

Lys Pro Ile Ser Ile Asn Tyr Arg Thr
            180                 185

<210> SEQ ID NO 111
<211> LENGTH: 184
<212> TYPE: PRT
<213> ORGANISM: Homo sapiens

<400> SEQUENCE: 111

Gly Leu Asp Ser Pro Thr Gly Ile Asp Phe Ser Asp Ile Thr Ala Ala
1               5                   10                  15

Ser Phe Thr Val His Trp Ile Ala Pro Arg Ala Thr Ile Thr Gly Tyr
            20                  25                  30

Arg Ile Arg His His Pro Glu His Phe Ser Gly Arg Pro Arg Glu Asp
        35                  40                  45

Arg Val Pro His Ser Arg Asn Ser Ile Thr Leu Thr Asn Leu Thr Pro
    50                  55                  60

Gly Thr Glu Tyr Val Val Ser Ile Val Ala Leu Asn Gly Arg Glu Glu
65                  70                  75                  80

Ser Pro Pro Leu Ile Gly Gln Gln Ser Thr Val Ser Asp Val Pro Arg
                85                  90                  95

Asp Leu Glu Val Val Ala Ala Thr Pro Thr Ser Leu Leu Ile Ser Trp
            100                 105                 110

Asp Ala Pro Ala Val Thr Val Arg Tyr Tyr Arg Ile Thr Tyr Gly Glu
        115                 120                 125

Thr Gly Gly Asn Ser Pro Val Gln Glu Phe Thr Val Pro Gly Ser Lys
    130                 135                 140

Ser Thr Ala Thr Ile Ser Gly Leu Lys Pro Gly Val Asp Tyr Thr Ile
145                 150                 155                 160

Thr Val Tyr Ala Cys Arg Ala Arg Gly Asp Asn Pro Asp Cys Ser Lys
                165                 170                 175

Pro Ile Ser Ile Asn Tyr Arg Thr
            180

<210> SEQ ID NO 112
<211> LENGTH: 184
<212> TYPE: PRT
<213> ORGANISM: Homo sapiens

<400> SEQUENCE: 112

Gly Leu Asp Ser Pro Thr Gly Ile Asp Phe Ser Asp Ile Thr Ala Asn
1               5                   10                  15

Ser Phe Thr Val His Trp Ile Ala Pro Arg Ala Thr Ile Thr Gly Tyr
            20                  25                  30

Arg Ile Arg His His Pro Glu His Phe Ser Gly Arg Pro Arg Glu Asp
        35                  40                  45

Arg Val Pro Pro Ser Arg Asn Ser Ile Thr Leu Thr Asn Leu Thr Pro

```
                 50                  55                  60
Gly Thr Glu Tyr Val Val Ser Ile Val Ala Leu Asn Gly Arg Glu Glu
 65                  70                  75                  80

Ser Pro Pro Leu Ile Gly Gln Gln Ser Thr Val Ser Asp Val Pro Arg
                 85                  90                  95

Asp Leu Glu Val Val Ala Ala Thr Pro Thr Ser Leu Leu Ile Ser Trp
            100                 105                 110

Asp Ala Pro Ala Val Thr Val Arg Tyr Tyr Arg Ile Thr Tyr Gly Glu
            115                 120                 125

Thr Gly Gly Asn Ser Pro Val Gln Glu Phe Thr Val Pro Gly Ser Lys
        130                 135                 140

Ser Thr Ala Thr Ile Ser Gly Leu Lys Pro Gly Val Asp Tyr Thr Ile
145                 150                 155                 160

Thr Val Tyr Ala Cys Arg Ala Arg Gly Asp Asn Pro Asp Cys Ser Lys
                165                 170                 175

Pro Ile Ser Ile Asn Tyr Arg Thr
            180
```

<210> SEQ ID NO 113
<211> LENGTH: 184
<212> TYPE: PRT
<213> ORGANISM: Homo sapiens

<400> SEQUENCE: 113

```
Gly Leu Asp Ser Pro Thr Gly Ile Asp Phe Ser Asp Ile Thr Ala Asn
  1               5                  10                  15

Ser Phe Thr Val His Trp Ile Ala Pro Arg Ala Thr Ile Thr Gly Tyr
                 20                  25                  30

Arg Ile Arg His His Pro Glu His Phe Ser Gly Arg Pro Arg Glu Asp
            35                  40                  45

Arg Val Lys His Ser Arg Asn Ser Ile Thr Leu Thr Asn Leu Thr Pro
 50                  55                  60

Gly Thr Glu Tyr Val Val Ser Ile Val Ala Leu Asn Gly Arg Glu Glu
 65                  70                  75                  80

Ser Pro Pro Leu Ile Gly Gln Gln Ser Thr Val Ser Asp Val Pro Arg
                 85                  90                  95

Asp Leu Glu Val Val Ala Ala Thr Pro Thr Ser Leu Leu Ile Ser Trp
            100                 105                 110

Asp Ala Pro Ala Val Thr Val Arg Tyr Tyr Arg Ile Thr Tyr Gly Glu
            115                 120                 125

Thr Gly Gly Asn Ser Pro Val Gln Glu Phe Thr Val Pro Gly Ser Lys
        130                 135                 140

Ser Thr Ala Thr Ile Ser Gly Leu Lys Pro Gly Val Asp Tyr Thr Ile
145                 150                 155                 160

Thr Val Tyr Ala Cys Arg Ala Arg Gly Asp Asn Pro Asp Cys Ser Lys
                165                 170                 175

Pro Ile Ser Ile Asn Tyr Arg Thr
            180
```

<210> SEQ ID NO 114
<211> LENGTH: 184
<212> TYPE: PRT
<213> ORGANISM: Homo sapiens

<400> SEQUENCE: 114

Gly Leu Asp Ser Pro Thr Gly Ile Asp Phe Ser Asp Ile Thr Ala Asn

```
                1               5                  10                 15
Ser Phe Thr Val His Trp Ile Ala Pro Arg Ala Thr Ile Thr Gly Tyr
                20                  25                 30

Arg Ile Arg His His Pro Glu His Phe Ser Gly Arg Pro Arg Glu Asp
                35                  40                 45

Arg Val Asp His Ser Arg Asn Ser Ile Thr Leu Thr Asn Leu Thr Pro
        50                  55                 60

Gly Thr Glu Tyr Val Val Ser Ile Val Ala Leu Asn Gly Arg Glu Glu
65                  70                  75                 80

Ser Pro Pro Leu Ile Gly Gln Gln Ser Thr Val Ser Asp Val Pro Arg
                85                  90                 95

Asp Leu Glu Val Val Ala Ala Thr Pro Thr Ser Leu Leu Ile Ser Trp
                100                 105                110

Asp Ala Pro Ala Val Thr Val Arg Tyr Tyr Arg Ile Thr Tyr Gly Glu
                115                 120                125

Thr Gly Gly Asn Ser Pro Val Gln Glu Phe Thr Val Pro Gly Ser Lys
        130                 135                140

Ser Thr Ala Thr Ile Ser Gly Leu Lys Pro Gly Val Asp Tyr Thr Ile
145                 150                 155                160

Thr Val Tyr Ala Cys Arg Ala Arg Gly Asp Asn Pro Asp Cys Ser Lys
                165                 170                175

Pro Ile Ser Ile Asn Tyr Arg Thr
            180
```

```
<210> SEQ ID NO 115
<211> LENGTH: 9
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gly, Ala or Pro
<220> FEATURE:
<221> NAME/KEY: MOD_RES
<222> LOCATION: (6)..(6)
<223> OTHER INFORMATION: Ser, Met, Asn or Trp
<220> FEATURE:
<221> NAME/KEY: MOD_RES
<222> LOCATION: (7)..(7)
<223> OTHER INFORMATION: Pro or Asn
<220> FEATURE:
<221> NAME/KEY: MOD_RES
<222> LOCATION: (8)..(8)
<223> OTHER INFORMATION: Ala, Asp or Glu

<400> SEQUENCE: 115

Cys Xaa Arg Gly Asp Xaa Xaa Xaa Cys
1               5

<210> SEQ ID NO 116
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Thr, Arg or Ile
<220> FEATURE:
<221> NAME/KEY: MOD_RES
```

```
<222> LOCATION: (3)..(3)
<223> OTHER INFORMATION: Gly, Ala or Pro
<220> FEATURE:
<221> NAME/KEY: MOD_RES
<222> LOCATION: (7)..(7)
<223> OTHER INFORMATION: Phe, Arg, Asp, Ser, Met or Asn
<220> FEATURE:
<221> NAME/KEY: MOD_RES
<222> LOCATION: (9)..(9)
<223> OTHER INFORMATION: Ala or Asp

<400> SEQUENCE: 116

Cys Xaa Xaa Arg Gly Asp Xaa Pro Xaa Cys
1               5                   10

<210> SEQ ID NO 117
<211> LENGTH: 10
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(9)
<223> OTHER INFORMATION: Any naturally occurring amino acid

<400> SEQUENCE: 117

Cys Xaa Xaa Xaa Xaa Xaa Xaa Xaa Xaa Cys
1               5                   10

<210> SEQ ID NO 118
<211> LENGTH: 10
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any naturally occurring amino acid
<220> FEATURE:
<221> NAME/KEY: MOD_RES
<222> LOCATION: (7)..(9)
<223> OTHER INFORMATION: Any naturally occurring amino acid

<400> SEQUENCE: 118

Cys Xaa Xaa Arg Gly Asp Xaa Xaa Xaa Cys
1               5                   10

<210> SEQ ID NO 119
<211> LENGTH: 9
<212> TYPE: PRT
<213> ORGANISM: artificial sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(8)
<223> OTHER INFORMATION: Any naturally occurring amino acid

<400> SEQUENCE: 119

Cys Xaa Xaa Xaa Xaa Xaa Xaa Xaa Cys
1               5

<210> SEQ ID NO 120
<211> LENGTH: 9
<212> TYPE: PRT
<213> ORGANISM: artificial sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (6)..(8)
<223> OTHER INFORMATION: Any naturally occurring amino acid

<400> SEQUENCE: 120

Cys Xaa Arg Gly Asp Xaa Xaa Xaa Cys
1               5

<210> SEQ ID NO 121
<211> LENGTH: 8
<212> TYPE: PRT
<213> ORGANISM: artificial sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any naturally occurring amino acid, which can
      repeat 1, 2 or 3 times
<220> FEATURE:
<221> NAME/KEY: MOD_RES
<222> LOCATION: (6)..(7)
<223> OTHER INFORMATION: Any naturally occurring amino acid, each of
      which can repeat 1, 2 or 3 times

<400> SEQUENCE: 121

Cys Xaa Arg Gly Asp Xaa Xaa Cys
1               5

<210> SEQ ID NO 122
<211> LENGTH: 12
<212> TYPE: PRT
<213> ORGANISM: artificial sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (6)..(11)
<223> OTHER INFORMATION: Any naturally occurring amino acid

<400> SEQUENCE: 122

Cys Xaa Arg Gly Asp Xaa Xaa Xaa Xaa Xaa Xaa Cys
1               5                   10

<210> SEQ ID NO 123
<211> LENGTH: 11
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Thr or Arg
<220> FEATURE:
<221> NAME/KEY: MOD_RES
<222> LOCATION: (3)..(3)
<223> OTHER INFORMATION: Ala or Pro
```

```
<220> FEATURE:
<221> NAME/KEY: MOD_RES
<222> LOCATION: (7)..(7)
<223> OTHER INFORMATION: Met, Trp or Asn
<220> FEATURE:
<221> NAME/KEY: MOD_RES
<222> LOCATION: (8)..(8)
<223> OTHER INFORMATION: Pro or Asn
<220> FEATURE:
<221> NAME/KEY: MOD_RES
<222> LOCATION: (9)..(9)
<223> OTHER INFORMATION: Asp or Glu
<220> FEATURE:
<221> NAME/KEY: MOD_RES
<222> LOCATION: (10)..(10)
<223> OTHER INFORMATION: Ser or Gly

<400> SEQUENCE: 123

Val Xaa Xaa Arg Gly Asp Xaa Xaa Xaa Xaa Ser
1               5                   10
```

MODIFIED FIBRONECTIN FRAGMENTS OR VARIANTS AND USES THEREOF

SEQUENCE LISTING

The instant application contains a Sequence Listing, which has been submitted electronically in ASCII format, and is hereby incorporated by reference in its entirety. Said ASCII copy, created on Jan. 5, 2018, is named 564169-LLB-011US_SL.txt and is 209,396 bytes in size.

FIELD OF THE INVENTION

The present invention generally relates to cell biology and, in particular, the function and interaction of extracellular matrix proteins with integrins. More specifically, the present invention relates to human fibronectin fragments and/or variants thereof as specific antagonists for integrins, in particular integrin $\alpha5\beta1$ and integrin $\alpha v\beta3$. The sequence txt file submitted herewith is incorporated by reference in its entirety.

BACKGROUND OF THE INVENTION

Integrins are a family of glycoprotein membrane receptors that mediate cell-matrix and cell-cell interactions. Integrins are heterodimers, consisting of $\alpha$ and $\beta$ subunits. To date at least 24 distinct integrin heterodimers have been described, including $18\alpha$ and $8\beta$ subunits. Integrins mediate anchorage and migration of cells via specific interaction with different extracellular matrix (ECM) proteins. In addition, cell survival, division and differentiation also rely on effective cell-ECM associations (Morgan et al. 2009, *IUBMB Life*, 61:731-38).

Integrins $\alpha5\beta1$ and $\alpha v\beta3$ are localized in the adhesion contacts of cultured cells. The integrin-ECM complex not only serves to sustain cell-cell and cell-matrix interactions needed for anchorage and migration, the formation of cell-ECM complex also triggers integrin-mediated intra-cellular signaling by recruiting enzymes and adaptors into dynamic complexes inside a cell. The intracellular signals downstream of integrin can influence gene expression, cell survival, differentiation and proliferation. Integrins have been implicated in many pathological conditions such as angiogenesis and tumor progression.

Several integrins were known to interact with fibronectin via the Arg-Gly-Asp (RGD) motif present in fibronectin. These integrins include 5 $\alpha v$ integrins ($\alpha v\beta1$, $\alpha v\beta3$, $\alpha v\beta5$, $\alpha v\beta6$, and $\alpha v\beta8$) and two $\beta1$ integrins ($\alpha5\beta1$ and $\alpha8\beta1$) (Smith, W., 2008, *J. Allergy Clin. Immunol.* 121:S375-S379). Fibronectin is a high-molecular weight (about 440 kDa) glycoprotein of the extracellular matrix that binds to integrins as well as other extracellular matrix proteins. Fibronectin exists as a dimer of two monomers linked by disulfide bonds at the C-terminus. Each fibronectin monomer has a molecular weight of 230-250 kDa that contains three types of domains: type I, II, and III. Type I and II domains are stabilized by intra-chain disulfide bonds, while type III domains do not contain any disulfide bonds. The absence of disulfide bonds can result in flexibility in the structure of FN type III domain.

Each domain contains a number of modules organized to form functional and protein-binding regions along the length of a fibronectin monomer. For example, modules in type I domains are required for initiation of fibronectin matrix assembly, and modules in both type I and type III domains are important for association with other fibronectin molecules. The RGD motif is located in module 10 of the type III domain (FNIII 10), and constitutes the binding site of fibronectin to integrins $\alpha5\beta1$ and $\alpha v\beta3$. The sequence in type III domain module 9 (FNIII 9), especially the PHSRN synergy loop, facilitates the binding of fibronectin to integrin $\alpha5\beta1$. Integrin $\alpha v\beta3$ binding of fibronectin does not require the synergistic effect of module 9.

Because integrins' roles in regulating a variety of cellular functions, the feasibility of using integrin antagonists as treatments of diseases has been studied. For example, antagonists for integrin $\alpha$IIb$\beta3$, the integrin that activates platelet aggregation, were experimented as an anti-coagulant for treating thrombosis-related ischemic vascular diseases (Coller et al., 2008, *Blood*, 112:3011-25). Disintegrin, such as Rhodostomin, is a family of small protein integrin antagonists naturally found in snake venom that inhibits integrin-mediated platelet aggregation and cell adhesion. Disintegrin, however, is non-specific and highly immunogenic. It competes with fibronectin for binding to $\beta1$- and $\beta3$-containing integrins on the cell surface and non-discriminatively inhibits the activities of integrins $\alpha5\beta1$, $\alpha v\beta3$ and integrin $\alpha$IIb$\beta3$. Thus, the use of disintegrin as an antagonist for integrins $\alpha5\beta1$ and $\alpha v\beta3$ posts a high risk of hemorrhage due to its $\alpha$IIb$\beta3$ antagonist activity that prevents platelet aggregation and blood clotting.

Similarly, the *Yersinia pseudotuberculosis* protein invasin is an integrin-binding protein. The bacterial invasin protein facilitates bacteria entry into cells by binding to integrins. The use of invasin as an integrin antagonist is problematic because the bacterial protein is likely highly immunogenic and because the specificity of the invasin protein is not defined.

At high concentrations, FNIII 9-10 to some extent mimics the biological activity of the full-length fibronectin molecule (van der Walle et al., 2002, *Protein Engineering* 15:1021-24). FNIII9-10 competes with other ECM proteins for binding to integrins. Such truncated fibronectin molecule or fragment comprising the binding domain for integrin, e.g., FNIII 10 or FNIII 9-10, is less immunogenic in human and has higher specificity, as compared with distintegrins, and thus does not cause hemorrhage. However, difficulties exist when using truncated fibronectin as integrin antagonists. One of the difficulties is stability and solubility. Human FNIII 9 or FNIII 9-10 alone is structurally unstable (see van der Walle, supra). Further, FNIII 9-10 at high concentration is insoluble, which presents great challenges to its large scale preparation and production. Therefore, there is a need for a better designed integrin antagonist with low immunogenicity, high specificity, and enhanced stability and solubility.

SUMMARY OF THE INVENTION

The invention provides, inter alia, integrin antagonists and uses thereof that are not hampered by the limitations found in the prior art.

It was unexpectedly discovered by the instant inventors that mutant or modified human fibronectin (FN) fragments disclosed herein exhibited integrin antagonist activity. In addition, the FNIII 10 or FNIII 9-10 mutants or variants disclosed herein showed increased solubility and stability as compared to FN fragments with wild type sequences.

In human FN, the RGD motif is located in a loop of type III domain 10 that is largely disordered and mobile, the flexibility presumably being important for its function. The instant inventors unexpectedly discovered that, increased intradomain rigidity by introducing an engineered di-sulfide bond within FNIII 10 conferred improved solubility and stability and/or maintained or improved antagonist activity for integrin α5β1 and/or integrin αvβ3. In certain particular embodiments, the FNIII fragments of the invention demonstrate a solubility of at least from about 20 to about 24 mg/ml in a solution at pH 7.0. In certain other particular embodiments, the FNIII fragments of the invention demonstrate a solubility of at least from about 7 to about 27 mg/ml. In certain particular embodiments, the solubility is achieved in the absence of free amino acids Arg and Glu. In certain other embodiments, the FNIII fragments of the invention demonstrate an increased solubility by from about 10% to about 300%, in particular from about 20% to about 280%, 25% to about 250%, 30% to about 200%, 20% to about 150%, as compared to FNIII fragments having the wild type human sequences.

While not required for binding to integrin αvβ3, module 9 is believed to provide synergistic enhancement of binding to integrin α5β1. The instant inventors surprisingly discovered that, in the presence of FNIII 9, a di-sulfide bond introduced in module 10 via two Cys substitutions flanking the RGD motif, for example comprising the formula Cys-$X_8$-Cys (SEQ ID NO:117), further for example comprising the formula $Cys^{1490}X_2RGDX_3Cys^{1499}$ (SEQ ID NO:118), can improve the solubility and stability of the FNIII 9-10 variants and increase their integrin α5β1 antagonist activity. Further, the present inventors unexpectedly discovered that an engineered di-sulfide bond in FNIII module 10 flanking the RGD motif, for example comprising the formula Cys-$X_7$-Cys (SEQ ID NO:119), further for example comprising the formula $Cys^{1491}XRGDX_3Cys^{1499}$ (SEQ ID NO:120), can improve the solubility and stability of the FNIII 10 variants and their antagonist activity for integrin αvβ3. Further, the instant inventors surprisingly discovered that, in the context of FNIII 9-10, variants with the Cys substitutions comprising the formula for example Cys-X7-Cys (SEQ ID NO:119), and further for example $Cys^{1491}XRGDX_3Cys^{1499}$ (SEQ ID NO:120) exhibited binding specificity for integrin αvβ3 instead of integrin α5β1.

Thus, in one aspect, the invention provides isolated polypeptides comprising a modified human fibronectin fragment that comprises human fibronectin type III domain module 10 (FNIII 10), wherein the FNIII 10 comprises an Arg-Gly-Asp (RGD) motif and two Cys substitutions to form a di-sulfide bond, wherein one Cys substitution is N-terminal to the RGD motif and the other Cys substitution is C-terminal to the RGD motif, and wherein the FNIII 10 comprises an amino acid sequence that is at least 85%, at least 90%, at least 95% or at least 98% homologous to SEQ ID NO:2. In certain embodiments, the polypeptide inhibits or is capable of inhibiting integrin α5β1 or integrin αvβ3 activity and does not inhibit integrin αIIbβ3 activity. Throughout the instant application, the modified human fibronectin fragment can optionally further comprise other modules and/or domains of human fibronectin. In certain embodiments, the modified human fibronectin further comprises type III domain module 9, and the human fibronectin type III domain module 9 and 10 (FNIII 9-10) comprises an amino acid sequence that is at least 85%, at least 90%, at least 95% or at least 98% homologous to SEQ ID NO:4. In certain other embodiments, the FNIII 9-10 optionally further comprises the Leu to Pro substitution at amino acid position 1408 in module 9.

In certain embodiments, the two Cys substitutions are separated by about 6 to about 9 amino acid residues, flanking the RGD motif. In certain other embodiments, the two Cys substitutions are separated by 7 or 8 amino acid residues. In certain embodiments, the two Cys substitutions are located within amino acid positions 1487-1501. In certain other embodiments, the FNIII 10 further comprises at least one amino acid substitution at amino acid position 1491, 1492, 1496, 1497 or 1498, and wherein the amino acid substitution at position 1491 is Arg or Ile, the amino acid substitution at position 1492 is Ala or Pro, the amino acid substitution at position 1496 is Met, Asn or Trp, the amino acid substitution at position 1497 is Asn, and the amino acid substitution at position 1498 is Asp or Glu. The amino acid numbering used throughout the application is based on the amino acid numbering of the full length human fibronectin protein (SEQ ID NO:74). For instance, the Thr residue at amino acid position 1491 based on the sequence of SEQ ID NO:74 refers to the Thr residue at amino acid position 76 of FNIII 10 as shown in SEQ ID NO:2.

In certain particular embodiments, the Cys substitutions are Thr to Cys substitution at amino acid position 1491 (T1491C) and Ser to Cys substitution at amino acid position 1499 (S1499C). In certain embodiments, the FNIII 10 comprises the formula $C^{1491}X_{1(n)}RGDX_{2(n)}C^{1499}$ (SEQ ID NO:121) wherein said n is 1, 2 or 3, wherein $X_1$ and $X_2$ can represent the same or different amino acid residues. In certain particular embodiments, the FNIII 10 comprises the formula $C^{1491}X_{1(1)} RGDX_{2(3)}C^{1499}$ (SEQ ID NO:122). In certain particular embodiments, the polypeptide inhibits integrin αvβ3 activity.

In yet other embodiments, the FNIII 10 comprises the formula $Cys^{1491}$-$X_1$-Arg-Gly-Asp-$X_2$-$X_3$-$X_4$-$Cys^{1499}$ (SEQ ID NO: 115), wherein $X_1$ is Gly, Ala or Pro; $X_2$ is Ser, Met, Asn or Trp; $X_3$ is Pro or Asn; and $X_4$ is Ala, Asp or Glu. In certain particular embodiments, $X_1$ is Pro, $X_2$ is Met, $X_3$ is Pro, and $X_4$ is Asp. In certain other particular embodiments, $X_1$ is Pro, $X_2$ is Trp, $X_3$ is Asn, and $X_4$ is Glu. In yet other particular embodiments, $X_1$ is Ala, $X_2$ is Asn, $X_3$ is Pro, and $X_4$ is Asp. In certain particular embodiments, $X_1$ is Gly, $X_2$ is Ser, $X_3$ is Pro, and $X_4$ is Ala. In certain other embodiments, the polypeptide has the amino acid sequence of SEQ ID NO:6, SEQ ID NO:8, SEQ ID NO:10 or SEQ ID NO:12. In certain particular embodiments, the polypeptide has the amino acid sequence of SEQ ID NO:6. In certain other particular embodiments, the polypeptide selectively inhibits or is capable of selectively inhibiting integrin αvβ3 activity.

In certain other embodiments, wherein the modified human fibronectin fragment further comprises human fibronectin type III domain module 9 (FNIII 9) that optionally comprises Leu to Pro substitution at amino acid position 1408, and wherein the FNIII 9 and FNIII 10 (FNIII 9-10) comprises an amino acid sequence that is at least 85%, at least 90%, at least 95% or at least 98% homologous to the amino acid sequence of SEQ ID NO:4. In certain embodiments, the polypeptide has the amino acid sequence of SEQ ID NO:20, SEQ ID NO:22, SEQ ID NO:24, or SEQ ID NO:26. In certain particular embodiments, the polypeptide has the amino acid sequence of SEQ ID NO:20.

In certain other embodiments, the Cys substitutions are Val to Cys substitution at amino acid position 1490 (V1490C) and Ser to Cys substitution at amino acid position 1499 (S1499C), wherein the modified human fibronectin fragment optionally further comprises human fibronectin type III domain module 9 that optionally further comprises the Leu to Pro substitution at amino acid position 1408. In certain embodiments, the FNIII 10 comprises the formula $Cys^{1490}$-$X_1$-$X_2$-Arg-Gly-Asp-$X_3$-Pro-$X_4$-$Cys^{1499}$ (SEQ ID NO: 116), wherein, $X_1$ is Thr, Arg or Ile; $X_2$ is Gly, Ala or Pro; $X_3$ is Phe, Arg, Asp, Ser, Met or Asn; and $X_4$ is Ala or Asp. In certain particular embodiments, $X_1$ is Arg, $X_2$ is Ala, $X_3$ is Asn, and $X_4$ is Asp. In certain other embodiments, the polypeptide has the amino acid sequence of SEQ ID NO:28, SEQ ID NO:30, SEQ ID NO:32, SEQ ID NO:34, SEQ ID NO:108, SEQ ID NO:109 or SEQ ID NO:110. In certain particular embodiments, the polypeptide has the amino acid sequence of SEQ ID NO:32, SEQ ID NO:108, SEQ ID NO:109 or SEQ ID NO:110. In certain particular embodiments, the polypeptide selectively inhibits or is capable of selectively inhibiting integrin α5β1 activity. In certain embodiment, the Cys substitutions are Val to Cys substitution at amino acid position 1490 (V1490C) and Ser to Cys substitution at amino acid position 1499 (S1499C), wherein the modified human fibronectin fragment optionally further comprises human fibronectin type III domain module 9 that optionally further comprises the Leu to Pro substitution at amino acid position 1408 and optional the Asn to Ala substitution at amino acid position 1341, the His to Pro substitution at amino acid position 1377, the Pro to Lys substitution at amino acid 1376, or the Pro to Asp substitution at amino acid position 1376. In certain particular embodiments, the polypeptide has the amino acid sequence of SEQ ID NO:111, SEQ ID NO:112, SEQ ID NO:113 or SEQ ID NO:114. In certain particular embodiments, the polypeptide selectively inhibits or is capable of selectively inhibiting integrin α5β1 activity.

Flexibility of the FNIII 9-10 interdomain linkage was thought to allow large scale conformational changes in the human FN protein. Partial structural uncoupling of FNIII 9 and FNIII 10 by the extension of the linker at the FNIII 9-10 interface led to loss of the synergistic binding of module 9 (Altroff et al., 2004, *J. Biological Chemistry*, 279:55995-56003). Previous results showed that interdomain rigidity introduced by a di-sulfide bond across the junction of modules 9 and 10 abolished the synergistic cell adhesion activity of FNIII 9-10 via binding to integrin α5β1, and reduced its affinity to FNIII 9-independent integrin αvβ3 binding (Altroff et al., supra).

The instant inventors, however, surprisingly discovered that an interdomain linkage between modules 9 and 10 created by a non-covalent linkage maintained its binding affinity to integrins α5β1. The non-covalent linkage can provide proper orientation for FNIII 9 and FNIII10 and facilitate binding to integrin α5β1.

Thus, in another aspect, the invention provides isolated polypeptides comprising a modified human fibronectin fragment that comprises human fibronectin type III domain module 9 and human fibronectin type III domain module 10 (FNIII 9-10), wherein FNIII 9 optionally comprises Leu to Pro substitution at amino acid position 1408, wherein FNIII 9 and/or FNIII 10 comprises at least one amino acid substitution, wherein the amino acid residues in FNIII 9 and FNIII 10 form a non-covalent bond, and wherein FNIII 9 and FNIII 10 comprises an amino acid sequence that is at least 85%, at least 90%, at least 95% or at least 98% homologous to the amino acid sequence of SEQ ID NO:4 and that is not SEQ ID NO:64. In certain particular embodiments, the polypeptide inhibits or is capable of inhibiting integrin α5β1 activity.

Figure 4:
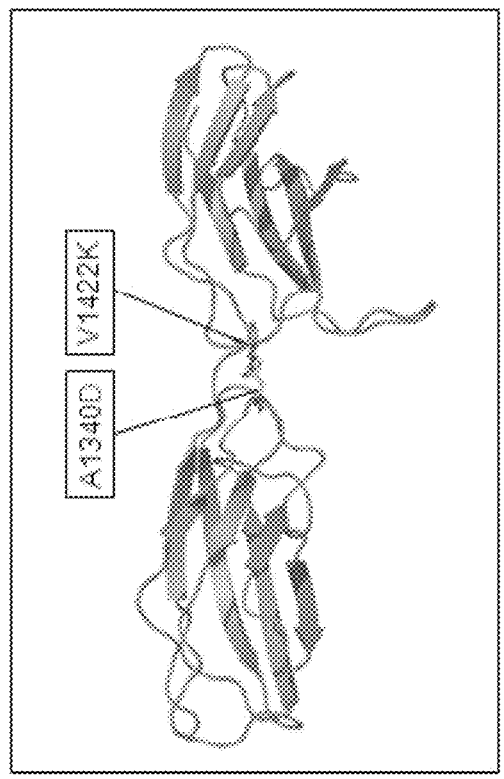

In accordance with this aspect of the invention, in certain embodiments, the amino acid substitutions in FNIII 9 and FNIII 10 form an interdomain di-sulfide bond. In certain other embodiments, the amino acid substitutions in FNIII 9 and FNIII 10 form an interdomain hydrogen bond. In certain particular embodiments, the amino acid substitution in FNIII 9 is Ala to Asp substitution at amino acid position 1340 (A1340D) and the amino acid substitution in FNIII 10 is Val to Lys substitution at amino acid position 1442 (V1442K) (FIG. 4). In certain further embodiments, the polypeptide has the amino acid sequence of SEQ ID NO:40. In certain other embodiments, the amino acid substitution in FNIII 10 is Thr to Arg substitution at amino acid position 1491 (T1491R). In certain particular embodiments, the non-covalent interdomain linkage is formed between Asn at amino acid position 1341 and the amino acid residue at position 1491. In certain further embodiments, the polypeptide has the amino acid sequence of SEQ ID NO:72.

In a further aspect, the invention provides isolated polypeptide comprising a modified human fibronectin fragment that comprises human fibronectin type III domain module 10 (FNIII 10) comprising the formula Val$^{1490}$-X$_1$-X$_2$-Arg-Gly-Asp-X$_3$-X$_4$-X$_5$-X$_6$-Ser$^{1500}$ (SEQ ID NO:123), wherein X$_1$ is Thr or Arg; X$_2$ is Ala or Pro; X$_3$ is Met, Trp or Asn; X$_4$ is Pro or Asn; X$_5$ is Asp or Glu; and X$_6$ is Ser or Gly, wherein the modified fibronectin fragment comprises an amino acid sequence that is at least 85%, at least 90%, at least 95% or at least 98% homologous to SEQ ID NO:2 and is not SEQ ID NO:50. In certain particular embodiment, X$_1$ is Thr; X$_2$ is Pro; X$_3$ is Met; X$_4$ is Pro; X$_5$ is Asp; and X$_6$ is Ser. In certain other particular embodiment, X$_1$ is Thr; X$_2$ is Ala; X$_3$ is Asn; X$_4$ is Pro; X$_5$ is Asp; and X$_6$ is Ser. In further embodiments, X$_1$ is Arg; X$_2$ is Ala; X$_3$ is Asn; X$_4$ is Pro; X$_5$ is Asp; and X$_6$ is Ser. In certain particular embodiments, the polypeptide inhibits or is capable of inhibiting integrin α5β1 activity and/or integrin αvβ3 activity. In certain other embodiments, the polypeptide has the amino acid sequence of SEQ ID NO:48, SEQ ID NO:52 or SEQ ID NO:54. In certain particular embodiments, the polypeptide has the amino acid sequence of SEQ ID NO:48.

In accordance with this aspect of the invention, in certain embodiments, the modified fibronectin fragment further comprises human fibronectin type III domain module 9 (FNIII 9) that optionally comprises Leu to Pro substitution at amino acid position 1408, and wherein the FNIII 9 and FNIII 10 (FNIII 9-10) comprises an amino acid sequence that is at least 85%, at least 90%, at least 95% or at least 98% homologous to the amino acid sequence of SEQ ID NO:4. In certain particular embodiments, the polypeptide has the amino acid sequence of SEQ ID NO:56, SEQ ID NO:58, SEQ ID NO:60 or SEQ ID NO:62. In certain particular embodiments, the polypeptide has the amino acid sequence of SEQ ID NO:60 or SEQ ID NO:62.

All embodiments described herein can be combined with other embodiments unless it is clear from the context that they cannot. For example, a modified fibronectin fragment comprising FNIII 9-10 that comprises an intradomain disulfide bond can further comprise an engineered interdomain linkage between FNIII 9 and FNIII 10. Other combinations are also understood to be encompassed by the instant invention.

In a further aspect, compositions are provided comprising the polypeptides described herein. In yet another aspect, the invention provides pharmaceutical compositions comprising the polypeptides of the invention and a pharmaceutical acceptable excipient, diluent or carrier. In certain particular embodiments, the pharmaceutical compositions comprise a therapeutically effective amount of the polypeptides described in various aspects described above.

In a further aspect, the invention provides methods of inhibiting integrin-mediated cell adhesion, growth, migration or differentiation, comprising the step of contacting a cell with an effective amount of the polypeptide of the instant invention, wherein the integrin comprises αvβ3 and/or α5β1 integrin. In accordance with these aspects of the invention, in certain embodiments the integrin is integrin αvβ3. In certain further embodiments, the polypeptide has the amino acid sequence of SEQ ID NO:6, SEQ ID NO:8, SEQ ID NO:10, SEQ ID NO:20, SEQ ID NO:44 or SEQ ID NO:56. In certain particular embodiments, the polypeptide has the amino acid sequence of SEQ ID NO:6. In certain other further embodiments, the integrin is integrin α5β1, and the polypeptide has the amino acid sequence of SEQ ID NO:28, SEQ ID NO:32, SEQ ID NO:34, SEQ ID NO:36, SEQ ID NO:38, SEQ ID NO:52, SEQ ID NO:54, SEQ ID NO:56 or SEQ ID NO:58. In certain particular embodiments, the polypeptide has the amino acid sequence of SEQ ID NO:32.

In yet another aspect, the invention provides methods of inhibiting integrin-mediated cell adhesion, growth, migration or differentiation in a mammal, comprising the step of administering to a mammal in need thereof a pharmaceutical composition comprising the inventive polypeptides described herein, wherein the integrin is αvβ3 or α5β1. In further aspects, the invention provides methods of inhibiting or treating tumor growth, tumor progression or tumor metastasis in a mammal, comprising the step of administering to a mammal a pharmaceutical composition comprising the inventive polypeptides described herein, wherein the tumor expresses αvβ3 or α5β1. In certain embodiments, the pharmaceutical composition comprises a therapeutic effective amount of the inventive polypeptides described herein. In accordance with these aspects, in certain embodiments, the integrin is integrin αvβ3, and the polypeptide has the amino acid sequence of SEQ ID NO:6, SEQ ID NO:8, SEQ ID NO:10, SEQ ID NO:20, SEQ ID NO:48 or SEQ ID NO:56. In certain other embodiments, the integrin is integrin α5β1, and the polypeptide has the amino acid sequence of SEQ ID NO:28, SEQ ID NO:32, SEQ ID NO:34, SEQ ID NO:40, SEQ ID NO:42, SEQ ID NO:56, SEQ ID NO:58, SEQ ID NO:60, SEQ ID NO:62 or SEQ ID NO:72. In certain particular embodiments, the mammal is a human.

In yet a further aspect, the invention provides methods of inhibiting an angiogenesis-related disease in a mammal comprising administering to a mammal in need thereof pharmaceutical compositions comprising the inventive polypeptides described herein, wherein the angiogenesis-related disease is cancer, macular degeneration, edema or arthritis. In accordance with this aspect, in certain particular embodiments, the angiogenesis-related disease comprises an disease mediated by integrin αvβ3 and/or α5β1; in certain other embodiments, the pharmaceutical composition comprises a polypeptide comprising the amino acid sequence of SEQ ID NO:6, SEQ ID NO:8, SEQ ID NO:10, SEQ ID NO:20, SEQ ID NO:28, SEQ ID NO:32, SEQ ID NO:34, SEQ ID NO:40, SEQ ID NO:42, SEQ ID NO:48, SEQ ID NO:56, SEQ ID NO:58, SEQ ID NO:60, SEQ ID NO:62 or SEQ ID NO:72.

In yet another aspect, the invention provides isolated polynucleotides comprising a nucleotide sequence that encodes the inventive polypeptide described herein. In certain embodiments, the polynucleotides comprise a nucleotide sequence of SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:51, SEQ ID NO:53, SEQ ID NO:55, SEQ ID NO:57, SEQ ID NO:59, or SEQ ID NO:61. In certain particular embodiments, the polynucleotides comprise a nucleotide sequence of SEQ ID NO:5, SEQ ID NO:7, SEQ ID NO:9, SEQ ID NO:19, SEQ ID NO:31, SEQ ID NO:33, SEQ ID NO:39, SEQ ID NO:41, SEQ ID NO:47, SEQ ID NO:55, SEQ ID NO:57, SEQ ID NO:59 or SEQ ID NO:61.

In further aspects, the invention provides expression vectors comprising the inventive polynucleotides described herein, or host cells comprising the expression vectors. In a further aspect, the invention provides methods of preparing a polypeptide comprising the steps of (a) culturing the host cell provided herein under conditions effective to allow expression of the polypeptide encoded from the expression vector; and (b) recovering the polypeptide from the culture. In certain particular embodiments, the isolated polypeptides are recovered in a buffer without free Arg and/or Glu.

Specific embodiments of the present invention will become evident from the following more detailed description of certain preferred embodiments and the claims.

BRIEF DESCRIPTIONS OF THE DRAWINGS

FIG. 1 is an illustration of an exemplary modified human FNIII 10 with an engineered intradomain disulfide bond formed in the RGD loop region between the T1491C and S1499C substitutions.

FIG. 2 shows amino acid sequence alignment of wild type human FNIII 9-10 (SEQ ID NO:4) with orthologs from different mammalian species: Chimpanzee (GenBank Accession Number: XP_003309506) (SEQ ID NO:66); Cow (DAA32456)(SEQ ID NO:67); Boar (XP_003133691)(SEQ ID NO:68); Mouse (BAE28040) (SEQ ID NO:69); and Rat (EDL75262) (SEQ ID NO:70). Key: "*" identical; ":" conserved substitution; "." semi-conservative substitution.

FIGS. 3A-C show thermostabiltiy and solubility of wild-type and mutant FN fragments as shown by NMR (FIG. 3A), differential scanning caliometry and ammonium sulfate precipitation (FIG. 3B, 3C). In FIG. 3B: FNIII 9-10 L1408P—middle peak, square; FNIII 9-10 L1408P (RARGDNPD) (SEQ ID NO:62)—left peak, triangle; and FNIII 9-10 L1408P (CRARGDNPDC) (SEQ ID NO:32)—right peak, circle. In FIG. 3C: FNIII 10—middle peak, circle; FNIII 10 (PRGDMPD) protein (SEQ ID NO:48)—left peak, square; and FNIII 10 (CPRGDMPDC) protein (SEQ ID NO: 6)—right peak, triangle.

FIG. 4 shows an illustration of an exemplary modified FNIII 9-10 with an engineered interdomain hydrogen bond formed between the A1340D substitution in module 9 and the V1422K substitution in module 10.

Figure 5:
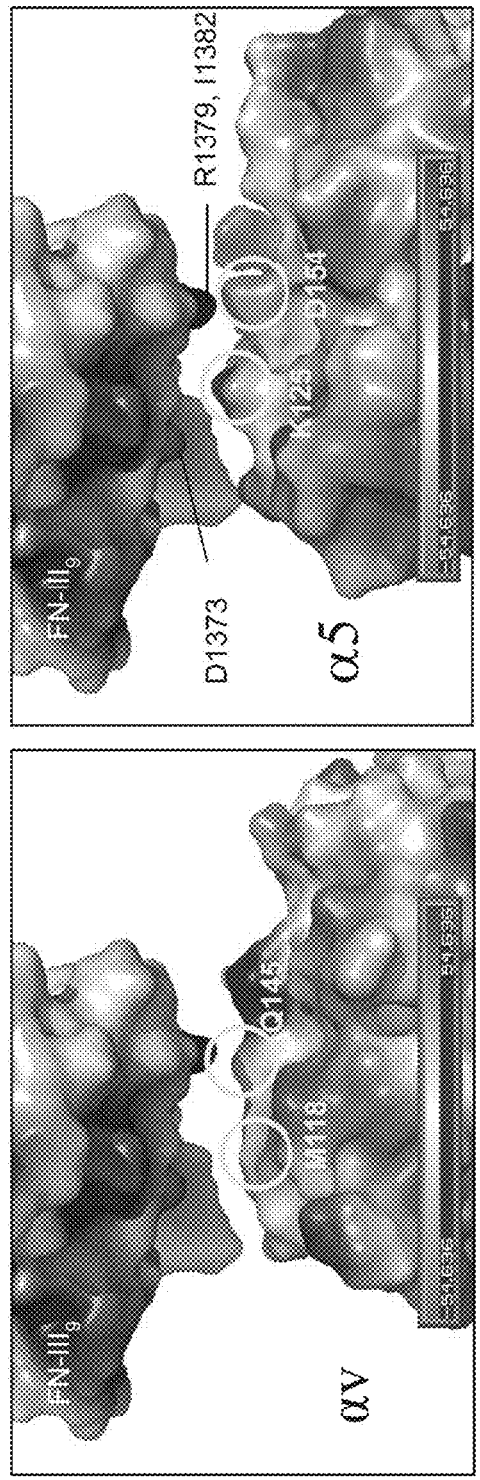
Figure 5:
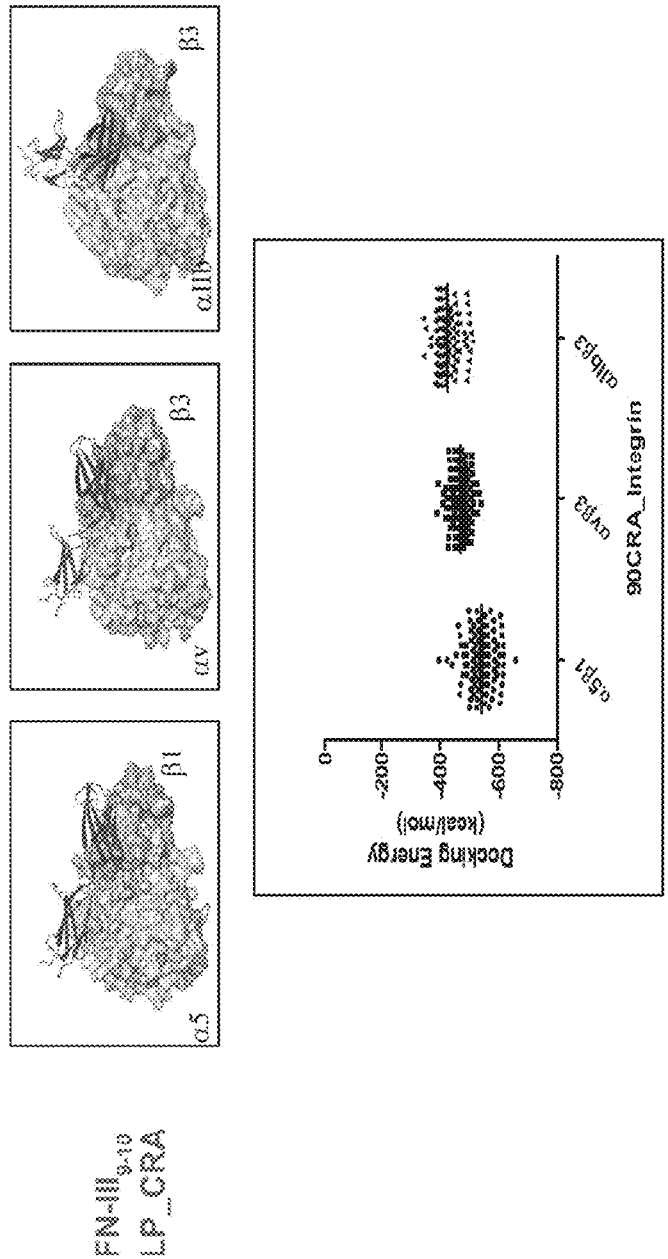

FIG. 5A presents computer-based models showing the interacting surface between FNIII 9 with integrin α5 subunit (right panel). Possible points of interaction are indicated. FIG. 5B shows computer docking models of FNIII 9-10 L1408P-CRA (SEQ ID NO:32)-integrin binding complexes and integrin binding selectivity based on the calculated docking energy.

FIGS. 6A-C show results of purification of different FNIII 9-10 variants by $Ni^{2+}$—chelating chromatography. The elution profile analyzed by measuring A280 (Absorbance) (left) and images of Coomassie blue staining of SDS gel electrophoresis (right) of FNIII 9-10 variants in the form of monomers or dimers formed by intermolecular S—S bond in the presence or absence of the reducing agent 2-mercaptoethanol.

Figure 7:
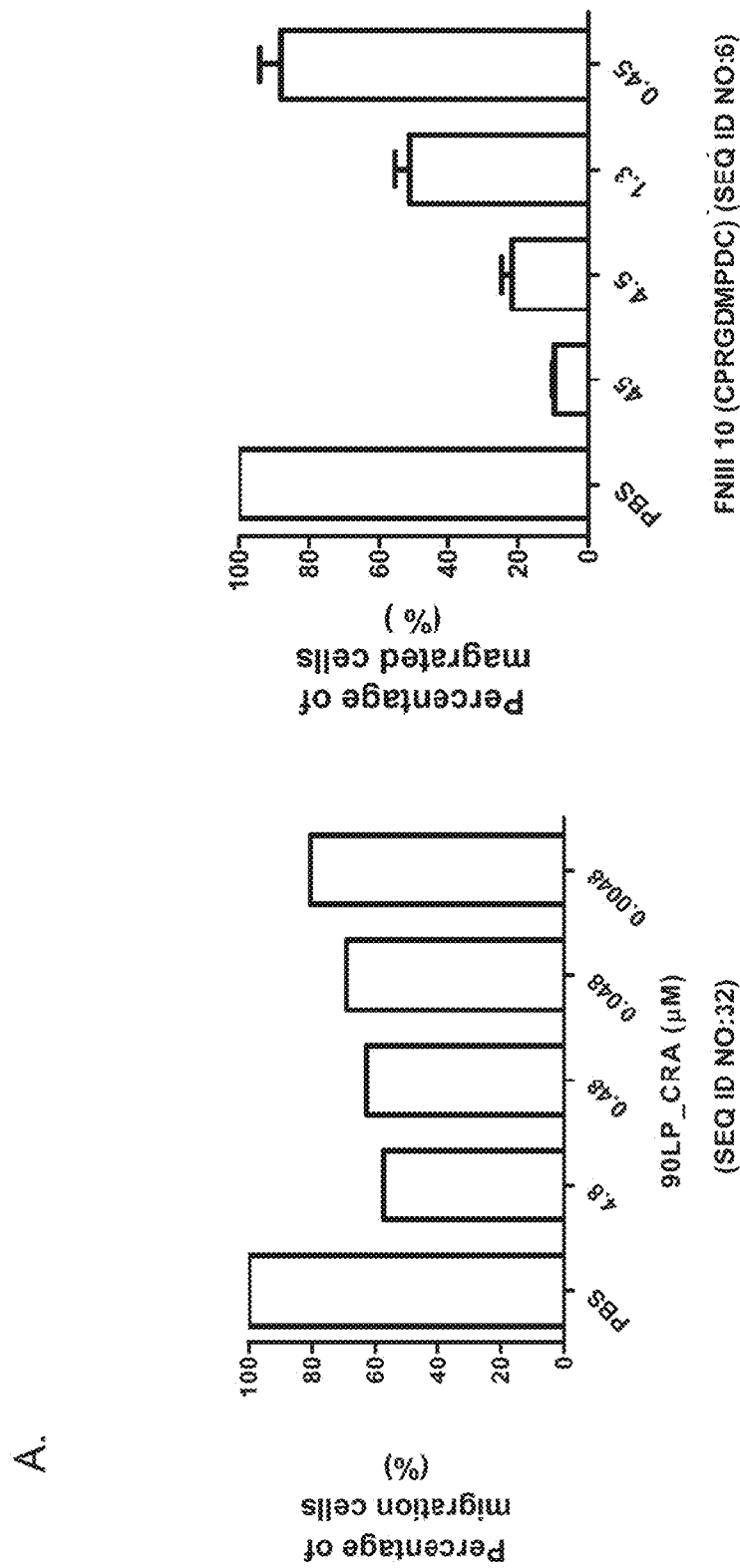
Figure 7:
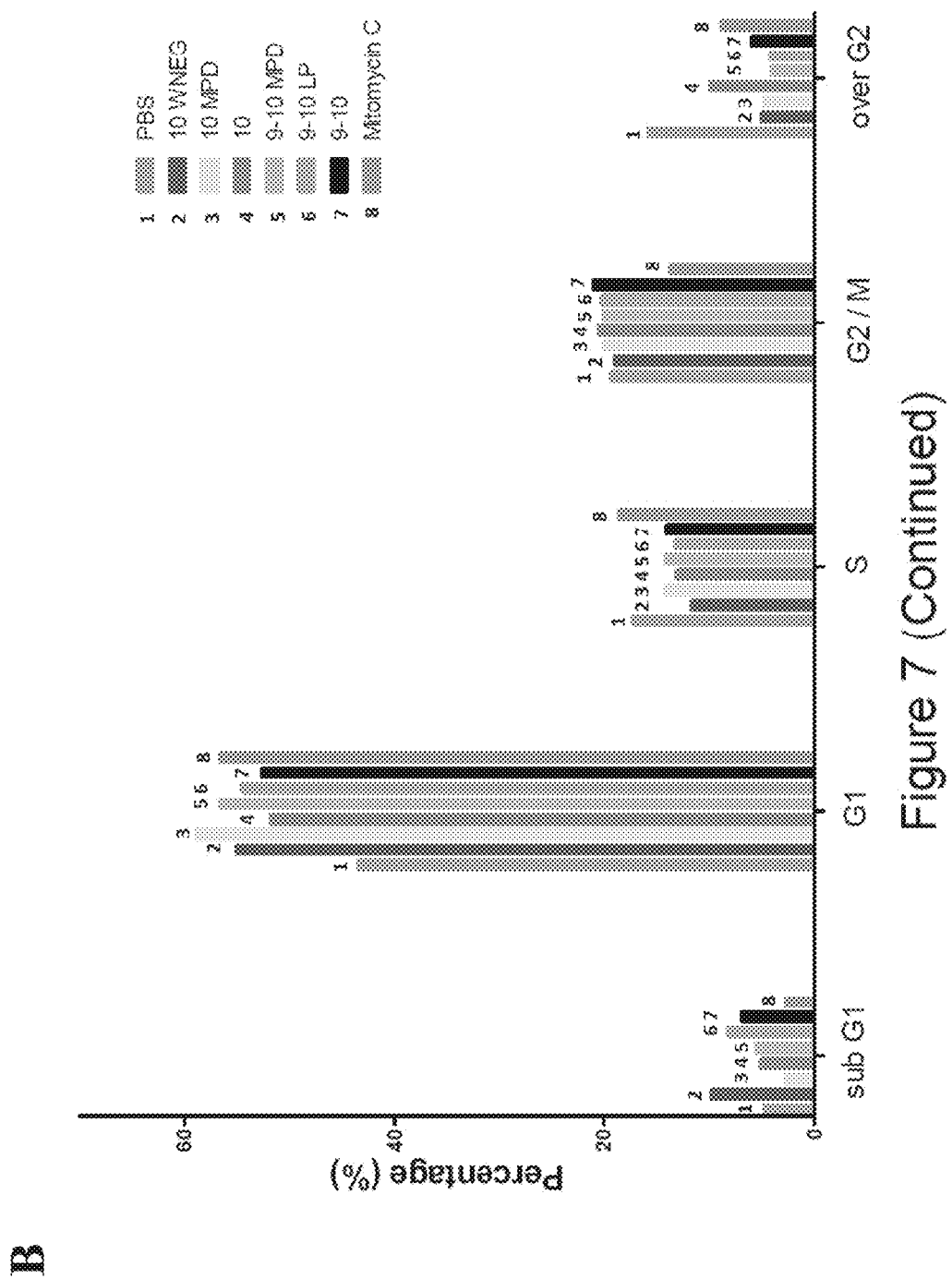
Figure 7:
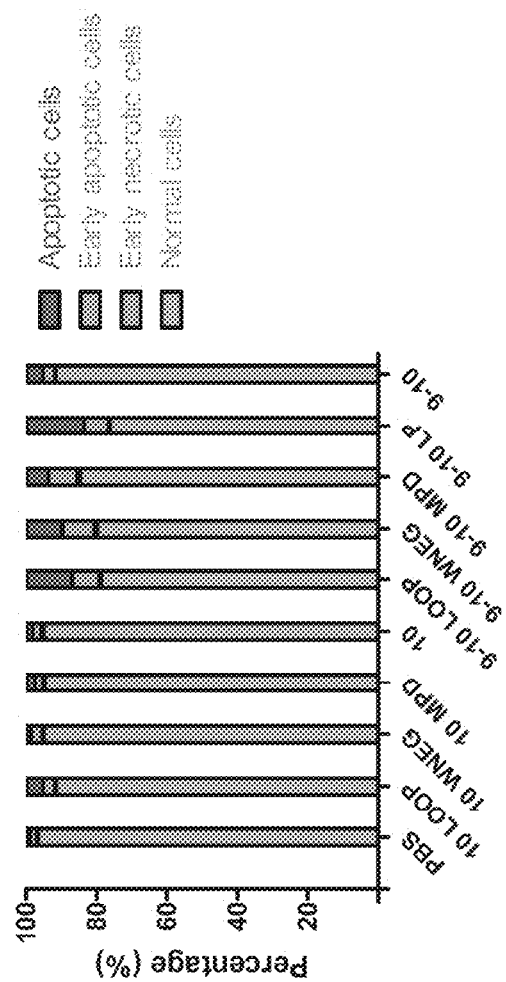
Figure 7:
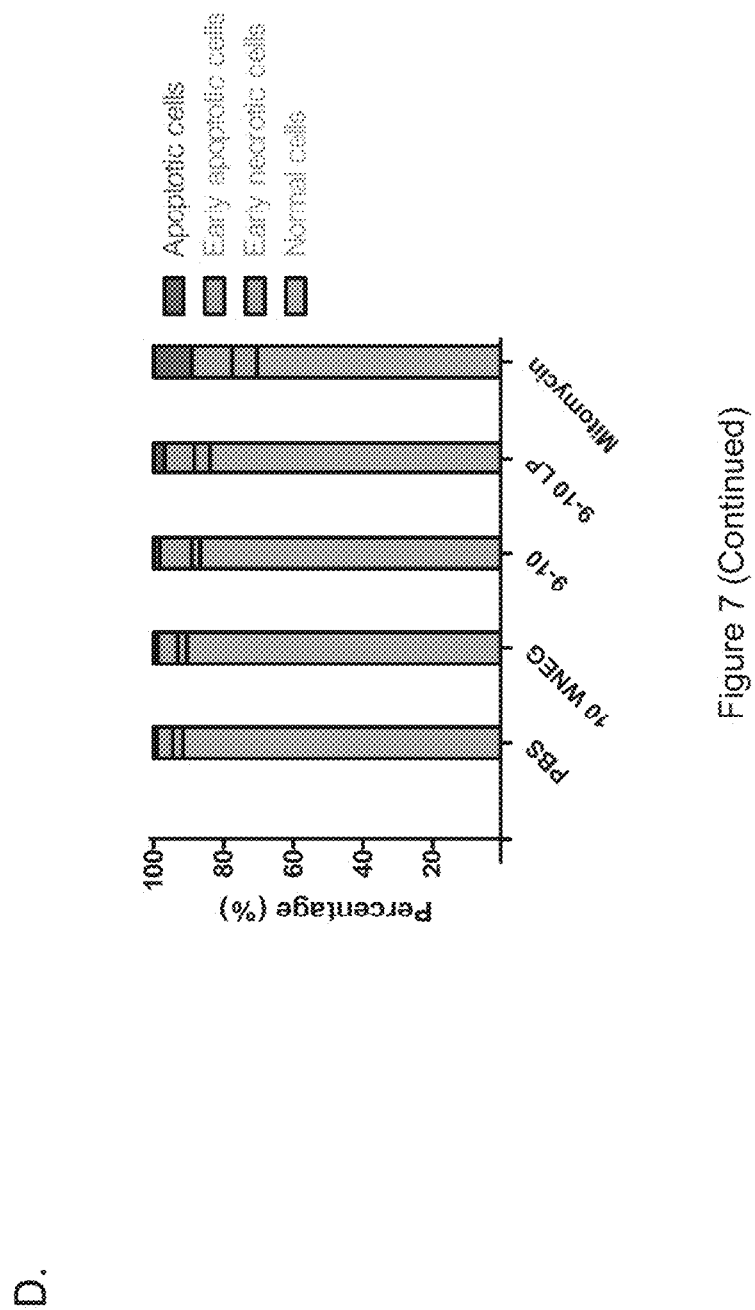

FIGS. 7A-D show results of the effects of various FNIII fragments on cell migration, cell survival and cell growth. FIG. 7A—the left panel presents a bar graph summarizing the inhibitory effect of FNIII 9-10 L1408P (CRARGDNPDC) (SEQ ID NO:32) on A549 cells migration and the right panel presents a bar graph summarizing the inhibitory effect of FNIII 10 (CPRGDMPDC) protein (SEQ ID NO:6) on A375 cells. FIG. 7B presents a bar graph showing that various FNIII variants induced G1 arrest in A375 melanoma cells. FIGS. 7C and 7D present bar graphs showing that various FNIII fragments induced apoptosis in A375 cells and A549 cells, respectively.

FIG. 8A-B present thermostability (A) and solubility (B) of $^9$FNIII 9-10 variants.

FIG. 9A-B present thermostability (A) and solubility (B) of FNIII 10 variants.

Figure 10:
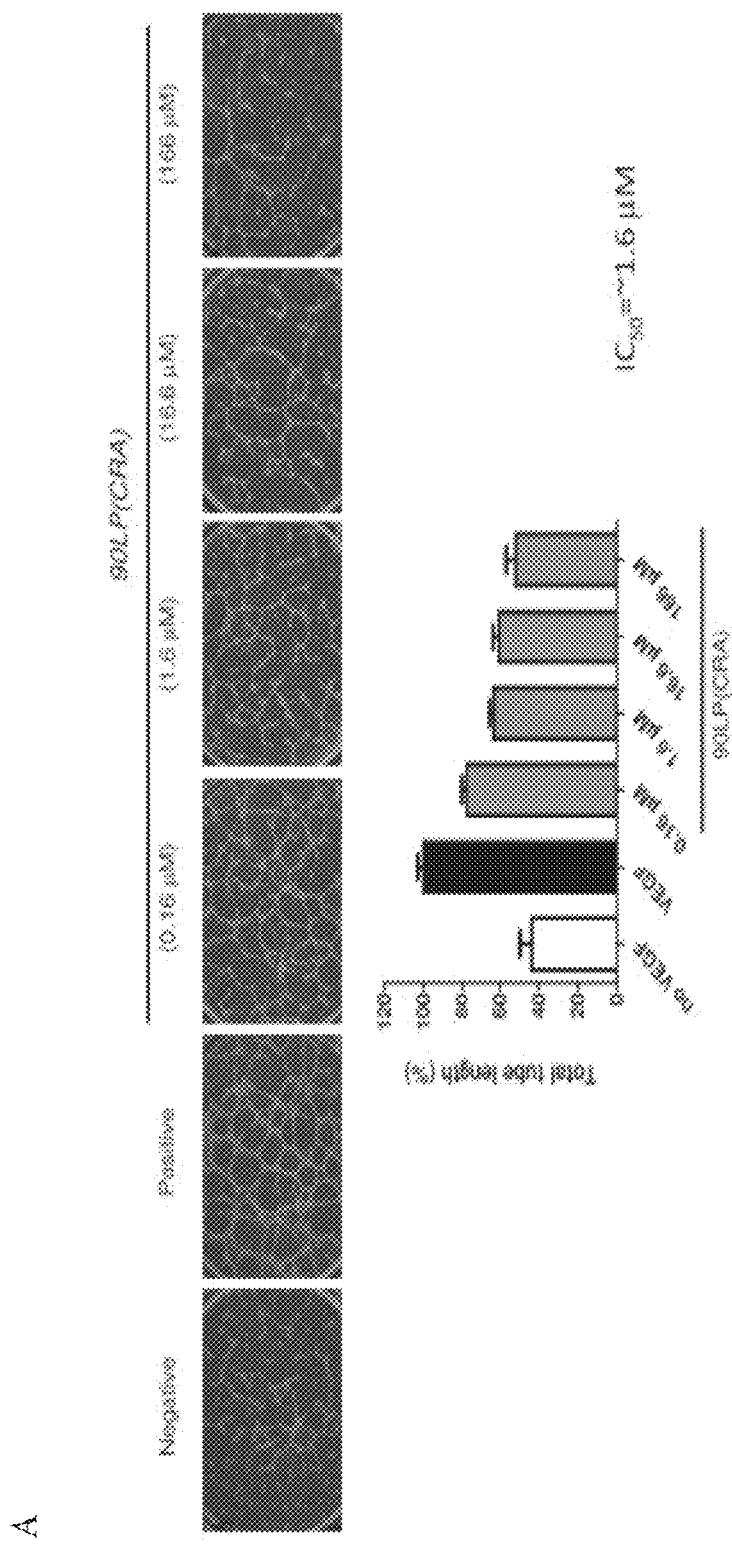
Figure 10:
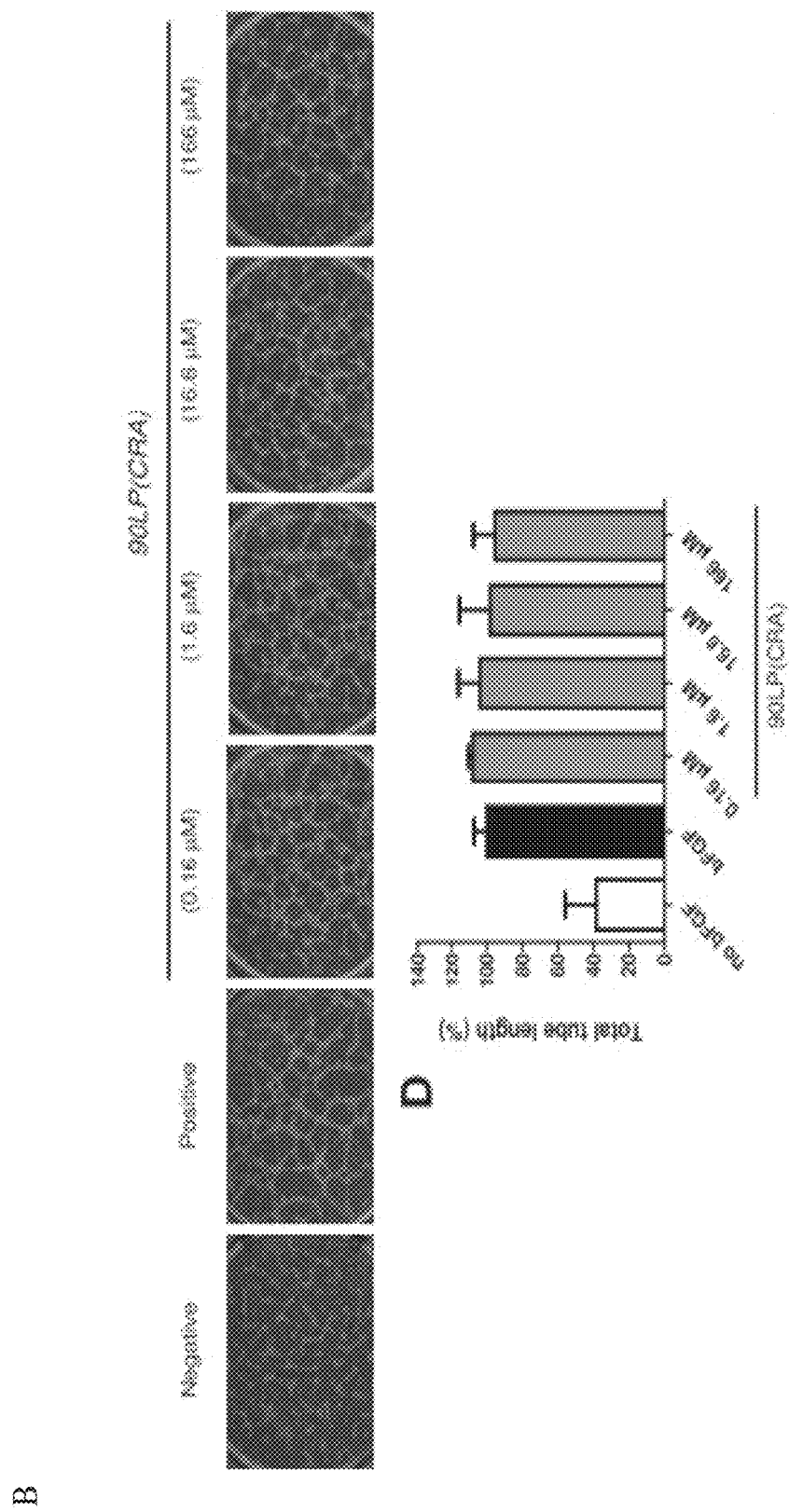

FIGS. 10A-B present inhibition of VEGF-induced tube formation (A) by FNIII 9-10 variant, an integrin α5β1-specific antagonist and no inhibition of bFGF-induced tube formation by $^{9,10}$Fn3 variant (B).

Figure 11:
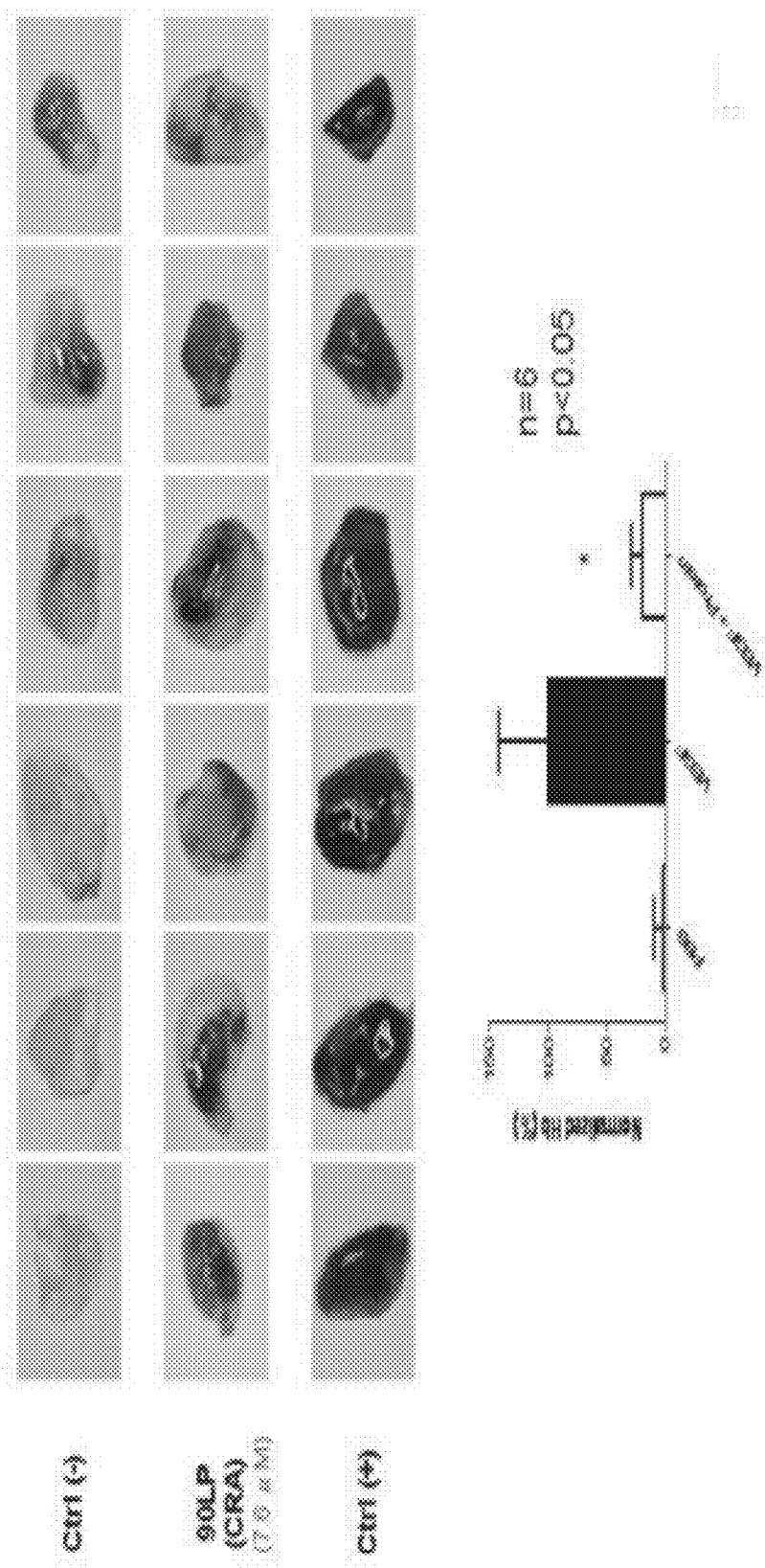

FIG. 11 presents the inhibition of VEGF-induced angiogenesis by FNIII 9-10 (CRARGDNPDC) variant (SEQ ID NO:32), an integrin α5β1-specific antagonist.

Figure 12:
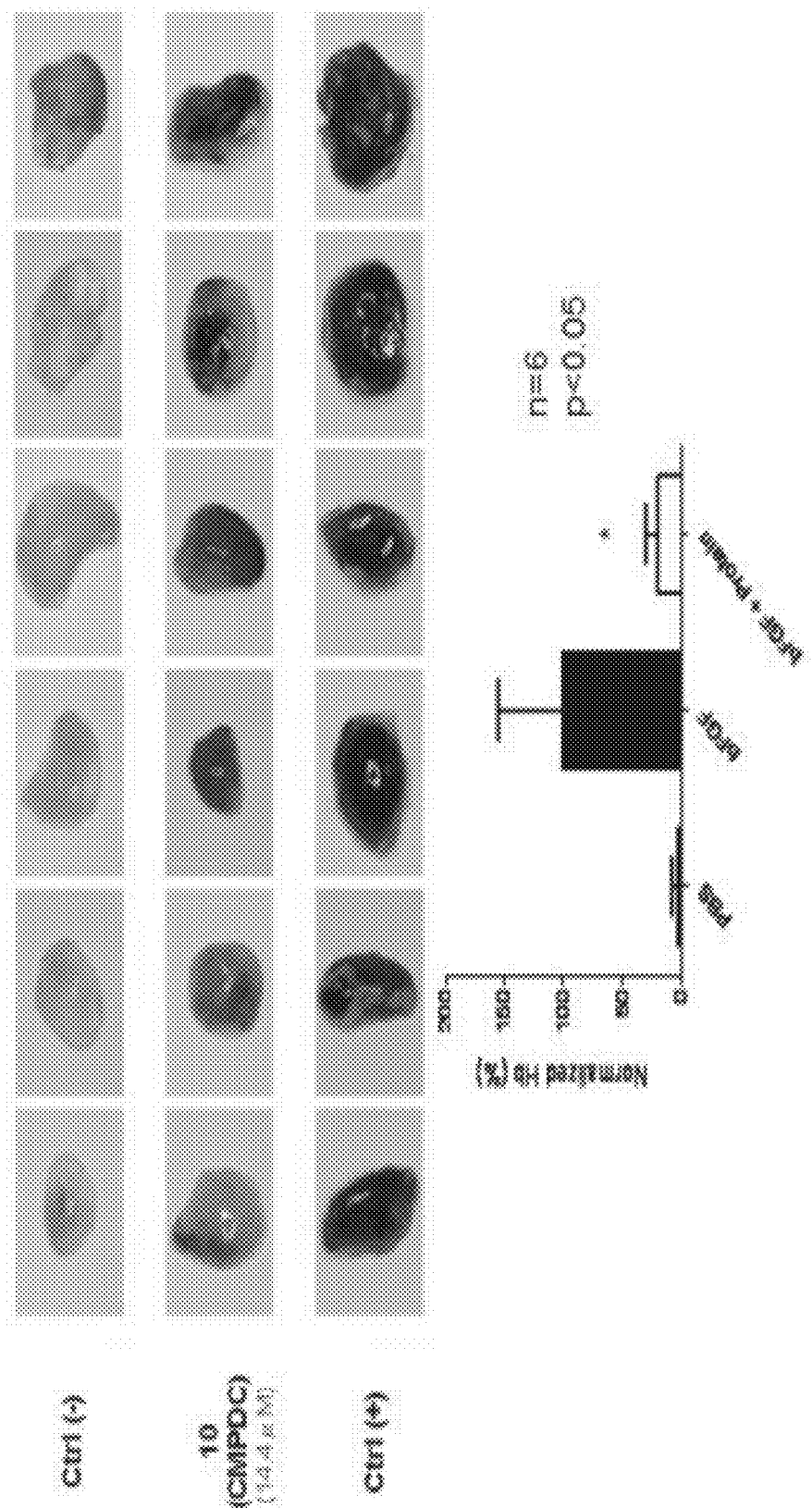

FIG. 12 presents the inhibition of bFGF-induced angiogenesis by FNIII 10 (CPRGDMPDC) variant (SEQ ID NO:6), an integrin αvβ3-specific antagonist.

Figure 13:
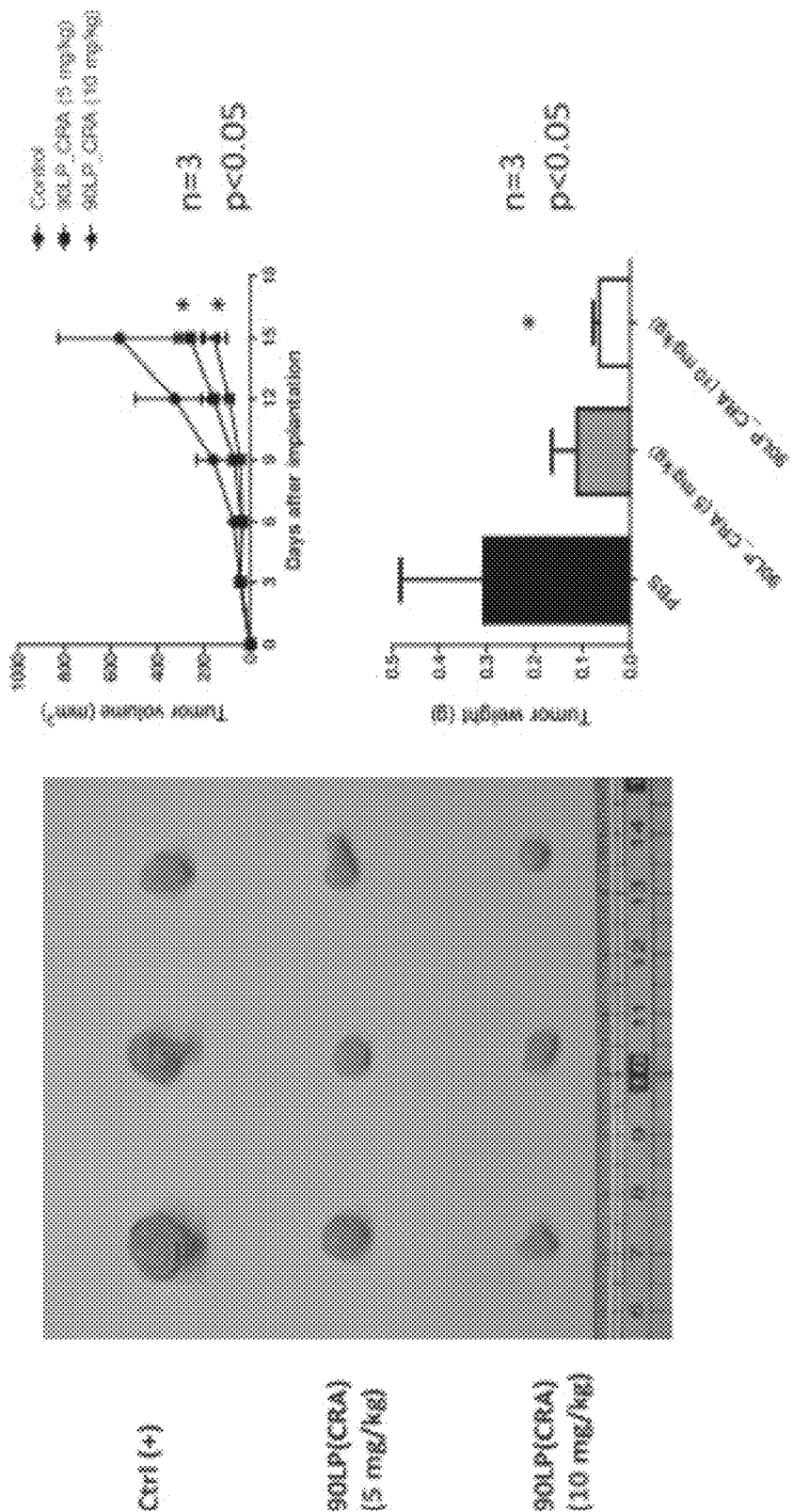

FIG. 13 presents the inhibition of tumor growth in A375-bearing NOD-SCID mice by FNIII 9-10 (CRARGDNPDC) variant (SEQ ID NO:32) in a dose-dependent manner.

Figure 14:
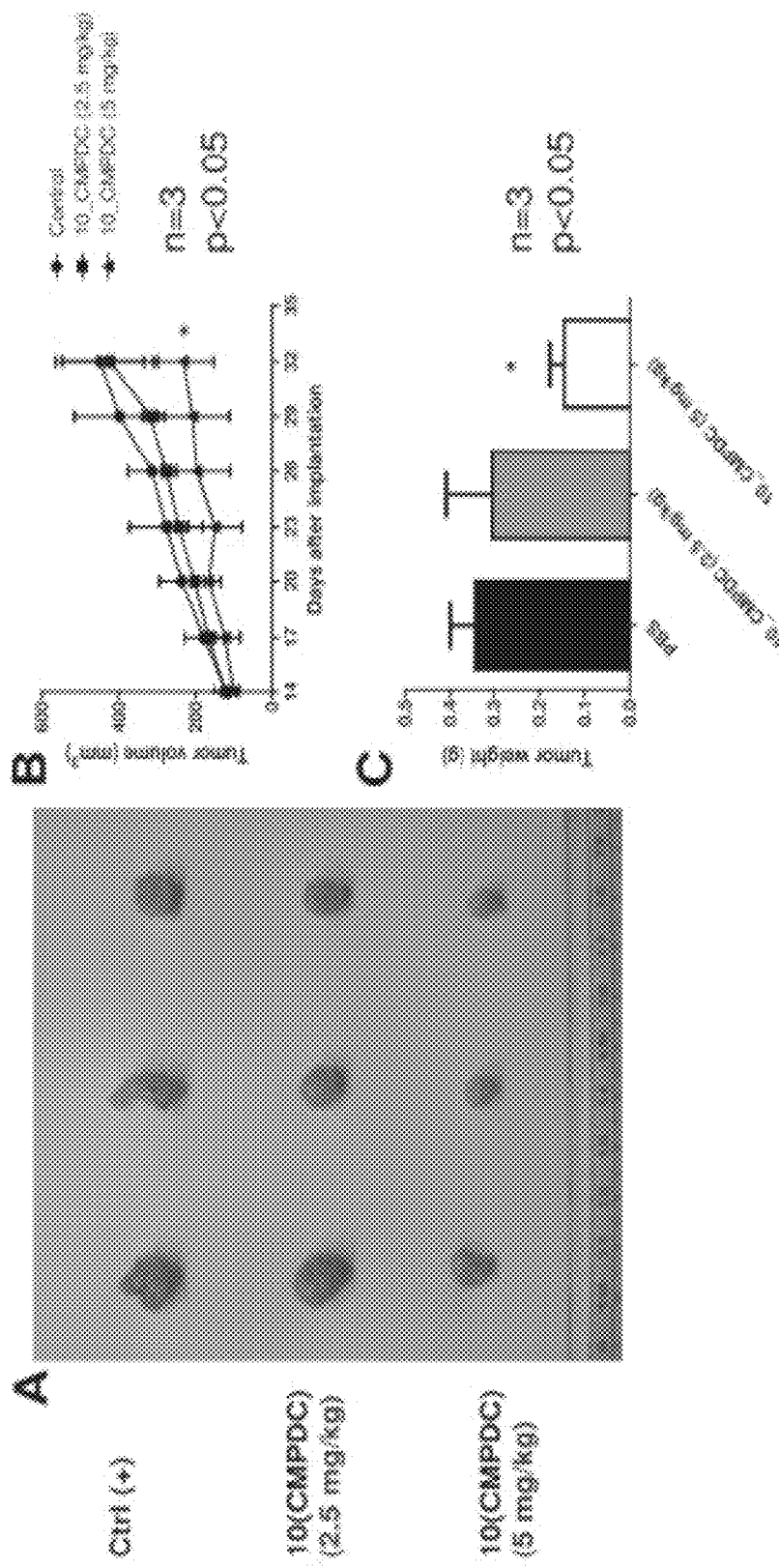

FIG. 14A-C presents the inhibition of tumor growth in A549-bearing NOD-SCID mice by FNIII 10 (CPRGDMPDC) variant (SEQ ID NO:6) in a dose-dependent manner

DETAILED DESCRIPTION OF THE INVENTION

All publications, patents and patent applications cited herein are hereby expressly incorporated by reference for all purposes.

Within this application, unless otherwise stated, the techniques utilized may be found in any of several well-known references such as: *Molecular Cloning: A Laboratory Manual* (Sambrook, et al., 1989, Cold Spring Harbor Laboratory Press) and *PCR Protocols: A Guide to Methods and Applications* (Innis, et al. 1990. Academic Press, San Diego, Calif.). Unless specific definitions are provided, the nomenclature utilized in connection with, and the laboratory procedures and techniques of molecular biology, genetic engineering, analytical chemistry, synthetic organic chemistry, and medicinal and pharmaceutical chemistry described herein are those well-known and commonly used in the art. Standard techniques can be used for chemical syntheses, chemical analyses, pharmaceutical preparation, formulation, and delivery, and treatment of patients.

Unless otherwise required by context, singular terms shall include pluralities and plural terms shall include the singular. For example, reference to a "polypeptide" means one or more polypeptides.

As described below, the invention provides isolated polypeptides comprising a modified human fibronectin fragment that comprises human fibronectin type III domain module 10 (FNIII 10), wherein the FNIII 10 comprises an Arg-Gly-Asp (RGD) motif, wherein the modified human fibronectin fragment comprises at least one amino acid substitution, and wherein the modified human fibronectin fragment comprises an amino acid sequence that is at least 85%, at least 90%, at least 95%, or at least 98% homologous to SEQ ID NO:2. In certain embodiments, the modified human fibronectin fragment further comprises FNIII 9, optionally further comprising Leu to Pro substitution at amino acid position 1408, and wherein the modified human fibronectin fragment comprises an amino acid sequence that is at least 85%, at least 90%, at least 95% or at least 98% homologous to SEQ ID NO:4. The amino acid numbering used throughout this application follows the amino acid numbering of full-length mature human fibronectin (SEQ ID NO:74). The full-length human fibronectin cDNA and protein sequences are based on Gen-Bank Accession Numbers NM_212476 (SEQ ID NO:73) and NP_997641 (SEQ ID NO:74), respectively.

Also encompassed within the instant invention are isolated polypeptides that comprise modified fibronectin fragments comprising, in addition to the inventive modified FNIII 10 or modified FNIII 9-10, additional modules and domains of fibronectin, including without limitation module 6, module 7 and/or module 8 of fibronectin type III domain. Full-length FN polypeptides with the one or more inventive mutations described herein are also encompassed within the scope of the invention.

Human fibronectin binds integrin α5β1 and integrin αvβ3 via the RGD motif, which resides in FNIII 10. See FIG. 1. FNIII 10 alone, however, shows only low affinity for integrin αvβ3. The instant inventors unexpectedly discovered that introducing into the RGD loop an intrachain di-sulfide bond formed between two Cys substitutions within FNIII 10 improved integrin binding and/or antagonist activity of FNIII 10. Further, it was unexpectedly discovered that Cys substitutions comprising the formula Cys$^{1491}$-X$_1$-RGD-X$_2$-X$_3$-X$_4$-Cys$^{1499}$ (SEQ ID NO: 115) improved integrin αvβ3 antagonist activity in the context of either FNIII 10 or FNIII 9-10. On the other hand, modified FNIII 9-10 comprising the formula Cys$^{1490}$-X$_1$-X$_2$-Arg-Gly-Asp-X$_3$-Pro-X$_4$-Cys$^{1499}$ (SEQ ID NO: 116) exhibited equal or superior integrin α5β1 antagonist activity as compared to FNIII 9-10 with the wild type sequence. In certain other embodiments, further mutations including conservative amino acid substitutions can be introduced in the modified inventive fibronectin fragment described herein without affecting the desirable activity of the modified fibronectin fragment.

It was believed that at high concentration, FNIII 9-10 at some extent mimics full-length FN biological activity. FNIII 9-10 or FNIII 10 was known to be structurally unstable in solution. It was previously reported that a Leu to Pro substitution at amino acid position 1408 (L1408P) improved stability of FNIII 9. See van der Walle et al., supra. It was also previously reported that an Asp to Asn substitution at amino acid position 1422 (D1422N) within FNIII 10 improved the stability of FNIII 10 (Koide A., et al. *Biochemistry* 2001, 40:10326-10333). The instant inventors, however, unexpectedly discovered that an engineered di-sulfide bond formed within the RGD loop, for example comprising the formula Cys$^{1491}$XRGDX$_3$Cys$^{1499}$ (SEQ ID NO: 120) increased the stability and solubility of the FN fragment FNIII 9-10 and FNIII 10, irrespective of the presence of the L1408P and/or the D1422N substitution. It was also discovered by the instant inventors that an engineered di-sulfide bond formed within the RGD loop comprising the formula Cys$^{1490}$X$_2$RGDX$_3$Cys$^{1499}$ (SEQ ID NO: 118) increased the stability and solubility of the FN fragment FNIII 9-10.

Unlike certain other naturally occurring integrin β1 binding protein such as invasin of *Yersinia pseudotuberculosi*, the α5β1 integrin interacting surface of FNIII 9-10 is less flexible due to minimal interaction between the two modules. See Hamburger et al., *Science*, 1999, 286:291. Structural flexibility between FN module 9 and module 10 has been suggested to be important in maintaining FN biological function. See Altroff et al., supra; Van Nhieu et al. 1996, *J. Biol. Chem.* 271:7665-72; and *Biochemistry* 37:10945 (1998). It was surprisingly discovered by the instant inventors, however, that restricted interdomain movement between FNIII 9 and FNIII 10 did not affect the integrin α5β1 antagonistic activity of FNIII 9-10.

In accordance with this aspect of the invention, in certain embodiments, the invention provides isolated polypeptides comprising a modified human fibronectin fragment that comprises human fibronectin type III domain module 9 and human fibronectin type III domain module 10 (FNIII 9-10), wherein the FNIII 9 optionally comprises Leu to Pro substitution at amino acid position 1408, wherein the FNIII 9 and the FNIII 10 each comprises at least one amino acid substitution, wherein the amino acid substitutions in the FNIII 9 and the FNIII 10 form a non-covalent bond, and wherein the FNIII 9 and FNIII 10 comprises an amino acid sequence that is at least 85%, at least 90%, at least 95% or at least 98% homologous to the amino acid sequence of SEQ ID NO:4 and that is not SEQ ID NO:64. In certain particular embodiments, the polypeptide inhibits integrin α5β1 activity.

By using computer-aided three-dimensional docking model, the instant inventors identified amino acid residues of FNIII 9 that are involved in interaction with integrin α5 subunit (FIG. 5A, right panel). The docking model also shows that FNIII 9 does not interact with the αIIb or αV subunit. Computer-generated docking model of FNIII 9-10 L1408P CRARGDNPDC (SEQ ID NO:32) demonstrates that this FNIII variant shows selectivity for integrin α5β1 binding as evidenced by favorable docking energy (FIG. 5B, lower panel).

In addition to the various embodiments described herein, polypeptides comprising modified FN fragment that comprises additional amino acid substitutions that do not affect the desirable antagonist activity and wherein the modified FN fragment is at least 85%, at least 90%, at least 95% or at least 98% homologous to the corresponding wild type FN sequence are also encompassed within the instant invention. The amino acid sequence of FN is highly conserved among different mammalian species. As an example, FIG. 2 shows amino acid sequence alignment of FNIII 9-10 from human and FNIII 9-10 from other indicated mammalian species, the sequences of which are available from the NCBI (National Center for Biotechnology Information) database. The sequences of full-length FN are also publicly available. Thus, it is within the ability of an ordinarily skilled artisan to determine whether FN variants of the invention with additional mutations, including without limitation insertion(s), deletion(s), and substitution(s), that are at least 85%, at least 90%, at least 95% or at least 98% homologous to SEQ ID NO:2 (or SEQ ID NO:4), and that would have maintained the desired activity of the FN fragments based on the conservation of the sequences among different mammalian species.

The term "isolated protein" or "isolated polypeptide" as used herein refers to a protein encoded by a nucleic acid including, inter alia, genomic DNA, cDNA, recombinant DNA, recombinant RNA, or nucleic acid of synthetic origin or some combination thereof, which (1) is free of at least some proteins with which it would normally be found, (2) is essentially free of other proteins from the same source, e.g., from the same cell or species, (3) is expressed by a cell from a different species, (4) has been separated from at least about 50 percent of polynucleotides, lipids, carbohydrates, or other materials with which it is naturally found when isolated from the source cell, (5) is not linked (by covalent or noncovalent interaction) to all or a portion of a polypeptide to which the "isolated protein" is linked in nature, (6) is operatively linked (by covalent or noncovalent interaction) to a polypeptide with which it is not linked in nature, or (7) does not occur in nature. Preferably, the isolated protein is substantially free from other contaminating proteins or polypeptides or other contaminants that are found in its natural environment that would interfere with its therapeutic, diagnostic, prophylactic or research use.

As used herein, the terms "polynucleotide," "nucleotide," "oligonucleotide," and "nucleic acid" may be used interchangeably to refer to nucleic acid comprising DNA, RNA, derivative thereof, or combination thereof.

As used herein, the terms "polypeptide" and "protein" may be used interchangeably to refer to proteins produced by naturally-occurring and non-recombinant cells, by genetically-engineered or recombinant cells, or by chemical synthesis, and comprise molecules having the amino acid sequence of the native protein, or sequences that have deletions, additions, and/or substitutions of one or more amino acids of the native sequence. In accordance with the instant invention, the polypeptide or protein specifically encompasses modified human fibronectin or fragments thereof or variants thereof. In certain particular embodiments, the polypeptide or protein encompasses human fibronectin fragments or variants thereof that inhibit integrin activity. In certain particular embodiments, the integrin is integrin α5β1 or αvβ3. In certain other particular embodiments, the integrin is not αIIbβ3.

The term "integrin antagonist" or "antagonist for integrin" as used herein refers to a molecule capable of inhibiting, blocking, neutralizing, reducing, abrogating or interfering with integrin activities. In certain embodiments, the antagonist inhibits integrin activities by binding to integrin and sequestering integrin from binding to other molecules, for example other ECM proteins. In certain other embodiments, the antagonist inhibits integrin activities by binding to integrin and preventing integrin from triggering downstream signaling events in the cells.

The term "inhibition" or "inhibit" in the context of integrin activity as used herein refers to a property of an integrin antagonist that reduces the activity of integrin as analyzed by various functional assays, including without limitation, binding assays, migration assays, apoptosis assays and cell adhesion assays. In certain embodiments of the invention, the polypeptide comprising a modified fibronectin fragment inhibit integrin activity, in certain particular embodiments, the integrin is integrin α5β1. In certain other particular embodiments, the integrin is integrin αvβ3. In certain further embodiments, the polypeptide inhibits integrin activity by from about 0% to about 100% as compared to the control in the absence of the polypeptide antagonist.

The term "selectively inhibit," "selective inhibition," "differentially inhibit" or "differential inhibition" as used herein refers to the property of an antagonist that shows differential specificity for a particular target molecule. For example, a polypeptide comprising a modified FN fragment that inhibits integrin αvβ3 activity but does not inhibit integrin α5β1 activity selectively inhibits integrin αvβ3. In certain embodiments, the polypeptide comprising a modified fibronectin fragment comprising FNIII 10, optimally further comprising FNIII 9, selectively inhibits integrin αvβ3 activities; in certain other embodiments, the polypeptide comprising a modified fibronectin fragment comprising FNIII 9-10 selectively inhibits integrin α5β1 activities. In certain alternative embodiments, the polypeptide comprising a modified fibronectin fragment comprising FNIII 9-10 specifically inhibits both integrin αvβ3 and integrin α5β1 activities.

The term "naturally-occurring" as used herein refers to an object that can be found in nature, for example, a polypeptide or polynucleotide sequence that is present in an organism (including a virus) that can be isolated from a source in nature and which has not been intentionally modified by man. The term "naturally occurring" or "native" when used in connection with biological materials such as nucleic acid molecules, polypeptides, host cells, and the like, refers to materials which are found in nature and are not manipulated by man. Similarly, "recombinant," "non-naturally occurring" or "non-native" as used herein refers to a material that is not found in nature or that has been structurally modified or synthesized by man.

The term "wild type" in the context of nucleic acid sequence or polypeptide sequence as used herein refers to native or naturally-occurring sequences that have not been intentionally modified by man. The wild type human fibronectin amino acid sequences are set forth in SEQ ID NO: 74. It is understood that naturally occurring allelic variants may exist that have amino acid sequences variation from the wild type sequence. The wild type human FN amino acid sequence is set forth in SEQ ID NO:74 as a reference to the numbering of amino acid residues used throughout the application.

The term "protein fragment" or "polypeptide fragment" as used herein refers to a polypeptide or protein that has an amino acid sequence less than the full length amino acid sequence of the corresponding wild type protein. A fragment of a protein can contain truncation(s) of the full-length protein from the N' terminus and/or from the C' terminus, or truncation(s) from the internal portion of the full-length protein. In certain embodiments, the fragment of a polypeptide retains the desirable activity of the full-length polypeptide. In certain other embodiments, the fragment of a polypeptide acquires desirable additional or altered activity as compared to the full-length protein. In certain particular embodiments, the protein fragment is a human fibronectin fragment, comprising a modified human fibronectin domain III module 10 (FNIII 10) or modules 9 and 10 (FNIII 9-10) that comprises one or more of the inventive modifications described herein. In certain other embodiments, polypeptides comprising the modified human fibronectin further comprising additional insertion(s), deletion(s), or substitution(s) and retaining the desirable activities are also encompassed by the instant invention.

The term "variant," "mutant" of "modified" as used herein refers to a sequence, either polynucleotide or polypeptide sequence, that contains at least one substitution or variation different from a wild type sequence. In certain embodiments, the variant comprises a modified human fibronectin fragment that comprises human fibronectin type III domain module 10 (FNIII 10) that contains at least one amino acid substitution. Modified FN variants further comprising post translational modifications are also contemplated and encompassed within the scope of the invention. Full length human FN comprises the corresponding inventive amino acid substitution(s) described herein is also contemplated and encompassed by the instant invention.

The term "homology" or "homologous" as used herein refers to the level of overall sequence similarity and/or identity between corresponding fibronectin fragments. High sequence homology suggests conservation of protein activity. A number of publicly available algorithms or software programs can be used to determine sequence homology. It is within the ability of one skilled in the art to determine the suitability of additional conservative or non-conservative amino acid substitutions and the level of sequence homology.

The phrase "N-terminal to" or "C-terminal to" is understood by an ordinarily skilled in the art to refer to the relative locations of two or more amino acid residues in a protein or fragment thereof. For example, an amino acid residue in a peptide sequence N-terminal to a reference amino acid residue is understood to reside in a position of the peptide sequence that is closer to the N-terminus of the peptide sequence than the reference amino acid residue is to the N-terminus. Similarly, an amino acid residue C-terminal to a reference amino acid residue is understood to reside in a position of the peptide sequence closer to the C-terminus of the peptide sequence than the reference amino acid residue is to the C-terminus.

The human FNIII 10 and FNIII 9-10 variants are summarized in Table 1 below:

TABLE 1

| Description | Sequence |
|---|---|
| Wild type FNIII 10 | V S D V P R D L E V V A<br>A T P T S L L I S W D A<br>P A V T V R Y Y R I T Y<br>G E T G G N S P V Q E F<br>T V P G S K S T A T I S<br>G L K P G V D Y T I T V<br>Y A V T G R G D S P A S<br>S K P I S I N Y R T<br>(SEQ ID NO: 2) |
| FNIII 10 (CX₇C) | V S D V P R D L E V V A<br>A T P T S L L I S W D A<br>P A V T V R Y Y R I T Y<br>G E T G G N S P V Q E F<br>T V P G S K S T A T I S<br>G L K P G V D Y T I T V<br>Y A V C X R G D X P X C<br>S K P I S I N Y R T<br>(SEQ ID NO: 6) |
| | V S D V P R D L E V V A<br>A T P T S L L I S W D A<br>P A V T V R Y Y R I T Y<br>G E T G G N S P V Q E F<br>T V P G S K S T A T I S<br>G L K P G V D Y T I T V<br>Y A V C X R G D X X X C<br>S K P I S I N Y R T<br>(SEQ ID NO: 8) |
| | V S D V P R D L E V V A<br>A T P T S L L I S W D A<br>P A V T V R Y Y R I T Y<br>G E T G G N S P V Q E F<br>T V P G S K S T A T I S<br>G L K TABLE 1-continued

| Description | Sequence |
|---|---|
|  | P A V T V R Y Y R I T Y<br>G E T G G N S P V Q E F<br>T V P G S K S T A T I S<br>G L K P G V D Y T I T V<br>Y A C R A R G D N P D C<br>S K P I S I N Y R T<br>(SEQ ID NO: 16) |
|  | V S D V P R D L E V V A<br>A T P T S L L I S W D A<br>P A V T V R Y Y R I T Y<br>G E T G G N S P V Q E F<br>T V P G S K S T A T I S<br>G L K P G V D Y T I T V<br>Y A C T G R G D S P A C<br>S K P I S I N Y R T<br>(SEQ ID NO: 18) |
| Wild type FN III 9-10 | G L D S P T G I D F S D<br>I T A N S F T V H W I A<br>P R A T I T G Y R I R H<br>H P E H F S G R P R E D<br>R V P H S R N S I T L T<br>N L T P G T E Y V V S I<br>V A L N G R E E S P L L<br>I G Q Q S T V S D V P R<br>D L E V V A A T P T S L<br>L I S W D A P A V T V R<br>Y Y R I T Y G E T G G N<br>S P V Q E F T V P G S K<br>S T A T I S G L K P G V<br>D Y T I T V Y A V T G R<br>G D S P A S S K P I S I<br>N Y R T (SEQ ID NO: 4) |
| FN III 9-10 (L1408P) | G L D S P T G I D F S D<br>I T A N S F T V H W I A<br>P R A T I T G Y R I R H<br>H P E H F S G R P R E D<br>R V P H S R N S I T L T<br>N L T P G T E Y V V S I<br>V A L N G R E E S P P L<br>I G Q Q S T V S D V P R<br>D L E V V A A T P T S L<br>L I S W D A P A V T V R<br>Y Y R I T Y G E T G G N<br>S P V Q E F T V P G S K<br>S T A T I S G L K P G V<br>D Y T I T V Y A V T G R<br>G D S P A S S K P I S I<br>N Y R T (SEQ ID NO: 63) |
| FN III 9-10 (CX<sub>7</sub>C) | G L D S P T G I D F S D<br>I T A N S F T V H W I A<br>P R A T I T G Y R I R H<br>H P E H F S G R P R E D<br>R V P H S R N S I T L T<br>N L T P G T E Y V V S I<br>V A L N G R E E S P L L<br>I G Q Q S T V S D V P R<br>D L E V V A A T P T S L<br>L I S W D A P A V T V R<br>Y Y R I T Y G E T G G N<br>S P V Q E F T V P G S K<br>S T A T I S G L K P G V<br>D Y T I T V Y A V C P R<br>G D N P D C S K P I S I<br>N Y R T (SEQ ID NO: 20) |
| FN III 9-10 (L1408P) (CX<sub>7</sub>C) | G L D S P T G I D F S D<br>I T A N S F T V H W I A<br>P R A T I T G Y R I R H<br>H P E H F S G R P R E D<br>R V P H S R N S I T L T<br>N L T P G T E Y V V S I<br>V A L N G R E E S P P L |

TABLE 1-continued

| Description | Sequence |
|---|---|
|  | I G Q Q S T V S D V P R<br>D L E V V A A T P T S L<br>L I S W D A P A V T V R<br>Y Y R I T Y G E T G G N<br>S P V Q E F T V P G S K<br>S T A T I S G L K P G V<br>D Y T I T V Y A V C A R<br>G D N P D C S K P I S I<br>N Y R T (SEQ ID NO: 22) |
| FN III 9-10 (L1408P) (CX<sub>7</sub>C) | G L D S P T G I D F S D<br>I T A N S F T V H W I A<br>P R A T I T G Y R I R H<br>H P E H F S G R P R E D<br>R V P H S R N S I T L T<br>N L T P G T E Y V V S I<br>V A L N G R E E S P P L<br>I G Q Q S T V S D V P R<br>D L E V V A A T P T S L<br>L I S W D A P A V T V R<br>Y Y R I T Y G E T G G N<br>S P V Q E F T V P G S K<br>S T A T I S G L K P G V<br>D Y T I T V Y A V C G R<br>G D S P A C S K P I S I<br>N Y R T (SEQ ID NO: 24) |
| FN III 9-10 (CX<sub>7</sub>C) | G L D S P T G I D F S D<br>I T A N S F T V H W I A<br>P R A T I T G Y R I R H<br>H P E H F S G R P R E D<br>R V P H S R N S I T L T<br>N L T P G T E Y V V S I<br>V A L N G R E E S P L L<br>I G Q Q S T V S D V P R<br>D L E V V A A T P T S L<br>L I S W D A P A V T V R<br>Y Y R I T Y G E T G G N<br>S P V Q E F T V P G S K<br>S T A T I S G L K P G V<br>D Y T I T V Y A V C G R<br>G D S P A C S K P I S I<br>N Y R T (SEQ ID NO: 26) |
| FN III 9-10 (L1408P) (CX<sub>8</sub>C) | G L D S P T G I D F S D<br>I T A N S F T V H W I A<br>P R A T I T G Y R I R H<br>H P E H F S G R P R E D<br>R V P H S R N S I T L T<br>N L T P G T E Y V V S I<br>V A L N G R E E S P P L<br>I G Q Q S T V S D V P R<br>D L E V V A A T P T S L<br>L I S W D A P A V T V R<br>Y Y R I T Y G E T G G N<br>S P V Q E F T V P G S K<br>S T A T I S G L K P G V<br>D Y T I T V Y A C T G R<br>G D S P A C S K P I S I<br>N Y R T (SEQ ID NO: 28) |
| FN III 9-10 (L1408P) (CX<sub>8</sub>C) | G L D S P T G I D F S D<br>I T A N S F T V H W I A<br>P R A T I T G Y R I R H<br>H P E H F S G R P R E D<br>R V P H S R N S I T L T<br>N L T P G T E Y V V S I<br>V A L N G R E E S P P L<br>I G Q Q S T V S D V P R<br>D L E V V A A T P T S L<br>L I S W D A P A V T V R<br>Y Y R I T Y G E T G G N<br>S P V Q E F T V P G S K<br>S T A T I S G L K P G V |

TABLE 1-continued

| Description | Sequence |
|---|---|
| | D Y T I T V Y A C I P R G D M P D C S K P I S I N Y R T (SEQ ID NO: 30) |
| FN III 9-10 (L1408P) (CX$_8$C) | G L D S P T G I D F S D I T A N S F T V H W I A P R A T I T G Y R I R H H P E H F S G R P R E D R V P H S R N S I T L T N L T P G T E Y V V S I V A L N G R E E S P P L I G Q Q S T V S D V P R D L E V V A A T P T S L L I S W D A P A V T V R Y Y R I T Y G E T G G N S P V Q E F T V P G S K S T A T I S G L K P G V D Y T I T V Y A C R R R G D N P D C S K P I S I N Y R T (SEQ ID NO: 32) |
| FN III 9-10 (L1408P) (CX$_8$C) | G L D S P T G I D F S D I T A N S F T V H W I A P R A T I T G Y R I R H H P E H F S G R P R E D R V P H S R N S I T L T N L T P G T E Y V V S I V A L N G R E E S P P L I G Q Q S T V S D V P R D L E V V A A T P T S L L I S W D A P A V T V R Y Y R I T Y G E T G G N S P V Q E F T V P G S K S T A T I S G L K P G V D Y T I T V Y A V C R A R G D F P D C S K P I S I N Y R T (SEQ ID NO: 108) |
| FN III 9-10 (L1408P) (CX$_8$C) | G L D S P T G I D F S D I T A N S F T V H W I A P R A T I T G Y R I R H H P E H F S G R P R E D R V P H S R N S I T L T N L T P G T E Y V V S I V A L N G R E E S P P L I G Q Q S T V S D V P R D L E V V A A T P T S L L I S W D A P A V T V R Y Y R I T Y G E T G G N S P V Q E F T V P G S K S T A T I S G L K P G V D Y T I T V Y A V C R A R G D R P D C S K P I S I N Y R T (SEQ ID NO: 109) |
| FN III 9-10 (L1408P) (CX$_8$C) | G L D S P T G I D F S D I T A N S F T V H W I A P R A T I T G Y R I R H H P E H F S G R P R E D R V P H S R N S I T L T N L T P G T E Y V V S I V A L N G R E E S P P L I G Q Q S T V S D V P R D L E V V A A T P T S L L I S W D A P A V T V R Y Y R I T Y G E T G G N S P V Q E F T V P G S K S T A T I S G L K P G V D Y T I T V Y A V C R A R G D D P D C S K P I S I N Y R T (SEQ ID NO: 110) |
| FNIII 9-10 (L1408P, N1341A) (CX$_8$C) | G L D S P T G I D F S D I T A A S F T V H W I A P R A T I T G Y R I R H H P E H F S G R P R E D R V P H S R N S I T L T N L T P G T E Y V V S I V A L N G R E E S P P L I G Q Q S T V S D V P R D L E V V A A T P T S L L I S W D A P A V T V R Y Y R I T Y G E T G G N S P V Q E F T V P G S K S T A T I S G L K P G V D Y T I T V Y A C R A R G D N P D C S K P I S I N Y R T (SEQ ID NO: 111) |
| FNIII 9-10 (L1408P, PPSRN) (CX$_8$C) | G L D S P T G I D F S D I T A N S F T V H W I A P R A T I T G Y R I R H H P E H F S G R P R E D R V P P S R N S I T L T N L T P G T E Y V V S I V A L N G R E E S P P L I G Q Q S T V S D V P R D L E V V A A T P T S L L I S W D A P A V T V R Y Y R I T Y G E T G G N S P V Q E F T V P G S K S T A T I S G L K P G V D Y T I T V Y A C R A R G D N P D C S K P I S I N Y R T (SEQ ID NO: 112) |
| FNIII 9-10 (L1408P, KHSRN) (CX$_8$C) | G L D S P T G I D F S D I T A N S F T V H W I A P R A T I T G Y R I R H H P E H F S G R P R E D R V K H S R N S I T L T N L T P G T E Y V V S I V A L N G R E E S P P L I G Q Q S T V S D V P R D L E V V A A T P T S L L I S W D A P A V T V R Y Y R I T Y G E T G G N S P V Q E F T V P G S K S T A T I S G L K P G V D Y T I T V Y A C R A R G D N P D C S K P I S I N Y R T (SEQ ID NO: 113) |
| FNIII 9-10 (L1408P, DHSRN) (CX$_8$C) | G L D S P T G I D F S D I T A N S F T V H W I A P R A T I T G Y R I R H H P E H F S G R P R E D R V D H S R N S I T L T N L T P G T E Y V V S I V A L N G R E E S P P L I G Q Q S T V S D V P R D L E V V A A T P T S L L I S W D A P A V T V R Y Y R I T Y G E T G G N S P V Q E F T V P G S K S T A T I S G L K P G V D Y T I T V Y A C R A R G D N P D C S K P I S I N Y R T (SEQ ID NO: 114) |
| FN III 9-10 (CX$_8$C) | G L D S P T G I D F S D I T A N S F T V H W I A P R A T I T G Y R I R H |

TABLE 1-continued

| Description | Sequence |
|---|---|
| | H P E H F S G R P R E D<br>R V P H S R N S I T L T<br>N L T P G T E Y V V S I<br>V A L N G R E E S P L L<br>I G Q Q S T V S D V P R<br>D L E V V A A T P T S L<br>L I S W D A P A V T V R<br>Y Y R I T Y G E T G G N<br>S P V Q E F T V P G S K<br>S T A T I S G L K P G V<br>D Y T I T V Y A C T G R<br>G D S P A C S K P I S I<br>N Y R T (SEQ ID NO: 34) |
| FNIII 9-10<br>L1408P, A1340D | G L D S P T G I D F S D<br>I T D N S F T V H W I A<br>P R A T I T G Y R I R H<br>H P E H F S G R P R E D<br>R V P H S R N S I T L T<br>N L T P G T E Y V V S I<br>V A L N G R E E S P P L<br>I G Q Q S T V S D V P R<br>D L E V V A A T P T S L<br>L I S W D A P A V T V R<br>Y Y R I T Y G E T G G N<br>S P V Q E F T V P G S K<br>S T A T I S G L K P G V<br>D Y T I T V Y A V T G R<br>G D S P A S S K P I S I<br>N Y R T (SEQ ID NO: 36) |
| FNIII 9-10<br>L1408P, V1442K | G L D S P T G I D F S D<br>I T A N S F T V H W I A<br>P R A T I T G Y R I R H<br>H P E H F S G R P R E D<br>R V P H S R N S I T L T<br>N L T P G T E Y V V S I<br>V A L N G R E E S P P L<br>I G Q Q S T V S D V P R<br>D L E V V A A T P T S L<br>L I S W D A P A K T V R<br>Y Y R I T Y G E T G G N<br>S P V Q E F T V P G S K<br>S T A T I S G L K P G V<br>D Y T I T V Y A V T G R<br>G D S P A S S K P I S I<br>N Y R T (SEQ ID NO: 38) |
| FNIII 9-10<br>L1408P, A1340D,<br>V1442K | G L D S P T G I D F S D<br>I T D N S F T V H W I A<br>P R A T I T G Y R I R H<br>H P E H F S G R P R E D<br>R V P H S R N S I T L T<br>N L T P G T E Y V V S I<br>V A L N G R E E S P P L<br>I G Q Q S T V S D V P R<br>D L E V V A A T P T S L<br>L I S W D A P A K T V R<br>Y Y R I T Y G E T G G N<br>S P V Q E F T V P G S K<br>S T A T I S G L K P G V<br>D Y T I T V Y A V T G R<br>G D S P A S S K P I S I<br>N Y R T (SEQ ID NO: 40) |
| FNIII 9-10<br>L1408P, T1491R | G L D S P T G I D F S D<br>I T A N S F T V H W I A<br>P R A T I T G Y R I R H<br>H P E H F S G R P R E D<br>R V P H S R N S I T L T<br>N L T P G T E Y V V S I<br>V A L N G R E E S P P L<br>I G Q Q S T V S D V P R<br>D L E V V A A T P T S L<br>L I S W D A P A V T V R |
| | Y Y R I T Y G E T G G N<br>S P V Q E F T V P G S K<br>S T A T I S G L K P G V<br>D Y T I T V Y A V G R<br>G D S P A S S K P I S I<br>N Y R T (SEQ ID NO: 72) |
| FNIII 9-10<br>L1408P, A1340C,<br>V1442C | G L D S P T G I D F S D<br>I T C N S F T V H W I A<br>P R A T I T G Y R I R H<br>H P E H F S G R P R E D<br>R V P H S R N S I T L T<br>N L T P G T E Y V V S I<br>V A L N G R E E S P P L<br>I G Q Q S T V S D V P R<br>D L E V V A A T P T S L<br>L I S W D A P A C T V R<br>Y Y R I T Y G E T G G N<br>S P V Q E F T V P G S K<br>S T A T I S G L K P G V<br>D Y T I T V Y A V T G R<br>G D S P A S S K P I S I<br>N Y R T (SEQ ID NO: 64) |
| FNIII 9-10,<br>L1408P, D1373R | G L D S P T G I D F S D<br>I T A N S F T V H W I A<br>P R A T I T G Y R I R H<br>H P E H F S G R P R E R<br>R V P H S R N S I T L T<br>N L T P G T E Y V V S I<br>V A L N G R E E S P P L<br>I G Q Q S T V S D V P R<br>D L E V V A A T P T S L<br>L I S W D A P A V T V R<br>Y Y R I T Y G E T G G N<br>S P V Q E F T V P G S K<br>S T A T I S G L K P G V<br>D Y T I T V Y A V T G R<br>G D S P A S S K P I S I<br>N Y R T (SEQ ID NO: 42) |
| FNIII 9-10,<br>L1408P, R1379D | G L D S P T G I D F S D<br>I T A N S F T V H W I A<br>P R A T I T G Y R I R H<br>H P E H F S G R P R E D<br>R V P H S D N S I T L T<br>N L T P G T E Y V V S I<br>V A L N G R E E S P P L<br>I G Q Q S T V S D V P R<br>D L E V V A A T P T S L<br>L I S W D A P A V T V R<br>Y Y R I T Y G E T G G N<br>S P V Q E F T V P G S K<br>S T A T I S G L K P G V<br>D Y T I T V Y A V T G R<br>G D S P A S S K P I S I<br>N Y R T (SEQ ID NO: 44) |
| FNIII 9-10,<br>L1408P, D1373R,<br>R1379D | G L D S P T G I D F S D<br>I T A N S F T V H W I A<br>P R A T I T G Y R I R H<br>H P E H F S G R P R E R<br>R V P H S D N S I T L T<br>N L T P G T E Y V V S I<br>V A L N G R E E S P P L<br>I G Q Q S T V S D V P R<br>D L E V V A A T P T S L<br>L I S W D A P A V T V R<br>Y Y R I T Y G E T G G N<br>S P V Q E F T V P G S K<br>S T A T I S G L K P G V<br>D Y T I T V Y A V T G R<br>G D S P A S S K P I S I<br>N Y R T (SEQ ID NO: 46) |

TABLE 1-continued

| Description | Sequence |
|---|---|
| FNIII 10 variant | V S D V P R D L E V V A<br>A T P T S L L I S W D A<br>P A V T V R Y Y R I T Y<br>G E T G G N S P V Q E F<br>T V P G S K S T A T I S<br>G L K P G V D Y T I T V<br>Y A V T E R G D N P E S<br>S K P I S I N Y R T<br>(SEQ ID NO: 48) |
| FNIII 10 variant | V S D V P R D L E V V A<br>A T P T S L L I S W D A<br>P A V T V R Y Y R I T Y<br>G E T G G N S P V Q E F<br>T V P G S K S T A T I S<br>G L K P G V D Y T I T V<br>Y A V T E R G D N E G<br>S K P I S I N Y R T<br>(SEQ ID NO: 50) |
| FNIII 10 variant | V S D V P R D L E V V A<br>A T P T S L L I S W D A<br>P A V T V R Y Y R I T Y<br>G E T G G N S P V Q E F<br>T V P G S K S T A T I S<br>G L K P G V D Y T I T V<br>Y A V T A R G D N P E S<br>S K P I S I N Y R T<br>(SEQ ID NO: 52) |
| FNIII 10 variant | V S D V P R D L E V V A<br>A T P T S L L I S W D A<br>P A V T V R Y Y R I T Y<br>G E T G G N S P V Q E F<br>T V P G S K S T A T I S<br>G L K P G V D Y T I T V<br>Y A V A A R G D N P E S<br>S K P I S I N Y R T<br>(SEQ ID NO: 54) |
| FNIII 10 variant, D1422N | V S D V P R N L E V V A<br>A T P T S L L I S W D A<br>P A V T V R Y Y R I T Y<br>G E T G G N S P V Q E F<br>T V P G S K S T A T I S<br>G L K P G V D Y T I T V<br>Y A V T G R G D S P A S<br>S K P I S I N Y R T<br>(SEQ ID NO: 65) |
| FNIII 9-10 variant | G L D S P T G I D F S D<br>I T A N S F T V H W I A<br>P R A T I T G Y R I R H<br>H P E H F S G R P R E D<br>R V P H S R N S I T L T<br>N L T P G T E Y V V S I<br>V A L N G R E E S P L L<br>I G Q Q S T V S D V P R<br>D L E V V A A T P T S L<br>L I S W D A P A V T V R<br>Y Y R I T Y G E T G G N<br>S P V Q E F T V P G S K<br>S T A T I S G L K P G V<br>D Y T I T V Y A V T E R<br>G D N P E S S K P I S I<br>N Y R T (SEQ ID NO: 56) |
| FNIII 9-10 variant | G L D S P T G I D F S D<br>I T A N S F T V H W I A<br>P R A T I T G Y R I R H<br>H P E H F S G R P R E D<br>R V P H S R N S I T L T<br>N L T P G T E Y V V S I<br>V A L N G R E E S P L L<br>I G Q Q S T V S D V P R<br>D L E V V A A T P T S L<br>L I S W D A P A V T V R<br>Y Y R I T Y G E T G G N<br>S P V Q E F T V P G S K<br>S T A T I S G L K P G V<br>D Y T I T V Y A V T E R<br>G D N E G S K P I S I<br>N Y R T (SEQ ID NO: 58) |
| FNIII 9-10 variant (L1408P) | G L D S P T G I D F S D<br>I T A N S F T V H W I A<br>P R A T I T G Y R I R H<br>H P E H F S G R P R E D<br>R V P H S R N S I T L T<br>N L T P G T E Y V V S I<br>V A L N G R E E S P P L<br>I G Q Q S T V S D V P R<br>D L E V V A A T P T S L<br>L I S W D A P A V T V R<br>Y Y R I T Y G E T G G N<br>S P V Q E F T V P G S K<br>S T A T I S G L K P G V<br>D Y T I T V Y A V T A R<br>G D N P E S S K P I S I<br>N Y R T (SEQ ID NO: 60) |
| FNIII 9-10 variant (L1408P) | G L D S P T G I D F S D<br>I T A N S F T V H W I A<br>P R A T I T G Y R I R H<br>H P E H F S G R P R E D<br>R V P H S R N S I T L T<br>N L T P G T E Y V V S I<br>V A L N G R E E S P P L<br>I G Q Q S T V S D V P R<br>D L E V V A A T P T S L<br>L I S W D A P A V T V R<br>Y Y R I T Y G E T G G N<br>S P V Q E F T V P G S K<br>S T A T I S G L K P G V<br>D Y T I T V Y A V A A R<br>G D N P E S S K P I S I<br>N Y R T (SEQ ID NO: 62) |

As used herein, the twenty conventional amino acids and their abbreviations follow conventional usage. See IMMUNOLOGY—A SYNTHESIS, 2nd Edition, (E. S. Golub and D. R. Gren, Eds.), 1991, Sinauer Associates, Sunderland, Mass., which is incorporated herein by reference for any purpose. According to certain embodiments, single or multiple amino acid substitutions (in certain embodiments, conservative amino acid substitutions) may be made in the naturally-occurring sequence (in certain embodiments, in the portion of the polypeptide outside the domain(s) forming intermolecular contacts or comprising functional domains). In certain embodiments, a conservative amino acid substitution does not substantially change the structural characteristics of the parent sequence (e.g., a replacement amino acid should not disrupt secondary structure that characterizes the parent or native protein, such as a helix). Examples of art-recognized polypeptide secondary and tertiary structures are described in PROTEINS, STRUCTURES AND MOLECULAR PRINCIPLES (Creighton, Ed.), 1984, W. H. New York: Freeman and Company; INTRODUCTION TO PROTEIN STRUCTURE (Branden and Tooze, eds.), 1991, New York: Garland Publishing; and Thornton et at., 1991, *Nature* 354: 105, which are each incorporated herein by reference.

Naturally occurring residues may be divided into classes based on common side chain properties: 1) hydrophobic: norleucine, Met, Ala, Val, Leu, Ile; 2) neutral hydrophilic:

Cys, Ser, Thr, Asn, Gln; 3) acidic: Asp, Glu; 4) basic: His, Lys, Arg; 5) residues that influence chain orientation: Gly, Pro; and 6) aromatic: Trp, Tyr, Phe.

Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties.

In contrast, non-conservative substitutions may involve the exchange of a member of one of these classes for a member from another class. Such substituted residues may be introduced into homologous or non-homologous or non-conserved regions of the molecule.

In making such changes, according to certain embodiments, the hydropathic index of amino acids may be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5) (Kyte et al., 1982, *J. Mol. Biol.* 157: 105-131).

The importance of the hydropathic amino acid index in conferring interactive biological function on a protein is understood in the art (see, for example, Kyte et al., 1982, ibid.). It is known that certain amino acids may be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those that are within ±1 are included, and in certain embodiments, those within ±0.5 are included.

It is also understood in the art that the substitution of like amino acids can be made effectively on the basis of hydrophilicity, particularly where the biologically functional protein or peptide thereby created is intended for use in immunological embodiments, as in the present case. In certain embodiments, the greatest local average hydrophilicity of a protein, as governed by the hydrophilicity of its adjacent amino acids, correlates with its immunogenicity and antigen-binding or immunogenicity, i.e., with a biological property of the protein.

As described in U.S. Pat. No. 4,554,101, the following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in certain embodiments, those that are within ±1 are included, and in certain embodiments, those within ±0.5 are included. Exemplary amino acid substitutions are set forth in Table 2.

TABLE 2

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, Gln, Asn, 1,4 Diamine-butyric Acid | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan can determine suitable variants of the polypeptide as set forth herein using well-known techniques. In certain embodiments, one skilled in the art can identify suitable areas of the molecule that can be changed without destroying activity by targeting regions not believed to be important for activity. In certain embodiments, one can identify residues and portions of the molecules that are conserved among similar polypeptides (by for example analysis of sequence alignment). In certain embodiments, even areas that are important for biological activity or for structure can be subject to conservative amino acid substitutions without destroying the biological activity or without adversely affecting the polypeptide structure.

Additionally, one skilled in the art can identify amino acid residues in similar or related polypeptides that are important for activity or maintaining structure. In view of such a comparison, one can predict the importance of amino acid residues in a protein that correspond to amino acid residues important for activity or structure in similar proteins. One skilled in the art may opt for chemically similar amino acid substitutions for such predicted important amino acid residues. An amino acid sequence alignment of FNIII 9-10 from different mammalian species is shown in FIG. 2.

One skilled in the art can also analyze the three-dimensional structure and amino acid sequence in relation to that structure in similar polypeptides. In view of such information, one skilled in the art can predict the alignment of amino acid residues of a polypeptide with respect to its three dimensional structure. In certain embodiments, one skilled in the art may choose not to make radical changes to amino acid residues predicted to be on the surface of the protein, since such residues may be involved in important interactions with other molecules. Moreover, one skilled in the art may generate test variants containing a single amino acid substitution at each desired amino acid residue. The variants can then be screened using activity assays known to those skilled in the art. Such variants can be used to gather information about suitable variants. For example, if it was discovered that a change to a particular amino acid residue resulted in destroyed, undesirably reduced, or unsuitable activity, variants with such a change can be avoided. In other words, based on information gathered from such routine experiments, one skilled in the art can readily determine the amino acids where further substitutions should be avoided either alone or in combination with other mutations.

Stereoisomers (e.g., D-amino acids) of the twenty conventional amino acids, non-naturally occurring amino acids such as α-,α-disubstituted amino acids, N-alkyl amino acids, lactic acid, and other unconventional amino acids may also be suitable components for polypeptides of the present invention. Examples of unconventional amino acids include but are not limited to: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

In certain other embodiments, the polypeptide comprising human fibronectin fragment further comprises a heterologous entity to form a fusion protein. The heterologous entity can facilitate detection and/or purification of the recombinantly synthesized human fibronectin fragment. Suitable heterologous entity includes without limitation a multi-histidine tag, GFP (green fluorescence protein) tag, GST (glutathione S-transferase) tag, and maltose binding protein tag, FLAG tag or HA tag. It is within the ability of one of skill in the art the selection of a suitable tag and construction of an expression vector that expresses the protein of interest with a heterologous tag (or epitope tag). The target protein linked to a desired epitope tag can be created by PCR, in which the sequence encoding the epitope tag is incorporated in the primer sequence. Expression vector designed for recombinant expression of a protein of interest conjugated to a heterologous tag is commercially available, for example, pGEX-2KS (GE Healthcare Life Sciences, Piscataway, N.J.) and pET21a (Novagen). In certain embodiments, the heterologous entity or epitope tag is removed by for example protease cleavage at a built-in protease cleavage site after purification of the recombinantly synthesized polypeptide.

The term "expression vector" refers to a vector that is suitable for transformation of a host cell or a target cell and contains nucleic acid sequences that direct and/or control the expression of inserted heterologous nucleic acid sequences. Expression includes, but is not limited to, processes such as transcription, translation, and RNA splicing, if introns are present. In certain embodiments, an expression vector comprises a polynucleotide sequence that encodes a human fibronectin fragment or variant thereof. In certain particular embodiments, the expression vector comprises a polynucleotide sequence that encodes a hexa-histidine-conjugated human fibronectin fragment or variant thereof.

Typically, expression vectors used in any of the host cells or target cells contain sequences for vector maintenance and for cloning and expression of exogenous nucleotide sequences. Such sequences, collectively referred to as "flanking sequences" in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation signal sequence, a polylinker region comprising one or a plurality of restriction endonuclease sites for inserting nucleic acid encoding the polypeptide to be expressed, and a selectable marker element.

The term "transduction" is used to refer to the transfer of genes from one bacterium to another, usually by a phage. "Transduction" also refers to the acquisition and transfer of eukaryotic cellular sequences by viruses such as retroviruses.

The term "transfection" is used to refer to the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., 1973, *Virology* 52: 456; Sambrook et al., 2001, MOLECULAR CLONING: A LABORATORY MANUAL, 3d ed., Cold Spring Harbor Laboratory Press, Cold Spring Harbor, N.Y.; Davis et al., 1986, BASIC METHODS IN MOLECULAR BIOLOGY (Elsevier); and Chu et al., 1981, *Gene* 13: 197. Such techniques can be used to introduce one or more exogenous DNA moieties into suitable host cells.

The term "transformation" as used herein refers to a change in a cell's genetic characteristics, and a cell has been transformed when it has been modified to contain a new DNA. For example, a cell is transformed where it is genetically modified from its native state. Following transfection or transduction, the transforming DNA may recombine with that of the cell by physically integrating into a chromosome of the cell, may be maintained transiently as an episomal element without being replicated, or may replicate independently as a plasmid. A cell is stably transformed when the DNA is replicated with the division of the cell.

The term "host cell" is used to refer to a cell into which has been introduced, or that is capable of having introduced, a nucleic acid sequence and then of expressing a gene of interest. The term includes the progeny of the parent cell, whether or not the progeny is identical in morphology or in genetic make-up to the original parent, so long as the gene is present. In preferred embodiments, the host cell is a eukaryotic cell, more preferably a mammalian cell and most preferably a rodent or human cell.

In another aspect, the invention provides methods of methods of inhibiting integrin-mediated cell adhesion, growth, migration or differentiation, comprising the step of contacting a cell with a therapeutically effective amount of the polypeptide of the instant invention, wherein the integrin is αvβ3 and/or α5β1 integrin. In yet another aspect, the invention provides methods of inhibiting or treating tumor growth, tumor progression or tumor metastasis in a mammal, comprising the step of administering to a mammal a pharmaceutical composition comprising the inventive polypeptides described herein, wherein the tumor expresses αvβ3 and/or α5β1. Non-exhaustive examples of suitable tumors include lung carcinoma, breast tumor, colon tumor, osteosarcoma, pancreatic tumor, ovarian tumor, cervical tumor, glioblastoma, prostate tumor, liver tumor and melanoma. In certain embodiments, the tumor expresses integrin α5β1, and the non-exhaustive examples of suitable tumors include lung, breast, colon, melanoma, osteosarcoma and prostate tumor. In certain other embodiments, the tumor expresses integrin αvβ3, and the non-exhaustive examples of suitable tumors include breast, melanoma, pancreatic, ovarian, cervical glioblastoma and prostate tumor.

In a further aspect, the invention provides methods of inhibiting an angiogenesis-related disease in a mammal comprising administering to a mammal in need thereof pharmaceutical compositions comprising the inventive polypeptides described herein, wherein the angiogenesis-related disease is cancer, macular degeneration, edema, arthritis, multiple sclerosis, vascular malformations, obesity, psoriasis, warts, allergic dermatitis, Kaposi's sarcoma in AIDS, diabetic retinopathy, primary pulmonary hypertension, asthma, cystic fibrosis, inflammatory bowel disease, periodontal disease, liver cirrhosis, endometriosis, ovarian cysts, uterine bleeding, osteomyelitis or diabetic nephropathy. In accordance with this aspect, in certain particular embodiments, the angiogenesis-related disease comprises a disease mediated by integrin αvβ3 and/or α5β1.

As used herein, the term "effective amount" or a "therapeutically effective amount" of an isolated polypeptide refers to an amount sufficient to achieve the stated desired result, for example, inhibiting integrin-mediated cell adhesion, growth, migration or differentiation, or inhibiting or treating tumor growth, tumor progression or tumor metastasis. The amount of a polypeptide or compound which constitutes an "effective amount" or "therapeutically effective amount" will vary depending on the polypeptide or compound, the disorder and its severity, and the age of the subject to be treated, but can be determined routinely by one of ordinary skill in the art. In certain embodiments, the subject is a mammal. In certain particular embodiments, the mammal is a human.

"Treating" or "treatment" as used herein covers the treatment of a disease or disorder described herein, in a mammal, for example a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder.

Administration routes for the pharmaceutical compositions of the invention include orally, through injection by intravenous, intraperitoneal, intracerebral (intra-parenchymal), intracerebroventricular, subcutaneous, intramuscular, intra-ocular, intraarterial, intraportal, or intralesional routes; by sustained release systems or by implantation devices. The pharmaceutical compositions may be administered by bolus injection or continuously by infusion, or by implantation device. The pharmaceutical composition also can be administered locally via implantation of a membrane, sponge or another appropriate material onto which the desired molecule has been absorbed or encapsulated. Where an implantation device is used, the device may be implanted into any suitable tissue or organ, and delivery of the desired molecule may be via diffusion, timed-release bolus, or continuous administration.

The polypeptides of the invention can be formulated according to known methods for preparing pharmaceutical compositions, in which the polypeptide to be delivered is combined with a pharmaceutically acceptable carrier, diluent or excipient. Suitable carrier, diluent and excipient and the preparation thereof are described, for example, in Genaro, A. O. "Remington: The Science and Practice of Pharmacy." Lippincott Williams & Wilkins (2005).

For aqueous pharmaceutical compositions used in vivo, sterile pyrogen-free water is preferred. Such formulations will contain an effective amount of the polypeptide together with a suitable amount of pharmaceutically acceptable carrier, diluent or excipient in order to prepare pharmaceutically acceptable compositions suitable for administration to a mammal, especially human. It is within the knowledge of one ordinarily skilled artisan or physician, and further taught in the instant application, the effective amount of the composition to be administered to a mammal, preferably a human to achieve the desirable therapeutic effect.

In certain embodiments, the composition comprising modified FN fragments of the invention can further comprise other anti-cancer, anti-angiogenesis and chemotherapy drugs to provide therapeutic effects.

The modified FN fragments of the invention can be chemically modified to prevent or reduce proteolytic degradation. Methods for chemical modification or optimization of protein or fragments thereof are well known in the art, including without limitation substitution of natural amino acid residues with unnatural amino acid residues, amino acid bond replacement, blocking N or C-terminal ends by N-acylation, N-pyroglutamate, and/or C-amidation, and N-terminal esterification or pegylation modifications. See for example Vlieghe et al., 2010, Drug Discovery Today, 15:40-56.

In a further aspect, kits are provided that comprise the inventive polypeptides, composition or pharmaceutical composition described herein. The pharmaceutical compositions of the present invention may be in the form of an emulsion, gel, solution, suspension, etc. The compositions of the present invention can also be lyophilized to produce a composition in a dried form for ease in transportation and storage. The compositions of the present invention may be stored in a sealed vial, container, ampule or the like. In the case where the composition is in a dried form, the composition is dissolved or resuspended (e.g., in sterilized distilled water or a buffer) before administration. An inert carrier such as saline or phosphate buffered saline or any such carrier, in which the composition has suitable solubility, may be used.

The Examples, which follow, are illustrative of specific embodiments of the invention, and various uses thereof. They are set forth for explanatory purposes only, and are not to be taken as limiting the invention.

EXAMPLES

Example 1 Construction of Expression Vectors Expressing Wild-type and Variants of FNIII Fragments Wild-type human FN III 9-10 was cloned and expressed in the vector pET21a (Novagen). The DNA encoding FNIII variants was composed of codons preferentially used in *E. coli*. Wild-type FNIII 9-10 coding sequence was amplified by polymerase chain reaction (PCR) with the forward primer 5'-CATATGCATATGCACCACCACCACCACCACG-GTCTTGATTCCCCAACT-3' (SEQ ID NO:75) that had the Nde I recognition site and six histidine residues for affinity purification. The reverse primer is 5'-AAGCT-TAAGCTTTCATGTTCGGTAATTAATGGAAATTGG-3' (SEQ ID NO: 76) with the Hind III recognition site and a TCA (or TTA) stop codon. The PCR product was purified and then ligated into the Nde I and Hind III sites of the *E. coli* recombination vector, pET21a (Novagen). The recombinant plasmid was used to transform *E. coli* DH5a strain, and colonies were selected on agar plates with LB (1% tryptone, 0.5% yeast extract, 1.0% NaCl, 1.0% agar at pH 7.4) and 100 μg/ml antibiotic Ampicillin.

FNIII 9-10 variants were synthesized and amplified by PCR using an overlapping oligonucleotide strategy with primers containing Nde I and Hind III restriction sites. The nucleotide sequences of various primers used for synthesizing or confirming variants are listed in Table 3.

The polymerase chain reactions were performed according to the procedure described in US2008/0188413, which is incorporated by reference herein in its entirety. Briefly, the reaction was carried out at 95° C. for 1 min, 55° C. for 1 min, and 72° C. for 1 min for 25 cycles. A mixture of primers was also used for generating multiple mutation sites. The PCR products were separated on 2% agarose gel electrophoresis and visualized by ethidium bromide staining. The desired PCR products were purified and then ligated into the Eco RI and Sac II sites of the yeast transfer vector pPICZ alpha A. The recombinant plasmid was used to transform an *Escherichia coli* XL1-blue strain and colonies were selected on agar plates containing antibiotic Zeocin. Plasmid DNA from Zeocin-positive colonies was amplified and isolated, and the FNIII sequences contained in the plasmids were confirmed by DNA sequencing.

TABLE 3

| Primer | Sequence | SEQ ID NO: |
|---|---|---|
| NdeI--3FN9-10 (forward) | CATATGCATATGCACCACCACCAC CACCACGGTCTTGATTCCCCAACT | 75 |
| HindIII--3FN9-10 (reverse) | AAGCTTAAGCTTTCATGTTCGGTA ATTAATGGAAATTGG | 76 |
| NdeI--3FN10 (forward) | CATATGCATATGCACCACCACCAC CACCACGTTTCTGATGTTCCGA | 77 |
| RGD loop PRGDMPD (F) | CGTGGTGATATGCCTGACAGCAGC AAG | 78 |
| RGD loop PRGDMPD (R) | AGGCATATCACCACGAGGAGTGAC AGCATA | 79 |
| RGD loop ARGDNPD (F) | CGTGGTGATAATCCTGACAGCAGC AAG | 80 |
| RGD loop ARGDNPD (R) | AGGATTATCACCACGAGCAGTGAC AGCATA | 81 |
| RGD loop PRGDWNEG (F) | GGAGACTGGAATGAAGGAAGCAAG CCA | 82 |
| RGD loop PRGDWNEG (R) | ATTCCAGTCTCCACGCGGAGTGAC AGCATA | 83 |
| RGD loop RARGDNPD (F) | TATGCTGTCCGTGCTCGTGGTGAT | 84 |
| RGD loop RARGDNPD (R) | ACCACGAGCACGGACAGCATACAC | 85 |
| 3FN9 L1408P (F) | AGTCCCCCGTTGATTGGC | 86 |
| 3FN9 L1408P (R) | CAACGGGGGACTTTCCTC | 87 |
| 3FN10 D1442N (F) | CCGAGGAATCTGGAAGTTG | 88 |
| 3FN10 D1442N (R) | CAGATTCCTCGGAACATC | 89 |
| Interdomian linkage A1340D (F) | TCTGATATTACTGATAACTCTTTT ACTGTG | 90 |
| Interdomian linkage A1340D (R) | AGAGTTATCAGTAATATCAGAAAA GTCAAT | 91 |
| Interdomain linkage V1422K (F) | GCTAAAACAGTGAGATATTACAGG ATC | 92 |
| Interdomain linkage V1422K (R) | CACTGTTTTAGCAGGAGCATCCCA | 93 |
| D1373R (F) | GAACGTCGGGTGCCC | 94 |
| D1373R (R) | CCGACGTTCACGAGGTCT | 95 |
| R1379D (F) | GTGCCCCACTCTGATAATTCCATC ACC | 96 |
| R1379D (R) | GGTGATGGAATTATCAGAGTGGGG CAC | 97 |

TABLE 3-continued

| Primer | Sequence | SEQ ID NO: |
|---|---|---|
| CX₇C CARGDNPDC (F) | CGTGGTGATAATCCTGACTGTAGC AAGCCA | 98 |
| CARGDNPDC (R) | AGGATTATCACCACGAGCACAGAC AGCATA | 99 |
| CPRGDMPDC (F) | CGTGGTGATATGCCTGACTGTAGC AAGCCA | 100 |
| CPRGDMPDC (R) | AGGCATATCACCACGAGGACAGAC AGCATA | 101 |
| CPRGDWNEC (F) | GGAGACTGGAATGAATGTAGCAAG CCA | 102 |
| CPRGDWNEC (R) | ATTCCAGTCTCCACGCGGACAGAC AGCATA | 103 |
| CX₈C CRARGDNPDC (F) | CGTGGTGATAATCCTGACTGTAGC AAGCCA | 104 |
| CRARGDNPDC (R) | AGGATTATCACCACGAGCACGACA AGCATACAC | 105 |
| CTGRGDSPAC (F) | GGTCGTGGAGACAGCCCCGCATGT AGCAAGCCA | 106 |
| CTGRGDSPAC (R) | GTCTCCACGACCAGTACAAGCATA CAC | 107 |

Example 2 Expression and Purification of FNIII 9-10 and FNIII 10 Variants

Protein expression of wild-type FNIII 9-10, FNIII 10 or variants thereof was carried out using the *Pichia* EASY-COMP™ Transformation Kit (Invitrogen) according to the manufacturer's recommendations with minor modifications. Briefly, a total of 10 μg plasmids containing DNA encoding FNIII 9-10, FNIII 10 or variants thereof were digested with Sac I to linearize the plasmids. *Pichia* strain X33 was transformed with the linearized constructs by a heat shock method, using the *Pichia* EASYCOMP™ Kit. The linearized construct was integrated at the 5' AOX1 locus by a single crossover. *Pichia* cells were lysed by Lyticase (Sigma) and analyzed by PCR to verify integration of the FNIII sequences into the *Pichia* genome. Colonies were selected on agar plates containing YPD (1% yeast extract, 2% peptone, 2% glucose, and 2% agar) and 100 μg/ml Zeocin. A number of colonies with multiple copies of the FNIII insertions were selected for the highest FNIII 9-10 or FNIII 10 protein expression.

Figure 6:
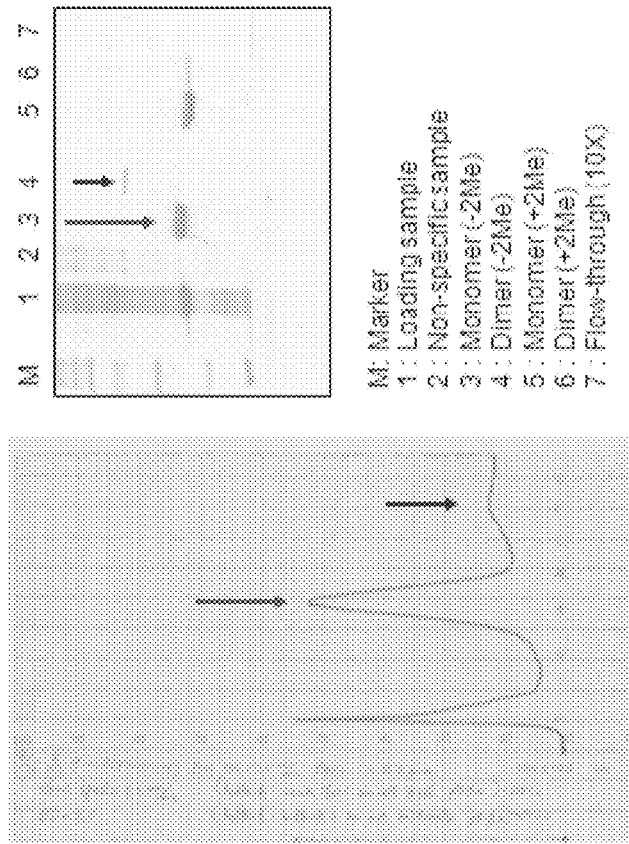
Figure 6:
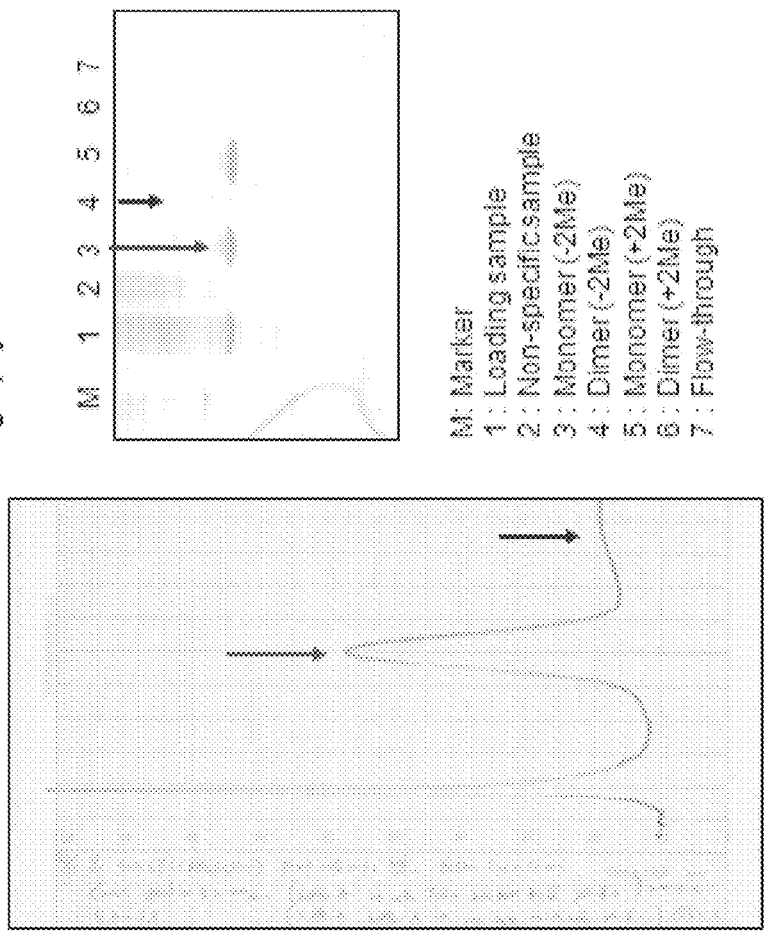
Figure 6:
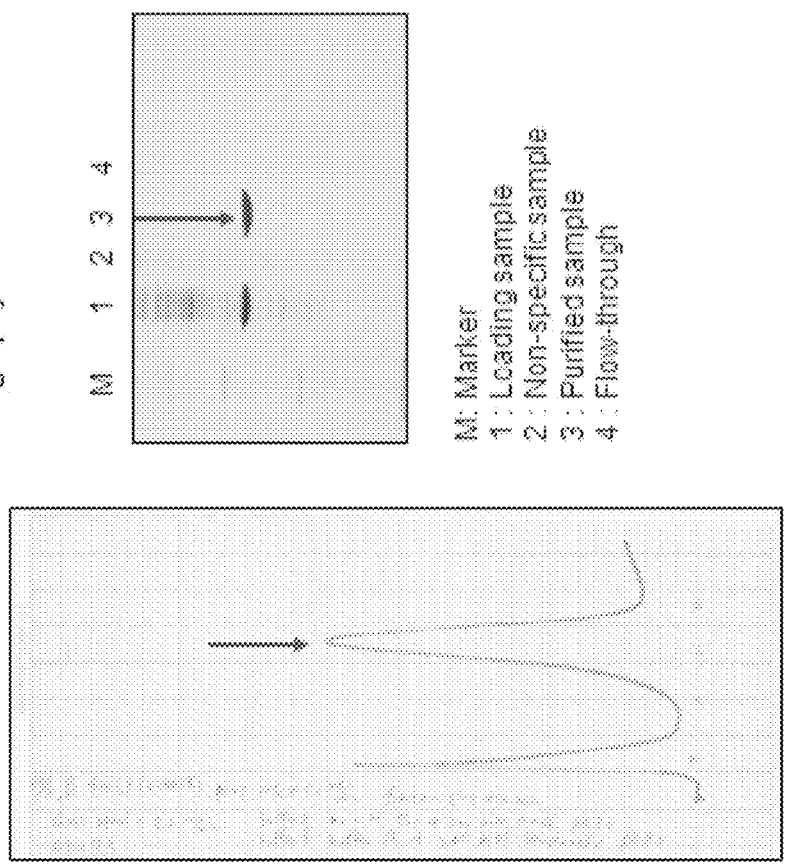

Recombinant FNIII 9-10, FNIII 10 and the variants were produced as follows: selected colonies were grown in the YPD medium (1% yeast extract, 2% peptone, and 2% dextrose) containing 100 μg/ml Zeocin at 30° C. After 48 hours, cells were collected by centrifugation and grown in 1 liter of minimal methanol medium (containing 1.34% yeast nitrogen base with ammonium sulfate without amino acids and $4 \times 10^{-5}$% biotin). A total of 1% methanol was added once every 24 hours to induce expression of FNIII or variants thereof for 2 days. The supernatant was collected by centrifugation and dialyzed twice against 5 liter buffer A (5 mM EDTA, 8M urea and 10 mM Na-phosphate buffer, pH 7.7). The final solution was loaded into a nickel-chelating column and eluted with a gradient of 200 mM imidazole. The recombinant FNIII 9-10, FNIII 10 and variants thereof were further purified by HPLC (reverse phase C18 HPLC). The purified recombinant FNIII had a purity of greater than 95% as judged by tricine-SDS-PAGE. Expression and purity of several FNIII variants is shown in FIG. 6. Representative HPLC profile and the purity of the FNIII 9-10 variants having the sequence of CPRGDMPDC (SEQ ID NO:20), L1408P (CARGDNPDC) protein (SEQ ID NO:22 and L1408P, V1442K substitution (SEQ ID NO:28) are shown in FIGS. 6A-C, respectively.

Example 3 FNIII 10 Intradomain Disulfide Bond Improved Stability and Solubility of FNIII 9-10 and FNIII 10

It was previously shown that a Leu to Pro substitution at amino acid position 1408 improved the stability of FNIII 9-10 (van der Walle et al., 2002, *Protein Engineering* 15:1021-24). The stability of intra-domain disulfide bond mutations in module 10 was tested by one-dimensional NMR spectrum analysis in buffer at different pH values. The presence of the L1408P mutation improved the stability of FNIII 9-10 at pH 5.0 as compared to wild type FNIII 9-10 in a solution containing 50 mM free arginine and glutamine. Free arginine and glutamine were added for the purpose of increasing maximal achievable protein concentration and improving long-term sample stability against precipitation and degradation (see Golovanov A. P., et al. J. Am. Chem. Soc. 126 (2004) 8933-8939). However, the stability of L1408P mutant decreased at higher pH, e.g., pH 6.0 (FIG. 3A, lower right panel), or lower pH, e.g., pH 3.5, in the absence of free arginine and glutamine. On the other hand, intradomain disulfide bond stabilized FNIII 9-10 in phosphate buffer even at pH 7.5 without the need for the L1408P mutation and without the need for free arginine and glutamine. As shown in FIG. 3A, upper right panel, FNIII 9-10 (CPRGDMPDC, SEQ ID NO:20) with the intradomain disulfide bond and without the L1408P mutation remained stable at pH 7.5, in a solution without arginine and glutamine. The intradomain disulfide bond also increased stability and solubility of FNIII 9-10 variants (FIG. 3B).

It has also been shown that substitution from Asp to Asn in module 10 at position 1422 (SEQ ID NO:65) improved stability of FNIII 10 in the presence of 50 mM free arginine and glutamine at pH 5. The stability of the D1422N mutant, however, decreased when the pH was increased to 5.4 and 6. See FIG. 3A, lower left panel. As shown in FIG. 3C, the intradomain disulfide bond present in FNIII 10 (CPRGDMPDC) protein (SEQ ID NO:6) improved stability and solubility of FNIII 10 without the need for the D1422N mutation (FIG. 3C).

Example 4 FNIII 9-10 or FNIII 10 Variants Inhibited Integrin α5β1- or αvβ3-mediated Cell Attachment The integrin antagonist activity of FNIII variants were evaluated by cell adhesion inhibition assays as described previously (Zhang, et al., 1998 *J Biol Chem* 273:7345-7350). Briefly, 96-well Immulon-2 microtiter plates (Costar, Corning, N.Y.) were coated with 100 µl of phosphate-buffered saline (PBS: 10 mM phosphate buffer, 0.15M NaCl, pH 7.4) containing substrates at a concentration of 50-500 nM, and incubated overnight at 4° C. The substrates for coating included: fibrinogen (FG) 50 µg/ml for α5β1, vitronectin (VN) 10 µg/ml for αvβ3, and fibronectin (FN) 25 µg/ml for αIIbβ3. Non-specific protein binding sites were blocked by incubating each well with 200 µl of heat-denatured 1% bovine serum albumin (BSA, Calbiochem) at room temperature (25° C.) for 1.5 hr. Afterwards, the blocking heat-denatured BSA was discarded and each well was washed twice with 200 µl of PBS.

Chinese hamster ovary (CHO) cells expressing αvβ3 (CHO-αvβ3) and α5β1 (CHO-α5β1) integrins were maintained in 100 µl of Dulbecco's Modified Eagle's Medium (DMEM) medium. Both CHO-αvβ3 and CHO-α5β1 were kind gifts of Dr. Y. Takada (Scripps Research Institute) established by stable transfection with a neomycin-resistant gene. CHO cells growing in log phase were detached by trypsinization and used in the assay at $3 \times 10^5$ cells/ml. FNIII 9-10, FNIII 10 and variants thereof were added to the cultured cells at the concentrations of 0.001-500 µM and incubated at 37° C. in 5% $CO_2$ for 15 minutes. The treated cells were then added into the coated plate and incubated at 37° C. in 5% $CO_2$ for 1 hour. The incubation solution was then discarded and non-adhered cells were removed by washing twice with 200 µl PBS.

Bound cells were quantified by crystal violet staining. Briefly, the well was fixed with 100 µl of 10% formalin for 10 minutes and dried. Fifty microliters of 0.05% crystal violet were then added into the well at room temperature for 20 minutes. Each well was washed with 200 µl of distilled water four times and dried. Colorization was carried out by adding 150 µl of colorizing solution (50% alcohol and 0.1% acetic acid). The resulting absorbance was read at 600 nm and the readings were correlated with the number of adhering cells. Inhibition was defined as % inhibition=100−[$OD_{600}$ (FNIII wild type or variant-treated sample)/$OD_{600}$ (untreated sample)]×100. $IC_{50}$ was defined as the concentration (nM) required for 50% inhibition of cell adhesion. Therefore, lower $IC_{50}$ indicates grater specificity or potency of the variant in inhibiting the cell adhesion activity of respective integrin. The results are summarized in Tables 4 and 5 below.

Wild type FNIII 10 did not effectively compete with FN for binding to integrin αvβ3 and thus did not show integrin αvβ3 antagonist activity in the cell adhesion assay. FNIII 10 with the sequence PRGDWNEGSK at amino acid positions 1492-1451 (SEQ ID NO:50) showed integrin αvβ3 binding activity, and competed with full length FN for binding to integrin αvβ3. See Table 4 and Richards et al., J Mol Biol. 2003, 326(5):1475-88.

It was unexpectedly discovered that introducing into the RGD loop a di-sulfide bond between two Cys substitutions flanking the RGD motif in a sequence comprising the formula of Cys-X7-Cys, for example between the T1491C and S1499C substitutions, greatly enhanced integrin αvβ3 antagonist activity (see e.g., Table 4, SEQ ID NO:6, 8 and 10 as compared to SEQ ID NO:2). In addition, the engineered di-sulfide bond further enhanced integrin αvβ3 antagonist activity of an FNIII 10 variant that already exhibited integrin αvβ3 antagonist activity. For example, two cysteine substitutions flanking the RGD motif in the background of FNIII 10 PRGDMPD (i.e., SEQ ID NO:6 with CPRGDMPDC) increased integrin αvβ3 binding affinity as compared to the variant without the Cys substitutions (SEQ ID NO:48) by 7 fold, and thus decreased the concentration required to inhibit 50% of cell adhesion (compare results of SEQ ID NO:6 with SEQ ID NO:48).

In summary, introduction of a di-sulfide bond within the loosely structured RGD loop substantially increased the binding affinity of FNIII variants for integrin αvβ3, and thus increased integrin αvβ3 antagonist activity as measured by the cell adhesion assay.

TABLE 4

| FIII Fragment | α5β1 (cell adhesion assay) | αvβ3 (cell adhesion assay) | αIIbβ3 (cell adhesion assay) | Platelet Aggregation (Inhibition of ADP-induced platelet aggregation) |
|---|---|---|---|---|
| Wild type FNIII 10 (SEQ ID NO: 2, VTGRGDSPASSK) (Control) | >4590 (39%)* | 4579 | >9180 (0%) | ~45000 |
| Control FNIII 10 mutant (SEQ ID NO: 50, VTPRGDWNEGSK) (Control) | >4513 (32.5%) | 908 | >9027 (0%) | >6454 (14%) |
| FNIII 10 C-$X_7$-C (SEQ ID NO: 6, VCPRGDMPDCSK) | >73218 (42%) | 93 | >62124 (19%) | ~62000 |
| FNIII 10 C-$X_7$-C (SEQ ID NO: 8, VCPRGDWNECSK) | >4494 (48%) | 418 | >4494 (0%) | ~10000 |
| FNIII 10 C-$X_7$-C (SEQ ID NO: 10, VCARGDNPDCSK) | >4546 (0%) | 432 | >4546 (0%) | >25463 (2%) |
| FNIII 10 variant (SEQ ID NO: 48, VTPRGDMPDSSK) | >6805 (31.7%) | 645 | >9073 (0%) | >22155 (4%) |
| FNIII 9-10 C-$X_7$-C (SEQ ID NO: 20, VCPRGDMPDCSK) | ~4765 | 112 | >2382 (26%) | >5003 (12%) |

*percentages in parentheses represent percentage of inhibition compared with control in the absence of the FN fragments Wild type FNIII 9-10 binds to integrin α5β1 but not integrin αvβ3. See results of wild type FNIII 9-10 (SEQ ID NO:4) in Table 5. Interestingly, FNIII 9-10 variants having an engineered di-sulfide bond flanking the RGD motif in the formula C—$X_7$—C exhibited altered binding specificity. For example, FNIII 9-10 having the amino acid sequence VCP RGDMPDCSK at amino acid positions 1490-1501 (SEQ ID NO:20) showed, instead of integrin α5β1, integrin αvβ3 antagonist activity, even though FNIII 9-10 has been considered an integrin α5β1 binder. See Table 4, comparing results of SEQ ID NOs:6 and 20 with those of Table 5, results of SEQ ID NO:4.

On the other hand, an intradomain di-sulfide bond formed by Cys substitutions in a sequence comprising the formula C—$X_8$—C did not alter the binding specificity of FNIII 9-10, and in some instances improved the binding affinity to integrin α5β1 (see e.g., Table 5, results of SEQ ID NO:32 as compared with results of SEQ ID NO:4 or SEQ ID NO:63).

It was previously shown that an interdomain di-sulfide bond between modules 9 and 10 (in the background of the L1408P substitution), although stabilized the FNIII 9-10 fragment, decreased the synergistic effect of module 9 to bind integrin α5β1 (Altroff et al., supra). The instant inventors, however, unexpectedly discovered that FNIII 9-10 (in the background of the L1408P substitution) with an interdomain linkage formed between an engineered Asp and Lys at positions 1340 and 1442 (A1340D and V1442K substitutions) maintained the binding affinity as compared to integrin α5β1 (see Table 5, results of SEQ ID NO:40 as compared to results of SEQ ID NO:4 or SEQ ID NO:63).

In addition, some of the FNIII 9-10 variants also acquired binding affinity to integrin αvβ3 (see Table 4, results of SEQ ID NO:60 as compared to results of SEQ ID NO:4 or SEQ ID NO:63).

TABLE 5

| FIII Fragment | α5β1 | αvβ3 | αIIbβ3 | Platelet Aggregation |
|---|---|---|---|---|
| Wild type FNIII 9-10 (SEQ ID NO: 4) (Control) | 245 | >3119 (33.2%) | >4798 (0%) | ~20000 |
| Control FNIII 9-10 mutant, L1408P (SEQ ID NO: 63) | 200 | >4802 (43.1%) | >4802 (0%) | ~30000 |
| FNIII 9-10, L1408P, C-$X_8$-C (SEQ ID NO: 32, CRARGDNPDCSK) | 67 | ~4766 | >19064 (39%) | >24781 (1.3%) |

TABLE 5-continued

| FIII Fragment | α5β1 | αvβ3 | αIIbβ3 | Platelet Aggregation |
|---|---|---|---|---|
| FNIII 9-10, L1408P, C-X$_8$-C (SEQ ID NO: 34, CTG<u>RGD</u>SPACSK) | 250 | 2092 | >4797 (0%) | >23508 (24%) |
| FNIII 9-10, L1408P, A1340D, V1442K (SEQ ID NO: 40) | 214 | 4240 | >4779 (2%) | >8602 (35.8%) |
| FNIII 9-10, L1408P, D1373R (SEQ ID NO: 42) | 224 | 3845 | >4791 (9%) | >12410 (40%) |
| FNIII 9-10 variant (SEQ ID NO: 56, VTP<u>RGD</u>MPDSSK) | 284 | 1728 | >4250 (0%) | >11446 (0%) |
| FNIII 9-10 variant (SEQ ID NO: 58, VTP<u>RGD</u>WNEGSK) | 270 | 1289 | >1250 (0%) | >4919 (28.5%) |
| FNIII 9-10 variant, L1408P (SEQ ID NO: 60, VTA<u>RGD</u>NPDSSK) | 165 | 423 | >4782 (0%) | >66959 (14.2%) |
| FNIII 9-10 variant, L1408P (SEQ ID NO: 62, VRA<u>RGD</u>NPDSSK) | 149 | ~3714 | >1250 (0%) | >21466 (7.8%) |
| FNIII 9-10, L1408P, C-X$_8$-C (SEQ ID NO: 108, CRA<u>RGD</u>FPDC) | 45 | | | |
| FNIII 9-10, L1408P, C-X$_8$-C (SEQ ID NO: 109, CRA<u>RGD</u>RPDC) | 53 | | | |
| FNIII 9-10, L1408P, C-X$_8$-C (SEQ ID NO: 110, CRA<u>RGD</u>DPDC) | 82 | | | |
| FNIII 9-10, L1408P, N1341A, C-X$_8$-C (SEQ ID NO: 111, CRA<u>RGD</u>NPDC) | 111 | | | |
| FNIII 9-10, L1408P, PPSRN, C-X$_8$-C (SEQ ID NO: 112, CRA<u>RGD</u>NPDC) | 66 | | | |
| FNIII 9-10, L1408P, KHSRN, C-X$_8$-C (SEQ ID NO: 113, CRA<u>RGD</u>NPDC) | 175 | | | |
| FNIII 9-10, L1408P, DHSRN, C-X$_8$-C (SEQ ID NO: 114, CRA<u>RGD</u>NPDC) | 562 | | | |

In summary, a di-sulfide bond introduced in the RGD loop of FNIII 9-10 in a sequence comprising the formula C—X$_8$—C can improve integrin α5β1 antagonist activity (Table 5, comparing results of SEQ ID NO:32 with SEQ ID NO:4, SEQ ID NO:63 and SEQ ID NO:62).

Example 5 FNIII 10 and FNIII 9-10 Variants Did Not Bind to Integrin αIIbβ3 and Did Not Induce Platelet Aggregation Venous blood (9 parts) samples from healthy donors who had not received any medication for at least two weeks were collected in 3.8% sodium citrate (1 part). Blood samples were centrifuged at 150×g for 10 min to obtain platelet-rich plasma (PRP) and allowed to stand for 5 min, and PRP was collected. The platelet-poor plasma (PPP) was prepared from the remaining blood by centrifuging at 2000×g for 25 min. The PPP platelet count was measured on a hematology analyzer and diluted to 250,000 platelets/µl. A solution of 190 µl of PRP and 10 µl of FNIII 10 or FNIII 9-10 variants at different concentrations or PBS buffer were incubated for 5 min in a Hema Tracer 601 aggregometer at 37° C. Ten microliters of 200 µM adenosine diphosphate (ADP) were further added to monitor the response of platelet aggregation by light transmission. As shown in Tables 4 and 5, none of the wild type or variants tested bound to integrin WIND or promoted platelet aggregation.

Example 6 The Effects of FNIII 10 or FNIII 9-10 Variants on Integrin-Mediated Cell Migration, Cell Survival and Cell Growth The effects of FNIII 10 or FNIII 9-10 variants on integrin-mediated biological process were analyzed. Human melanoma cells A375 or A549 stably expressing αvβ3 or α5β1 as confirmed by flow cytometry were incubated with FNIII 10 CPRGDMPDC (SEQ ID NO:6 with CPRGDMPDC) or FNIII 9-10 L1408P CRARGDNPDCSK (SEQ ID NO:32) and the effects on cell migration was examined by transwell assay. Cell migration (Haptotaxis) assays were performed as described previously (Bisanz et al., 2005, Model. Mol. Ther. 12:4 634-643). Inserts (Falcon) with 8-µm pore polycarbonate were coated with 200 µl of Fibronectin (50 µg/ml) on the underside of the porous membrane at room temperature for 2 h and then subjected to washing and blocking with 1% (w/v) heat-denatured BSA at room temperature for 2 h followed by two washes with PBS. Chambers were assembled with serum-free DMEM and then 1×10$^5$ cells were placed on the upper chamber. Each experiment was accompanied by a control consisting of a polycarbonate filter coated on the underside with PBS/1% (w/v) BSA, and this consistently demonstrated no migration. After 6-h incubation, cells were fixed with 3.7% formaldehyde and stained with crystal violet. Cells remaining in the upper chamber were removed with a cotton swab and migrating cells were photographed and quantified Inhibition of migration by FN-III variants were performed as above with the exception of adding different dosages of FN-III variants to the upper chambers at the time of plating. The results are summarized in FIG. 7A, which show that FN III variants inhibited cell migration.

In addition, the effects of the FNIII 10 or FNIII 9-10 variants on cell cycle arrest were examined. Cell cycle analyses were done as described previously (Brooks et al., 1994, Cell 79:1157-1164) with some modifications. Briefly, FN-III variants were added 24 hours after seeding, when the cells were well spread. 48 hours after treatment, floating and attached cells were washed and collected in PBS. Cells were centrifuged at 1,000 rpm for 10 min and resuspended in 3 ml of cold 70% PBS before stored at −80° C. overnight. After incubation at 4° C. for 45 min, cells were harvested and centrifuged at 1,300 rpm for 10 min at 4° C. Subsequently cells were resuspended in 1 ml PI staining solution (200 µl of 1 mg/ml propidium iodide, 200 µl RNase A and 200 µl 5% Triton X-100 in 9.4 ml PBS) at 37° C. for 15 min. Cell fluorescence was measured using a FACScan flow cytometer (Becton-Dickinson) as described above. The results are summarized in FIG. 7B. In summary, treatment of FNIII wild type fragments caused increased percentage of G1 cells as compared to control (PBS), and treatment of FN III variants further induced cell cycle arrest.

Further, the ability of FNIII or FNIII 9-10 variants to induce apoptosis was analyzed. Cell apoptosis experiments were done as described previously (Maubant et al., 2006, *Blood* 108: 3035-3044) with some modification. Briefly, FN-III variants were added 24 hours after seeding, when the cells were well spread. 48 hours after treatment, floating and attached cells were collected and subjected to 100 µlannexin V/propidium iodide (PI) staining using annexin V-Alexa Fluor 488 (Molecular Probes) and PI (Sigma) at 37° C. for 15 min. The resultant fluorescence was measured by flow cytometry. Staining cells with a combination of annexin V and PI revealed nonapoptotic cells (annexin $V^-/PI^-$), early apoptotic cells (annexin $V^+/PI^-$), late apoptotic cells (annexin $V^+/PI^+$), and necrotic cells (annexin $V^-/PI^+$). The results are summarized in FIGS. 7C-7D. In summary, FNIII and variants thereof induced apoptosis in integrin-expressing cells.

Having described the invention in detail and by reference to specific embodiments thereof, it will be apparent that modifications and variations are possible without departing from the scope of the invention defined in the appended claims. More specifically, although some aspects of the present invention are identified herein as particularly advantageous, it is contemplated that the present invention is not necessarily limited to these particular aspects of the invention.

Example 6 Thermostability and Solubility of the Variants of the Invention

Thermostability Measured by Differential Scanning Calorimetry (DSC)

It is important for a biotherapeutic to remain stable throughout manufacturing, storage, and delivery to the patients. Differential scanning calorimetry (DSC) allows for the accurate, rapid and easy measurement of Tm, the thermal transition midpoint of a protein, which has been shown to be a good indicator of the relative stability of biotherapeutics in solution (Demarest et al., 2004; Sanchez-Ruiz et al., 1988; Vermeer and Norde, 2000). Consequently, DSC was applied to: (1) screen buffers and excipients for formulation; (2) screen therapeutic candidates with reasonable stability in addition to activity; and (3) predict protein aggregation tendency. For the above reasons, we characterized the stability of our designed proteins, Tm of $^{9,10}$Fn3 variants and $^{10}$Fn3 variants by DSC.

DSC analysis was performed using a VP-DSC microcalorimeter (MicroCal). Samples were dialyzed into prepared buffer using a 3-kDa molecular mass cutoff membrane, and the final concentration of sample were adjusted to ~0.7 mg/ml. All experiments were heated from 20 to 110° C. at a scan rate of 60° C./hr. Buffer-buffer baselines were obtained under the same experimental conditions and subtracted from sample traces. Data analysis was performed in Origin 7.0 (OriginLab Corp, Northampton, Mass.) equipped with the DSC analysis add-on (MicroCal). Each protein excess heat capacity curve was corrected by reference subtraction of a matching buffer scan followed by concentration normalization of the data. The transition midpoint or melting temperature (apparent Tm) was determined by calculating the apex of the thermal denaturation curve from the normalized data.

Differential scattering calorimetry (DSC) experiment has been used to study thermally induced transitions of biological macromolecules by monitoring the excess heat capacity of a solution (Cp) of the molecule of interest as a function of temperature (Bruylants et al., 2005; Spink, 2008). We carried out DSC experiments of a series of our engineered proteins for thermal stability comparison in PBS buffer. Since thermal denaturation process for our proteins was irreversible, the melting temperature (Tm) instead of transition enthalpy (ΔH°m) was used to reflect the stability for our proteins. The heat-induced unfolding of these proteins produced a DSC profile consisting of one endothermic transition. Deconvolution of the DSC trace using a non-two-state transition model yielded one endotherm with a Tm. The fitness of the model was confirmed by comparison of the experimental and calculated traces. A denaturation curve with only one peak is usually taken to indicate the presence in the protein molecule of more than one domain, with the various domains undergoing denaturation not independently of each other. DSC experiments on three representative proteins exhibited a Tm value of 62.4° C., 60.8° C. and 58.7° C. in FNIII 9-10 L1408P (CRARGDNPDC) variant (SEQ ID NO:32), FNIII 9-10, L1408P (SEQ ID NO:63) and FNIII 9-10 L1408P (RARGDNPD) variant (SEQ ID NO:62), respectively (see Table 6 and FIG. 8A). Stability of FNIII 10 wild type (SEQ ID NO:2), FNIII 10, FNIII 10 PRGDMPD variant (SEQ ID NO:48) and FNIII 10 (CPRGDMPDC) variant (SEQ ID NO: 6) variants is 80.7° C., 74.3° C. and 85.0° C., respectively (see Table 7 and FIG. 9A). The presence of only one predominant endotherm confirmed the lack of heterogeneity due to the product with or without a disulfide bond. In this study, the Tm values of the DSC transitions were reproducible and therefore may be assumed to reflect the relative thermal stabilities of WT and its mutants.

TABLE 6

After the incorporation of a disulfide bond, FNIII 9-10 variant increased their thermostability (3.7° C.) and solubility (~6-fold).

| Protein | Thermostability (° C.) | Solubility (mg/ml) |
|---|---|---|
| FNIII 9-10, L1408P (SEQ ID NO: 63) | 60.8 | 19.9 |
| FNIII 9-10 RARGDNPD (SEQ ID NO: 62) | 58.7 | 4.0 |
| FNIII 9-10 CRARGDNPDC (SEQ ID NO: 32) | 62.4 | 24.4 |

TABLE 7

After the incorporation of a disulfide bond, FN-III10 variant increased their thermostability (10.7° C.) and solubility (~4-fold).

| Protein | Thermostability (° C.) | Solubility (mg/ml) |
| --- | --- | --- |
| FNIII 10 wild type (SEQ ID NO: 2) | 80.7 | 7.3 |
| FNIII 10 variant (TPRGDMPD; SEQ ID NO: 48) | 74.3 | 5.3 |
| FNIII 10 variant (CPRGDMPDC, SEQ ID NO: 6) | 85.0 | 27.8 |

Solubility Measured by Ammonium Sulfate Precipitation

Solubility is a concern of physicochemical properties studied during pharmaceutical preformulation. For liquid dosage form development, accurate solubility data are essential to ensure the robustness of the finished product. For solid dosage forms, solubility data are important in determining if an adequate amount of drug is available for absorption in vivo. If a compound has a low aqueous solubility, it may be subject to dissolution rate-limited or solubility-limited absorption within the gastrointestinal (GI) residence time. Methods that can be used to increase protein solubility are useful in high resolution structural studies and pharmaceutical applications. Several studies have succeeded in using site-directed mutagenesis of surface residues to enhance protein solubility. Here, we investigate the intrinsic determinants of protein solubility by studying how mutation on RGD loop of folded proteins influences their solubilities.

Protein precipitation using ammonium sulfate has been successful in measuring protein solubility. (Trevino, S. R., Scholtz, J. M., and Pace, C. N. (2008). Measuring and increasing protein solubility. Journal of pharmaceutical sciences 97, 4155-4166). Although ammonium sulfate precipitation can give quick and accurate information on relative solubility values of variants of the same protein. This method is experimentally reliable since factors which are difficult to control such as the water/buffer content of lyophilized protein or incidental ions that might get introduced during the course of the experiment become masked by the high concentration of salt. Besides, this method produces precipitated solutions with well-defined aqueous and solid phases, and it requires relatively small amounts of protein (10 mg or less)—even when studying a highly soluble protein.

All measurements were performed at room temperature (25° C.) as previously described (Trevino, S. R., Scholtz, J. M., and Pace, C. N. (2008). Measuring and increasing protein solubility. Journal of pharmaceutical sciences 97, 4155-4166. Briefly, three solutions (50 mM buffer, 3.0 M ammonium sulfate in 50 mM buffer, and a protein stock solution in 50 mM buffer) were mixed together in a 0.2 ml PCR tube for a final sample volume of 15 µl with the desired ammonium sulfate and protein concentrations. The sample was allowed to equilibrate for >1 min for amorphous salting-out processes. Then the sample was transferred to 1.5 ml Eppendorf tubes and centrifuged for 1 min at 16,000 g for the removal of aggregation. The spectrophotometer was blanked with 495 µl of a 1.1 M ammonium sulfate solution. After centrifugation, 5 µl of the sample was added to the 495 µl blanking solution and mixed to generate a 100-fold dilution for the absorbance measurements.

Protein solubility determination bt ammonium sulfate method was used for inducing amorphous precipitation (Trevino, S. R., Scholtz, J. M., and Pace, C. N. (2008). Measuring and increasing protein solubility. Journal of pharmaceutical sciences 97, 4155-4166). Solubility curves as a function of ammonium sulfate concentration for proteins were used to indicate the solubility of protein of interest. Solubility of FNIII 9-10 L1408P (CRARGDNPDC) variant (SEQ ID NO:32), wild type protein and FNIII 9-10 L1408P (RARGDNPD) variant is 24.4, 19.9 and 4.0 mg/ml (see Table 6 and FIG. 8B). Solubility of FNIII 10, FNIII 10 wild type (SEQ ID NO:2), FNIII 10 (TPRGDMPD) variant (SEQ ID NO:48) and FNIII 10 (CPRGDMPDC) variant (SEQ ID NO:6) is 7.3, 5.3 and 27.8 mg/ml (see Table 7 and FIG. 9B). Each solubility value was repeated three times and therefore may be assumed to reflect the relative solubility of WT and its mutants. Taken together, the incorporation of disulfide bond into integrin α5β1-specific FNIII 9-10 L1408P (CRARGDNPDC) variant (SEQ ID NO:32) and integrin αvβ3-specific FNIII 10 (CPRGDMPDC) variant (SEQ ID NO:6) had increased their stability and solubility (see FIGS. 8B and 9B).

Example 7 The Effects on Growth Factor-induced Vascular Tube Formation in Vitro

One of the common used in vitro assays to model the reorganization stage of angiogenesis is the tube formation assay (Arnaoutova, I., and Kleinman, H. K. (2010). In vitro angiogenesis: endothelial cell tube formation on gelled basement membrane extract. Nature protocols 5, 628-635). The assay measures the ability of endothelial cells, plated at subconfluent densities with the appropriate extracellular matrix support, to form capillary-like structures. Typically, the ability can be quantified by measuring the number, length, or area of these capillary-like structures in microscope images of the culture dish. Given that compounds are able to inhibit tube formation, they should be useful in various diseases, such as cancer, where tumors stimulate new blood vessel formation to receive oxygen and nutrients for growth beyond a relatively small size. Here, we examined the ability of our designed mutants to promote or inhibit tube formation.

To evaluate the effect of Fn3 mutants on bFGF or VEGF-mediated endothelial tube formation in vitro, 15-well µ-slides (ibidi GmbH) were coated with 10 µL of Matrigel (BD Biosciences). HUVECs preincubated with Fn3 mutants for 15 minutes were added to the wells in M199 containing 2% FBS and endothelial cell growth supplement, and finally with 50 ng/ml bFGF or 20 ng/ml VEGF. The total tube length was measured using ImajeJ software and compared with the control at the indicated times. The micrographs of tube formation were taken and processed by an inverted microscope (Leica DM IRE2) equipped with a N PLAN 10x/0.25 objective lens and a CCD camera (CoolSNAP fx; Photometrics).

Inhibition on VEGF-induced Tube Formation by FNIII 9-10 (CRARGDNPDC) Variant (SEQ ID NO:32)

It was known that integrin α5β1 is involved in VEGF-induced angiogenesis. And blockade of integrin α5β1 could inhibit VEGF-induced angiogenesis in vitro and in vivo. To assess whether our integrin α5β1-specific antagonist may suppress capillary tube formation and the Matrigel plug assay. Flow cytometry analysis showed that integrin α5β1 is overexpressed on HUVECs. We chose FNIII 9-10 L1408P (CRARGDNPDC) variant (SEQ ID NO:32) for this study, as it had the strongest binding and robust biophysical property. FNIII 9-10 L1408P (CRARGDNPDC) variant (SEQ ID NO:32) inhibited VEGF-induced capillary tube formation by HUVECs grown on Matrigel, an extracellular basement membrane matrix (Kleinman et al., 1986), with $IC_{50}$ values of approximately 1.6 µM (FIG. 10A). However, FNIII 9-10 L1408P (CRARGDNPDC) variant (SEQ ID NO:32) did not inhibit bFGF-induced capillary tube formation by HUVECs grown on Matrigel (FIG. 10B). The results suggest that our integrin α5β1-specific antagonist can specifically target integrin α5β1 on HUVECs cells and interfere with its involvement in VEGF-inducing tube formation.

No Inhibition on bFGF-induced Tube Formation by FNIII 10 (CPRGDMPDC) Variant (SEQ ID NO: 6)

$^{10}$Fn3(CPRGDMPDC) variant (SEQ ID NO:6) did not inhibit VEGF-induced and bFGF-induced capillary tube formation by HUVECs grown on Matrigel respectively. However, FNIII 10 (CPRGDMPDC) variant (SEQ ID NO:6) did inhibit bFGF-induced angiogenesis in vivo. In addition to tube formation, HUVECs migration also is involved in the process of angiogenesis. Therefore, we speculated that our integrin αvβ3-specific antagonist may interfere with migration but not tube formation under bFGF-inducing condition. This will be further confirmed in bFGF-induced transwell migration assay.

Example 8 In vivo Matrigel Plug Angiogenesis Assay

The Matrigel plug angiogenesis assay is a simple in vivo technique to detect the newly formed blood vessels in the transplanted gel plugs in nude mice). The Matrigel matrix composition is comparable to the basement membrane proteins. It can induce differentiation of a variety of cell types such as endothelial cells. The levels of activity of angiogenic or antiangiogenic compounds can be visually assessed by color differences in the plugs compared to the controls. Further quantitation can be performed using a variety of methods like hemoglobin detection. In our case, growth factors (VEGF or bFGF) with or without proteins are mixed with the Matrigel then is injected into the mice to determine the antiangiogenic activities of proteins.

To assess angiogenic effects in vivo, growth factor-reduced liquid Matrigel (0.25 mL) containing heparin (500 U/mL) with combinations of 125 ng bFGF/VEGF and Fn3 mutants were subcutaneously injected into C57BL/6 mice near the abdominal midline. Four days after implantation, mice were euthanized and the Matrigel plugs were surgically removed, photographed with a CMOS camera (600D, Canon), and the hemoglobin content of each Matrigel plug was measured with hemoglobin colorimetric assay kit (Cayman).

Inhibition on VEGF-induced Angiogenesis by FNIII 9-10 Variant (CRARGDNPDC) (SEQ ID NO:32)

We next measured the ability of the FNIII 9-10 L1408P (CRARGDNPDC) variant (SEQ ID NO:32) to block angiogenesis in vivo using a Matrigel plug assay. (Passaniti, R. M. Taylor, R. Pili, Y. Guo, P. V. Long, J. A. Haney, R. R. Pauly, D. S. Grant, G. R. Martin. A simple, quantitative method for assessing angiogenesis and antiangiogenic agents using reconstituted basement membrane, heparin, and fibroblast growth factor., Lab. Invest., 67 (1992), pp. 519-528)). Strikingly, FNIII 9-10 L1408P (CRARGDNPDC) variant (SEQ ID NO:32) inhibited angiogenesis to levels approaching that of the negative control (see FIG. 11). It indicates that integrin α5β1 play a role in VEGF-induced angiogenesis and this biological process can be blocked by our designed α5β1-specific antagonist.

(SEQ ID NO: 6)
Inhibition on bFGF-induced Angiogenesis by FNIII 10 (CPRGDMPDC) Variant We also measured the ability of the FNIII 10 (CPRGDMPDC) variant (SEQ ID NO:6) to block angiogenesis in vivo using a Matrigel plug assay. Strikingly, FNIII 10 (CPRGDMPDC) variant (SEQ ID NO:6) inhibited angiogenesis to levels approaching that of the negative control (FIG. 12). It indicates that integrin αvβ3 play a role in bFGF-induced angiogenesis and this biological process can be blocked by our designed αvβ3-specific antagonist.

Example 9 The Effects on the Growth of Human Tumor Xenografts in SCID Mice

The major preclinical screen for the development of novel cancer therapeutics is to be achieved by heterotransplantation of human cancer cells into immunodeficient rodents (xenograft models)(Christopher L Morton & Peter J Houghton, NATURE PROTOCOLS. 2007 247-250). These models have identified clinically efficacious agents, and still is the 'workhorse' of the pharmaceutical industry. To uncover the proposed mechanism of therapeutic approaches, molecular characteristics of tumor could be identified by immunohistochemistry staining of tumor bioposies. In this study, we establish two xenograft models to test the anti-tumor activities of two integrin antagonists respectively.

To assess the effect of FNIII mutant on tumor angiogenesis, NOD-SCID mice were given subcutaneous dorsal injections of $1 \times 10^6$ human melanoma/lung carcinoma cells. The mice were given s.c. injections of various amounts of E. coli-expressed FNIII mutants (5 or 10 mg/kg body weight) once daily. Tumors were harvested, photographed with a camera (T30, Sony), and sectioned. Intratumoral microvessels and cells were detected using IHC staining with Ab against CD31 (BD Biosciences) and Ki-67 (Leica) respectively. The images were captured using a BX51 microscope (Olympus, Tokyo, Japan). Intratumoral microvessel density and cells were quantified. Briefly, integrated optical density (IOD) of microvessels and cells were calculated in each section of the tumor at 10× magnification by using the Image-Pro Plus software.

Immunohistochemistry.

All tissue sections were deparaffinized, rehydrated and subjected to heat-induced antigen retrieval by autoclaving them for 6 min in 10 mM Tris-EDTA buffer (pH 9.0). Incubation with 3% $H_2O_2$ in methanol for 5 min, following 2 washes in TBS, the tissue sections were incubated with protein block (NovoLink™) for 5 min. Then the samples were mixed with primary antibodies in antibody diluents and incubated at room temperature for 30 min. Following 3 washes in TBS, the sections were incubated with secondary antibodies at room temperature for 10 min. After 3 washes in TBS, the samples were developed using DAB working solution (NovoLink™) for 3 min, counterstained with 0.02% hematoxylin for 5 min, and mounted with xylene. Finally, the sections were visualized using an inverted microscope (IX71; Olympus, Tokyo, Japan).

Statistical Analysis.

Data are expressed as mean±SD. Values of $P<0.05$ were considered statistically significant.

(SEQ ID NO: 32)
Inhibition on A375 Tumor Growth by
FNIII 9-10 (CRARGDNPDC) Variant The antiangiogenic activity of FNIII 9-10 L1408P (CRARGDNPDC) variant (SEQ ID NO:32) encouraged us to determine whether it could suppress pathological angiogenesis. Tumor growth is angiogenesis-dependent, and suppression of angiogenesis has been shown to inhibit tumor growth. To study the possible antitumor activity of FNIII 9-10 L1408P (CRARGDNPDC) variant (SEQ ID NO:32), we used human A375 melanoma xenografts. Flow cytometry analysis showed that integrin α5β1 is overexpressed on A375 tumor cells. In vivo subcutaneous administration of FNIII 9-10 L1408P (CRARGDNPDC) variant (SEQ ID NO:32) resulted in dose-dependent suppression of tumor growth. After a 3-wk treatment, reduction of tumor volumes and weights was observed (see FIG. 13). To elucidate the cellular basis for the observed defects in tumor burden, we evaluated the effects of FNIII 9-10 L1408P (CRARGDNPDC) variant (SEQ ID NO:32) on proliferation, and angiogenesis of A375-induced tumors by performing immunohistochemistry on paraffin-embedded tumor sections with the appropriate markers. Tumors exhibited a very slight defect in proliferative status, as reflected by the quantification of the cellular Ki67 expression levels. It is consistent with our in vitro results that FNIII 9-10 L1408P (CRARGDNPDC) variant (SEQ ID NO:32) showed slight inhibition on tumor cell proliferation. Another possible explanation for the observed growth defects may be an inability to efficiently recruit tumor vasculature, as β1-integrin has been previously implicated in promoting tumor angiogenesis. To test this possibility, we performed immunohistochemical analyses on the tumors by using an anti-CD31 antibody. Interestingly, protein-treated tumors exhibited a different pattern of CD31 staining compared with their proficient counterparts. The number of CD31-positive pixels observed from total vessels within protein-treated tumors was reduced by nearly an average of one-fold. Neovascularization of FNIII 9-10 L1408P (CRARGDNPDC) variant (SEQ ID NO:32)-treated tumors was significantly reduced as compared with control tumors (see FIG. 13). These results reflected a diminution in the average diameter of the tumor-infiltrated vessels observed in A375-induced tumors and suggested an overall impaired blood supply to these tumors. It is in accordance with our in vitro results that FNIII 9-10 L1408P (CRARGDNPDC) variant (SEQ ID NO:32) showed significant suppression on tube formation and Matrigel plug assay. Collectively, these observations indicate that the defects in A375-induced tumor growth and progression by integrin α5β1-antagonist treatment are correlated with reduced angiogenesis but not tumor cell survival.

(SEQ ID NO: 6)
Inhibition on A549 Tumor Growth by
FNIII 10 (CPRGDMPDC) Variant

The antiangiogenic activity of FNIII 10 (CPRGDMPDC) variant (SEQ ID NO:6) encouraged us to determine whether it could suppress pathological angiogenesis. To study the possible antitumor activity of $^{10}$Fn3 (CPRGDMPDC) variant (SEQ ID NO:6), we used human A549 melanoma xenografts. Flow cytometry analysis showed that integrin αvβ3 is not overexpressed on A549 tumor cells. Surprisingly, in vivo subcutaneous administration of FNIII 10 (CPRGDMPDC) variant (SEQ ID NO:6) resulted in dose-dependent suppression of tumor growth. After a 3-wk treatment, reduction of tumor volumes and weights was observed (see FIG. 14). To elucidate the cellular basis for the observed defects in tumor burden, we evaluated the effects of FNIII 10 (CPRGDMPDC) variant (SEQ ID NO:6) on proliferation, and angiogenesis of A375-induced tumors by performing immunohistochemistry on paraffin-embedded tumor sections with the appropriate markers. Tumors exhibited dramatic defect in proliferative status, as reflected by the quantification of the cellular Ki67 expression levels (see FIG. 14).

What is claimed is:

1. An isolated polypeptide comprising a modified human fibronectin fragment that comprises human fibronectin type III domain module 10 (FNIII 10), wherein the FNIII 10 comprises an Arg-Gly-Asp (RGD) motif and two Cys substitutions to form a di-sulfide bond, wherein the two Cys substitutions are a Thr to Cys substitution at amino acid position 1491 and a Ser to Cys substitution at amino acid position 1499 and the FNIII 10 comprising an RGD motif has the formula $Cys^{1491}$-$X_1$-Arg-Gly-Asp-$X_2$-$X_3$-$X_4$-$Cys^{1499}$ (SEQ ID NO: 115), wherein $X_1$ is Ala or Pro;
$X_2$ is Ser, Met, Asn or Trp;
$X_3$ is Pro or Asn; and
$X_4$ is Asp or Glu, and wherein the amino acid position numbering is based on the amino acid numbering of the full length human fibronectin protein (SEQ ID NO:74).

2. The polypeptide of claim 1, wherein the polypeptide inhibits integrin α5β1 or integrin αvβ3 activity and does not inhibit integrin αIIβ3 activity.

3. The polypeptide of claim 1, wherein the amino acid substitution at amino acid position 1492 is Ala or Pro, the amino acid substitution at position 1496 is Met, Asn or Trp, the amino acid substitution at position 1497 is Asn, and the amino acid substitution at position 1498 is Asp or Glu, wherein the amino acid position numbering is based on the amino acid numbering of the full length human fibronectin protein (SEQ ID NO:74).

4. The polypeptide of claim 1, wherein the polypeptide has the amino acid sequence of SEQ ID NO:6, SEQ ID NO:8 or SEQ ID NO:10.

5. The polypeptide of claim 1, wherein $X_1$ is Pro, $X_2$ is Met, $X_3$ is Pro, and $X_4$ is Asp.

6. The polypeptide of claim 5, wherein the polypeptide has the amino acid sequence of SEQ ID NO:6.

7. The polypeptide of claim 1, wherein the modified human fibronectin fragment further comprises human fibronectin type III domain module 9 (FNIII 9) that comprises Leu to Pro substitution at amino acid position 1408, and wherein the FNIII 9 and FNIII 10 (FNIII 9-10) comprises the amino acid sequence of SEQ ID NO:4.

8. The polypeptide of claim 7, wherein the polypeptide has the amino acid sequence of SEQ ID NO: 20 or SEQ ID NO: 22.

9. The polypeptide of claim 8, wherein the polypeptide has the amino acid sequence of SEQ ID NO:20.

10. The polypeptide of claim 1, wherein the polypeptide inhibits integrin αvβ3 activity.

11. The polypeptide of claim 3, wherein the modified human fibronectin fragment further comprises human fibronectin type III domain module 9 (FNIII 9) that comprises Leu to Pro substitution at amino acid position 1408, and wherein the FNIII 9 and FNIII 10 (FNIII 9-10) comprises the amino acid sequence of SEQ ID NO:4.

12. A pharmaceutical composition comprising a therapeutically effective amount of the polypeptide of claim 1, and a pharmaceutically acceptable excipient, diluent or carrier.

13. A method of inhibiting tumor progression in a mammal comprising administering to a mammal in need thereof the pharmaceutical composition of claim 12, wherein the tumor cell expresses αvβ3 or α5β1.

14. The method of claim 13, where the tumor is lung carcinoma, breast tumor, colon tumor, osteosarcoma, pancreatic tumor, ovarian tumor, cervical tumor, glioblastoma, prostate tumor, liver tumor or melanoma.

15. A method of inhibiting an angiogenesis-related disease in a mammal comprising administering to a mammal in need thereof the pharmaceutical composition of claim 12, wherein the angiogenesis-related disease is cancer, macular degeneration, edema or arthritis.

* * * * *